United States Patent
Ikawa et al.

(10) Patent No.: US 11,739,153 B2
(45) Date of Patent: Aug. 29, 2023

(54) ANTI-HLA-DQ2.5 ANTIBODY AND ITS USE FOR THE TREATMENT OF CELIAC DISEASE

(71) Applicant: Chugai Seiyaku Kabushiki Kaisha, Tokyo (JP)

(72) Inventors: Yuri Ikawa, Singapore (SG); Yuu Okura, Kanagawa (JP); Akihiko Mizoroki, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 17/477,651

(22) Filed: Sep. 17, 2021

(65) Prior Publication Data

US 2022/0089743 A1 Mar. 24, 2022

(30) Foreign Application Priority Data

Sep. 18, 2020 (JP) .................. 2020-157873

(51) Int. Cl.
  C07K 16/28 (2006.01)
(52) U.S. Cl.
  CPC ...... C07K 16/2833 (2013.01); C07K 2317/24 (2013.01); C07K 2317/31 (2013.01); C07K 2317/55 (2013.01); C07K 2317/565 (2013.01); C07K 2317/622 (2013.01)
(58) Field of Classification Search
  USPC ...................................... 424/133.1
  See application file for complete search history.

(56) References Cited

U.S. PATENT DOCUMENTS

| | | | |
|---|---|---|---|
| 5,965,787 A | 10/1999 | Luthra et al. | |
| 2014/0370020 A1 | 12/2014 | Kuramochi et al. | |
| 2017/0304445 A1 | 10/2017 | Ogez et al. | |
| 2020/0040085 A1* | 2/2020 | Okura | G01N 33/577 |
| 2020/0317790 A1* | 10/2020 | Okura | C07K 16/2833 |
| 2021/0147552 A1* | 5/2021 | Løset | A61P 37/00 |
| 2022/0153847 A1 | 5/2022 | Okura et al. | |
| 2023/0118024 A1 | 4/2023 | Okura et al. | |

FOREIGN PATENT DOCUMENTS

| | | |
|---|---|---|
| AU | 2013/204429 | 5/2013 |
| CN | 103209709 | 7/2013 |
| JP | 2011-519347 | 7/2011 |
| JP | 2015-042638 | 3/2015 |
| JP | 2022-051553 | 3/2022 |
| WO | WO 02/083722 | 10/2002 |
| WO | WO 2009/099641 | 8/2009 |
| WO | WO 2010/141658 | 12/2010 |
| WO | WO 2012/017003 | 2/2012 |
| WO | WO 2016/202805 | 12/2016 |
| WO | WO 2017/184880 | 10/2017 |
| WO | WO 2018/155692 | 8/2018 |
| WO | WO 2019/069993 | 4/2019 |
| WO | WO 2019/158602 | 8/2019 |
| WO | WO 2020/204054 | 10/2020 |

OTHER PUBLICATIONS

Biesiekierski (Journal of Gastroenterology and Hepatology 2017; 32 (Suppl. 1): 78-81).*
Wieser (Food Microbiology 24 (2007) 115-119).*
Falcigno et al (Int. J. Mol. Sci. 2020, 21, 9301; Published: Dec. 6, 2020).*
Dørum et al, (PLoS One Nov. 19, 2010;5(11):e14056. doi: 10.1371/journal.pone.0014056).*
Høydahl et al (Gastroenterology. Apr. 2019 ; 156(5): 1428-1439. e10. doi:10.1053/j.gastro.2018.12.013).*
Frick et al (Protein Eng Des Sel Feb. 17, 2022;35:gzac005. doi: 10.1093/protein/gzac005).*
Frick et al (Sci Immunol Aug. 20, 2021;6(62):eabg4925. doi: 10.1126/sciimmunol.abg4925).*
Dieli-Crimi et al, "The genetics of celiac disease: A comprehensive review of clinical implications," J Autoimmun, Nov. 2015, 64:26-41.
U.S. Appl. No. 16/488,336, Okura et al., filed Aug. 23, 2019.
U.S. Appl. No. 16/652,707, Okura et al., filed Apr. 1, 2020.
U.S. Appl. No. 17/438,496, Okura et al., filed Sep. 13, 2021.
U.S. Appl. No. 16/488,336, filed Aug. 23, 2019, Okura et al.
U.S. Appl. No. 17/438,496, filed Sep. 13, 2021, Okura et al.
Anderson et al., "Small Intestine-T cells in peripheral blood after gluten challenge in coeliac disease," Gut, Sep. 2005, 54(9):1217-1223.
Catassi et al., "A prospective, double-blind, placebo-controlled trial to establish a safe gluten threshold for patients with celiac disease," Am J Clin Nutr, Jan. 2007, 85(1):160-166.
Colman, "Effects of amino acid sequence changes on antibody-antigen interactions," Research in Immunology, Elsevier, NY, 1994, 145(1):33-36.
Du Pre et al., "Tolerance to Ingested Deamidated Gliadin in Mice is Maintained by Splenic, Type 1 Regulatory T Cells," Gastroenterology, Aug. 2011, 141(2):610-620, 620.e1-2. doi: 10.1053/j.gastro.2011.04.048. Epub Apr. 28, 2011.
Frick et al., "A high-affinity human TCR-like antibody detects celiac disease gluten peptide-MHC complexes and inhibits T cell activation," Sci Immunol, Aug. 20, 2021, 6(62):eabg4925, 17 pages.
Goel et al., "Efficacy, Safety, Tolerability, and Immunological Effects of Nexvax2®, a Peptide-Based Therapeutic Vaccine, Administered by Intra-Dermal (ID) Injection Twice-Weekly for 8-Weeks in HLA-DQ2.5+ Celiac Disease (CeD)," Gastroenterology, 2016, 150(4 Supplement 1):S-180, #846, 1 page.

(Continued)

Primary Examiner — Lynn A Bristol
(74) Attorney, Agent, or Firm — Fish & Richardson P.C.

(57) ABSTRACT

The present invention relates to anti-HLA-DQ2.5 antibodies and its use for the treatment of celiac disease.
The present invention provides anti-HLA-DQ2.5 antibodies that have been modified. The anti-HLA-DQ2.5 antibodies of the invention have binding activity to complexes formed by HLA-DQ2.5 and a gluten peptide, but have substantially no binding activity to complexes formed by HLA-DQ2.5 and an irrelevant peptide. Furthermore, the antibodies of the invention are shown to have inhibitory effects on T cell activation by gluten peptides.

22 Claims, 41 Drawing Sheets

Specification includes a Sequence Listing.

(56) References Cited

OTHER PUBLICATIONS

Green et al., "Medical Progress—Celiac Disease," N Engl J Med, Oct. 25, 2007, 357(17):1731-1743.
Hoydahl et al., "Plasma Cells are the Most Abundant Gluten Peptide MHC-expressing Cells in Inflamed Intestinal Tissues From Patients with Celiac Disease," Gastroenterology, Apr. 2019, 156(5):1428-1439.e10. doi: 10.1053/j.gastro.2018.12.013. Epub Dec. 26, 2018.
Kagnoff, "Celiac disease: pathogenesis of a model immunogenetic disease," J Clin Invest, Jan. 2007, 117(1):41-49.
Lahdeaho et al., "Glutenase ALV003 Attenuates Gluten-Induced Mucosal Injury in Patients With Celiac Disease," Gastroenterology, Jun. 2014, 146(7):1649-1658. doi: 10. 1053/j.gastro. 2014.02.031. Epub Feb. 25, 2014.
Maki et al., "Prevalence of Celiac Disease among Children in Finland," N Engl J Med, Jun. 19, 2003, 348(25):2517-2524.
Megiorni et al., "HLA-DQA1 and HLA-DQB1 in Celiac disease predisposition: practical implications of the HLA molecular typing," J Biomed Sci, Oct. 11, 2012, 19:88, 5 pages. doi: 10.1186/1423-0127-19-88.
Moldenhauer et al., "Surface-expressed invariant chain (CD74) is required for internalization of human leucocyte antigen-DR molecules to early endosomal compartments," Immunology, Mar. 1999, 96(3):473-484.
Pisapia et al., "HLA-DQ2.5 genes associated with celiac disease risk are preferentially expressed with respect to non-predisposing HLA genes: Implication for anti-gluten T cell response," J Autoimmun, Jun. 2016, 70:63-72. doi: 10.1016/j.jaut.2016.03.016. Epub Apr. 12, 2016. PMID: 27083396.
Paul, Chapter 9 "Structure and Function of Immunoglobulins," Fundamental Immunology, 3rd ed, Raven Press, NY, 1993, pp. 292-295.
Rudikoff et al., "Single amino acid substitution altering antigen-binding specificity," Proc Natl Acad Sci USA, Mar. 1982, 79:1979-1983.
Stein et al., "CD74: A New Candidate Target for the Immunotherapy of B-Cell Neoplasms," Clin Cancer Res, Sep. 15, 2007, 13(18 Pt 2):5556s-5563s.
Tatar et al., "Screening of Tissue Transglutaminase Antibody in Healthy Blood Donors for Celiac Disease Screening in the Turkish Population," Dig Dis Sci, Sep. 2004, 49(9):1479-1484.
Tye-Din Ja et al., "Comprehensive, Quantitative Mapping of T Cell Epitopes in Gluten in Celiac Disease," Sci Transl Med, Jul. 21, 2010, 2(41):41ra51, pp. 1-14.
West et al., "Small Intestine—Seroprevalence, correlates, and characteristics of undetected coeliac disease in England," Gut, Jul. 2003, 52(7):960-965.
Wierdsma et al., "Vitamin and Mineral Deficiencies Are Highly Prevalent in Newly Diagnosed Celiac Disease Patients," Nutrients, Sep. 30, 2013, 5(10):3975-3992. doi: 10.3390/nu5103975.
International Search Report in International Application No. PCT/JP2021/034240, dated Nov. 30, 2021, 2 pages.
USPTO Restriction Requirement in U.S. Appl. No. 16/652,707, dated Oct. 29, 2021, 7 pages.
USPTO Non-Final Office Action in U.S. Appl. No. 16/652,707, dated Apr. 12, 2022, 12 pages.
U.S. Appl. No. 17/974,949, Okura et al., filed Oct. 27, 2022.
U.S. Appl. No. 17/974,949, filed Oct. 27, 2022, Okura et al.
Ozuna et al., "Diversification of the celiac disease α-gliadin complex in wheat: a 33-mer peptide with six overlapping epitopes, evolved following polyploidization," Plant J, Jun. 2015, 82(5):794-805.
Tollefsen et al., "HLA-DQ2 and -DQ8 signatures of gluten T cell epitopes in celiac disease," J Clin Invest, Aug. 2006, 116(8):2226-2236.
Cornell et al., "A Second Generation Force Field for the Simulation of Proteins, Nucleic Acids, and Organic Molecules," J Am Chem Soc, May 1, 1995, 117(19):5179-5197.
Gerhardt et al., "Protein Aggregation and Particle Formation in Prefilled Glass Syringes," J Pharm Sci, Jun. 2014, 103(6):1601-1612.
Gerhardt et al., "Effect of the Siliconization Method on Particle Generation in a Monoclonal Antibody Formulation in Pre-filled Syringes," J Pharm Sci, May 2015, 104(5):1601-1609.
Giannos et al., "Formulation Stabilization and Disaggregation of Bevacizumab, Ranibizumab and Aflibercept in Dilute Solutions," Pharm Res, Feb. 28, 2018, 35(4):78, 15 pages.
Grapentin et al., "Protein-Polydimethylsiloxane Particles in Liquid Vial Monoclonal Antibody Formulations Containing Poloxamer 188," J Pharm Sci, Aug. 2020, 109(8):2393-2404.
Jetha et al., "Homology modeling and structure-based design improve hydrophobic interaction chromatography behavior of integrin binding antibodies," mAbs, Aug./Sep. 2018, 10(6):890-900.
Jones et al., "Prediction of Protein-Protein Interaction Sites using Patch Analysis," J Mol Biol, Sep. 12, 1997, 272(1):133-143.
Melchore, "Sound Practices for Consistent Human Visual Inspection," AAPS PharmSciTech, Mar. 2011, 12(1):215-221.
Torisu et al., "Friability Testing as a New Stress-Stability Assay for Biopharmaceuticals," J Pharm Sci, Oct. 2017, 106(10):2966-2978.
Wildman et al., "Prediction of Physicochemical Parameters by Atomic Contributions," J Chem Inf Comput Sci, Aug. 19, 1999, 39(5):868-873.

* cited by examiner

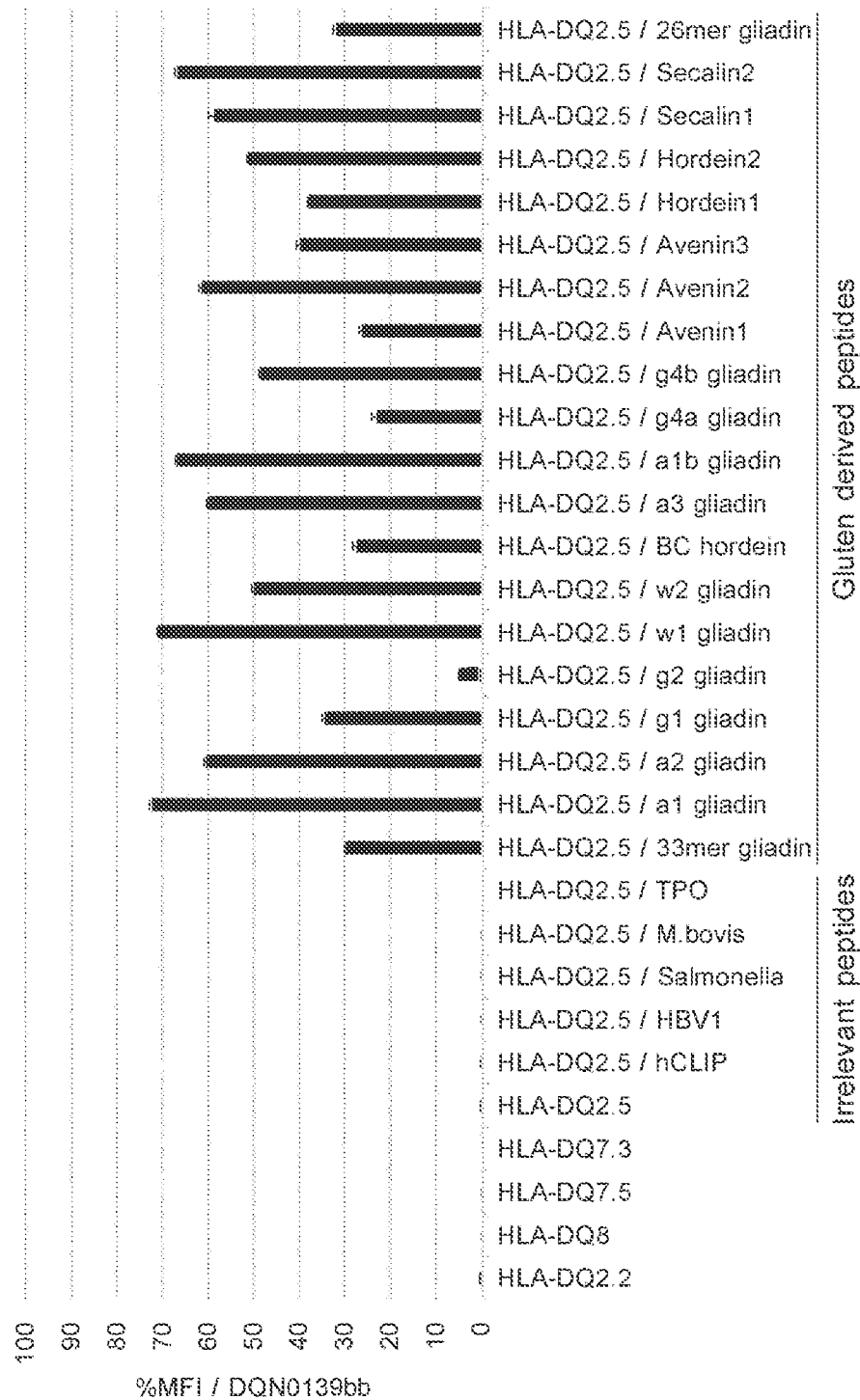
[Fig. 1-1]

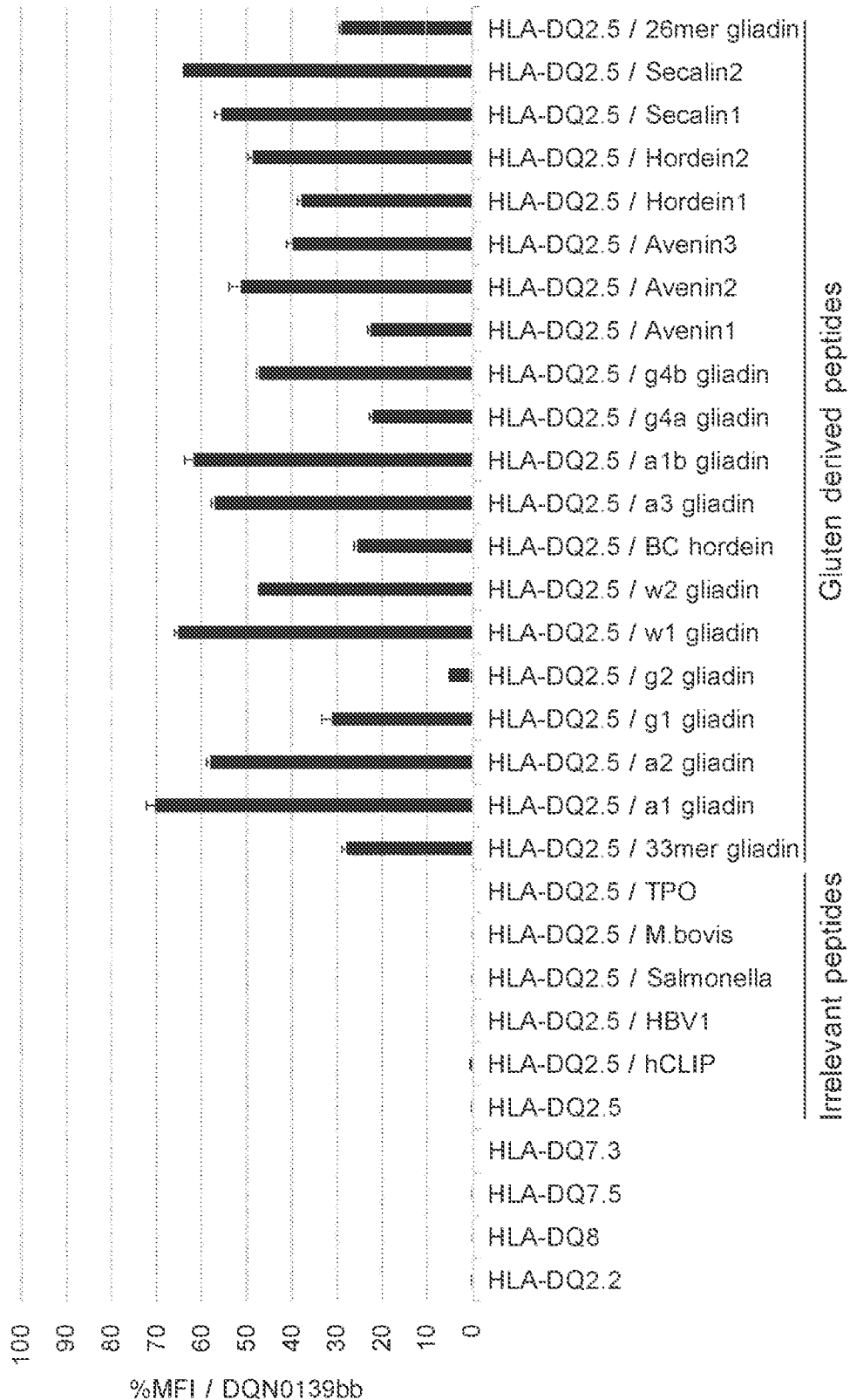

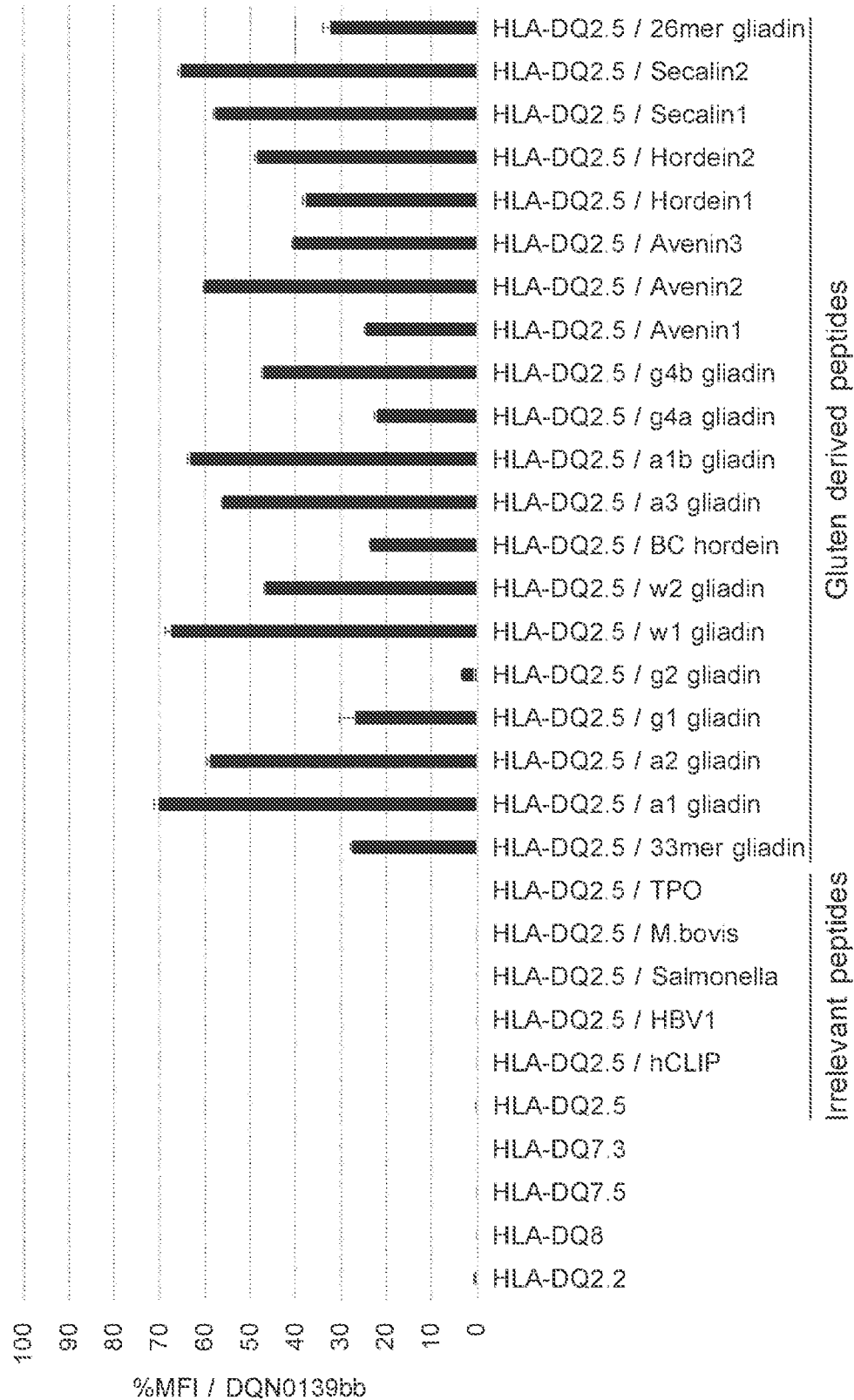

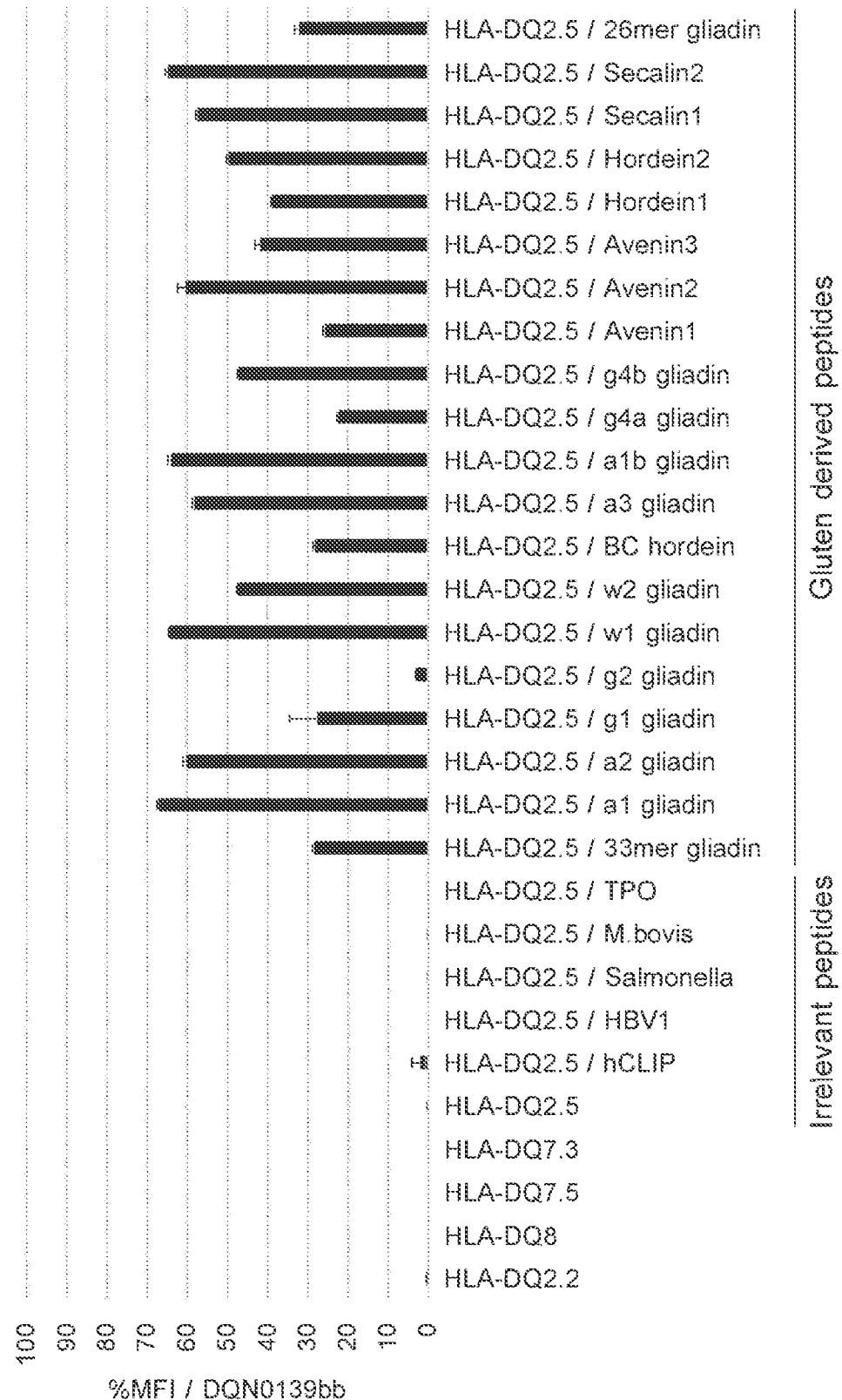

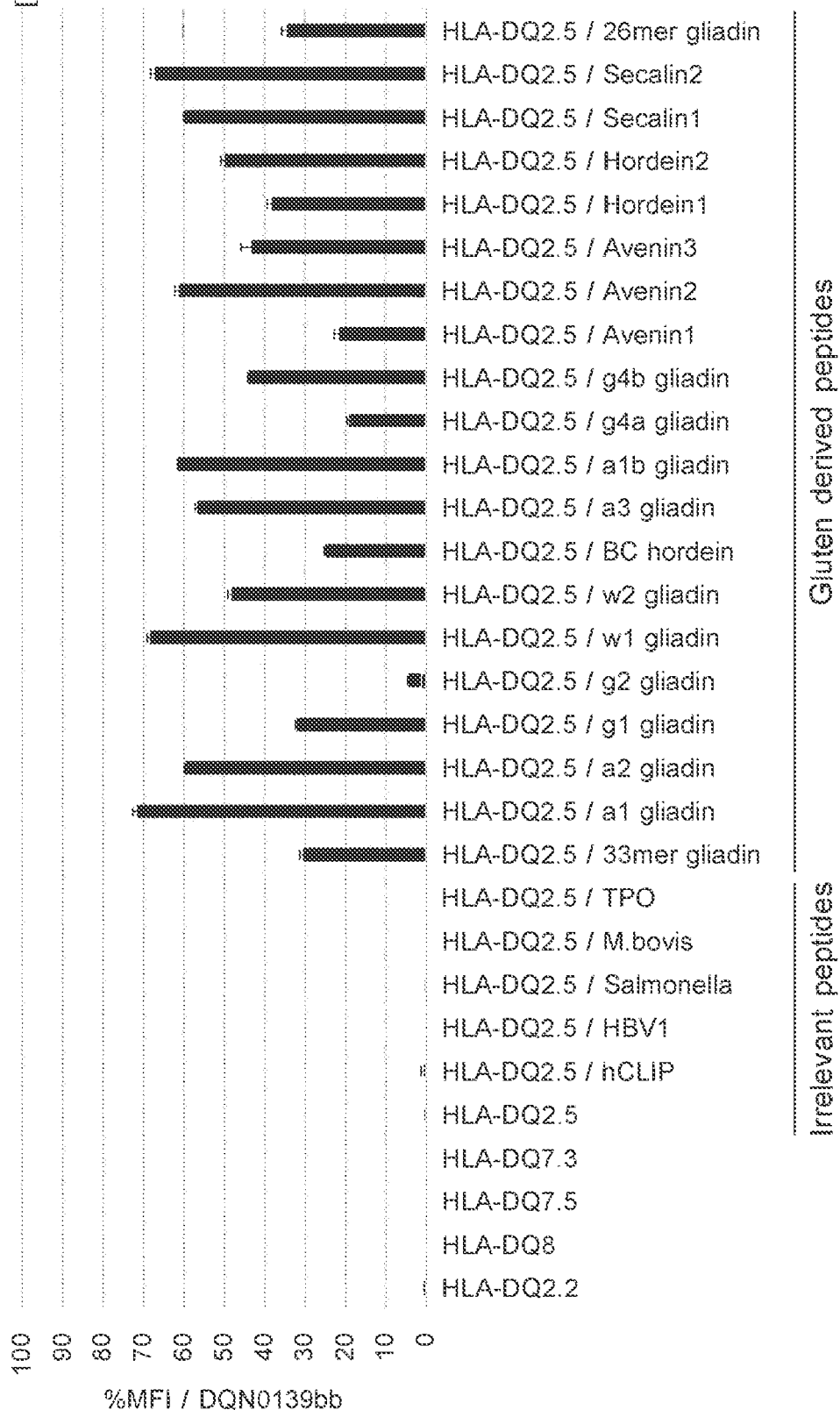

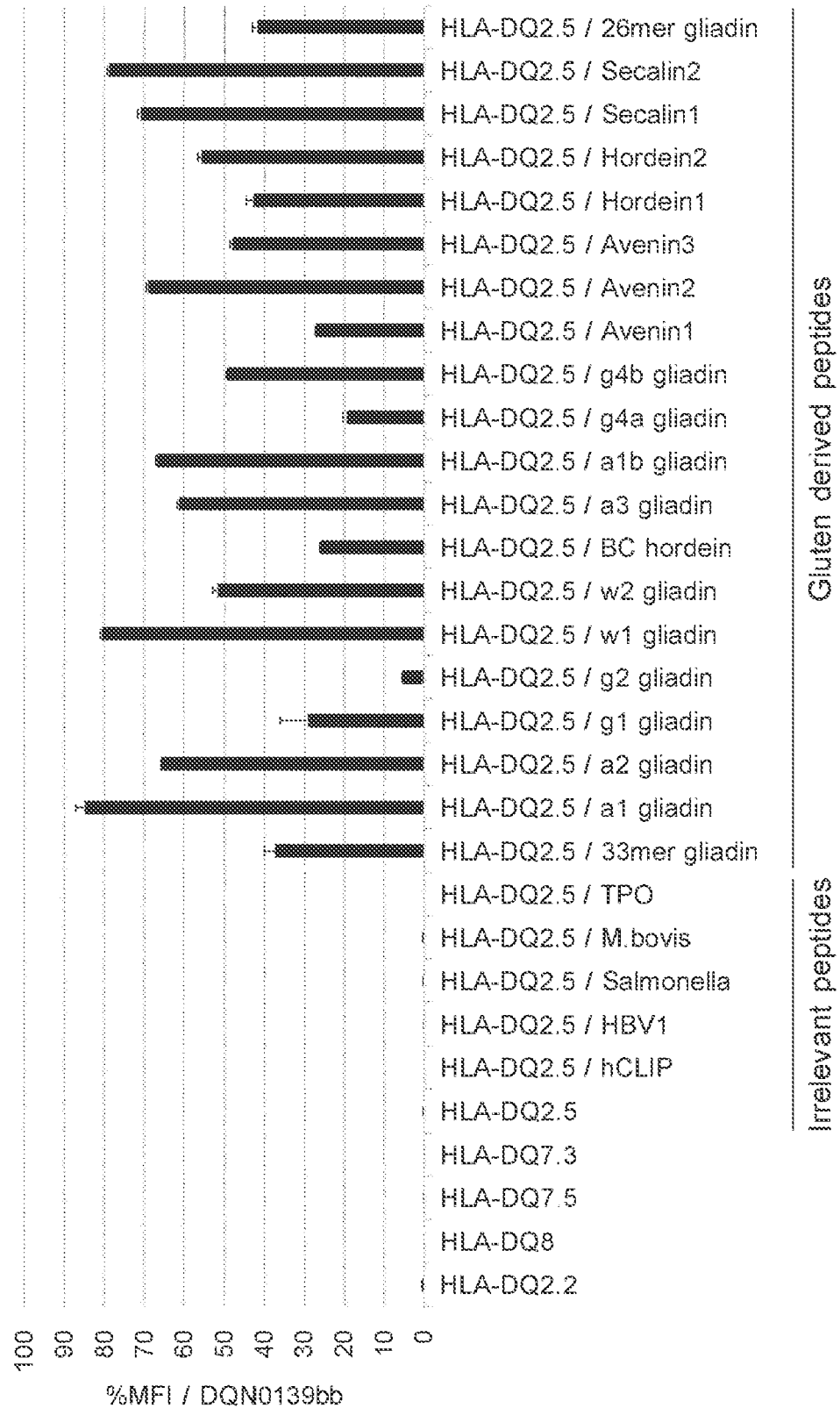
[Fig. 1-6]

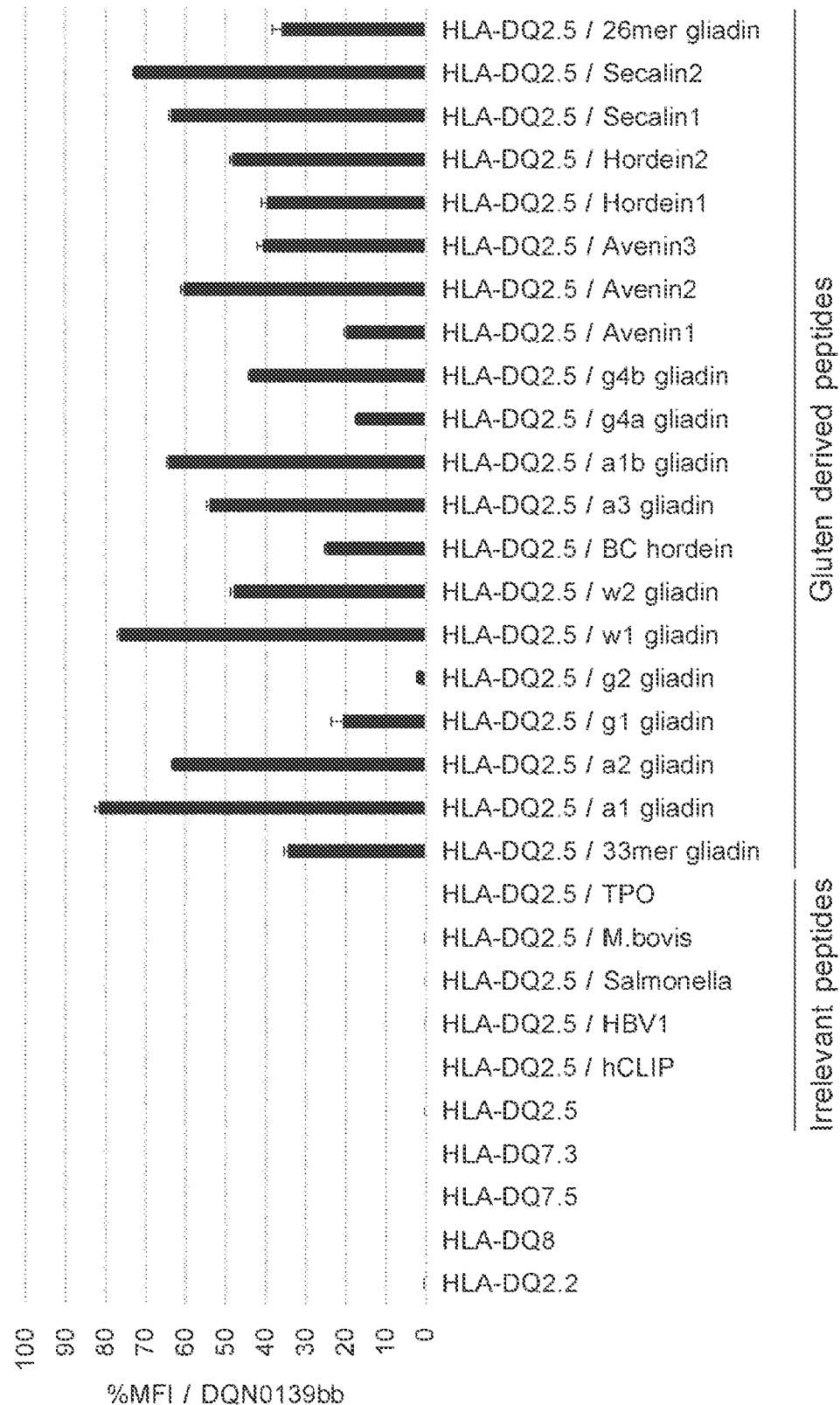

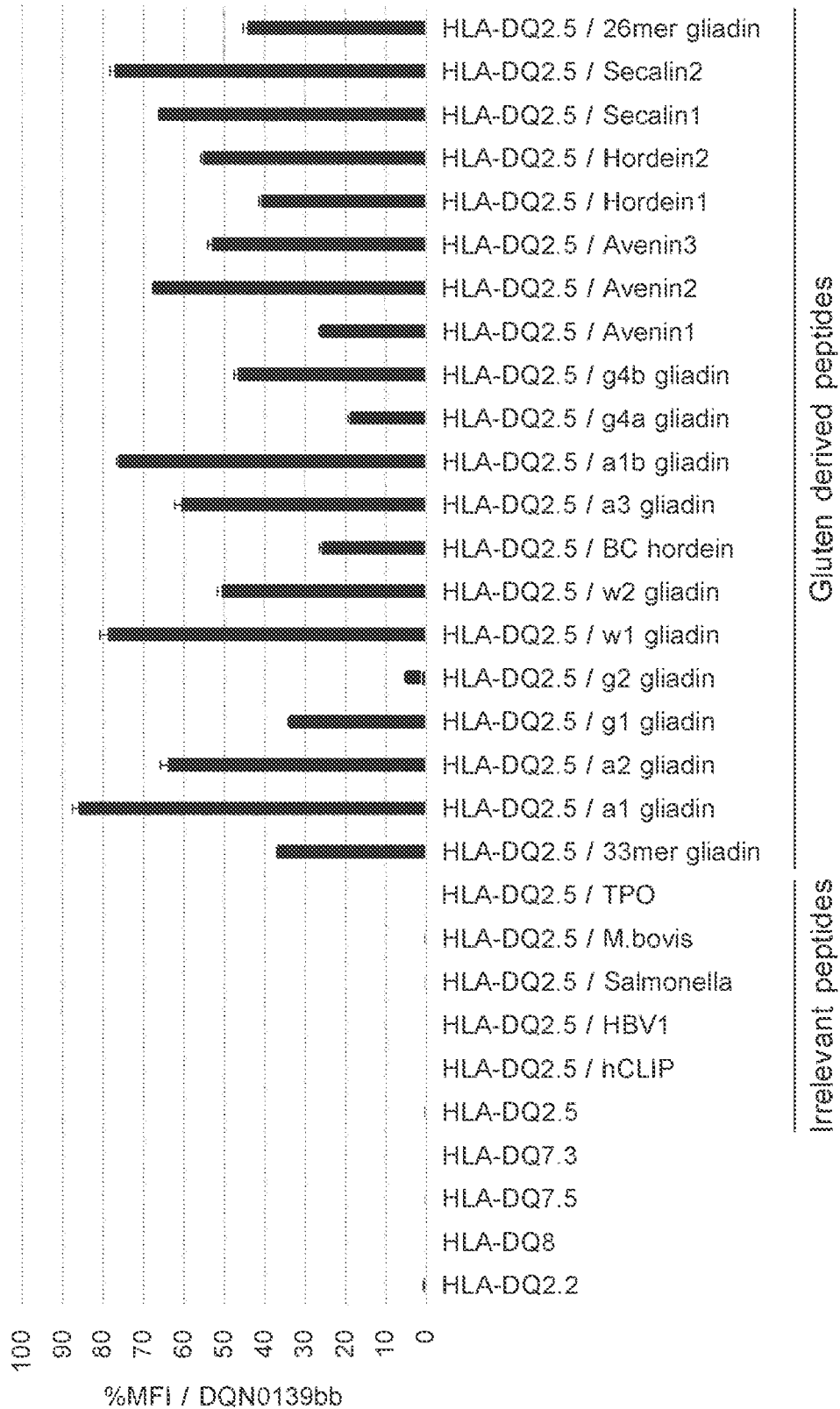
[Fig. 1-8]

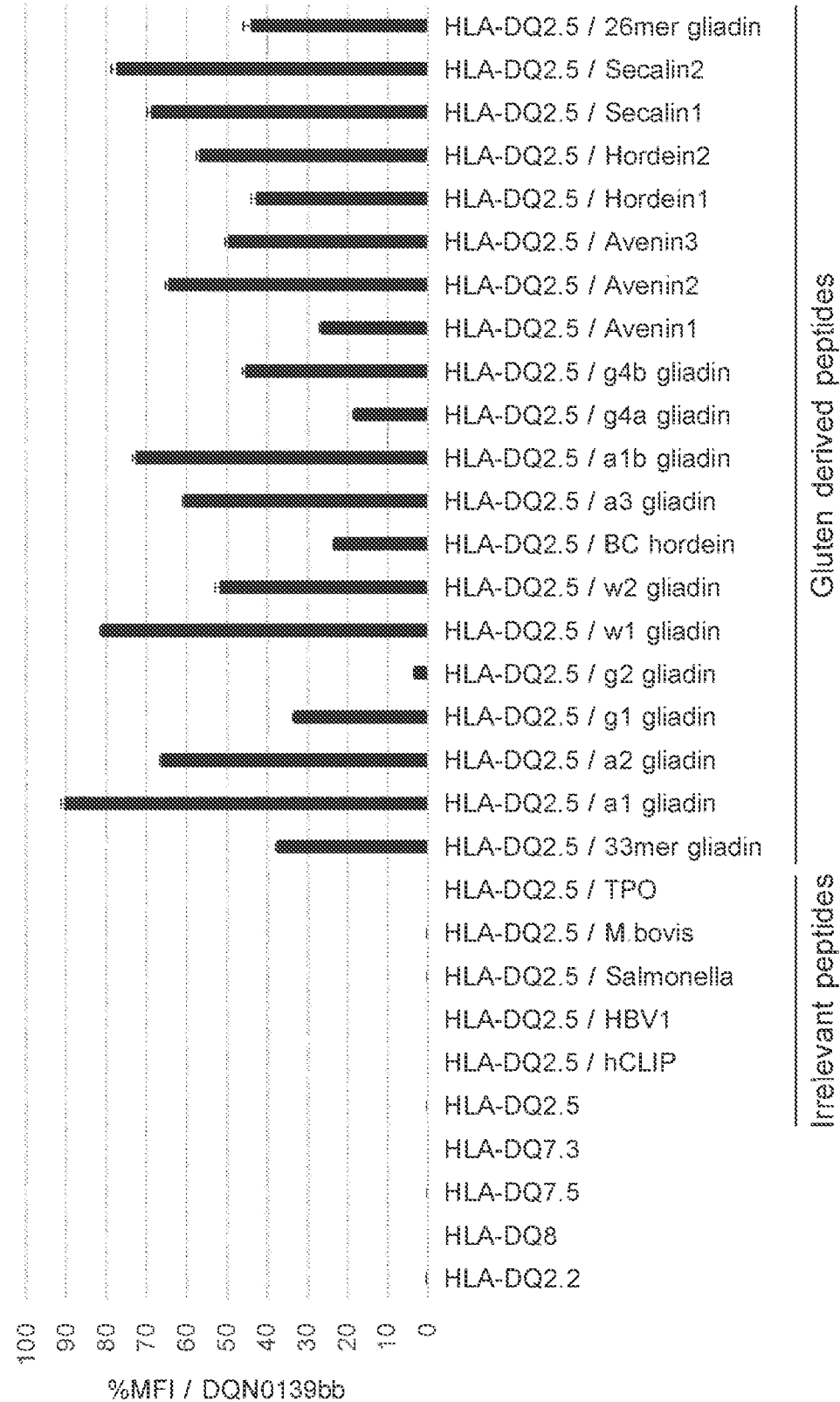

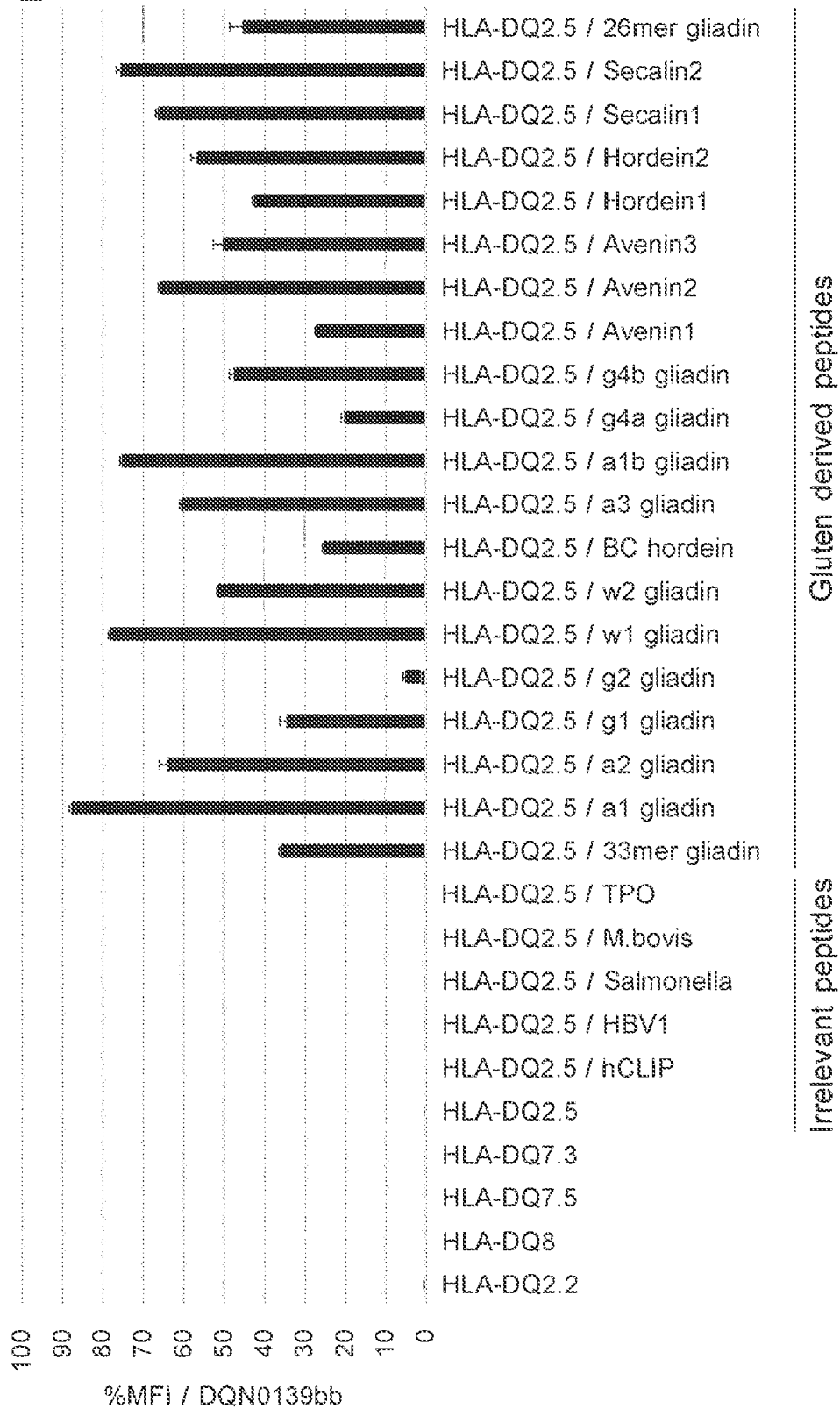
[Fig. 1-10]

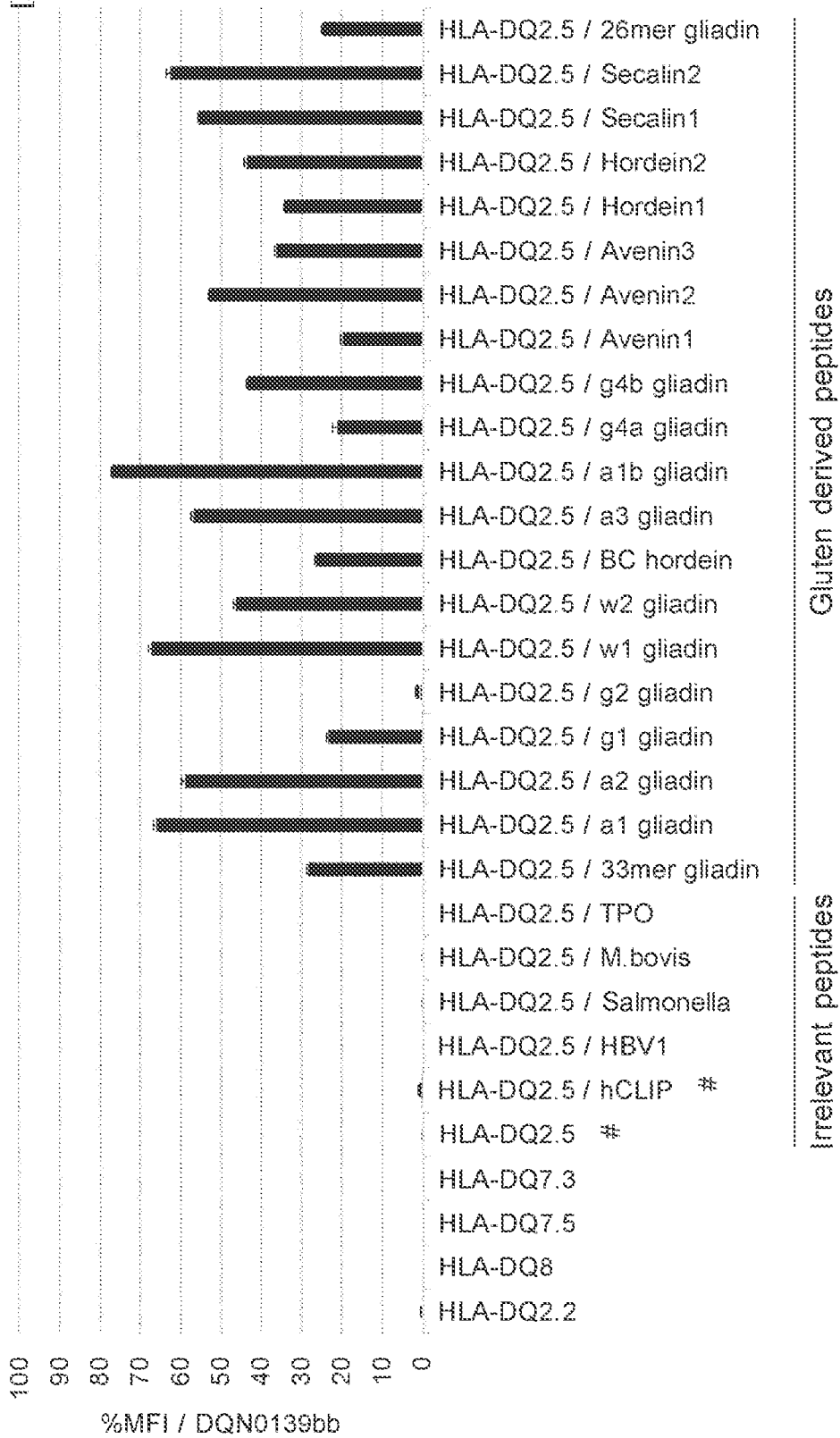

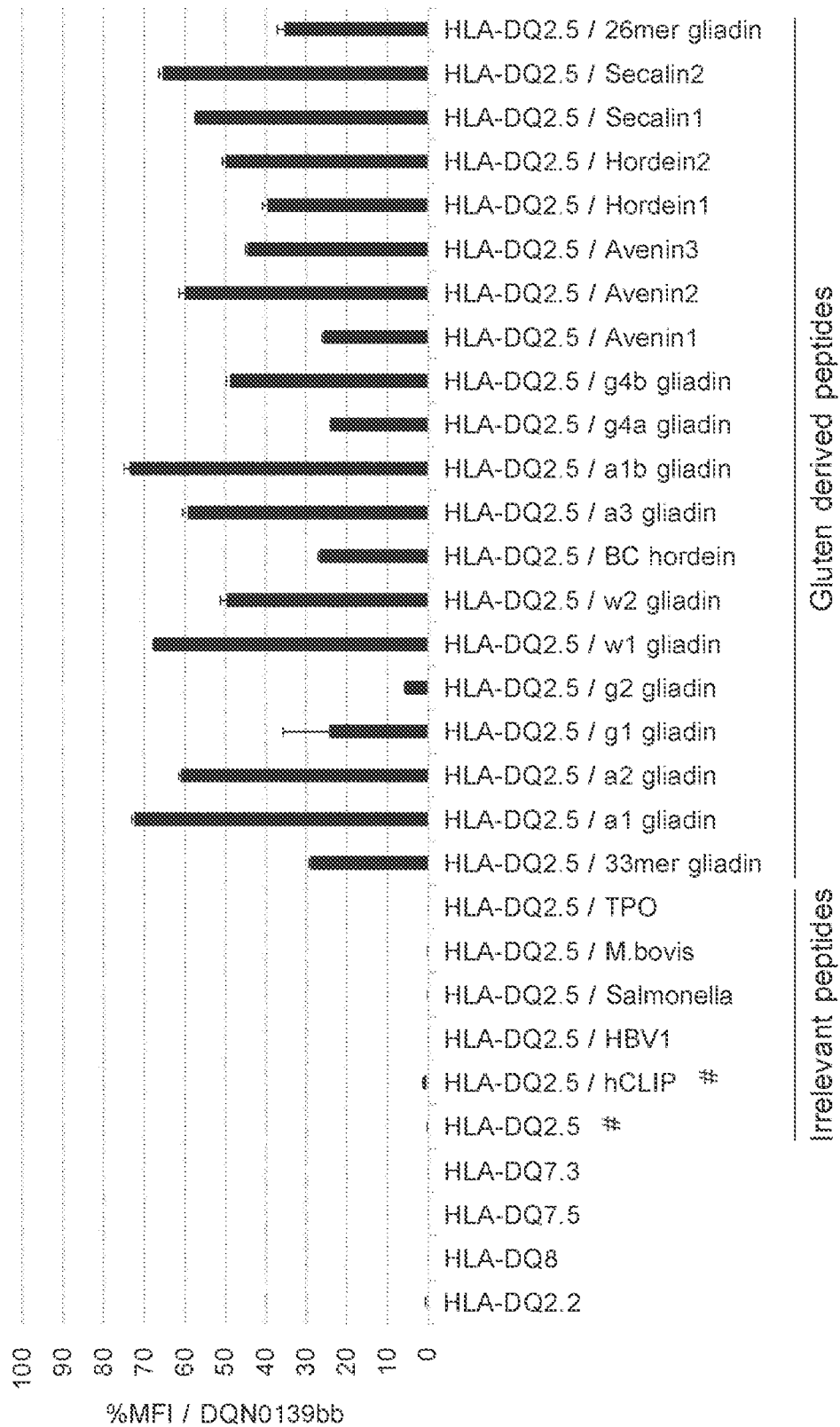
[Fig. 1-12]

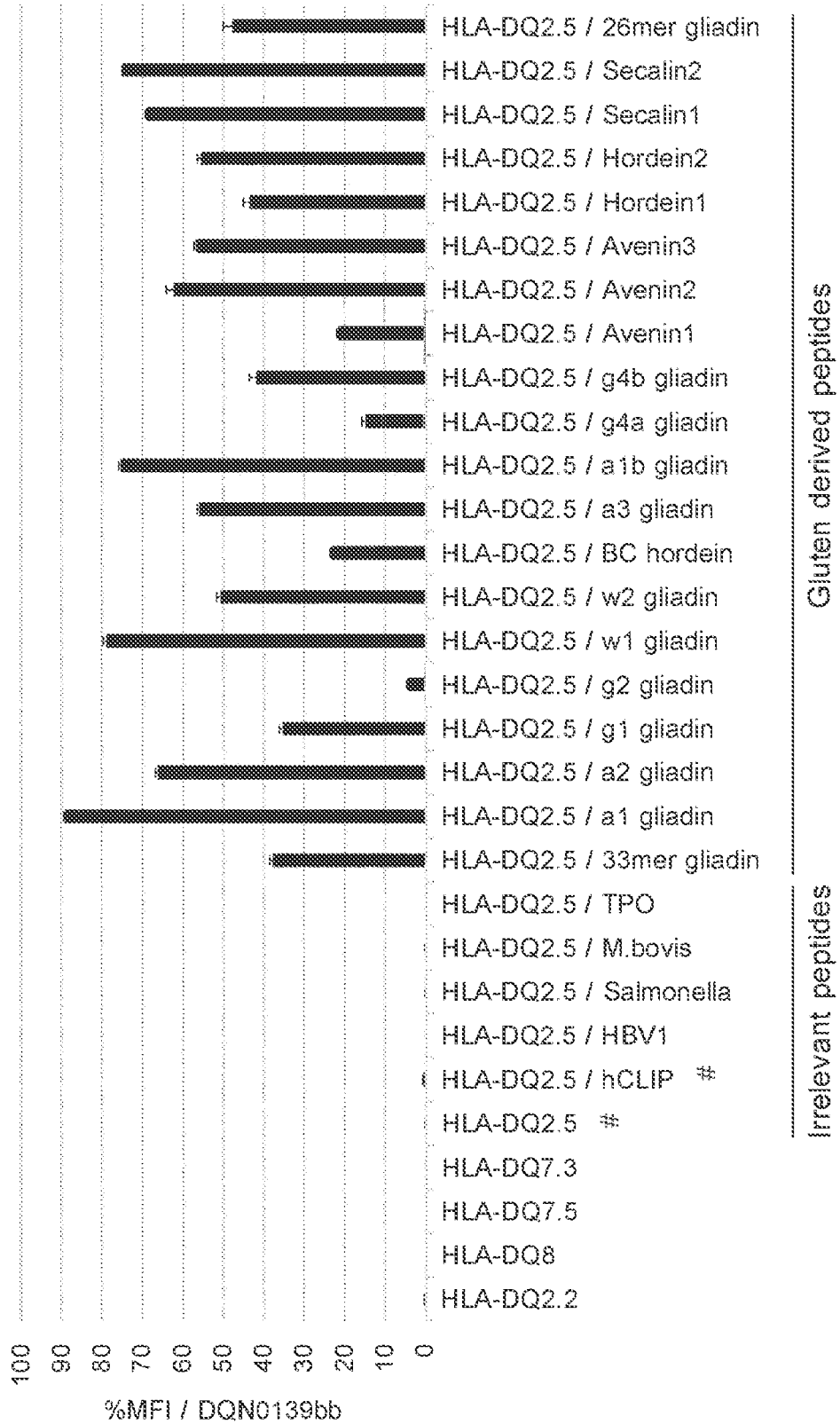
[Fig. 1-13]

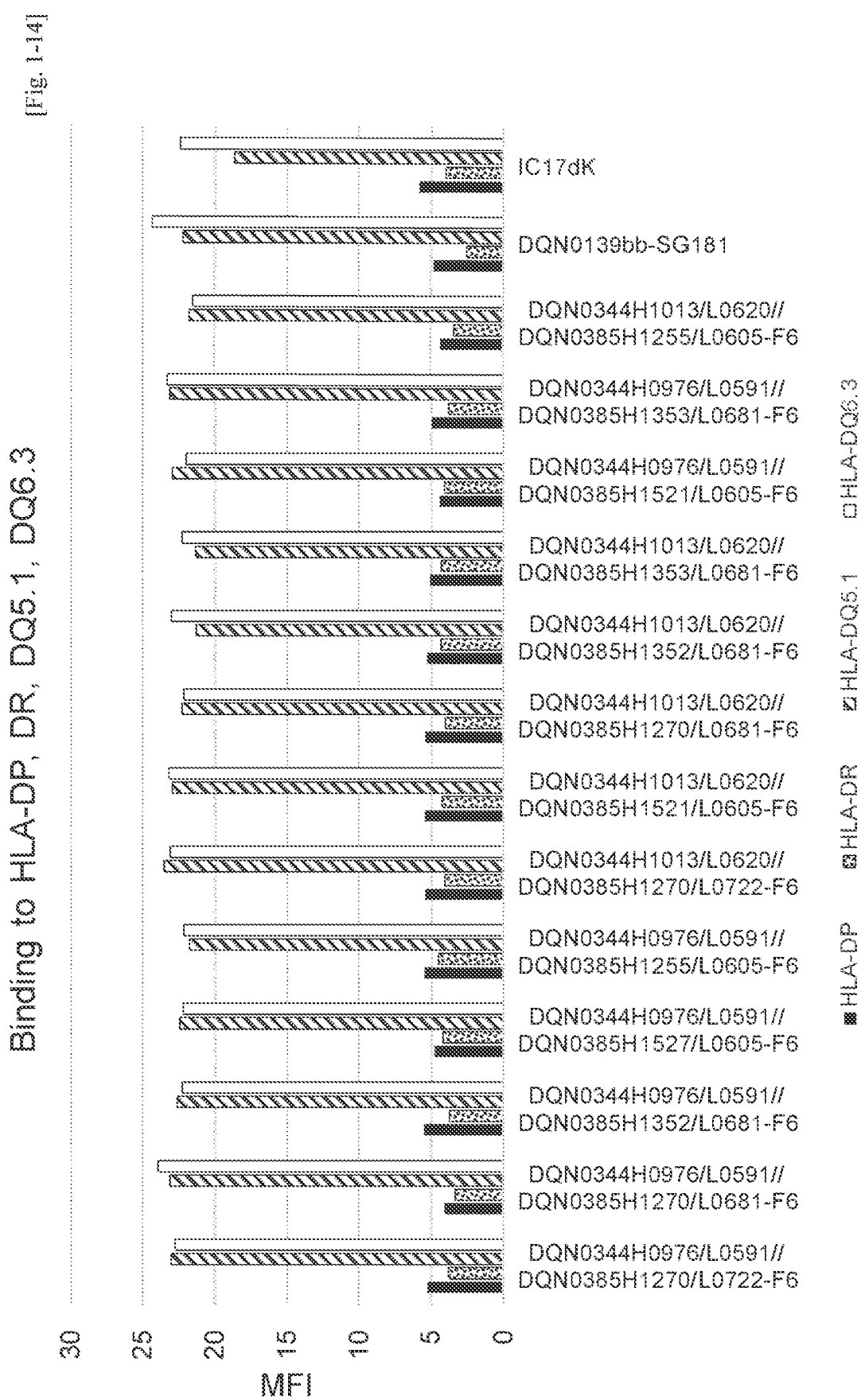

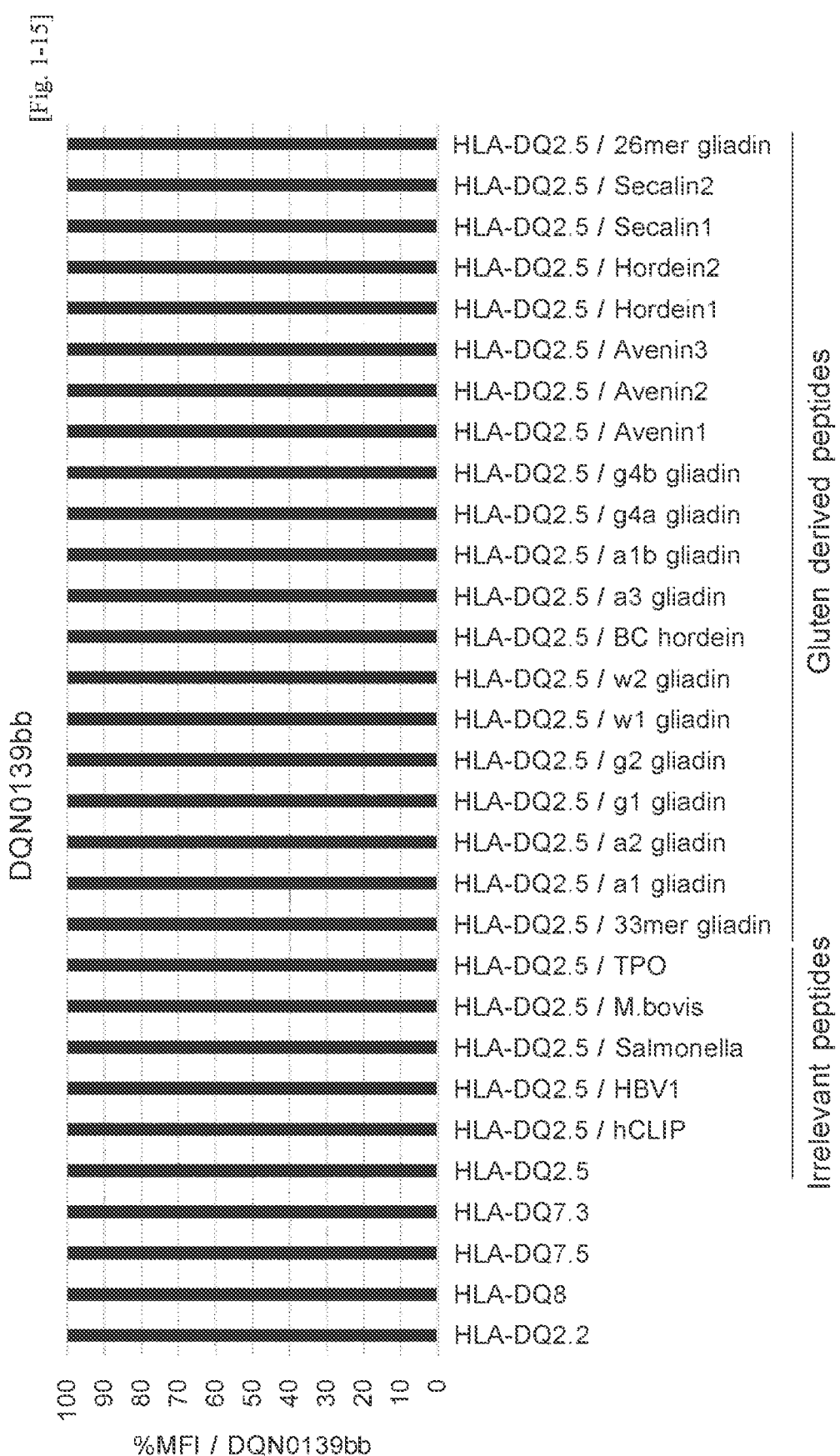

[Fig. 1-16]
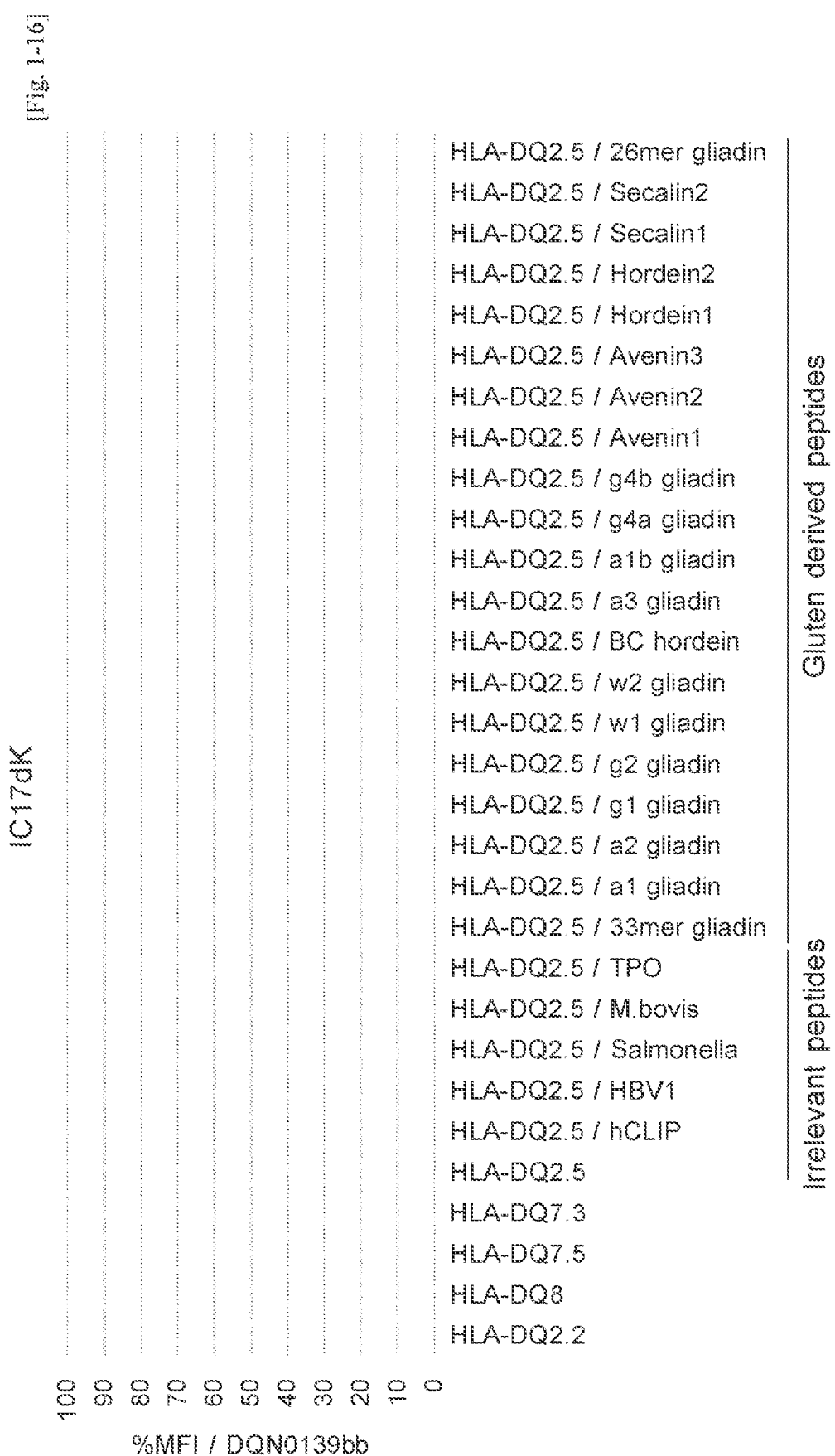

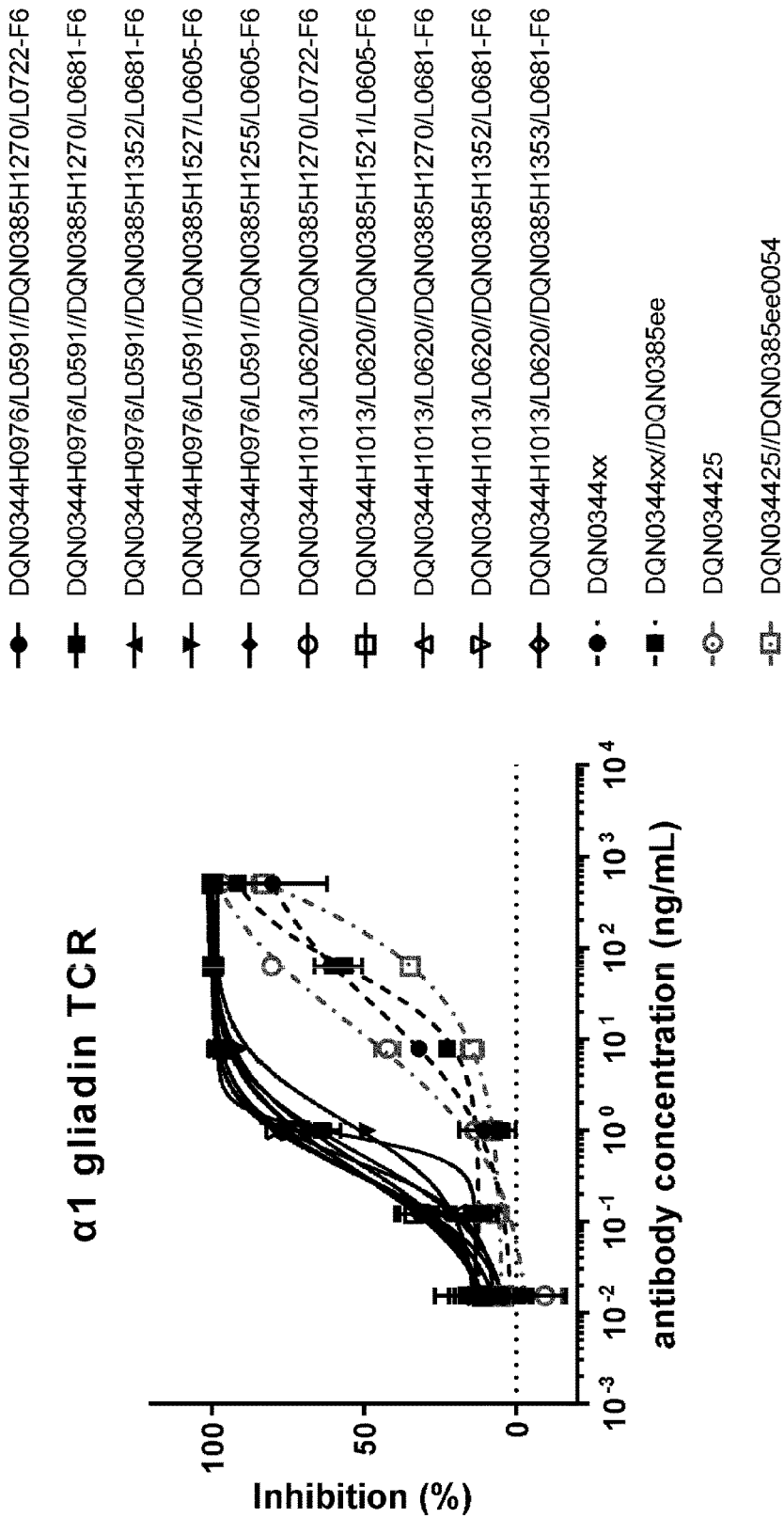

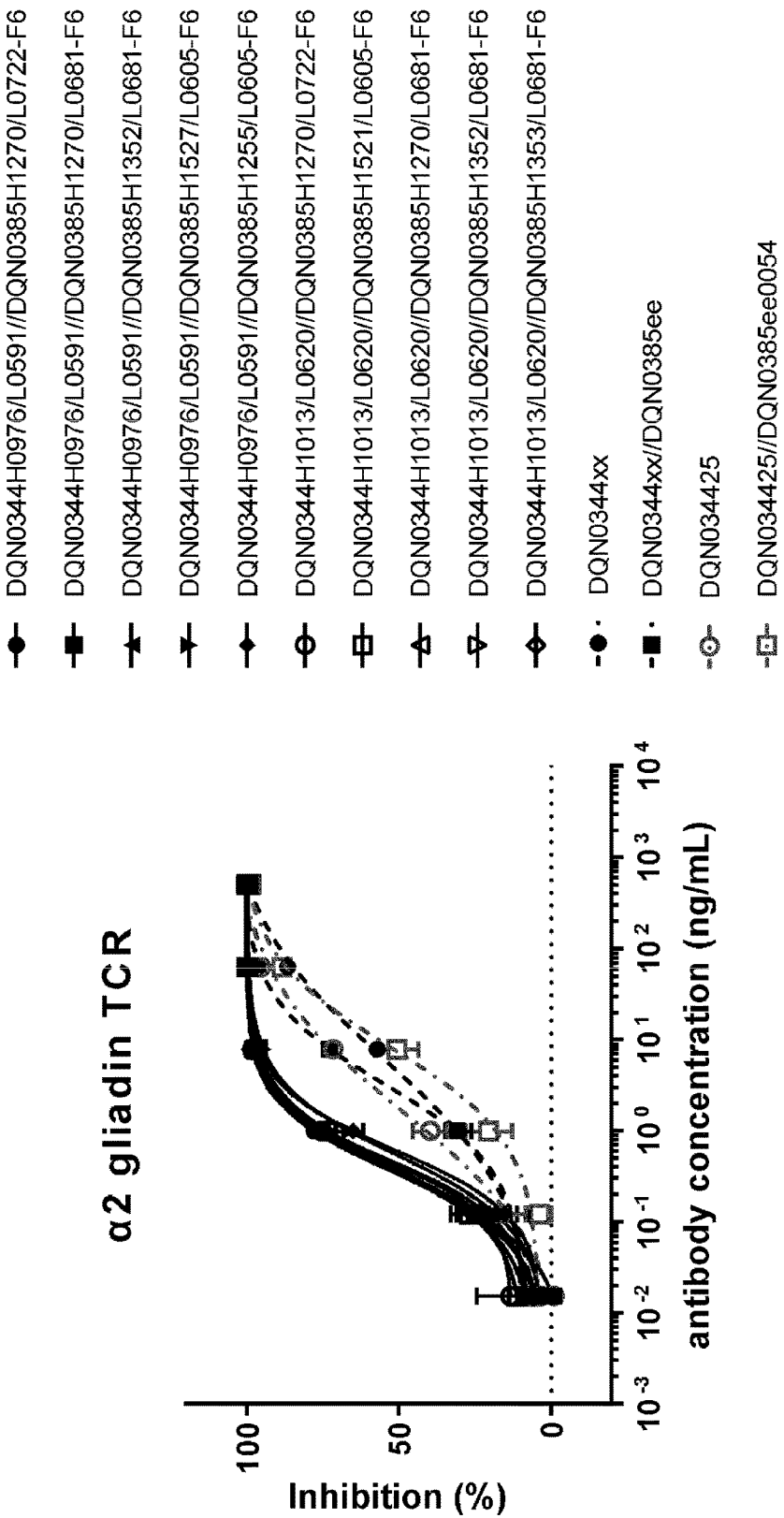

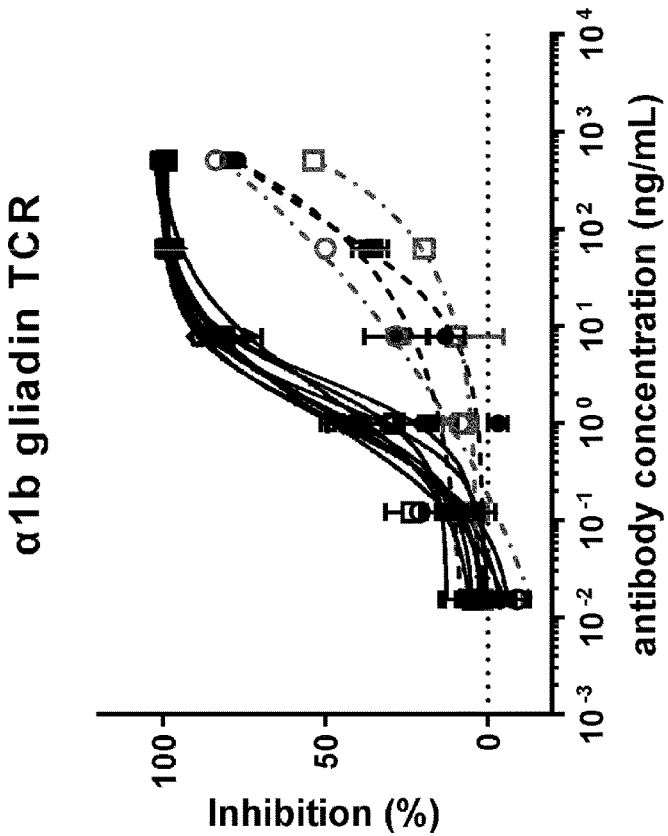

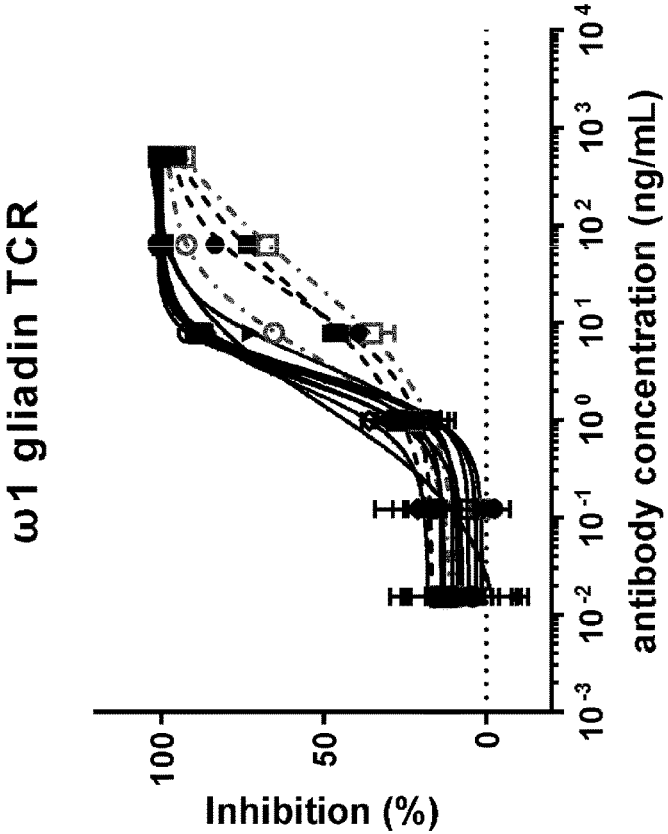
[Fig. 3-4]

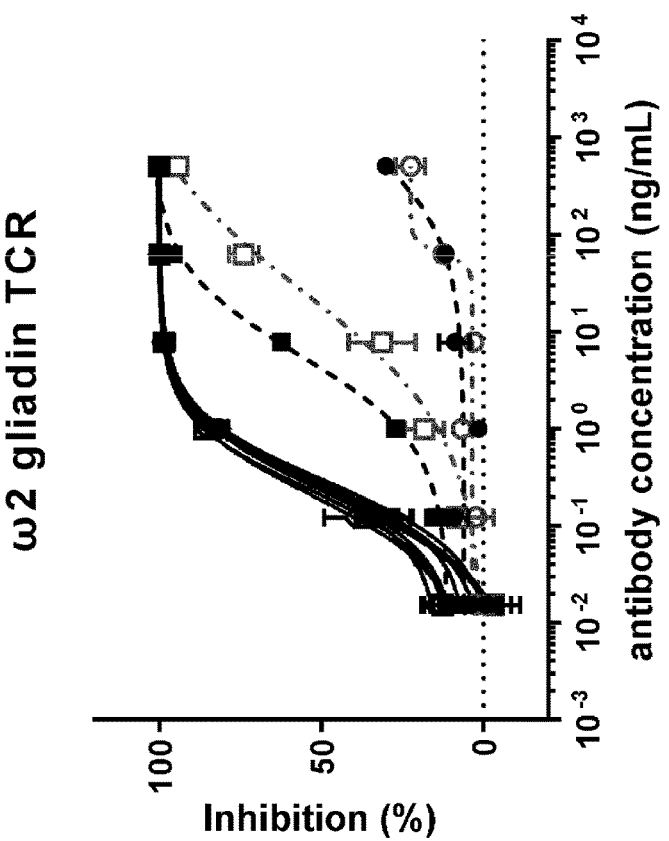

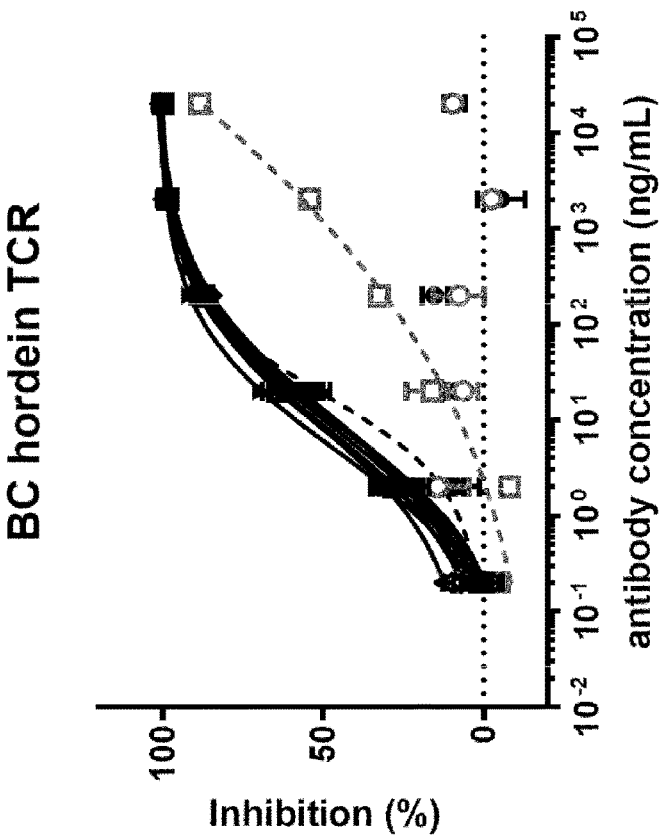

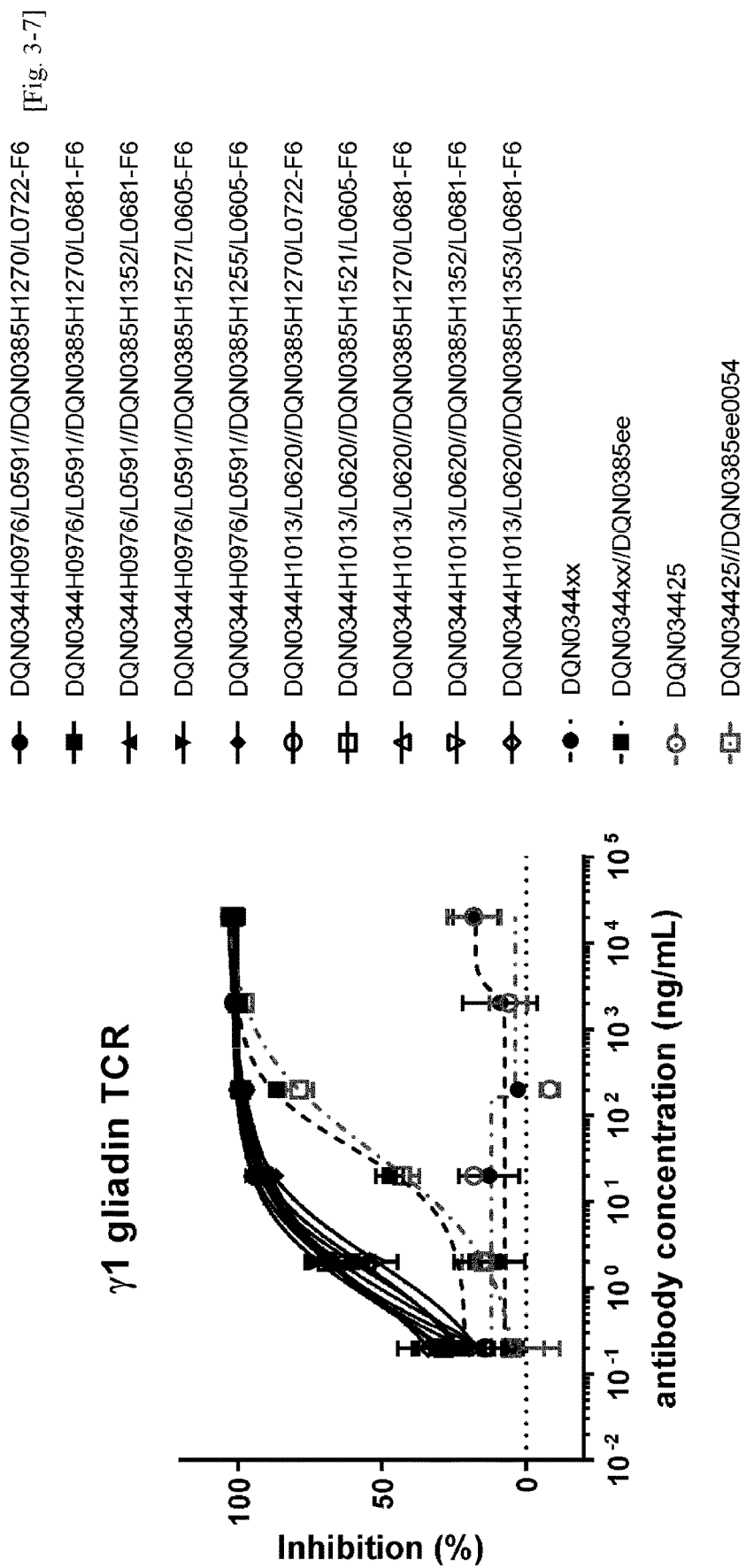

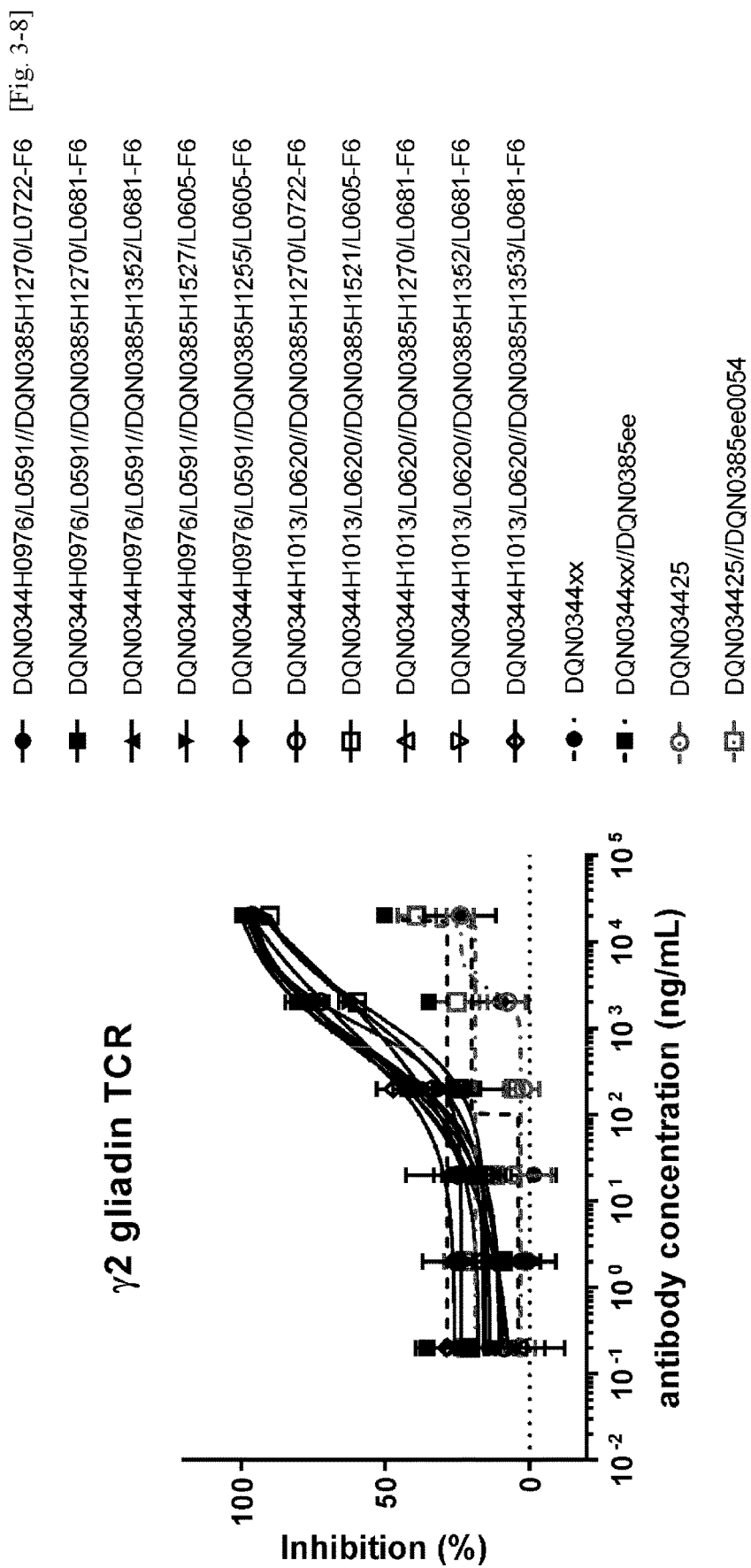

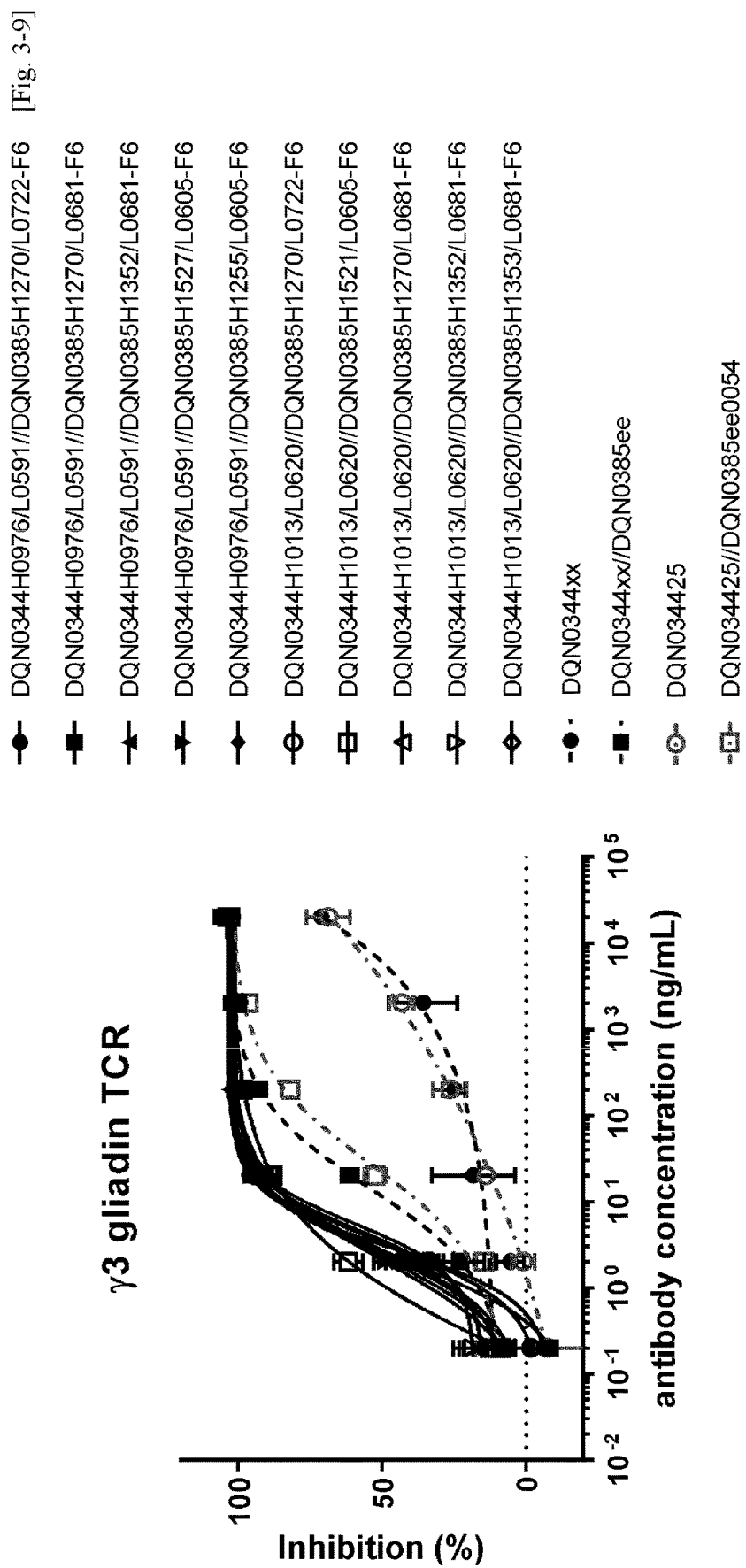

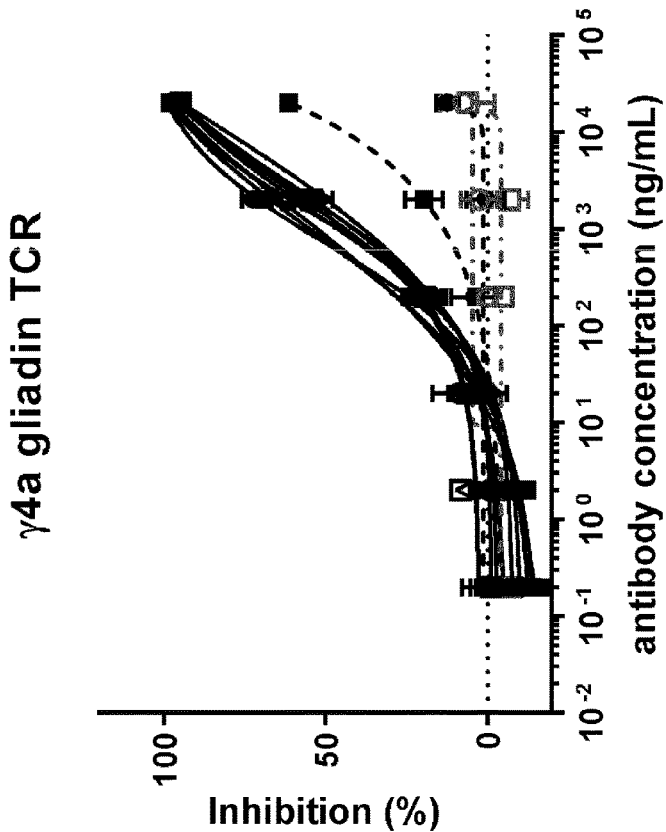

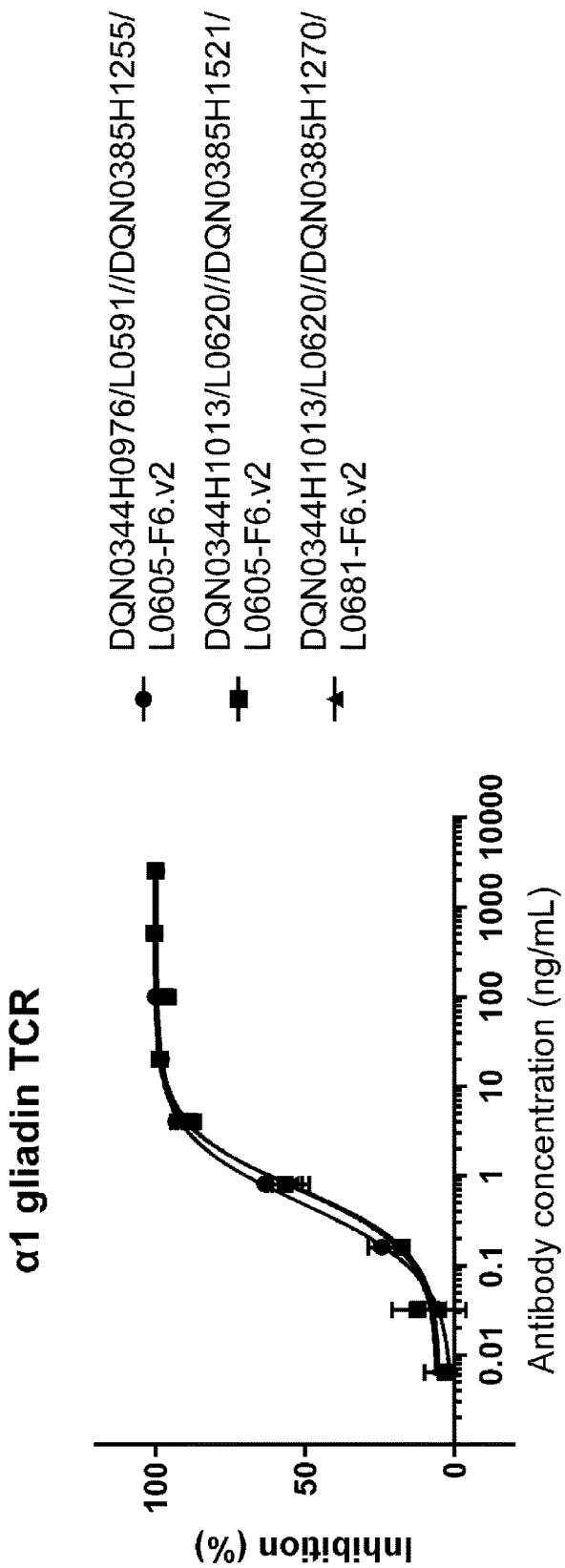

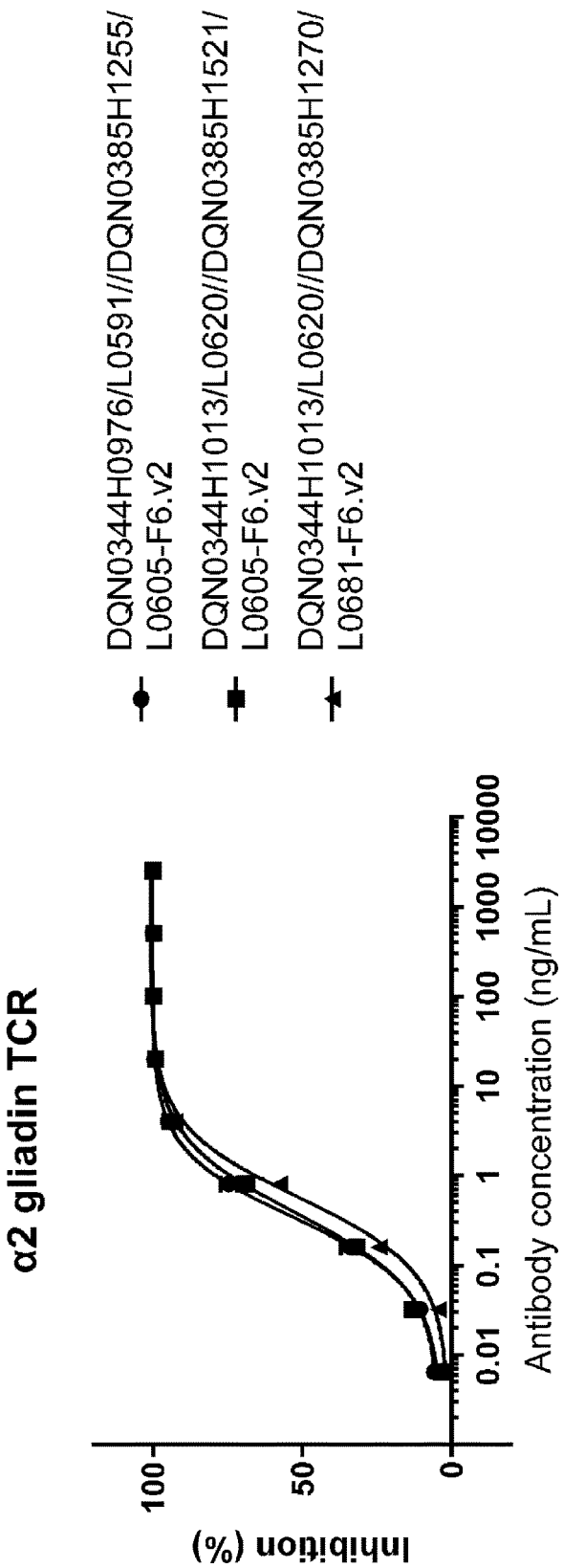

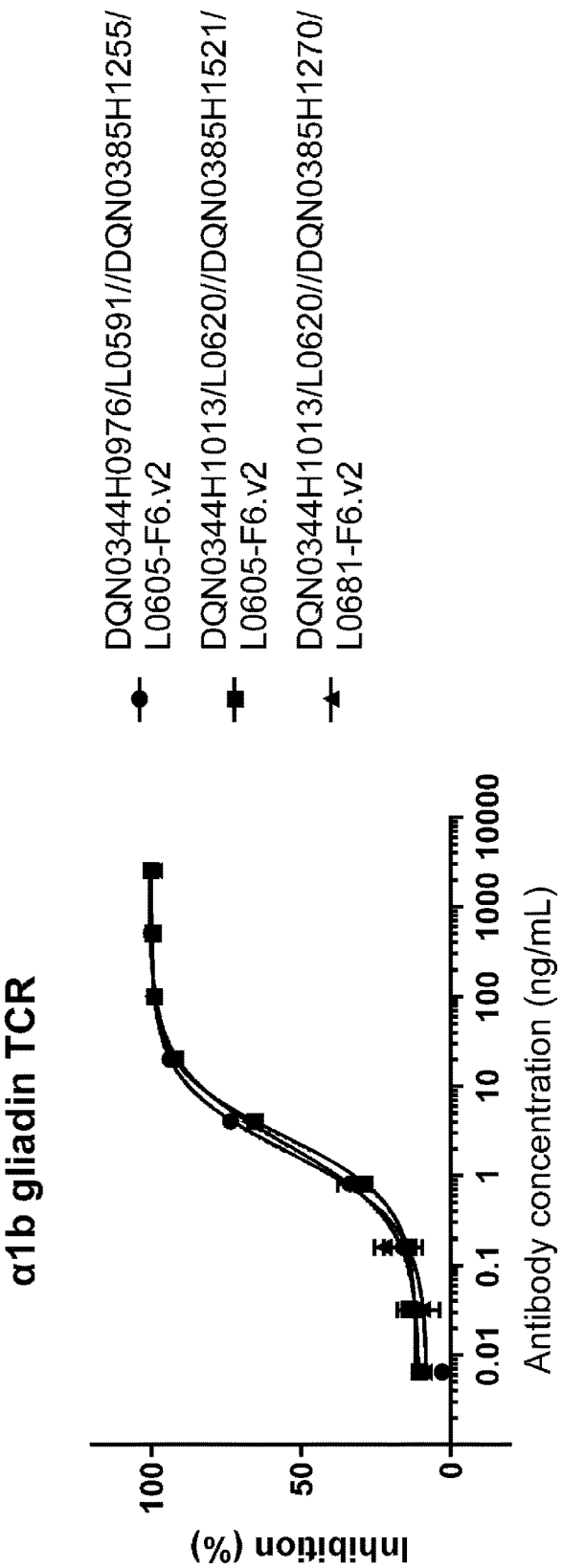

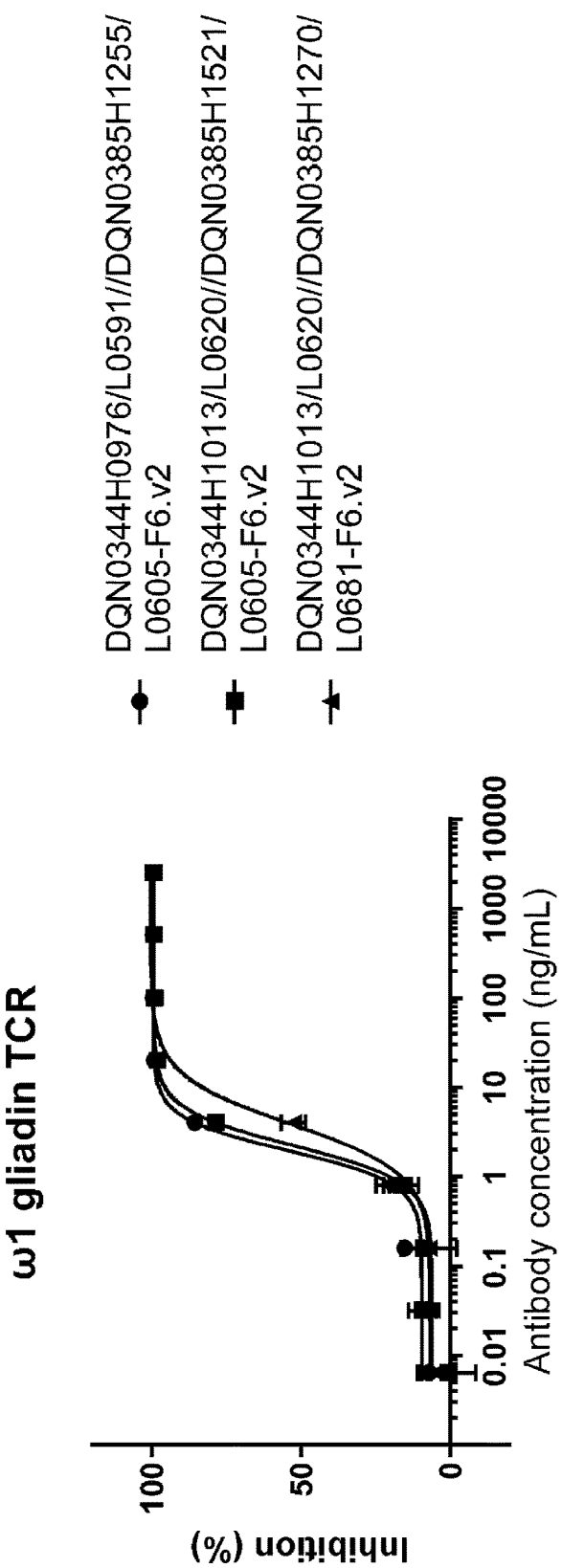

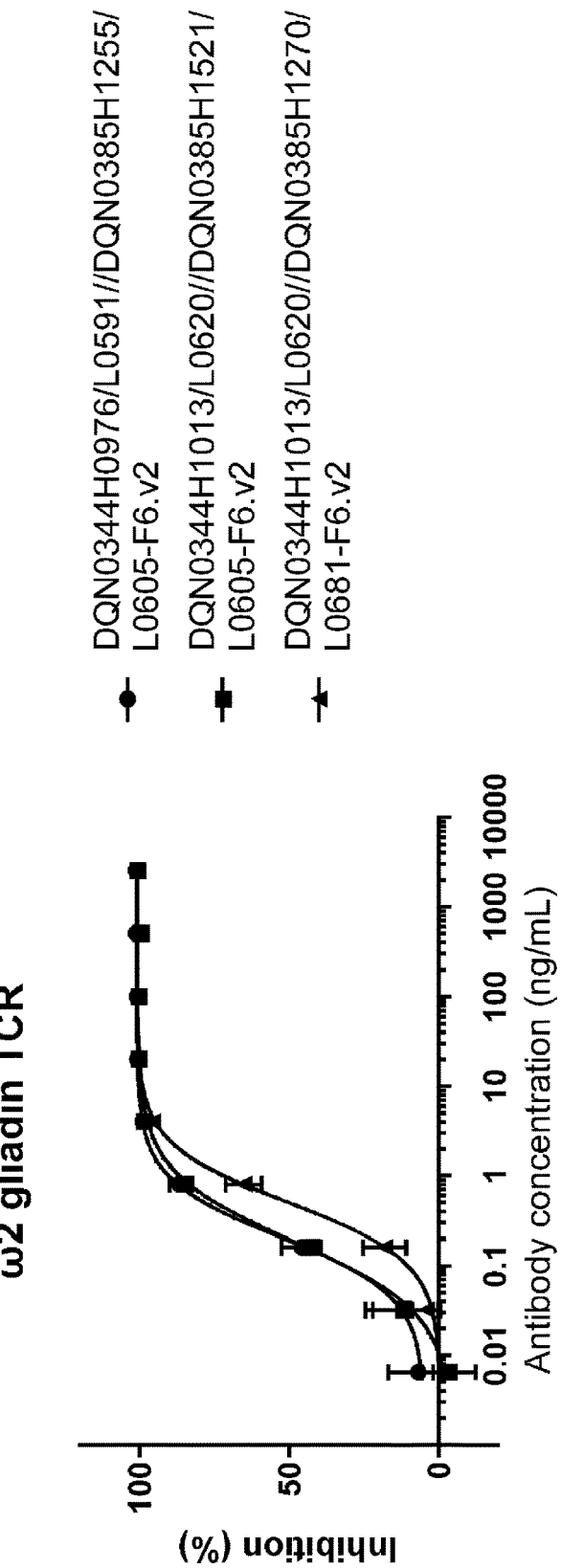
[Fig. 4-5]

[Fig. 4-6]

BC hordein TCR

- ● DQN0344H0976/L0591//DQN0385H1255/L0605-F6.v2
- ■ DQN0344H1013/L0620//DQN0385H1521/L0605-F6.v2
- ▲ DQN0344H1013/L0620//DQN0385H1270/L0681-F6.v2

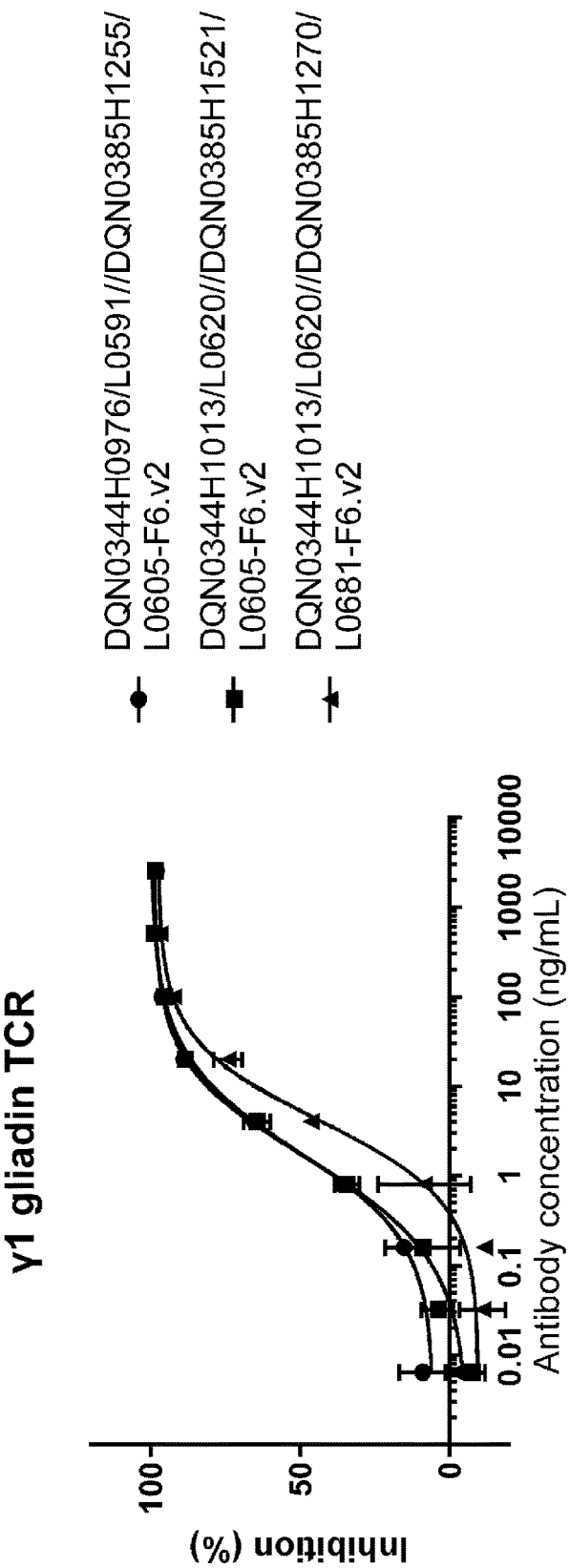

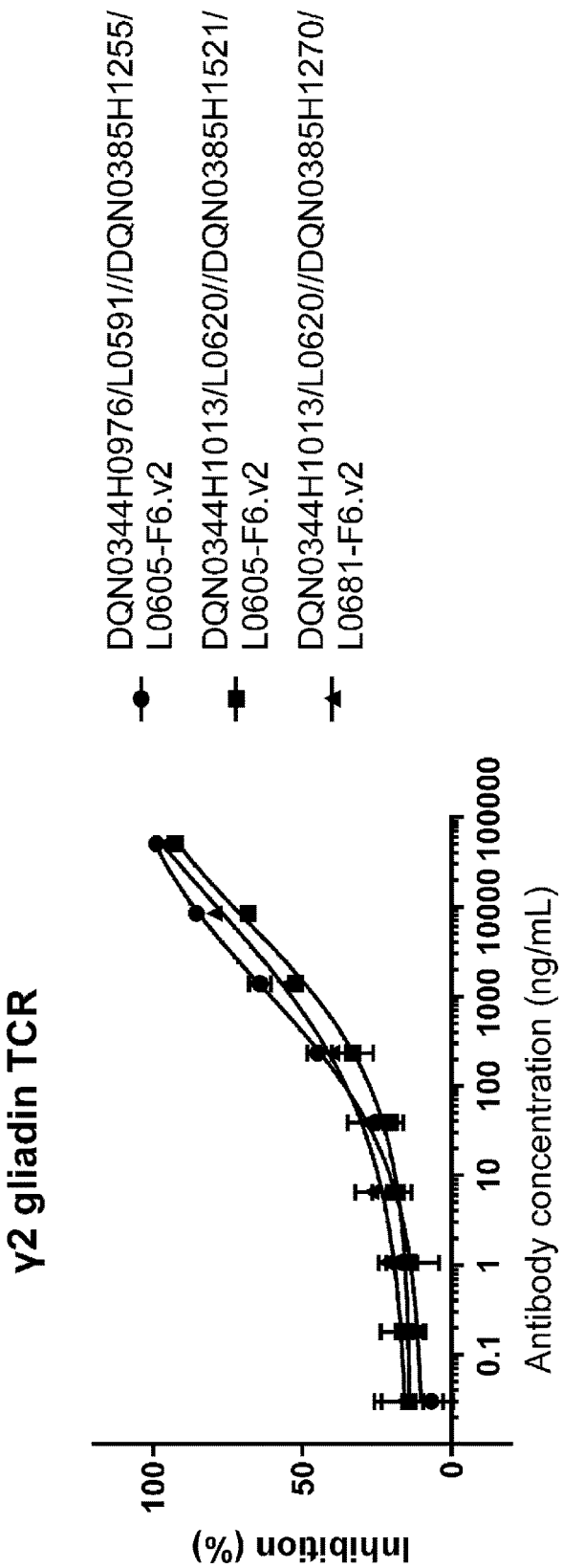
[Fig. 4-8]

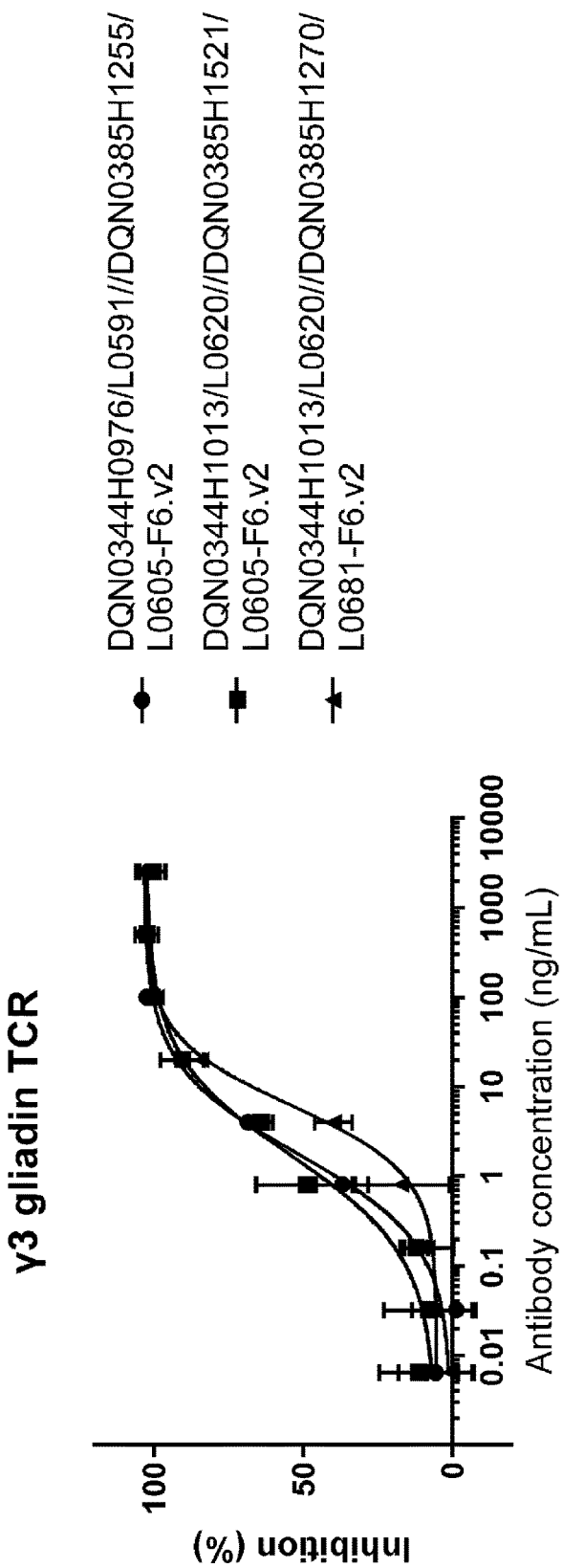

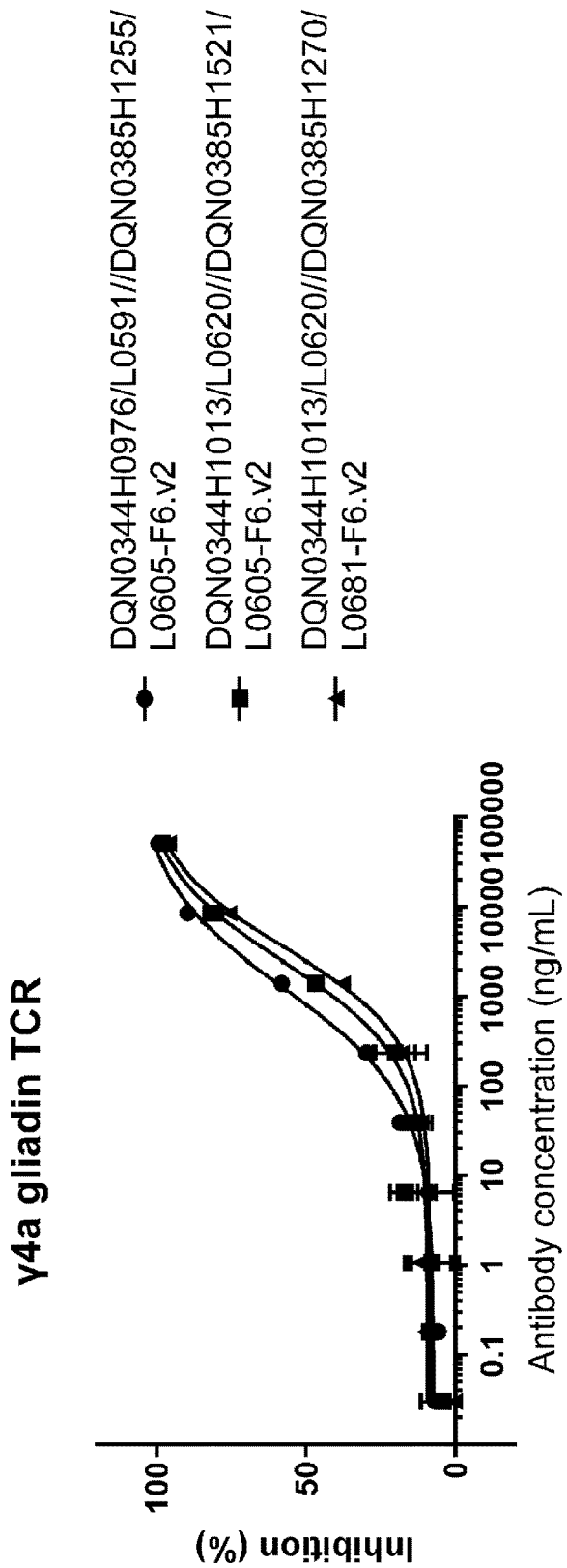
[Fig. 4-10]

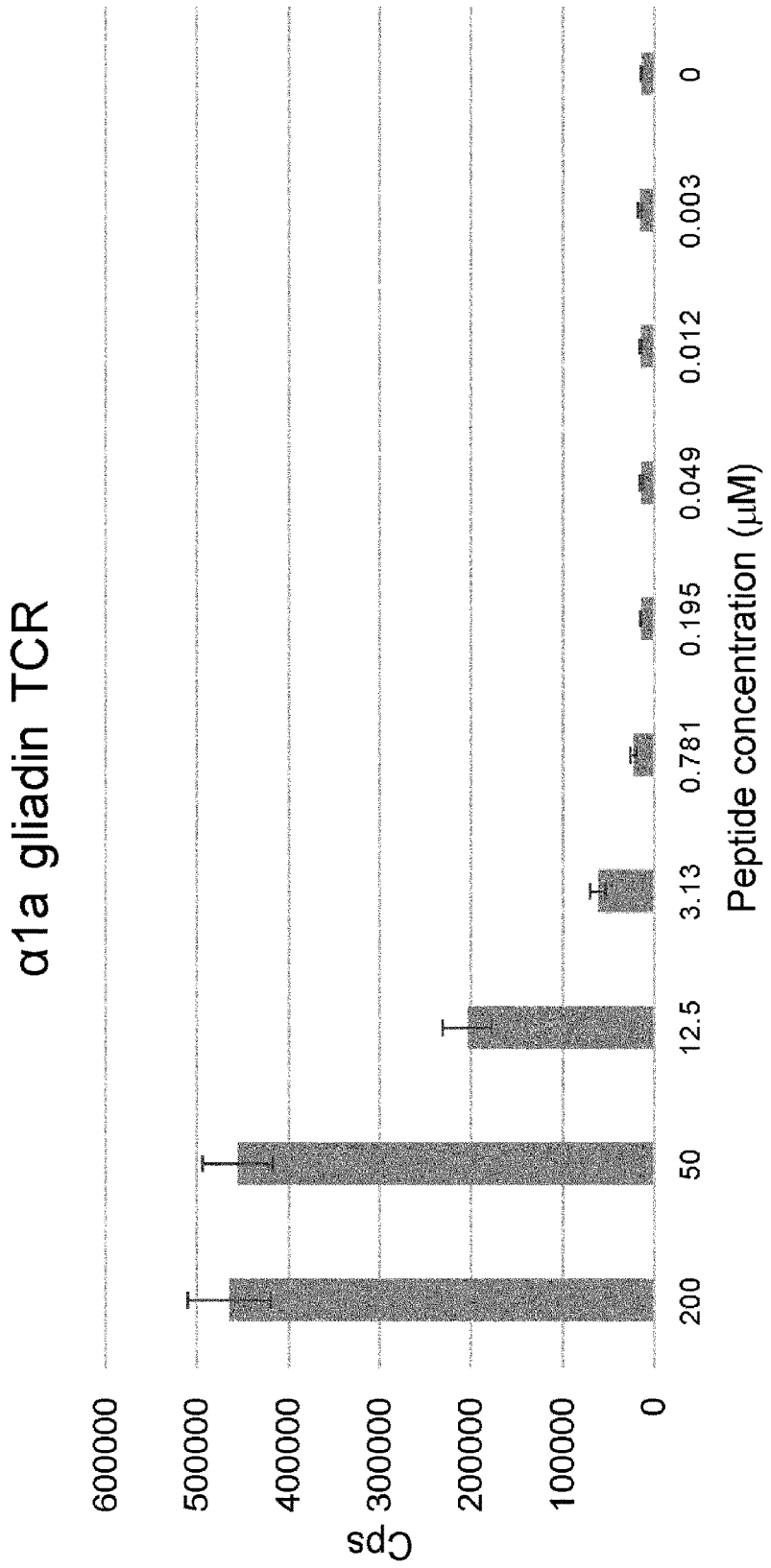
[Fig. 5-1]

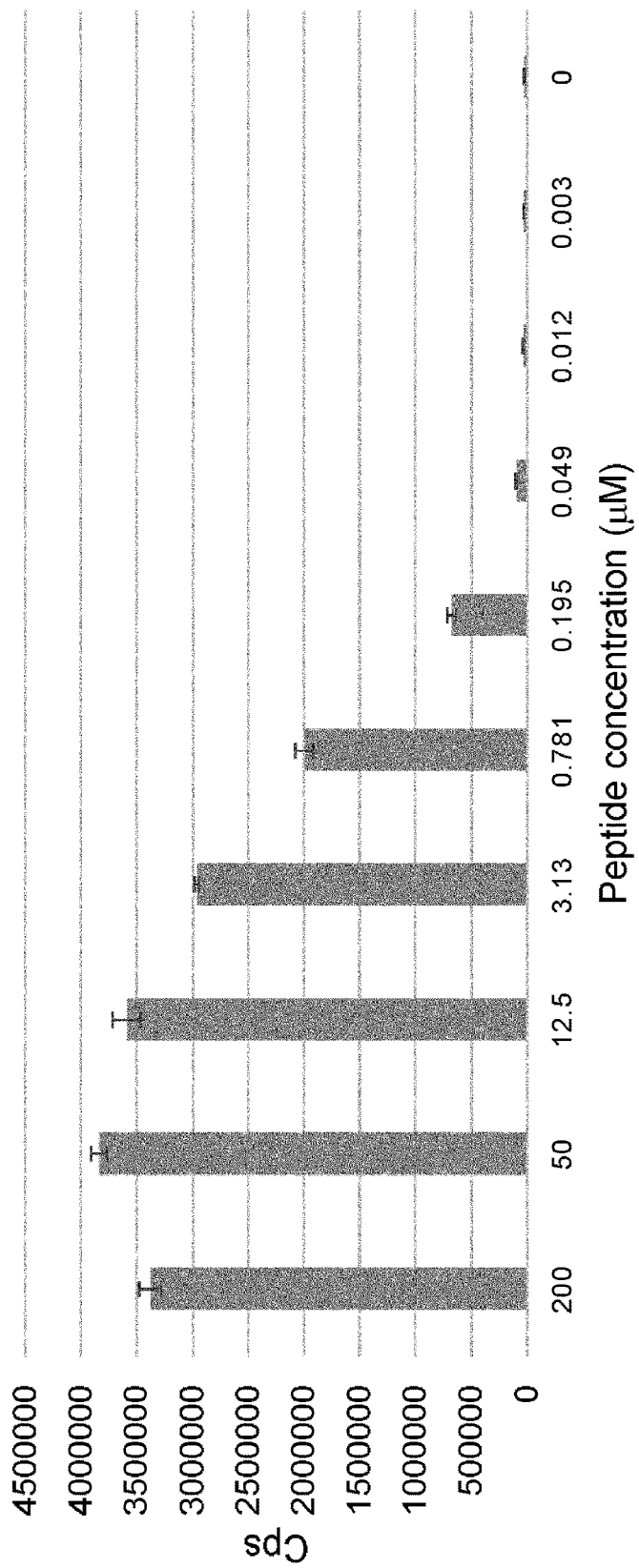
[Fig. 5-2]

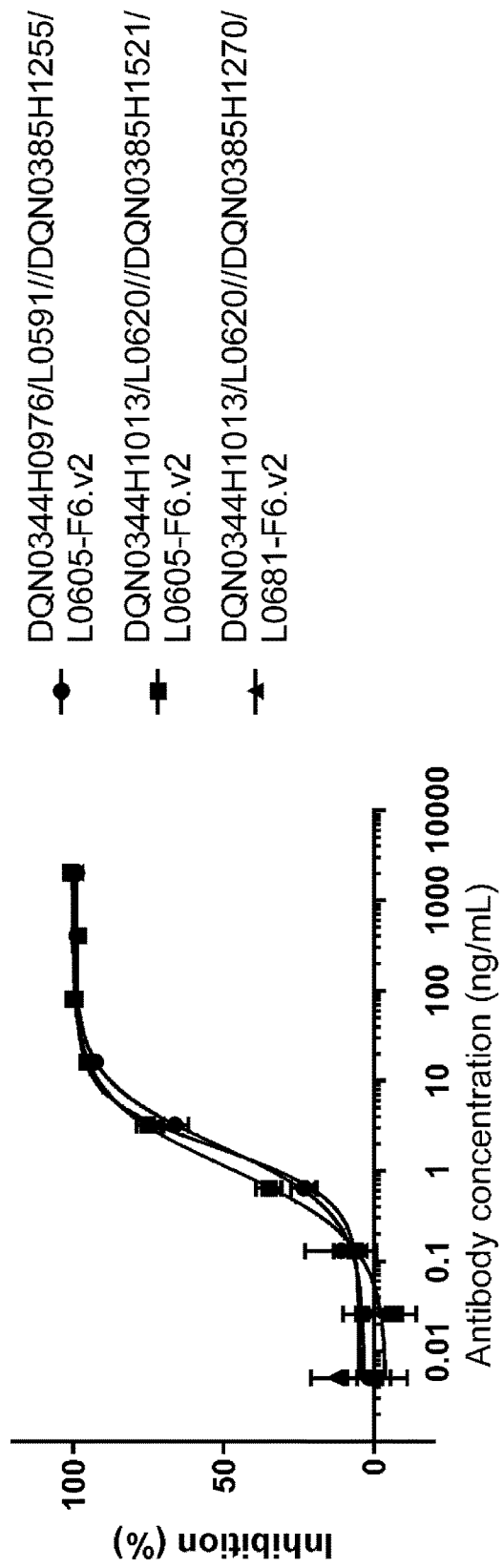
[Fig. 5-3]

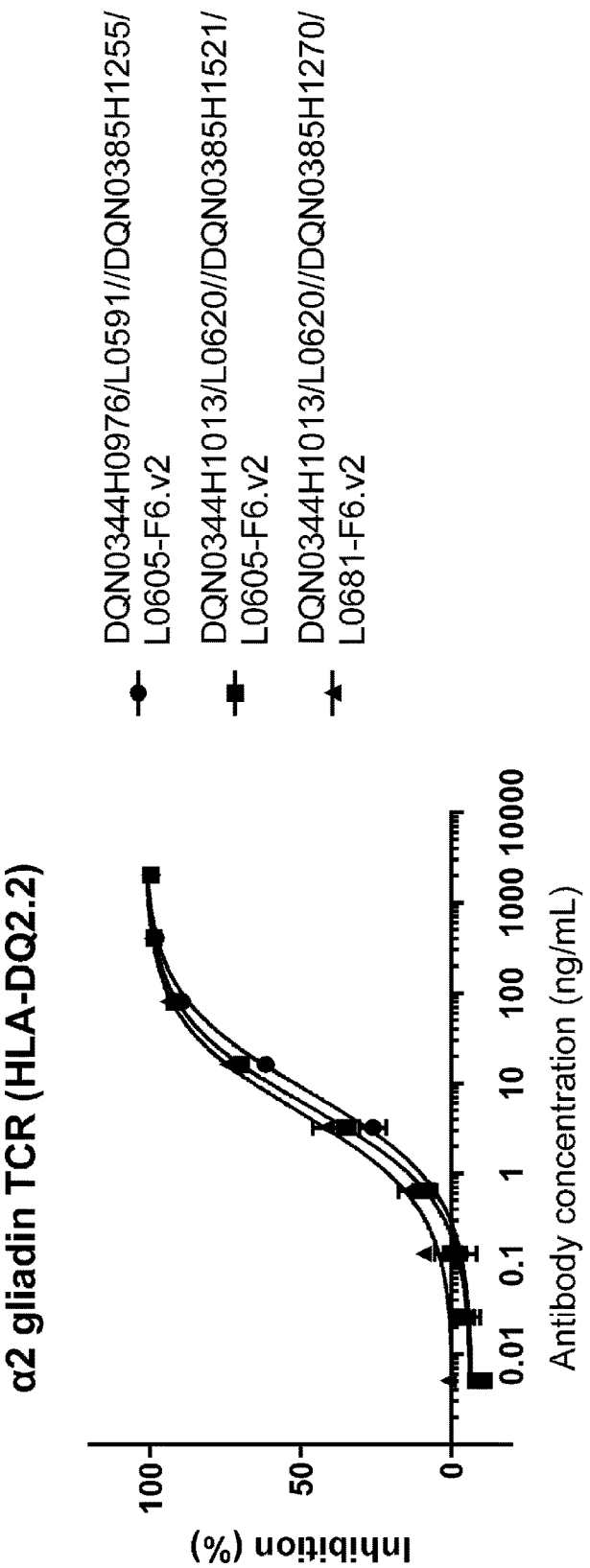

SEQUENCE LISTING

<160> NUMBER OF SEQ ID NOS: 210

<210> SEQ ID NO 1
<211> LENGTH: 30
<212> TYPE: PRT
<213> ORGANISM: Artificial Sequence
<220> FEATURE:
<223> OTHER INFORMATION: VH1a

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
            20                  25                  30

-continued

```
<210> SEQ ID NO 2
<211> LENGTH: 30
<212> TYPE: PRT
<213> ORGANISM: Artificial Sequence
<220> FEATURE:
<223> OTHER INFORMATION: VH1b

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: VH2

<400> SEQUENCE: 3

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: VH3

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: VH4

<400> SEQUENCE: 5

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: VH5

<400> SEQUENCE: 6

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr
            20                  25                  30
```

```
<210> SEQ ID NO 7
<211> LENGTH: 30
<212> TYPE: PRT
<213> ORGANISM: Artificial Sequence
<220> FEATURE:
<223> OTHER INFORMATION: VH6

<400> SEQUENCE: 7

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser
            20                  25                  30

<210> SEQ ID NO 8

<400> SEQUENCE: 8

000

<210> SEQ ID NO 9
<211> LENGTH: 14
<212> TYPE: PRT
<213> ORGANISM: Artificial Sequence
<220> FEATURE:
<223> OTHER INFORMATION: VH1a

<400> SEQUENCE: 9

Trp Val Arg Gln Ala Pro Gly Gln Gly Leu Glu Trp Met Gly
1               5                   10

<210> SEQ ID NO 10
<211> LENGTH: 14
<212> TYPE: PRT
<213> ORGANISM: Artificial Sequence
<220> FEATURE:
<223> OTHER INFORMATION: VH3

<400> SEQUENCE: 10

Trp Val Arg Gln Ala Pro Gly Lys Gly Leu Glu Trp Val Ser
1               5                   10

<210> SEQ ID NO 11
<211> LENGTH: 32
<212> TYPE: PRT
<213> ORGANISM: Artificial Sequence
<220> FEATURE:
<223> OTHER INFORMATION: VH1a

<400> SEQUENCE: 11

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: VH1b

<400> SEQUENCE: 12

Arg Val Thr Met Thr Arg Asp Thr Ser Ile Ser Thr Ala Tyr Met Glu
1               5                   10                  15

Leu Ser Ser Leu Arg Ser Glu Asp Thr Ala Val Tyr Tyr Cys Ala Arg
```

```
            20                  25                  30
```

<210> SEQ ID NO 13
<211> LENGTH: 32
<212> TYPE: PRT
<213> ORGANISM: Artificial Sequence
<220> FEATURE:
<223> OTHER INFORMATION: VH2

<400> SEQUENCE: 13

```
Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30
```

<210> SEQ ID NO 14
<211> LENGTH: 32
<212> TYPE: PRT
<213> ORGANISM: Artificial Sequence
<220> FEATURE:
<223> OTHER INFORMATION: VH3

<400> SEQUENCE: 14

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30
```

<210> SEQ ID NO 15
<211> LENGTH: 32
<212> TYPE: PRT
<213> ORGANISM: Artificial Sequence
<220> FEATURE:
<223> OTHER INFORMATION: VH4

<400> SEQUENCE: 15

```
Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30
```

<210> SEQ ID NO 16
<211> LENGTH: 32
<212> TYPE: PRT
<213> ORGANISM: Artificial Sequence
<220> FEATURE:
<223> OTHER INFORMATION: VH5

<400> SEQUENCE: 16

```
Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30
```

<210> SEQ ID NO 17
<211> LENGTH: 32
<212> TYPE: PRT
<213> ORGANISM: Artificial Sequence
<220> FEATURE:
<223> OTHER INFORMATION: VH6

<400> SEQUENCE: 17

```
Arg Ile Thr Ile Asn Pro Asp Thr Ser Lys Asn Gln Phe Ser Leu Gln
1               5                   10                  15
```

Leu Asn Ser Val Thr Pro Glu Asp Thr Ala Val Tyr Tyr Cys Ala Arg
            20                  25                  30

<210> SEQ ID NO 18
<211> LENGTH: 11
<212> TYPE: PRT
<213> ORGANISM: Artificial Sequence
<220> FEATURE:
<223> OTHER INFORMATION: VH1a

<400> SEQUENCE: 18

Trp Gly Gln Gly Thr Leu Val Thr Val Ser Ser
1               5                   10

<210> SEQ ID NO 19
<211> LENGTH: 11
<212> TYPE: PRT
<213> ORGANISM: Artificial Sequence
<220> FEATURE:
<223> OTHER INFORMATION: VH6

<400> SEQUENCE: 19

Trp Gly Pro Gly Thr Leu Val Thr Val Ser Ser
1               5                   10

<210> SEQ ID NO 20
<211> LENGTH: 23
<212> TYPE: PRT
<213> ORGANISM: Artificial Sequence
<220> FEATURE:
<223> OTHER INFORMATION: VK1

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 21
<211> LENGTH: 23
<212> TYPE: PRT
<213> ORGANISM: Artificial Sequence
<220> FEATURE:
<223> OTHER INFORMATION: VK2

<400> SEQUENCE: 21

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 22
<211> LENGTH: 23
<212> TYPE: PRT
<213> ORGANISM: Artificial Sequence
<220> FEATURE:
<223> OTHER INFORMATION: VK3

<400> SEQUENCE: 22

Asp Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 23

```
<211> LENGTH: 23
<212> TYPE: PRT
<213> ORGANISM: Artificial Sequence
<220> FEATURE:
<223> OTHER INFORMATION: VK4

<400> SEQUENCE: 23

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 24
<211> LENGTH: 15
<212> TYPE: PRT
<213> ORGANISM: Artificial Sequence
<220> FEATURE:
<223> OTHER INFORMATION: VK1

<400> SEQUENCE: 24

Trp Tyr Gln Gln Lys Pro Gly Lys Ala Pro Lys Leu Leu Ile Tyr
1               5                   10                  15

<210> SEQ ID NO 25

<400> SEQUENCE: 25

000

<210> SEQ ID NO 26
<211> LENGTH: 32
<212> TYPE: PRT
<213> ORGANISM: Artificial Sequence
<220> FEATURE:
<223> OTHER INFORMATION: VK1

<400> SEQUENCE: 26

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 27
<211> LENGTH: 32
<212> TYPE: PRT
<213> ORGANISM: Artificial Sequence
<220> FEATURE:
<223> OTHER INFORMATION: VK2

<400> SEQUENCE: 27

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 28
<211> LENGTH: 32
<212> TYPE: PRT
<213> ORGANISM: Artificial Sequence
<220> FEATURE:
<223> OTHER INFORMATION: VK3

<400> SEQUENCE: 28

Gly Val Pro Ala Arg Phe Ser Gly Ser Gly Ser Gly Thr Asp Phe Thr
1               5                   10                  15
```

Leu Thr Ile Ser Ser Leu Glu Pro Glu Asp Phe Ala Val Tyr Tyr Cys
            20                  25                  30

<210> SEQ ID NO 29
<211> LENGTH: 32
<212> TYPE: PRT
<213> ORGANISM: Artificial Sequence
<220> FEATURE:
<223> OTHER INFORMATION: VK4

<400> SEQUENCE: 29

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 30
<211> LENGTH: 10
<212> TYPE: PRT
<213> ORGANISM: Artificial Sequence
<220> FEATURE:
<223> OTHER INFORMATION: VK1

<400> SEQUENCE: 30

Phe Gly Gly Gly Thr Lys Val Glu Ile Lys
1               5                   10

<210> SEQ ID NO 31
<211> LENGTH: 328
<212> TYPE: PRT
<213> ORGANISM: Artificial Sequence
<220> FEATURE:
<223> OTHER INFORMATION: SG1

<400> SEQUENCE: 31

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn 195                 200                 205
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 32
<211> LENGTH: 107
<212> TYPE: PRT
<213> ORGANISM: Artificial Sequence
<220> FEATURE:
<223> OTHER INFORMATION: SK1

<400> SEQUENCE: 32

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 33
<211> LENGTH: 14
<212> TYPE: PRT
<213> ORGANISM: Artificial Sequence
<220> FEATURE:
<223> OTHER INFORMATION: VH3 (54H)

<400> SEQUENCE: 33

Trp Val Arg Gln Ala Pro Gly Lys Gly Leu Glu Trp Val Ala
1               5                   10

<210> SEQ ID NO 34
<211> LENGTH: 15
<212> TYPE: PRT
<213> ORGANISM: Artificial Sequence
<220> FEATURE:
<223> OTHER INFORMATION: VK4 (38509L)

<400> SEQUENCE: 34

```
Trp Tyr Gln Gln Lys Pro Gly Gln Pro Pro Lys Leu Leu Ile Tyr
1               5                   10                  15
```

<210> SEQ ID NO 35
<211> LENGTH: 449
<212> TYPE: PRT
<213> ORGANISM: Artificial Sequence
<220> FEATURE:
<223> OTHER INFORMATION: DQN0344Hx-SG1310.A5

<400> SEQUENCE: 35

```
Gln Ser Leu Glu Glu Ser Gly Gly Leu Val Lys Pro Gly Gly Thr
1               5                   10                  15

Leu Thr Leu Thr Cys Thr Ala Ser Gly Phe Ser Phe Ser Ser Tyr
                20                  25                  30

Trp Met Cys Trp Val Arg Gln Ala Pro Gly Lys Gly Leu Glu Trp Val
                35                  40                  45

Ala Cys Val Tyr Gly Gly Ser Asp Thr Thr Tyr Ala Ser Trp Thr
                50                  55                  60

Lys Gly Arg Phe Thr Ile Ser Lys Gly Ser Thr Thr Val Ala Leu
65                  70                  75                  80

Gln Val Thr Ser Leu Thr Ala Ala Asp Thr Ala Thr Tyr Phe Cys Ala
                85                  90                  95

Arg Asp Pro Leu Asn Tyr Tyr Tyr Gly Glu Leu Asn Leu Trp Gly
                100                 105                 110

Pro Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Lys Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Arg Arg
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350
```

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Tyr Leu Asp Ser Asp Gly Ser Phe Phe Leu Tyr Ser Lys Leu Thr Val
                405                 410                 415

Asp Lys Ser Arg Trp Gln Glu Gly Asn Val Phe Ser Cys Ser Val Leu
            420                 425                 430

His Glu Ala Leu His Ala His Tyr Thr Arg Glu Glu Leu Ser Leu Ser
        435                 440                 445

Pro

<210> SEQ ID NO 36
<211> LENGTH: 449
<212> TYPE: PRT
<213> ORGANISM: Artificial Sequence
<220> FEATURE:
<223> OTHER INFORMATION: DQN0344Hx-SG1399.A5

<400> SEQUENCE: 36

Gln Ser Leu Glu Glu Ser Gly Gly Gly Leu Val Lys Pro Gly Gly Thr
1               5                   10                  15

Leu Thr Leu Thr Cys Thr Ala Ser Gly Phe Ser Phe Ser Ser Ser Tyr
            20                  25                  30

Trp Met Cys Trp Val Arg Gln Ala Pro Gly Lys Gly Leu Glu Trp Val
        35                  40                  45

Ala Cys Val Tyr Gly Gly Ser Asp Thr Thr Tyr Tyr Ala Ser Trp Thr
    50                  55                  60

Lys Gly Arg Phe Thr Ile Ser Lys Gly Ser Thr Thr Val Ala Leu
65                  70                  75                  80

Gln Val Thr Ser Leu Thr Ala Ala Asp Thr Ala Thr Tyr Phe Cys Ala
                85                  90                  95

Arg Asp Pro Leu Asn Tyr Tyr Tyr Gly Glu Leu Asn Leu Trp Gly
            100                 105                 110

Pro Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Lys Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Arg Arg
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Asp Val Ser His
          260                 265                 270

Glu Asp Pro Glu Val Lys Phe Asn Trp Tyr Val Asp Gly Val Glu Val
      275                 280                 285

His Asn Ala Lys Thr Lys Pro Arg Glu Glu Gln Tyr Asn Ser Thr Tyr
  290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
              325                 330                 335

Glu Lys Thr Ile Ser Lys Ala Lys Gly Gln Pro Arg Glu Pro Gln Val
          340                 345                 350

Tyr Thr Leu Pro Pro Ser Arg Glu Glu Met Thr Lys Asn Gln Val Ser
      355                 360                 365

Leu Thr Cys Leu Val Lys Gly Phe Tyr Pro Ser Asp Ile Ala Val Glu
  370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
              405                 410                 415

Asp Lys Ser Arg Trp Gln Glu Gly Asn Val Phe Ser Cys Ser Val Leu
          420                 425                 430

His Glu Ala Leu His Ala His Tyr Thr Arg Glu Leu Ser Leu Ser
      435                 440                 445

Pro

<210> SEQ ID NO 37
<211> LENGTH: 215
<212> TYPE: PRT
<213> ORGANISM: Artificial Sequence
<220> FEATURE:
<223> OTHER INFORMATION: DQN0344Lx-SK1004

<400> SEQUENCE: 37

Ala Val Val Leu Thr Gln Thr Ala Ser Pro Val Ser Ala Ala Val Gly
1               5                   10                  15

Gly Thr Val Thr Ile Arg Cys Gln Ala Thr Glu Asn Ile Tyr Ser Gly
              20                  25                  30

Leu Ala Trp Tyr Gln Gln Lys Pro Gly Gln Pro Lys Val Leu Ile
          35                  40                  45

Tyr Tyr Val Ser Thr Leu Ala Ser Gly Val Pro Ser Arg Phe Lys Gly
 50                  55                  60

Ser Gly Ser Gly Thr Glu Tyr Thr Leu Thr Ile Ser Gly Val Gln Cys
65                  70                  75                  80

Asp Asp Ala Ala Thr Tyr Tyr Cys Gln Thr Tyr His Asp Ile Ser Asn
              85                  90                  95

Val Thr Phe Gly Gly Gly Thr Lys Val Glu Ile Lys Arg Thr Val Ala
          100                 105                 110

Ala Pro Ser Val Phe Ile Phe Pro Pro Ser Asp Glu Gln Leu Lys Ser
      115                 120                 125

Gly Thr Ala Glu Val Val Cys Leu Leu Asn Asn Phe Tyr Pro Arg Glu
  130                 135                 140

Ala Lys Val Gln Trp Lys Val Asp Asn Ala Leu Gln Ser Gly Asn Ser
145                 150                 155                 160

Glu Glu Ser Val Thr Glu Gln Asp Ser Lys Asp Ser Thr Tyr Ser Leu

```
                165                 170                 175
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 38
<211> LENGTH: 451
<212> TYPE: PRT
<213> ORGANISM: Artificial Sequence
<220> FEATURE:
<223> OTHER INFORMATION: DQN034425H-SG1310.A5

<400> SEQUENCE: 38

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Ser
            20                  25                  30

Tyr Trp Met Cys Trp Val Arg Gln Ala Pro Gly Gln Gly Leu Glu Trp
        35                  40                  45

Met Gly Cys Val Tyr Gly Gly Ser Asp Thr Thr Tyr Tyr Ala Ser Trp
    50                  55                  60

Thr Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Pro Leu Asn Tyr Tyr Tyr Gly Glu Leu Asn Leu
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Lys Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Arg Arg Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
```

```
                305                 310                 315                 320
Asn Gly Lys Glu Tyr Lys Cys Lys Val Ser Asn Lys Ala Leu Pro Ala
                325                 330                 335
Pro Ile Glu Lys Thr Ile Ser Lys Ala Lys Gly Gln Pro Arg Glu Pro
                340                 345                 350
Gln Val Tyr Thr Leu Pro Pro Ser Arg Glu Glu Met Thr Lys Asn Gln
                355                 360                 365
Val Ser Leu Thr Cys Leu Val Lys Gly Phe Tyr Pro Ser Asp Ile Ala
370                 375                 380
Val Glu Trp Glu Ser Asn Gly Gln Pro Glu Asn Asn Tyr Lys Thr Thr
385                 390                 395                 400
Pro Pro Tyr Leu Asp Ser Asp Gly Ser Phe Phe Leu Tyr Ser Lys Leu
                405                 410                 415
Thr Val Asp Lys Ser Arg Trp Gln Glu Gly Asn Val Phe Ser Cys Ser
                420                 425                 430
Val Leu His Glu Ala Leu His Ala His Tyr Thr Arg Glu Glu Leu Ser
                435                 440                 445
Leu Ser Pro
    450

<210> SEQ ID NO 39
<211> LENGTH: 451
<212> TYPE: PRT
<213> ORGANISM: Artificial Sequence
<220> FEATURE:
<223> OTHER INFORMATION: DQN034425H-SG1399.A5

<400> SEQUENCE: 39

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Ser
                20                  25                  30
Tyr Trp Met Cys Trp Val Arg Gln Ala Pro Gly Gln Gly Leu Glu Trp
                35                  40                  45
Met Gly Cys Val Tyr Gly Gly Ser Asp Thr Thr Tyr Tyr Ala Ser Trp
        50                  55                  60
Thr Lys Gly Arg Phe Thr Ile Ser Arg Asp Asn Ser Lys Asn Thr Leu
65              70                  75                  80
Tyr Leu Gln Met Asn Ser Leu Arg Ala Glu Asp Thr Ala Val Tyr Tyr
                85                  90                  95
Cys Ala Arg Asp Pro Leu Asn Tyr Tyr Tyr Gly Glu Leu Asn Leu
                100                 105                 110
Trp Gly Gln Gly Thr Leu Val Thr Val Ser Ser Ala Ser Thr Lys Gly
                115                 120                 125
Pro Ser Val Phe Pro Leu Ala Pro Ser Ser Lys Ser Thr Ser Gly Gly
                130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Lys Ser Ser Gly Leu Tyr Ser Leu Ser Ser Val Val
                180                 185                 190
Thr Val Pro Ser Ser Ser Leu Gly Thr Gln Thr Tyr Ile Cys Asn Val
                195                 200                 205
Asn His Lys Pro Ser Asn Thr Lys Val Asp Lys Arg Val Glu Pro Lys
```

-continued

```
                210                 215                 220
Ser Cys Asp Lys Thr His Thr Cys Pro Pro Cys Pro Ala Pro Glu Leu
225                 230                 235                 240

Arg Arg Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
                355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Leu His Glu Ala Leu His Ala His Tyr Thr Arg Glu Glu Leu Ser
                435                 440                 445

Leu Ser Pro
    450

<210> SEQ ID NO 40
<211> LENGTH: 215
<212> TYPE: PRT
<213> ORGANISM: Artificial Sequence
<220> FEATURE:
<223> OTHER INFORMATION: DQN034409L-SK1004

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Gln Ala Thr Glu Asn Ile Tyr Ser Gly
                20                  25                  30

Leu Ala Trp Tyr Gln Gln Lys Pro Gly Lys Ala Pro Lys Leu Leu Ile
            35                  40                  45

Tyr Tyr Val Ser Thr Leu Ala Ser Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Thr Tyr His Asp Ile Ser Asn
                85                  90                  95

Val Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
```

```
            115                 120                 125
Gly Thr Ala Glu Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Glu Glu Ser Val Thr Glu Gln Asp Ser Lys Asp Ser Thr Tyr Ser Leu
                    165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
                210                 215

<210> SEQ ID NO 41
<211> LENGTH: 451
<212> TYPE: PRT
<213> ORGANISM: Artificial Sequence
<220> FEATURE:
<223> OTHER INFORMATION: ssVH3.30DQN034425H0976-SG1310.A5

<400> SEQUENCE: 41

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Ala
                20                  25                  30

Tyr Trp Met Val Trp Val Arg Gln Ala Pro Gly Gln Gly Leu Glu Trp
            35                  40                  45

Met Gly Ala Val Tyr Gly Gly Ser Asp Thr Thr Tyr Tyr Ala Lys Trp
        50                  55                  60

Thr Glu Gly Arg Phe Thr Ile Ser Arg Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Glu Pro Leu Asn Tyr Tyr Tyr Gly Glu Leu Asn Leu
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                    165                 170                 175

Pro Ala Val Leu Lys Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Arg Val Glu Pro Lys
            210                 215                 220

Ser Cys Asp Lys Thr His Thr Cys Pro Pro Cys Pro Ala Pro Glu Leu
225                 230                 235                 240

Arg Arg Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
```

```
                    260                 265                 270
        Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
        305                 310                 315                 320

Asn Gly Lys Glu Tyr Lys Cys Lys Val Ser Asn Lys Ala Leu Pro Ala
                        325                 330                 335

Pro Ile Glu Lys Thr Ile Ser Lys Ala Lys Gly Gln Pro Arg Glu Pro
                    340                 345                 350

Gln Val Tyr Thr Leu Pro Pro Ser Arg Glu Glu Met Thr Lys Asn Gln
                    355                 360                 365

Val Ser Leu Thr Cys Leu Val Lys Gly Phe Tyr Pro Ser Asp Ile Ala
                    370                 375                 380

Val Glu Trp Glu Ser Asn Gly Gln Pro Glu Asn Asn Tyr Lys Thr Thr
        385                 390                 395                 400

Pro Pro Tyr Leu Asp Ser Asp Gly Ser Phe Phe Leu Tyr Ser Lys Leu
                        405                 410                 415

Thr Val Asp Lys Ser Arg Trp Gln Glu Gly Asn Val Phe Ser Cys Ser
                    420                 425                 430

Val Leu His Glu Ala Leu His Ala His Tyr Thr Arg Glu Glu Leu Ser
                    435                 440                 445

Leu Ser Pro
            450

<210> SEQ ID NO 42
<211> LENGTH: 451
<212> TYPE: PRT
<213> ORGANISM: Artificial Sequence
<220> FEATURE:
<223> OTHER INFORMATION: ssVH3.30DQN034425H0976-SG1399.A5

<400> SEQUENCE: 42

Gln Val Gln Leu Val Glu Ser Gly Gly Gly Val Val Gln Pro Gly Gly
        1               5                   10                  15

Ser Leu Arg Leu Ser Cys Ala Ala Ser Gly Phe Thr Phe Ser Ser Ala
                    20                  25                  30

Tyr Trp Met Val Trp Val Arg Gln Ala Pro Gly Gln Gly Leu Glu Trp
                35                  40                  45

Met Gly Ala Val Tyr Gly Gly Ser Asp Thr Thr Tyr Tyr Ala Lys Trp
        50                  55                  60

Thr Glu Gly Arg Phe Thr Ile Ser Arg Asp Thr Ser Lys Asn Thr Leu
        65                  70                  75                  80

Tyr Leu Gln Met Asn Ser Leu Arg Ala Glu Asp Thr Ala Val Tyr Tyr
                        85                  90                  95

Cys Ala Arg Glu Pro Leu Asn Tyr Tyr Tyr Gly Glu Leu Asn Leu
                    100                 105                 110

Trp Gly Gln Gly Thr Leu Val Thr Val Ser Ser Ala Ser Thr Lys Gly
                    115                 120                 125

Pro Ser Val Phe Pro Leu Ala Pro Ser Ser Lys Ser Thr Ser Gly Gly
                    130                 135                 140

Thr Ala Ala Leu Gly Cys Leu Val Lys Asp Tyr Phe Pro Glu Pro Val
        145                 150                 155                 160

Thr Val Ser Trp Asn Ser Gly Ala Leu Thr Ser Gly Val His Thr Phe
```

165                 170                 175
Pro Ala Val Leu Lys Ser Ser Gly Leu Tyr Ser Leu Ser Val Val
            180                 185                 190

Thr Val Pro Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Arg Arg Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Leu His Glu Ala Leu His Ala His Tyr Thr Arg Glu Glu Leu Ser
        435                 440                 445

Leu Ser Pro
    450

<210> SEQ ID NO 43
<211> LENGTH: 215
<212> TYPE: PRT
<213> ORGANISM: Artificial Sequence
<220> FEATURE:
<223> OTHER INFORMATION: ssVK1.L1DQN034409L0591-SK1004

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Gln Ala Thr Glu Glu Ile Tyr Ser Gly
            20                  25                  30

Leu Ala Trp Tyr Gln Gln Lys Pro Gly Lys Ala Pro Lys Leu Leu Ile
        35                  40                  45

Tyr Tyr Val Ser Thr Leu Tyr Glu Gly Ile Pro Ala Arg Phe Ser Gly
    50                  55                  60

Ser Gly Ser Gly Thr Asp Phe Thr Leu Thr Ile Ser Ser Leu Glu Pro

```
              65                  70                  75                  80
        Glu Asp Phe Ala Val Tyr Tyr Cys Gln Thr Tyr Glu Asp Val Ser Ala
                         85                  90                  95

Val Thr Phe Gly Gln Gly Thr Lys Val Glu Ile Lys Arg Thr Val Ala
                        100                 105                 110

Ala Pro Ser Val Phe Ile Phe Pro Pro Ser Asp Glu Gln Leu Lys Ser
                        115                 120                 125

Gly Thr Ala Glu Val Val Cys Leu Leu Asn Asn Phe Tyr Pro Arg Glu
                        130                 135                 140

Ala Lys Val Gln Trp Lys Val Asp Asn Ala Leu Gln Ser Gly Asn Ser
        145                 150                 155                 160

Glu Glu Ser Val Thr Glu Gln Asp Ser Lys Asp Ser Thr Tyr Ser Leu
                        165                 170                 175

Ser Ser Thr Leu Thr Leu Ser Lys Ala Asp Tyr Glu Lys His Lys Val
                        180                 185                 190

Tyr Ala Cys Glu Val Thr His Gln Gly Leu Ser Ser Pro Val Thr Lys
                        195                 200                 205

Ser Phe Asn Arg Gly Glu Cys
                        210                 215

<210> SEQ ID NO 44
<211> LENGTH: 451
<212> TYPE: PRT
<213> ORGANISM: Artificial Sequence
<220> FEATURE:
<223> OTHER INFORMATION: ssVH3.30DQN034425H1013-SG1310.A5

<400> SEQUENCE: 44

Gln Val Gln Leu Val Glu Ser Gly Gly Gly Val Val Gln Pro Gly Arg
        1               5                   10                  15

Ser Leu Arg Leu Ser Cys Ala Ala Ser Gly Phe Thr Phe Ser Ser Ala
                        20                  25                  30

Tyr Trp Met Val Trp Val Arg Gln Ala Pro Gly Gln Gly Leu Glu Trp
                        35                  40                  45

Met Gly Ala Val Tyr Gly Gly Ser Asp Thr Thr Tyr Tyr Ala Lys Trp
                        50                  55                  60

Thr Glu Gly Arg Phe Thr Ile Ser Arg Asp Thr Ser Lys Asn Thr Leu
        65                  70                  75                  80

Tyr Leu Gln Met Asn Ser Leu Arg Ala Glu Asp Thr Ala Val Tyr Tyr
                        85                  90                  95

Cys Ala Arg Glu Pro Leu Asn Tyr Tyr Tyr Gly Glu Leu Asn Val
                        100                 105                 110

Trp Gly Gln Gly Thr Leu Val Thr Val Ser Ser Ala Ser Thr Lys Gly
                        115                 120                 125

Pro Ser Val Phe Pro Leu Ala Pro Ser Ser Lys Ser Thr Ser Gly Gly
                        130                 135                 140

Thr Ala Ala Leu Gly Cys Leu Val Lys Asp Tyr Phe Pro Glu Pro Val
        145                 150                 155                 160

Thr Val Ser Trp Asn Ser Gly Ala Leu Thr Ser Gly Val His Thr Phe
                        165                 170                 175

Pro Ala Val Leu Lys Ser Ser Gly Leu Tyr Ser Leu Ser Ser Val Val
                        180                 185                 190

Thr Val Pro Ser Ser Ser Leu Gly Thr Gln Thr Tyr Ile Cys Asn Val
                        195                 200                 205

Asn His Lys Pro Ser Asn Thr Lys Val Asp Lys Arg Val Glu Pro Lys
```

Ser Cys Asp Lys Thr His Thr Cys Pro Pro Cys Pro Ala Pro Glu Leu
225                 230                 235                 240

Arg Arg Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Tyr Leu Asp Ser Asp Gly Ser Phe Phe Leu Tyr Ser Lys Leu
                405                 410                 415

Thr Val Asp Lys Ser Arg Trp Gln Glu Gly Asn Val Phe Ser Cys Ser
                420                 425                 430

Val Leu His Glu Ala Leu His Ala His Tyr Thr Arg Glu Glu Leu Ser
            435                 440                 445

Leu Ser Pro
    450

<210> SEQ ID NO 45
<211> LENGTH: 451
<212> TYPE: PRT
<213> ORGANISM: Artificial Sequence
<220> FEATURE:
<223> OTHER INFORMATION: ssVH3.30DQN034425H1013-SG1399.A5

<400> SEQUENCE: 45

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Ala
            20                  25                  30

Tyr Trp Met Val Trp Val Arg Gln Ala Pro Gly Gln Gly Leu Glu Trp
        35                  40                  45

Met Gly Ala Val Tyr Gly Gly Ser Asp Thr Thr Tyr Tyr Ala Lys Trp
    50                  55                  60

Thr Glu Gly Arg Phe Thr Ile Ser Arg Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Glu Pro Leu Asn Tyr Tyr Tyr Gly Glu Leu Asn Val
            100                 105                 110

Trp Gly Gln Gly Thr Leu Val Thr Val Ser Ser Ala Ser Thr Lys Gly

```
            115                 120                 125
Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Lys Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Arg Arg Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Leu His Glu Ala Leu His Ala His Tyr Thr Arg Glu Glu Leu Ser
        435                 440                 445

Leu Ser Pro
    450

<210> SEQ ID NO 46
<211> LENGTH: 215
<212> TYPE: PRT
<213> ORGANISM: Artificial Sequence
<220> FEATURE:
<223> OTHER INFORMATION: ssVK1.L1DQN034409L0620-SK1004

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Gln Ala Thr Glu Asn Ile Tyr Ser Gly
```

```
                    20                  25                  30
Leu Ala Trp Tyr Gln Gln Lys Pro Gly Lys Ala Pro Lys Leu Leu Ile
            35                  40                  45

Tyr Tyr Val Ser Thr Leu Ala Tyr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Thr Tyr Glu Asp Val Ser Ala
                85                  90                  95

Val Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Glu Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Glu Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 47
<211> LENGTH: 445
<212> TYPE: PRT
<213> ORGANISM: Artificial Sequence
<220> FEATURE:
<223> OTHER INFORMATION: DQN0385He-SG1308.A5

<400> SEQUENCE: 47

Gln Glu Gln Leu Glu Glu Ser Gly Gly Asp Leu Val Lys Pro Gly Ala
1               5                   10                  15

Ser Leu Thr Leu Thr Cys Thr Ala Ser Gly Phe Ser Phe Tyr Ser Ser
            20                  25                  30

Tyr Trp Ile Cys Trp Val Arg Gln Ala Pro Gly Lys Gly Leu Glu Trp
        35                  40                  45

Ile Ala Cys Ile Asp Thr Gly Ser Gly Ser Ile Asp Tyr Ala Ser Trp
    50                  55                  60

Val Asn Gly Arg Phe Thr Ile Ser Lys Thr Ser Ser Thr Thr Val Thr
65                  70                  75                  80

Leu Gln Met Thr Ser Leu Thr Val Ala Asp Thr Ala Thr Tyr Phe Cys
                85                  90                  95

Ala Arg Asp Ile Gly Ile Asp Tyr Asn Phe Trp Gly Pro Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Glu Asp Tyr Phe Pro Glu Pro Val Thr Val Ser Trp Asn Ser
145                 150                 155                 160

Gly Ala Leu Thr Ser Gly Val His Thr Phe Pro Ala Val Leu Glu Ser
```

```
                165                 170                 175
Ser Gly Leu Tyr Ser Leu Ser Ser Val Val Thr Val Pro Ser Ser Ser
            180                 185                 190

Leu Gly Thr Lys Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Arg Arg Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Lys Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Tyr Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Leu His Glu Ala Leu
            420                 425                 430

His Ala His Tyr Thr Arg Lys Glu Leu Ser Leu Ser Pro
        435                 440                 445

<210> SEQ ID NO 48
<211> LENGTH: 445
<212> TYPE: PRT
<213> ORGANISM: Artificial Sequence
<220> FEATURE:
<223> OTHER INFORMATION: DQN0385He-SG1398.A5

<400> SEQUENCE: 48

Gln Glu Gln Leu Glu Glu Ser Gly Gly Asp Leu Val Lys Pro Gly Ala
1               5                   10                  15

Ser Leu Thr Leu Thr Cys Thr Ala Ser Gly Phe Ser Phe Tyr Ser Ser
            20                  25                  30

Tyr Trp Ile Cys Trp Val Arg Gln Ala Pro Gly Lys Gly Leu Glu Trp
        35                  40                  45

Ile Ala Cys Ile Asp Thr Gly Ser Gly Ser Ile Asp Tyr Ala Ser Trp
    50                  55                  60

Val Asn Gly Arg Phe Thr Ile Ser Lys Thr Ser Ser Thr Thr Val Thr
65                  70                  75                  80

Leu Gln Met Thr Ser Leu Thr Val Ala Asp Thr Ala Thr Tyr Phe Cys
```

```
            85                  90                  95
Ala Arg Asp Ile Gly Ile Asp Tyr Asn Phe Trp Gly Pro Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Glu Asp Tyr Phe Pro Glu Pro Val Thr Val Ser Trp Asn Ser
145                 150                 155                 160

Gly Ala Leu Thr Ser Gly Val His Thr Phe Pro Ala Val Leu Glu Ser
                165                 170                 175

Ser Gly Leu Tyr Ser Leu Ser Ser Val Val Thr Val Pro Ser Ser Ser
                180                 185                 190

Leu Gly Thr Lys Thr Tyr Ile Cys Asn Val Asn His Lys Pro Ser Asn
                195                 200                 205

Thr Lys Val Asp Lys Arg Val Glu Pro Lys Ser Cys Asp Lys Thr His
            210                 215                 220

Thr Cys Pro Pro Cys Pro Ala Pro Glu Leu Arg Arg Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Lys Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Leu His Glu Ala Leu
                420                 425                 430

His Ala His Tyr Thr Arg Lys Glu Leu Ser Leu Ser Pro
                435                 440                 445

<210> SEQ ID NO 49
<211> LENGTH: 213
<212> TYPE: PRT
<213> ORGANISM: Artificial Sequence
<220> FEATURE:
<223> OTHER INFORMATION: DQN0385Le-SK1014

<400> SEQUENCE: 49

Ala Phe Glu Leu Thr Gln Thr Pro Ser Phe Val Glu Ala Ala Val Gly
```

-continued

```
1               5                   10                  15
Gly Thr Val Thr Ile Lys Cys Gln Ala Thr Gln Ser Ile Ser Ser Tyr
                20                  25                  30

Leu Asn Trp Tyr Gln Gln Lys Pro Gly Gln Pro Pro Lys Leu Leu Ile
            35                  40                  45

Tyr Tyr Ala Ser Thr Leu Ala Ser Gly Val Pro Ser Arg Phe Lys Gly
        50                  55                  60

Ser Gly Ser Gly Thr Glu Phe Ser Leu Thr Ile Ser Gly Val Glu Cys
65                  70                  75                  80

Ala Asp Ala Ala Thr Tyr Tyr Cys His Tyr Gly Ile Ser Tyr Val Ser
                85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Lys Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Lys Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
            210
```

<210> SEQ ID NO 50
<211> LENGTH: 446
<212> TYPE: PRT
<213> ORGANISM: Artificial Sequence
<220> FEATURE:
<223> OTHER INFORMATION: DQN0385ee0054H-SG1308.A5

<400> SEQUENCE: 50

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Ser
                20                  25                  30

Tyr Trp Ile Cys Trp Val Arg Gln Ala Pro Gly Lys Gly Leu Glu Trp
            35                  40                  45

Val Ala Cys Ile Asp Thr Gly Ser Gly Ser Ile Asp Tyr Ala Ser Trp
        50                  55                  60

Val Asn Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ile Gly Ile Asp Tyr Asn Phe Trp Gly Pro Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Glu Asp Tyr Phe Pro Glu Pro Val Thr Val Ser Trp Asn
```

```
            145                 150                 155                 160
    Ser Gly Ala Leu Thr Ser Gly Val His Thr Phe Pro Ala Val Leu Glu
                    165                 170                 175

Ser Ser Gly Leu Tyr Ser Leu Ser Ser Val Thr Val Pro Ser Ser
                180                 185                 190

Ser Leu Gly Thr Lys Thr Tyr Ile Cys Asn Val Asn His Lys Pro Ser
                    195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Arg Arg Gly Pro Ser
    225                 230                 235                 240

Val Phe Leu Phe Pro Pro Lys Pro Lys Asp Thr Leu Met Ile Ser Arg
                    245                 250                 255

Thr Pro Glu Val Thr Cys Val Val Val Asp Val Ser His Glu Asp Pro
                    260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
    305                 310                 315                 320

Lys Cys Lys Val Ser Asn Lys Ala Leu Pro Ala Pro Ile Glu Lys Thr
                    325                 330                 335

Ile Ser Lys Ala Lys Gly Gln Pro Arg Glu Pro Gln Val Tyr Thr Leu
                340                 345                 350

Pro Pro Ser Arg Lys Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Tyr Leu Asp
    385                 390                 395                 400

Ser Asp Gly Ser Phe Phe Leu Tyr Ser Lys Leu Thr Val Asp Lys Ser
                    405                 410                 415

Arg Trp Gln Gln Gly Asn Val Phe Ser Cys Ser Val Leu His Glu Ala
                420                 425                 430

Leu His Ala His Tyr Thr Arg Lys Glu Leu Ser Leu Ser Pro
                435                 440                 445

<210> SEQ ID NO 51
<211> LENGTH: 446
<212> TYPE: PRT
<213> ORGANISM: Artificial Sequence
<220> FEATURE:
<223> OTHER INFORMATION: DQN0385ee0054H-SG1398.A5

<400> SEQUENCE: 51

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Ser
            20                  25                  30

Tyr Trp Ile Cys Trp Val Arg Gln Ala Pro Gly Lys Gly Leu Glu Trp
        35                  40                  45

Val Ala Cys Ile Asp Thr Gly Ser Gly Ser Ile Asp Tyr Ala Ser Trp
    50                  55                  60

Val Asn Gly Arg Phe Thr Ile Ser Arg Asp Asn Ser Lys Asn Thr Leu
```

```
            65                  70                  75                  80
Tyr Leu Gln Met Asn Ser Leu Arg Ala Glu Asp Thr Ala Val Tyr Tyr
                85                  90                  95

Cys Ala Arg Asp Ile Gly Ile Asp Tyr Asn Phe Trp Gly Pro Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Glu
                165                 170                 175

Ser Ser Gly Leu Tyr Ser Leu Ser Ser Val Val Thr Val Pro Ser Ser
            180                 185                 190

Ser Leu Gly Thr Lys Thr Tyr Ile Cys Asn Val Asn His Lys Pro Ser
            195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Arg Arg Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Lys Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Leu His Glu Ala
            420                 425                 430

Leu His Ala His Tyr Thr Arg Lys Glu Leu Ser Leu Ser Pro
            435                 440                 445

<210> SEQ ID NO 52
<211> LENGTH: 213
<212> TYPE: PRT
<213> ORGANISM: Artificial Sequence
<220> FEATURE:
<223> OTHER INFORMATION: DQN0385ee009L-SK1014
```

```
<400> SEQUENCE: 52

Asp Ile Gln Met Thr Gln Ser Pro Ser Leu Ser Ala Ser Val Gly
1               5                   10                  15

Asp Arg Val Thr Ile Thr Cys Gln Ala Thr Gln Ser Ile Ser Ser Tyr
            20                  25                  30

Leu Asn Trp Tyr Gln Gln Lys Pro Gly Gln Pro Lys Leu Leu Ile
        35                  40                  45

Tyr Tyr Ala Ser Thr Leu Ala Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys His Tyr Gly Ile Ser Tyr Val Ser
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Lys Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Lys Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 53
<211> LENGTH: 446
<212> TYPE: PRT
<213> ORGANISM: Artificial Sequence
<220> FEATURE:
<223> OTHER INFORMATION: ssVH3.30DQN0385ee0054H1270-SG1308.A5

<400> SEQUENCE: 53

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Glu Trp
            20                  25                  30

Tyr Phe Met Ser Trp Val Arg Gln Ala Pro Gly Lys Gly Leu Glu Trp
        35                  40                  45

Val Ala Ser Ile Asp Thr Gly Ser Gly Ser Ile Asp Tyr Ala Glu Trp
50                  55                  60

Val Glu Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ile Gly Ile Asp Tyr Asn Phe Trp Gly Pro Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
```

```
                130                 135                 140
Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Glu
                165                 170                 175

Ser Ser Gly Leu Tyr Ser Leu Ser Val Val Thr Val Pro Ser Ser
                180                 185                 190

Ser Leu Gly Thr Lys Thr Tyr Ile Cys Asn Val Asn His Lys Pro Ser
                195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Arg Arg Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Lys Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Tyr Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Leu His Glu Ala
                420                 425                 430

Leu His Ala His Tyr Thr Arg Lys Glu Leu Ser Leu Ser Pro
                435                 440                 445

<210> SEQ ID NO 54
<211> LENGTH: 446
<212> TYPE: PRT
<213> ORGANISM: Artificial Sequence
<220> FEATURE:
<223> OTHER INFORMATION: ssVH3.30DQN0385ee0054H1270-SG1398.A5

<400> SEQUENCE: 54

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Glu Trp
                20                  25                  30

Tyr Phe Met Ser Trp Val Arg Gln Ala Pro Gly Lys Gly Leu Glu Trp
                35                  40                  45

Val Ala Ser Ile Asp Thr Gly Ser Gly Ser Ile Asp Tyr Ala Glu Trp
```

Val Glu Gly Arg Phe Thr Ile Ser Arg Asp Asn Ser Lys Asn Thr Leu
50              55                  60
65                                                              80

Tyr Leu Gln Met Asn Ser Leu Arg Ala Glu Asp Thr Ala Val Tyr Tyr
            85                  90                  95

Cys Ala Arg Asp Ile Gly Ile Asp Tyr Asn Phe Trp Gly Pro Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Glu
                165                 170                 175

Ser Ser Gly Leu Tyr Ser Leu Ser Ser Val Val Thr Val Pro Ser Ser
                180                 185                 190

Ser Leu Gly Thr Lys Thr Tyr Ile Cys Asn Val Asn His Lys Pro Ser
                195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Arg Arg Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Lys Glu Met Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Leu His Glu Ala
                420                 425                 430

Leu His Ala His Tyr Thr Arg Lys Glu Leu Ser Leu Ser Pro
                435                 440                 445

<210> SEQ ID NO 55
<211> LENGTH: 213
<212> TYPE: PRT
<213> ORGANISM: Artificial Sequence
<220> FEATURE:
<223> OTHER INFORMATION: ssVK1.L1DQN0385ee009L0722-SK1014

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Gln Thr Gln Ser Ile Ser Ser Tyr
            20                  25                  30

Leu Asn Trp Tyr Gln Gln Lys Pro Gly Gln Pro Pro Lys Leu Leu Ile
        35                  40                  45

Tyr Tyr Ala Ser Thr Lys Ala Glu Gly Ile Pro Ala Arg Phe Ser Gly
    50                  55                  60

Ser Gly Leu Gly Thr Asp Phe Thr Leu Thr Ile Ser Ser Leu Gln Pro
65                  70                  75                  80

Glu Asp Phe Ala Val Tyr Tyr Cys His Tyr Gly Ile Ser Lys Val Ser
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Lys Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Lys Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 56
<211> LENGTH: 213
<212> TYPE: PRT
<213> ORGANISM: Artificial Sequence
<220> FEATURE:
<223> OTHER INFORMATION: ssVK1.L1DQN0385ee009L0681-SK1014

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Gln Thr Gln Ser Ile Ser Ser Tyr
            20                  25                  30

Leu Asn Trp Tyr Gln Gln Lys Pro Gly Gln Pro Pro Lys Leu Leu Ile
        35                  40                  45

Tyr Tyr Ala Ser Thr Lys Ala Glu Gly Ile Pro Ala Arg Phe Ser Gly
    50                  55                  60

Ser Gly Leu Gly Thr Asp Phe Thr Leu Thr Ile Ser Ser Leu Glu Pro
65                  70                  75                  80

Glu Asp Phe Ala Val Tyr Tyr Cys His Tyr Gly Ile Ser Lys Val Ser
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr

```
            115                 120                 125
Ala Lys Val Val Cys Leu Leu Asn Asn Phe Tyr Pro Arg Glu Ala Lys
        130                 135                 140
Val Gln Trp Lys Val Asp Asn Ala Leu Gln Ser Gly Asn Ser Lys Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
                195                 200                 205
Asn Arg Gly Glu Cys
        210

<210> SEQ ID NO 57
<211> LENGTH: 446
<212> TYPE: PRT
<213> ORGANISM: Artificial Sequence
<220> FEATURE:
<223> OTHER INFORMATION: ssVH3.30DQN0385ee0054H1352-SG1308.A5

<400> SEQUENCE: 57

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Glu Phe Ser Glu Trp
            20                  25                  30
Tyr Phe Met Ser Trp Val Arg Gln Ala Pro Gly Lys Gly Leu Glu Trp
        35                  40                  45
Val Ala Ser Ile Asp Thr Gly Ser Gly Ser Ile Asp Tyr Ala Glu Trp
    50                  55                  60
Val Glu Gly Arg Phe Thr Ile Ser Arg Asp Asn Ser Lys Asn Thr Leu
65                  70                  75                  80
Tyr Leu Gln Met Asn Ser Leu Arg Ala Glu Asp Thr Ala Val Tyr Tyr
                85                  90                  95
Cys Ala Arg Asp Ile Gly Ile Asp Tyr Asn Phe Trp Gly Pro Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Glu Asp Tyr Phe Pro Glu Pro Val Thr Val Ser Trp Asn
145                 150                 155                 160
Ser Gly Ala Leu Thr Ser Gly Val His Thr Phe Pro Ala Val Leu Glu
                165                 170                 175
Ser Ser Gly Leu Tyr Ser Leu Ser Ser Val Val Thr Val Pro Ser Ser
            180                 185                 190
Ser Leu Gly Thr Lys Thr Tyr Ile Cys Asn Val Asn His Lys Pro Ser
        195                 200                 205
Asn Thr Lys Val Asp Lys Arg Val Glu Pro Lys Ser Cys Asp Lys Thr
    210                 215                 220
His Thr Cys Pro Pro Cys Pro Ala Pro Glu Leu Arg Arg Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
```

```
            260                 265                 270
Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Lys Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Tyr Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Leu His Glu Ala
            420                 425                 430

Leu His Ala His Tyr Thr Arg Lys Glu Leu Ser Leu Ser Pro
        435                 440                 445

<210> SEQ ID NO 58
<211> LENGTH: 446
<212> TYPE: PRT
<213> ORGANISM: Artificial Sequence
<220> FEATURE:
<223> OTHER INFORMATION: ssVH3.30DQN0385ee0054H1352-SG1398.A5

<400> SEQUENCE: 58

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Glu Phe Ser Glu Trp
            20                  25                  30

Tyr Phe Met Ser Trp Val Arg Gln Ala Pro Gly Lys Gly Leu Glu Trp
        35                  40                  45

Val Ala Ser Ile Asp Thr Gly Ser Gly Ser Ile Asp Tyr Ala Glu Trp
    50                  55                  60

Val Glu Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ile Gly Ile Asp Tyr Asn Phe Trp Gly Pro Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Glu
                165                 170                 175

Ser Ser Gly Leu Tyr Ser Leu Ser Ser Val Val Thr Val Pro Ser Ser
```

```
              180                 185                 190
Ser Leu Gly Thr Lys Thr Tyr Ile Cys Asn Val Asn His Lys Pro Ser
          195                 200                 205

Asn Thr Lys Val Asp Lys Arg Val Glu Pro Lys Ser Cys Asp Lys Thr
      210                 215                 220

His Thr Cys Pro Pro Cys Pro Ala Pro Glu Leu Arg Arg Gly Pro Ser
225                 230                 235                 240

Val Phe Leu Phe Pro Pro Lys Pro Lys Asp Thr Leu Met Ile Ser Arg
              245                 250                 255

Thr Pro Glu Val Thr Cys Val Val Val Asp Val Ser His Glu Asp Pro
          260                 265                 270

Glu Val Lys Phe Asn Trp Tyr Val Asp Gly Val Glu Val His Asn Ala
      275                 280                 285

Lys Thr Lys Pro Arg Glu Glu Gln Tyr Asn Ser Thr Tyr Arg Val Val
  290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
              325                 330                 335

Ile Ser Lys Ala Lys Gly Gln Pro Arg Glu Pro Gln Val Tyr Thr Leu
          340                 345                 350

Pro Pro Ser Arg Lys Glu Met Thr Lys Asn Gln Val Ser Leu Thr Cys
      355                 360                 365

Leu Val Lys Gly Phe Tyr Pro Ser Asp Ile Ala Val Glu Trp Glu Ser
  370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
              405                 410                 415

Arg Trp Gln Gln Gly Asn Val Phe Ser Cys Ser Val Leu His Glu Ala
          420                 425                 430

Leu His Ala His Tyr Thr Arg Lys Glu Leu Ser Leu Ser Pro
      435                 440                 445

<210> SEQ ID NO 59
<211> LENGTH: 446
<212> TYPE: PRT
<213> ORGANISM: Artificial Sequence
<220> FEATURE:
<223> OTHER INFORMATION: ssVH3.30DQN0385ee0054H1527-SG1308.A5

<400> SEQUENCE: 59

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ala Ser Trp
              20                  25                  30

Tyr Phe Met Ser Trp Val Arg Gln Ala Pro Gly Lys Gly Leu Glu Trp
          35                  40                  45

Val Ala Ser Ile Asp Thr Gly Ser Gly Ser Ile Asp Tyr Ala Glu Trp
      50                  55                  60

Val Glu Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
              85                  90                  95

Cys Ala Arg Asp Ile Gly Ile Asp Tyr Asn Phe Trp Gly Pro Gly Thr
```

```
            100                 105                 110
Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Glu
                165                 170                 175

Ser Ser Gly Leu Tyr Ser Leu Ser Ser Val Val Thr Val Pro Ser Ser
            180                 185                 190

Ser Leu Gly Thr Lys Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Arg Arg Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Lys Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Tyr Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Leu His Glu Ala
            420                 425                 430

Leu His Ala His Tyr Thr Arg Lys Glu Leu Ser Leu Ser Pro
        435                 440                 445

<210> SEQ ID NO 60
<211> LENGTH: 446
<212> TYPE: PRT
<213> ORGANISM: Artificial Sequence
<220> FEATURE:
<223> OTHER INFORMATION: ssVH3.30DQN0385ee0054H1527-SG1398.A5

<400> SEQUENCE: 60

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ala Ser Trp
```

-continued

```
                20                  25                  30
Tyr Phe Met Ser Trp Val Arg Gln Ala Pro Gly Lys Gly Leu Glu Trp
            35                  40                  45
Val Ala Ser Ile Asp Thr Gly Ser Gly Ser Ile Asp Tyr Ala Glu Trp
 50                  55                  60
Val Glu Gly Arg Phe Thr Ile Ser Arg Asp Asn Ser Lys Asn Thr Leu
 65                  70                  75                  80
Tyr Leu Gln Met Asn Ser Leu Arg Ala Glu Asp Thr Ala Val Tyr Tyr
                85                  90                  95
Cys Ala Arg Asp Ile Gly Ile Asp Tyr Asn Phe Trp Gly Pro Gly Thr
               100                 105                 110
Leu Val Thr Val Ser Ser Ala Ser Thr Lys Gly Pro Ser Val Phe Pro
               115                 120                 125
Leu Ala Pro Ser Ser Lys Ser Thr Ser Gly Gly Thr Ala Ala Leu Gly
               130                 135                 140
Cys Leu Val Glu Asp Tyr Phe Pro Glu Pro Val Thr Val Ser Trp Asn
145                 150                 155                 160
Ser Gly Ala Leu Thr Ser Gly Val His Thr Phe Pro Ala Val Leu Glu
               165                 170                 175
Ser Ser Gly Leu Tyr Ser Leu Ser Ser Val Val Thr Val Pro Ser Ser
               180                 185                 190
Ser Leu Gly Thr Lys Thr Tyr Ile Cys Asn Val Asn His Lys Pro Ser
               195                 200                 205
Asn Thr Lys Val Asp Lys Arg Val Glu Pro Lys Ser Cys Asp Lys Thr
               210                 215                 220
His Thr Cys Pro Pro Cys Pro Ala Pro Glu Leu Arg Arg Gly Pro Ser
225                 230                 235                 240
Val Phe Leu Phe Pro Pro Lys Pro Lys Asp Thr Leu Met Ile Ser Arg
               245                 250                 255
Thr Pro Glu Val Thr Cys Val Val Val Asp Val Ser His Glu Asp Pro
               260                 265                 270
Glu Val Lys Phe Asn Trp Tyr Val Asp Gly Val Glu Val His Asn Ala
               275                 280                 285
Lys Thr Lys Pro Arg Glu Glu Gln Tyr Asn Ser Thr Tyr Arg Val Val
               290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
               325                 330                 335
Ile Ser Lys Ala Lys Gly Gln Pro Arg Glu Pro Gln Val Tyr Thr Leu
               340                 345                 350
Pro Pro Ser Arg Lys Glu Met Thr Lys Asn Gln Val Ser Leu Thr Cys
               355                 360                 365
Leu Val Lys Gly Phe Tyr Pro Ser Asp Ile Ala Val Glu Trp Glu Ser
               370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
               405                 410                 415
Arg Trp Gln Gln Gly Asn Val Phe Ser Cys Ser Val Leu His Glu Ala
               420                 425                 430
Leu His Ala His Tyr Thr Arg Lys Glu Leu Ser Leu Ser Pro
               435                 440                 445
```

<210> SEQ ID NO 61
<211> LENGTH: 213
<212> TYPE: PRT
<213> ORGANISM: Artificial Sequence
<220> FEATURE:
<223> OTHER INFORMATION: ssVK1.L1DQN0385ee009L0605-SK1014

<400> SEQUENCE: 61

```
Asp Ile Gln Met Thr Gln Ser Pro Ser Ser Leu Ser Ala Ser Val Gly
1               5                   10                  15

Asp Arg Val Thr Ile Thr Cys Gln Thr Gln Ser Ile Ser Ser Tyr
            20                  25                  30

Leu Asn Trp Tyr Gln Gln Lys Pro Gly Gln Pro Lys Leu Leu Ile
        35                  40                  45

Tyr Tyr Ala Ser Thr Lys Ala Glu Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys His Tyr Gly Ile Ser Lys Val Ser
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Lys Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Lys Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 62
<211> LENGTH: 446
<212> TYPE: PRT
<213> ORGANISM: Artificial Sequence
<220> FEATURE:
<223> OTHER INFORMATION: ssVH3.30DQN0385ee0054H1255-SG1308.A5

<400> SEQUENCE: 62

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Glu Trp
            20                  25                  30

Tyr Phe Met Ser Trp Val Arg Gln Ala Pro Gly Lys Gly Leu Glu Trp
        35                  40                  45

Val Ala Ser Ile Asp Thr Gly Ser Gly Ser Ile Asp Tyr Ala Gly Trp
    50                  55                  60

Val Glu Glu Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
```

```
                85                  90                  95
Cys Ala Arg Asp Ile Gly Ile Asp Tyr Asn Phe Trp Gly Pro Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Glu
            165                 170                 175

Ser Ser Gly Leu Tyr Ser Leu Ser Ser Val Val Thr Val Pro Ser Ser
            180                 185                 190

Ser Leu Gly Thr Lys Thr Tyr Ile Cys Asn Val Asn His Lys Pro Ser
            195                 200                 205

Asn Thr Lys Val Asp Lys Arg Val Glu Pro Lys Ser Cys Asp Lys Thr
            210                 215                 220

His Thr Cys Pro Pro Cys Pro Ala Pro Glu Leu Arg Arg Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Lys Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Tyr Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Leu His Glu Ala
            420                 425                 430

Leu His Ala His Tyr Thr Arg Lys Glu Leu Ser Leu Ser Pro
            435                 440                 445

<210> SEQ ID NO 63
<211> LENGTH: 446
<212> TYPE: PRT
<213> ORGANISM: Artificial Sequence
<220> FEATURE:
<223> OTHER INFORMATION: ssVH3.30DQN0385ee0054H1255-SG1398.A5

<400> SEQUENCE: 63

Gln Val Gln Leu Val Glu Ser Gly Gly Gly Val Val Gln Pro Gly Arg
```

-continued

```
 1               5               10              15
Ser Leu Arg Leu Ser Cys Ala Ala Ser Gly Phe Thr Phe Ser Glu Trp
            20                  25              30

Tyr Phe Met Ser Trp Val Arg Gln Ala Pro Gly Lys Gly Leu Glu Trp
            35                  40              45

Val Ala Ser Ile Asp Thr Gly Ser Gly Ser Ile Asp Tyr Ala Gly Trp
 50                          55                  60

Val Glu Glu Arg Phe Thr Ile Ser Arg Asp Asn Ser Lys Asn Thr Leu
 65                      70                  75              80

Tyr Leu Gln Met Asn Ser Leu Arg Ala Glu Asp Thr Ala Val Tyr Tyr
                    85                  90                  95

Cys Ala Arg Asp Ile Gly Ile Asp Tyr Asn Phe Trp Gly Pro Gly Thr
                        100                 105             110

Leu Val Thr Val Ser Ser Ala Ser Thr Lys Gly Pro Ser Val Phe Pro
                115                     120                 125

Leu Ala Pro Ser Ser Lys Ser Thr Ser Gly Gly Thr Ala Ala Leu Gly
 130                    135                     140

Cys Leu Val Glu Asp Tyr Phe Pro Glu Pro Val Thr Val Ser Trp Asn
145                     150                     155             160

Ser Gly Ala Leu Thr Ser Gly Val His Thr Phe Pro Ala Val Leu Glu
                165                     170                 175

Ser Ser Gly Leu Tyr Ser Leu Ser Ser Val Val Thr Val Pro Ser Ser
                180                     185                 190

Ser Leu Gly Thr Lys Thr Tyr Ile Cys Asn Val Asn His Lys Pro Ser
            195                     200                 205

Asn Thr Lys Val Asp Lys Arg Val Glu Pro Lys Ser Cys Asp Lys Thr
210                     215                     220

His Thr Cys Pro Pro Cys Pro Ala Pro Glu Leu Arg Arg Gly Pro Ser
225                     230                     235             240

Val Phe Leu Phe Pro Pro Lys Pro Lys Asp Thr Leu Met Ile Ser Arg
                245                     250                 255

Thr Pro Glu Val Thr Cys Val Val Val Asp Val Ser His Glu Asp Pro
                260                     265                 270

Glu Val Lys Phe Asn Trp Tyr Val Asp Gly Val Glu Val His Asn Ala
            275                     280                 285

Lys Thr Lys Pro Arg Glu Glu Gln Tyr Asn Ser Thr Tyr Arg Val Val
        290                     295                 300

Ser Val Leu Thr Val Leu His Gln Asp Trp Leu Asn Gly Lys Glu Tyr
305                     310                     315             320

Lys Cys Lys Val Ser Asn Lys Ala Leu Pro Ala Pro Ile Glu Lys Thr
                    325                     330                 335

Ile Ser Lys Ala Lys Gly Gln Pro Arg Glu Pro Gln Val Tyr Thr Leu
                340                     345                 350

Pro Pro Ser Arg Lys Glu Met Thr Lys Asn Gln Val Ser Leu Thr Cys
                355                     360                 365

Leu Val Lys Gly Phe Tyr Pro Ser Asp Ile Ala Val Glu Trp Glu Ser
            370                     375                 380

Asn Gly Gln Pro Glu Asn Asn Tyr Lys Thr Thr Pro Pro Val Leu Asp
385                     390                     395             400

Ser Asp Gly Ser Phe Phe Leu Tyr Ser Lys Leu Thr Val Asp Lys Ser
                    405                     410                 415

Arg Trp Gln Gln Gly Asn Val Phe Ser Cys Ser Val Leu His Glu Ala
                420                     425                 430
```

```
Leu His Ala His Tyr Thr Arg Lys Glu Leu Ser Leu Ser Pro
        435                 440                 445

<210> SEQ ID NO 64
<211> LENGTH: 446
<212> TYPE: PRT
<213> ORGANISM: Artificial Sequence
<220> FEATURE:
<223> OTHER INFORMATION: sVH3.30DQN0385ee0054H1521-SG1308.A5

<400> SEQUENCE: 64

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Glu Ser Trp
            20                  25                  30

Tyr Phe Met Ser Trp Val Arg Gln Ala Pro Gly Lys Gly Leu Glu Trp
        35                  40                  45

Val Ala Ser Ile Asp Thr Gly Ser Gly Ser Ile Asp Tyr Ala Glu Trp
    50                  55                  60

Val Glu Gly Arg Phe Thr Ile Ser Arg Asp Asn Ser Lys Asn Thr Leu
65              70                  75                  80

Tyr Leu Gln Met Asn Ser Leu Arg Ala Glu Asp Thr Ala Val Tyr Tyr
            85                  90                  95

Cys Ala Arg Asp Ile Gly Ile Asp Tyr Asn Phe Trp Gly Pro Gly Thr
        100                 105                 110

Leu Val Thr Val Ser Ser Ala Ser Thr Lys Gly Pro Ser Val Phe Pro
    115                 120                 125

Leu Ala Pro Ser Ser Lys Ser Thr Ser Gly Gly Thr Ala Ala Leu Gly
130             135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Glu
            165                 170                 175

Ser Ser Gly Leu Tyr Ser Leu Ser Ser Val Val Thr Val Pro Ser Ser
        180                 185                 190

Ser Leu Gly Thr Lys Thr Tyr Ile Cys Asn Val Asn His Lys Pro Ser
    195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Arg Arg Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350
```

```
Pro Pro Ser Arg Lys Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Tyr Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Leu His Glu Ala
                420                 425                 430

Leu His Ala His Tyr Thr Arg Lys Glu Leu Ser Leu Ser Pro
                435                 440                 445

<210> SEQ ID NO 65
<211> LENGTH: 446
<212> TYPE: PRT
<213> ORGANISM: Artificial Sequence
<220> FEATURE:
<223> OTHER INFORMATION: ssVH3.30DQN0385ee0054H1521-SG1398.A5

<400> SEQUENCE: 65

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Glu Ser Trp
            20                  25                  30

Tyr Phe Met Ser Trp Val Arg Gln Ala Pro Gly Lys Gly Leu Glu Trp
        35                  40                  45

Val Ala Ser Ile Asp Thr Gly Ser Gly Ser Ile Asp Tyr Ala Glu Trp
    50                  55                  60

Val Glu Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ile Gly Ile Asp Tyr Asn Phe Trp Gly Pro Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Glu
                165                 170                 175

Ser Ser Gly Leu Tyr Ser Leu Ser Val Val Thr Val Pro Ser Ser
            180                 185                 190

Ser Leu Gly Thr Lys Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Arg Arg Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

```
Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Lys Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Leu His Glu Ala
                420                 425                 430

Leu His Ala His Tyr Thr Arg Lys Glu Leu Ser Leu Ser Pro
            435                 440                 445

<210> SEQ ID NO 66
<211> LENGTH: 446
<212> TYPE: PRT
<213> ORGANISM: Artificial Sequence
<220> FEATURE:
<223> OTHER INFORMATION: ssVH3.30DQN0385ee0054H1353-SG1308.A5

<400> SEQUENCE: 66

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ala Glu Trp
            20                  25                  30

Tyr Phe Met Ser Trp Val Arg Gln Ala Pro Gly Lys Gly Leu Glu Trp
        35                  40                  45

Val Ala Ser Ile Asp Thr Gly Ser Gly Ser Ile Asp Tyr Ala Glu Trp
    50                  55                  60

Val Glu Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ile Gly Ile Asp Tyr Asn Phe Trp Gly Pro Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Glu
                165                 170                 175

Ser Ser Gly Leu Tyr Ser Leu Ser Val Val Thr Val Pro Ser Ser
            180                 185                 190
```

Ser Leu Gly Thr Lys Thr Tyr Ile Cys Asn Val Asn His Lys Pro Ser
            195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Arg Arg Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Lys Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Tyr Lys Thr Thr Pro Pro Tyr Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Leu His Glu Ala
            420                 425                 430

Leu His Ala His Tyr Thr Arg Lys Glu Leu Ser Leu Ser Pro
        435                 440                 445

<210> SEQ ID NO 67
<211> LENGTH: 446
<212> TYPE: PRT
<213> ORGANISM: Artificial Sequence
<220> FEATURE:
<223> OTHER INFORMATION: ssVH3.30DQN0385ee0054H1353-SG1398.A5

<400> SEQUENCE: 67

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ala Glu Trp
            20                  25                  30

Tyr Phe Met Ser Trp Val Arg Gln Ala Pro Gly Lys Gly Leu Glu Trp
        35                  40                  45

Val Ala Ser Ile Asp Thr Gly Ser Gly Ser Ile Asp Tyr Ala Glu Trp
    50                  55                  60

Val Glu Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ile Gly Ile Asp Tyr Asn Phe Trp Gly Pro Gly Thr
                100                 105                 110

-continued

```
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
        130                 135                 140
Cys Leu Val Glu Asp Tyr Phe Pro Glu Pro Val Thr Val Ser Trp Asn
145                 150                 155                 160
Ser Gly Ala Leu Thr Ser Gly Val His Thr Phe Pro Ala Val Leu Glu
                165                 170                 175
Ser Ser Gly Leu Tyr Ser Leu Ser Ser Val Val Thr Val Pro Ser Ser
            180                 185                 190
Ser Leu Gly Thr Lys Thr Tyr Ile Cys Asn Val Asn His Lys Pro Ser
        195                 200                 205
Asn Thr Lys Val Asp Lys Arg Val Glu Pro Lys Ser Cys Asp Lys Thr
    210                 215                 220
His Thr Cys Pro Pro Cys Pro Ala Pro Glu Leu Arg Arg Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Lys Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Leu His Glu Ala
            420                 425                 430
Leu His Ala His Tyr Thr Arg Lys Glu Leu Ser Leu Ser Pro
        435                 440                 445
```

<210> SEQ ID NO 68
<211> LENGTH: 6
<212> TYPE: PRT
<213> ORGANISM: Artificial Sequence
<220> FEATURE:
<223> OTHER INFORMATION: DQN0344Hx H_CDR1

<400> SEQUENCE: 68

```
Ser Ser Tyr Trp Met Cys
1               5
```

<210> SEQ ID NO 69

```
<211> LENGTH: 17
<212> TYPE: PRT
<213> ORGANISM: Artificial Sequence
<220> FEATURE:
<223> OTHER INFORMATION: DQN0344Hx H_CDR2

<400> SEQUENCE: 69

Cys Val Tyr Gly Gly Ser Asp Thr Thr Tyr Tyr Ala Ser Trp Thr Lys
1               5                   10                  15
Gly

<210> SEQ ID NO 70
<211> LENGTH: 13
<212> TYPE: PRT
<213> ORGANISM: Artificial Sequence
<220> FEATURE:
<223> OTHER INFORMATION: DQN0344Hx H_CDR3

<400> SEQUENCE: 70

Asp Pro Leu Asn Tyr Tyr Tyr Tyr Gly Glu Leu Asn Leu
1               5                   10

<210> SEQ ID NO 71
<211> LENGTH: 121
<212> TYPE: PRT
<213> ORGANISM: Artificial Sequence
<220> FEATURE:
<223> OTHER INFORMATION: DQN0344Hx

<400> SEQUENCE: 71

Gln Ser Leu Glu Glu Ser Gly Gly Gly Leu Val Lys Pro Gly Gly Thr
1               5                   10                  15

Leu Thr Leu Thr Cys Thr Ala Ser Gly Phe Ser Phe Ser Ser Ser Tyr
            20                  25                  30

Trp Met Cys Trp Val Arg Gln Ala Pro Gly Lys Gly Leu Glu Trp Val
        35                  40                  45

Ala Cys Val Tyr Gly Gly Ser Asp Thr Thr Tyr Tyr Ala Ser Trp Thr
    50                  55                  60

Lys Gly Arg Phe Thr Ile Ser Lys Gly Ser Ser Thr Thr Val Ala Leu
65                  70                  75                  80

Gln Val Thr Ser Leu Thr Ala Ala Asp Thr Ala Thr Tyr Phe Cys Ala
                85                  90                  95

Arg Asp Pro Leu Asn Tyr Tyr Tyr Tyr Gly Glu Leu Asn Leu Trp Gly
            100                 105                 110

Pro Gly Thr Leu Val Thr Val Ser Ser
        115                 120

<210> SEQ ID NO 72
<211> LENGTH: 11
<212> TYPE: PRT
<213> ORGANISM: Artificial Sequence
<220> FEATURE:
<223> OTHER INFORMATION: DQN0344Lx L_CDR1

<400> SEQUENCE: 72

Gln Ala Thr Glu Asn Ile Tyr Ser Gly Leu Ala
1               5                   10

<210> SEQ ID NO 73
<211> LENGTH: 7
<212> TYPE: PRT
<213> ORGANISM: Artificial Sequence
<220> FEATURE:
```

<223> OTHER INFORMATION: DQN0344Lx L_CDR2

<400> SEQUENCE: 73

Tyr Val Ser Thr Leu Ala Ser
1               5

<210> SEQ ID NO 74
<211> LENGTH: 10
<212> TYPE: PRT
<213> ORGANISM: Artificial Sequence
<220> FEATURE:
<223> OTHER INFORMATION: DQN0344Lx L_CDR3

<400> SEQUENCE: 74

Gln Thr Tyr His Asp Ile Ser Asn Val Thr
1               5                   10

<210> SEQ ID NO 75
<211> LENGTH: 108
<212> TYPE: PRT
<213> ORGANISM: Artificial Sequence
<220> FEATURE:
<223> OTHER INFORMATION: DQN0344Lx

<400> SEQUENCE: 75

Ala Val Val Leu Thr Gln Thr Ala Ser Pro Val Ser Ala Ala Val Gly
1               5                   10                  15

Gly Thr Val Thr Ile Arg Cys Gln Ala Thr Glu Asn Ile Tyr Ser Gly
            20                  25                  30

Leu Ala Trp Tyr Gln Gln Lys Pro Gly Gln Pro Pro Lys Val Leu Ile
        35                  40                  45

Tyr Tyr Val Ser Thr Leu Ala Ser Gly Val Pro Ser Arg Phe Lys Gly
    50                  55                  60

Ser Gly Ser Gly Thr Glu Tyr Thr Leu Thr Ile Ser Gly Val Gln Cys
65                  70                  75                  80

Asp Asp Ala Ala Thr Tyr Tyr Cys Gln Thr Tyr His Asp Ile Ser Asn
                85                  90                  95

Val Thr Phe Gly Gly Gly Thr Lys Val Glu Ile Lys
            100                 105

<210> SEQ ID NO 76
<211> LENGTH: 6
<212> TYPE: PRT
<213> ORGANISM: Artificial Sequence
<220> FEATURE:
<223> OTHER INFORMATION: DQN0385He H_CDR1

<400> SEQUENCE: 76

Ser Ser Tyr Trp Ile Cys
1               5

<210> SEQ ID NO 77
<211> LENGTH: 17
<212> TYPE: PRT
<213> ORGANISM: Artificial Sequence
<220> FEATURE:
<223> OTHER INFORMATION: DQN0385He H_CDR2

<400> SEQUENCE: 77

Cys Ile Asp Thr Gly Ser Gly Ser Ile Asp Tyr Ala Ser Trp Val Asn
1               5                   10                  15

Gly

```
<210> SEQ ID NO 78
<211> LENGTH: 8
<212> TYPE: PRT
<213> ORGANISM: Artificial Sequence
<220> FEATURE:
<223> OTHER INFORMATION: DQN0385He H_CDR3

<400> SEQUENCE: 78

Asp Ile Gly Ile Asp Tyr Asn Phe
1               5

<210> SEQ ID NO 79
<211> LENGTH: 117
<212> TYPE: PRT
<213> ORGANISM: Artificial Sequence
<220> FEATURE:
<223> OTHER INFORMATION: DQN0385He

<400> SEQUENCE: 79

Gln Glu Gln Leu Glu Glu Ser Gly Gly Asp Leu Val Lys Pro Gly Ala
1               5                   10                  15

Ser Leu Thr Leu Thr Cys Thr Ala Ser Gly Phe Ser Phe Tyr Ser Ser
            20                  25                  30

Tyr Trp Ile Cys Trp Val Arg Gln Ala Pro Gly Lys Gly Leu Glu Trp
        35                  40                  45

Ile Ala Cys Ile Asp Thr Gly Ser Gly Ser Ile Asp Tyr Ala Ser Trp
    50                  55                  60

Val Asn Gly Arg Phe Thr Ile Ser Lys Thr Ser Ser Thr Val Thr
65                  70                  75                  80

Leu Gln Met Thr Ser Leu Thr Val Ala Asp Thr Ala Thr Tyr Phe Cys
                85                  90                  95

Ala Arg Asp Ile Gly Ile Asp Tyr Asn Phe Trp Gly Pro Gly Thr Leu
            100                 105                 110

Val Thr Val Ser Ser
        115

<210> SEQ ID NO 80
<211> LENGTH: 11
<212> TYPE: PRT
<213> ORGANISM: Artificial Sequence
<220> FEATURE:
<223> OTHER INFORMATION: DQN0385Le L_CDR1

<400> SEQUENCE: 80

Gln Ala Thr Gln Ser Ile Ser Ser Tyr Leu Asn
1               5                   10

<210> SEQ ID NO 81
<211> LENGTH: 7
<212> TYPE: PRT
<213> ORGANISM: Artificial Sequence
<220> FEATURE:
<223> OTHER INFORMATION: DQN0385Le L_CDR2

<400> SEQUENCE: 81

Tyr Ala Ser Thr Leu Ala Ser
1               5

<210> SEQ ID NO 82
<211> LENGTH: 8
<212> TYPE: PRT
<213> ORGANISM: Artificial Sequence
<220> FEATURE:
```

```
<223> OTHER INFORMATION: DQN0385Le L_CDR3

<400> SEQUENCE: 82

His Tyr Gly Ile Ser Tyr Val Ser
1               5

<210> SEQ ID NO 83
<211> LENGTH: 106
<212> TYPE: PRT
<213> ORGANISM: Artificial Sequence
<220> FEATURE:
<223> OTHER INFORMATION: DQN0385Le

<400> SEQUENCE: 83

Ala Phe Glu Leu Thr Gln Thr Pro Ser Phe Val Glu Ala Ala Val Gly
1               5                   10                  15

Gly Thr Val Thr Ile Lys Cys Gln Ala Thr Gln Ser Ile Ser Ser Tyr
            20                  25                  30

Leu Asn Trp Tyr Gln Gln Lys Pro Gly Gln Pro Pro Lys Leu Leu Ile
        35                  40                  45

Tyr Tyr Ala Ser Thr Leu Ala Ser Gly Val Pro Ser Arg Phe Lys Gly
    50                  55                  60

Ser Gly Ser Gly Thr Glu Phe Ser Leu Thr Ile Ser Gly Val Glu Cys
65                  70                  75                  80

Ala Asp Ala Ala Thr Tyr Tyr Cys His Tyr Gly Ile Ser Tyr Val Ser
                85                  90                  95

Phe Gly Gly Gly Thr Lys Val Glu Ile Lys
            100                 105

<210> SEQ ID NO 84
<211> LENGTH: 123
<212> TYPE: PRT
<213> ORGANISM: Artificial Sequence
<220> FEATURE:
<223> OTHER INFORMATION: DQN034425H

<400> SEQUENCE: 84

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Ser
            20                  25                  30

Tyr Trp Met Cys Trp Val Arg Gln Ala Pro Gly Gln Gly Leu Glu Trp
        35                  40                  45

Met Gly Cys Val Tyr Gly Gly Ser Asp Thr Thr Tyr Tyr Ala Ser Trp
    50                  55                  60

Thr Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Pro Leu Asn Tyr Tyr Tyr Gly Glu Leu Asn Leu
            100                 105                 110

Trp Gly Gln Gly Thr Leu Val Thr Val Ser Ser
        115                 120

<210> SEQ ID NO 85
<211> LENGTH: 108
<212> TYPE: PRT
<213> ORGANISM: Artificial Sequence
<220> FEATURE:
<223> OTHER INFORMATION: DQN034409L
```

-continued

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Gln Ala Thr Glu Asn Ile Tyr Ser Gly
            20                  25                  30

Leu Ala Trp Tyr Gln Gln Lys Pro Gly Lys Ala Pro Lys Leu Leu Ile
        35                  40                  45

Tyr Tyr Val Ser Thr Leu Ala Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Thr Tyr His Asp Ile Ser Asn
                85                  90                  95

Val Thr Phe Gly Gln Gly Thr Lys Val Glu Ile Lys
            100                 105

<210> SEQ ID NO 86
<211> LENGTH: 106
<212> TYPE: PRT
<213> ORGANISM: Artificial Sequence
<220> FEATURE:
<223> OTHER INFORMATION: DQN0385ee009L

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Gln Ala Thr Gln Ser Ile Ser Ser Tyr
            20                  25                  30

Leu Asn Trp Tyr Gln Gln Lys Pro Gly Gln Pro Pro Lys Leu Leu Ile
        35                  40                  45

Tyr Tyr Ala Ser Thr Leu Ala Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys His Tyr Gly Ile Ser Tyr Val Ser
                85                  90                  95

Phe Gly Gln Gly Thr Lys Val Glu Ile Lys
            100                 105

<210> SEQ ID NO 87
<211> LENGTH: 118
<212> TYPE: PRT
<213> ORGANISM: Artificial Sequence
<220> FEATURE:
<223> OTHER INFORMATION: DQN0385ee0054H

<400> SEQUENCE: 87

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Ser
            20                  25                  30

Tyr Trp Ile Cys Trp Val Arg Gln Ala Pro Gly Lys Gly Leu Glu Trp
        35                  40                  45

Val Ala Cys Ile Asp Thr Gly Ser Gly Ser Ile Asp Tyr Ala Ser Trp
    50                  55                  60

Val Asn Gly Arg Phe Thr Ile Ser Arg Asp Asn Ser Lys Asn Thr Leu
65                  70                  75                  80

```
Tyr Leu Gln Met Asn Ser Leu Arg Ala Glu Asp Thr Ala Val Tyr Tyr
                85                  90                  95

Cys Ala Arg Asp Ile Gly Ile Asp Tyr Asn Phe Trp Gly Pro Gly Thr
            100                 105                 110

Leu Val Thr Val Ser Ser
        115
```

<210> SEQ ID NO 88
<211> LENGTH: 123
<212> TYPE: PRT
<213> ORGANISM: Artificial Sequence
<220> FEATURE:
<223> OTHER INFORMATION: DQN0344H0976

<400> SEQUENCE: 88

```
Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Ala
            20                  25                  30

Tyr Trp Met Val Trp Val Arg Gln Ala Pro Gly Gln Gly Leu Glu Trp
        35                  40                  45

Met Gly Ala Val Tyr Gly Gly Ser Asp Thr Thr Tyr Tyr Ala Lys Trp
    50                  55                  60

Thr Glu Gly Arg Phe Thr Ile Ser Arg Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Glu Pro Leu Asn Tyr Tyr Tyr Gly Glu Leu Asn Leu
            100                 105                 110

Trp Gly Gln Gly Thr Leu Val Thr Val Ser Ser
        115                 120
```

<210> SEQ ID NO 89
<211> LENGTH: 123
<212> TYPE: PRT
<213> ORGANISM: Artificial Sequence
<220> FEATURE:
<223> OTHER INFORMATION: DQN0344H1013

<400> SEQUENCE: 89

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Ala
            20                  25                  30

Tyr Trp Met Val Trp Val Arg Gln Ala Pro Gly Gln Gly Leu Glu Trp
        35                  40                  45

Met Gly Ala Val Tyr Gly Gly Ser Asp Thr Thr Tyr Tyr Ala Lys Trp
    50                  55                  60

Thr Glu Gly Arg Phe Thr Ile Ser Arg Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Glu Pro Leu Asn Tyr Tyr Tyr Gly Glu Leu Asn Val
            100                 105                 110

Trp Gly Gln Gly Thr Leu Val Thr Val Ser Ser
        115                 120
```

-continued

```
<210> SEQ ID NO 90
<211> LENGTH: 108
<212> TYPE: PRT
<213> ORGANISM: Artificial Sequence
<220> FEATURE:
<223> OTHER INFORMATION: DQN0344L0591

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Gln Ala Thr Glu Glu Ile Tyr Ser Gly
            20                  25                  30

Leu Ala Trp Tyr Gln Gln Lys Pro Gly Lys Ala Pro Lys Leu Leu Ile
        35                  40                  45

Tyr Tyr Val Ser Thr Leu Tyr Glu Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Thr Tyr Glu Asp Val Ser Ala
                85                  90                  95

Val Thr Phe Gly Gln Gly Thr Lys Val Glu Ile Lys
            100                 105

<210> SEQ ID NO 91
<211> LENGTH: 108
<212> TYPE: PRT
<213> ORGANISM: Artificial Sequence
<220> FEATURE:
<223> OTHER INFORMATION: DQN0344L0620

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Gln Ala Thr Glu Asn Ile Tyr Ser Gly
            20                  25                  30

Leu Ala Trp Tyr Gln Gln Lys Pro Gly Lys Ala Pro Lys Leu Leu Ile
        35                  40                  45

Tyr Tyr Val Ser Thr Leu Ala Tyr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Thr Tyr Glu Asp Val Ser Ala
                85                  90                  95

Val Thr Phe Gly Gln Gly Thr Lys Val Glu Ile Lys
            100                 105

<210> SEQ ID NO 92
<211> LENGTH: 118
<212> TYPE: PRT
<213> ORGANISM: Artificial Sequence
<220> FEATURE:
<223> OTHER INFORMATION: DQN0385H1270

<400> SEQUENCE: 92

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Glu Trp
            20                  25                  30

Tyr Phe Met Ser Trp Val Arg Gln Ala Pro Gly Lys Gly Leu Glu Trp
        35                  40                  45
```

Val Ala Ser Ile Asp Thr Gly Ser Gly Ser Ile Asp Tyr Ala Glu Trp
    50                  55                  60

Val Glu Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ile Gly Ile Asp Tyr Asn Phe Trp Gly Pro Gly Thr
            100                 105                 110

Leu Val Thr Val Ser Ser
            115

<210> SEQ ID NO 93
<211> LENGTH: 118
<212> TYPE: PRT
<213> ORGANISM: Artificial Sequence
<220> FEATURE:
<223> OTHER INFORMATION: DQN0385H1352

<400> SEQUENCE: 93

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Glu Phe Ser Glu Trp
            20                  25                  30

Tyr Phe Met Ser Trp Val Arg Gln Ala Pro Gly Lys Gly Leu Glu Trp
        35                  40                  45

Val Ala Ser Ile Asp Thr Gly Ser Gly Ser Ile Asp Tyr Ala Glu Trp
    50                  55                  60

Val Glu Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ile Gly Ile Asp Tyr Asn Phe Trp Gly Pro Gly Thr
            100                 105                 110

Leu Val Thr Val Ser Ser
            115

<210> SEQ ID NO 94
<211> LENGTH: 118
<212> TYPE: PRT
<213> ORGANISM: Artificial Sequence
<220> FEATURE:
<223> OTHER INFORMATION: DQN0385H1527

<400> SEQUENCE: 94

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ala Ser Trp
            20                  25                  30

Tyr Phe Met Ser Trp Val Arg Gln Ala Pro Gly Lys Gly Leu Glu Trp
        35                  40                  45

Val Ala Ser Ile Asp Thr Gly Ser Gly Ser Ile Asp Tyr Ala Glu Trp
    50                  55                  60

Val Glu Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ile Gly Ile Asp Tyr Asn Phe Trp Gly Pro Gly Thr

Leu Val Thr Val Ser Ser
        115

<210> SEQ ID NO 95
<211> LENGTH: 118
<212> TYPE: PRT
<213> ORGANISM: Artificial Sequence
<220> FEATURE:
<223> OTHER INFORMATION: DQN0385H1255

<400> SEQUENCE: 95

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Glu Trp
            20                  25                  30

Tyr Phe Met Ser Trp Val Arg Gln Ala Pro Gly Lys Gly Leu Glu Trp
        35                  40                  45

Val Ala Ser Ile Asp Thr Gly Ser Gly Ser Ile Asp Tyr Ala Gly Trp
    50                  55                  60

Val Glu Glu Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ile Gly Ile Asp Tyr Asn Phe Trp Gly Pro Gly Thr
            100                 105                 110

Leu Val Thr Val Ser Ser
        115

<210> SEQ ID NO 96
<211> LENGTH: 118
<212> TYPE: PRT
<213> ORGANISM: Artificial Sequence
<220> FEATURE:
<223> OTHER INFORMATION: DQN0385H1521

<400> SEQUENCE: 96

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Glu Ser Trp
            20                  25                  30

Tyr Phe Met Ser Trp Val Arg Gln Ala Pro Gly Lys Gly Leu Glu Trp
        35                  40                  45

Val Ala Ser Ile Asp Thr Gly Ser Gly Ser Ile Asp Tyr Ala Glu Trp
    50                  55                  60

Val Glu Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ile Gly Ile Asp Tyr Asn Phe Trp Gly Pro Gly Thr
            100                 105                 110

Leu Val Thr Val Ser Ser
        115

<210> SEQ ID NO 97
<211> LENGTH: 118
<212> TYPE: PRT
<213> ORGANISM: Artificial Sequence
<220> FEATURE:

<223> OTHER INFORMATION: DQN0385H1353

<400> SEQUENCE: 97

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ala Glu Trp
            20                  25                  30

Tyr Phe Met Ser Trp Val Arg Gln Ala Pro Gly Lys Gly Leu Glu Trp
        35                  40                  45

Val Ala Ser Ile Asp Thr Gly Ser Gly Ser Ile Asp Tyr Ala Glu Trp
    50                  55                  60

Val Glu Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ile Gly Ile Asp Tyr Asn Phe Trp Gly Pro Gly Thr
            100                 105                 110

Leu Val Thr Val Ser Ser
        115

<210> SEQ ID NO 98
<211> LENGTH: 106
<212> TYPE: PRT
<213> ORGANISM: Artificial Sequence
<220> FEATURE:
<223> OTHER INFORMATION: DQN0385L0722

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Gln Thr Thr Gln Ser Ile Ser Ser Tyr
            20                  25                  30

Leu Asn Trp Tyr Gln Gln Lys Pro Gly Gln Pro Pro Lys Leu Leu Ile
        35                  40                  45

Tyr Tyr Ala Ser Thr Lys Ala Glu Gly Ile Pro Ala Arg Phe Ser Gly
    50                  55                  60

Ser Gly Leu Gly Thr Asp Phe Thr Leu Thr Ile Ser Ser Leu Gln Pro
65                  70                  75                  80

Glu Asp Phe Ala Val Tyr Tyr Cys His Tyr Gly Ile Ser Lys Val Ser
                85                  90                  95

Phe Gly Gln Gly Thr Lys Val Glu Ile Lys
            100                 105

<210> SEQ ID NO 99
<211> LENGTH: 106
<212> TYPE: PRT
<213> ORGANISM: Artificial Sequence
<220> FEATURE:
<223> OTHER INFORMATION: DQN0385L0681

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Gln Thr Thr Gln Ser Ile Ser Ser Tyr
            20                  25                  30

Leu Asn Trp Tyr Gln Gln Lys Pro Gly Gln Pro Pro Lys Leu Leu Ile
        35                  40                  45

Tyr Tyr Ala Ser Thr Lys Ala Glu Gly Ile Pro Ala Arg Phe Ser Gly

```
                50                  55                  60
Ser Gly Leu Gly Thr Asp Phe Thr Leu Thr Ile Ser Ser Leu Glu Pro
 65                  70                  75                  80

Glu Asp Phe Ala Val Tyr Tyr Cys His Tyr Gly Ile Ser Lys Val Ser
                 85                  90                  95

Phe Gly Gln Gly Thr Lys Val Glu Ile Lys
            100                 105

<210> SEQ ID NO 100
<211> LENGTH: 106
<212> TYPE: PRT
<213> ORGANISM: Artificial Sequence
<220> FEATURE:
<223> OTHER INFORMATION: DQN0385L0605

<400> SEQUENCE: 100

Asp Ile Gln Met Thr Gln Ser Pro Ser Ser Leu Ser Ala Ser Val Gly
 1               5                  10                  15

Asp Arg Val Thr Ile Thr Cys Gln Thr Thr Gln Ser Ile Ser Ser Tyr
                 20                  25                  30

Leu Asn Trp Tyr Gln Gln Lys Pro Gly Gln Pro Pro Lys Leu Leu Ile
             35                  40                  45

Tyr Tyr Ala Ser Thr Lys Ala Glu Gly Ile Pro Ala Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys His Tyr Gly Ile Ser Lys Val Ser
                 85                  90                  95

Phe Gly Gln Gly Thr Lys Val Glu Ile Lys
            100                 105

<210> SEQ ID NO 101
<211> LENGTH: 328
<212> TYPE: PRT
<213> ORGANISM: Artificial Sequence
<220> FEATURE:
<223> OTHER INFORMATION: SG181.S3n

<400> SEQUENCE: 101

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Arg Arg Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Tyr Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 102
<211> LENGTH: 328
<212> TYPE: PRT
<213> ORGANISM: Artificial Sequence
<220> FEATURE:
<223> OTHER INFORMATION: SG181.S3p

<400> SEQUENCE: 102

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Arg Arg Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Lys Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Tyr Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 103
<211> LENGTH: 107
<212> TYPE: PRT
<213> ORGANISM: Artificial Sequence
<220> FEATURE:
<223> OTHER INFORMATION: SK1

<400> SEQUENCE: 103

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 104
<211> LENGTH: 328
<212> TYPE: PRT
<213> ORGANISM: Artificial Sequence
<220> FEATURE:
<223> OTHER INFORMATION: SG1308.A5

<400> SEQUENCE: 104

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Glu Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Glu Ser Ser Gly Leu Tyr Ser
    50                  55                  60

Leu Ser Ser Val Val Thr Val Pro Ser Ser Leu Gly Thr Lys Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Arg Arg Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Lys Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Tyr Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Leu His Glu Ala Leu His Ala His Tyr Thr
305                 310                 315                 320

Arg Lys Glu Leu Ser Leu Ser Pro
                325

<210> SEQ ID NO 105
<211> LENGTH: 328
<212> TYPE: PRT
<213> ORGANISM: Artificial Sequence
<220> FEATURE:
<223> OTHER INFORMATION: SG1310.A5

<400> SEQUENCE: 105

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Lys Ser Ser Gly Leu Tyr Ser
            50                  55                  60

Leu Ser Ser Val Val Thr Val Pro Ser Ser Leu Gly Thr Gln Thr
65                  70                  75                  80

```
Tyr Ile Cys Asn Val Asn His Lys Pro Ser Asn Thr Lys Val Asp Lys
                    85                  90                  95

Arg Val Glu Pro Lys Ser Cys Asp Lys Thr His Thr Cys Pro Pro Cys
            100                 105                 110

Pro Ala Pro Glu Leu Arg Arg Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Tyr Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Leu His Glu Ala Leu His Ala His Tyr Thr
305                 310                 315                 320

Arg Glu Glu Leu Ser Leu Ser Pro
                325

<210> SEQ ID NO 106
<211> LENGTH: 107
<212> TYPE: PRT
<213> ORGANISM: Artificial Sequence
<220> FEATURE:
<223> OTHER INFORMATION: SK1004

<400> SEQUENCE: 106

Arg Thr Val Ala Ala Pro Ser Val Phe Ile Phe Pro Pro Ser Asp Glu
1               5                   10                  15

Gln Leu Lys Ser Gly Thr Ala Glu Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Glu Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 107
<211> LENGTH: 107
<212> TYPE: PRT
<213> ORGANISM: Artificial Sequence
<220> FEATURE:
<223> OTHER INFORMATION: SK1014

<400> SEQUENCE: 107

Arg Thr Val Ala Ala Pro Ser Val Phe Ile Phe Pro Pro Ser Asp Glu
1               5                   10                  15

Gln Leu Lys Ser Gly Thr Ala Lys Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Lys Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 108
<211> LENGTH: 11
<212> TYPE: PRT
<213> ORGANISM: Artificial Sequence
<220> FEATURE:
<223> OTHER INFORMATION: DQN034409L0012 L_CDR1

<400> SEQUENCE: 108

Gln Ala Thr Glu Asn Ile Tyr Ser Gly Leu Ala
1               5                   10

<210> SEQ ID NO 109
<211> LENGTH: 7
<212> TYPE: PRT
<213> ORGANISM: Artificial Sequence
<220> FEATURE:
<223> OTHER INFORMATION: DQN034409L0012 L_CDR2

<400> SEQUENCE: 109

Tyr Val Ser Thr Leu Ala Ser
1               5

<210> SEQ ID NO 110
<211> LENGTH: 10
<212> TYPE: PRT
<213> ORGANISM: Artificial Sequence
<220> FEATURE:
<223> OTHER INFORMATION: DQN034409L0012 L_CDR3

<400> SEQUENCE: 110

Gln Thr Tyr His Asp Ile Ser Glu Val Thr
1               5                   10

<210> SEQ ID NO 111
<211> LENGTH: 108
<212> TYPE: PRT
<213> ORGANISM: Artificial Sequence
<220> FEATURE:
<223> OTHER INFORMATION: DQN034409L0012

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Gln Ala Thr Glu Asn Ile Tyr Ser Gly
            20                  25                  30

Leu Ala Trp Tyr Gln Gln Lys Pro Gly Lys Ala Pro Lys Leu Leu Ile
        35                  40                  45

Tyr Tyr Val Ser Thr Leu Ala Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Thr Tyr His Asp Ile Ser Glu
                85                  90                  95

Val Thr Phe Gly Gln Gly Thr Lys Val Glu Ile Lys
            100                 105

<210> SEQ ID NO 112
<211> LENGTH: 6
<212> TYPE: PRT
<213> ORGANISM: Artificial Sequence
<220> FEATURE:
<223> OTHER INFORMATION: DQN034425H H_CDR1

<400> SEQUENCE: 112

Ser Ser Tyr Trp Met Cys
1               5

<210> SEQ ID NO 113
<211> LENGTH: 17
<212> TYPE: PRT
<213> ORGANISM: Artificial Sequence
<220> FEATURE:
<223> OTHER INFORMATION: DQN034425H H_CDR2

<400> SEQUENCE: 113

Cys Val Tyr Gly Gly Ser Asp Thr Thr Tyr Tyr Ala Ser Trp Thr Lys
1               5                   10                  15

Gly

<210> SEQ ID NO 114
<211> LENGTH: 13
<212> TYPE: PRT
<213> ORGANISM: Artificial Sequence
<220> FEATURE:
<223> OTHER INFORMATION: DQN034425H H_CDR3

<400> SEQUENCE: 114

Asp Pro Leu Asn Tyr Tyr Tyr Gly Glu Leu Asn Leu
1               5                   10

<210> SEQ ID NO 115
<211> LENGTH: 6
<212> TYPE: PRT
<213> ORGANISM: Artificial Sequence
<220> FEATURE:
<223> OTHER INFORMATION: DQN0385ee0054H H_CDR1

<400> SEQUENCE: 115

Ser Ser Tyr Trp Ile Cys
1               5

<210> SEQ ID NO 116

```
<211> LENGTH: 17
<212> TYPE: PRT
<213> ORGANISM: Artificial Sequence
<220> FEATURE:
<223> OTHER INFORMATION: DQN0385ee0054H H_CDR2

<400> SEQUENCE: 116

Cys Ile Asp Thr Gly Ser Gly Ser Ile Asp Tyr Ala Ser Trp Val Asn
1               5                   10                  15
Gly

<210> SEQ ID NO 117
<211> LENGTH: 8
<212> TYPE: PRT
<213> ORGANISM: Artificial Sequence
<220> FEATURE:
<223> OTHER INFORMATION: DQN0385ee0054H H_CDR3

<400> SEQUENCE: 117

Asp Ile Gly Ile Asp Tyr Asn Phe
1               5

<210> SEQ ID NO 118
<211> LENGTH: 11
<212> TYPE: PRT
<213> ORGANISM: Artificial Sequence
<220> FEATURE:
<223> OTHER INFORMATION: DQN0385ee009L L_CDR1

<400> SEQUENCE: 118

Gln Ala Thr Gln Ser Ile Ser Ser Tyr Leu Asn
1               5                   10

<210> SEQ ID NO 119
<211> LENGTH: 7
<212> TYPE: PRT
<213> ORGANISM: Artificial Sequence
<220> FEATURE:
<223> OTHER INFORMATION: DQN0385ee009L L_CDR2

<400> SEQUENCE: 119

Tyr Ala Ser Thr Leu Ala Ser
1               5

<210> SEQ ID NO 120
<211> LENGTH: 8
<212> TYPE: PRT
<213> ORGANISM: Artificial Sequence
<220> FEATURE:
<223> OTHER INFORMATION: DQN0385ee009L L_CDR3

<400> SEQUENCE: 120

His Tyr Gly Ile Ser Tyr Val Ser
1               5

<210> SEQ ID NO 121
<211> LENGTH: 5
<212> TYPE: PRT
<213> ORGANISM: Artificial Sequence
<220> FEATURE:
<223> OTHER INFORMATION: IC17HdK H_CDR1

<400> SEQUENCE: 121

Ser Tyr Trp Met His
1               5
```

```
<210> SEQ ID NO 122
<211> LENGTH: 17
<212> TYPE: PRT
<213> ORGANISM: Artificial Sequence
<220> FEATURE:
<223> OTHER INFORMATION: IC17HdK H_CDR2

<400> SEQUENCE: 122

Met Ile Asp Pro Ser Tyr Ser Glu Thr Arg Leu Asn Gln Lys Phe Lys
1               5                   10                  15

Asp

<210> SEQ ID NO 123
<211> LENGTH: 7
<212> TYPE: PRT
<213> ORGANISM: Artificial Sequence
<220> FEATURE:
<223> OTHER INFORMATION: IC17HdK H_CDR3

<400> SEQUENCE: 123

Tyr Gly Asn Tyr Phe Asp Tyr
1               5

<210> SEQ ID NO 124
<211> LENGTH: 116
<212> TYPE: PRT
<213> ORGANISM: Artificial Sequence
<220> FEATURE:
<223> OTHER INFORMATION: IC17HdK

<400> SEQUENCE: 124

Gln Val Gln Leu Gln Gln Ser Gly Pro Gln Leu Val Arg Pro Gly Ala
1               5                   10                  15

Ser Val Lys Ile Ser Cys Lys Ala Ser Gly Tyr Ser Phe Thr Ser Tyr
            20                  25                  30

Trp Met His Trp Val Asn Gln Arg Pro Gly Gln Gly Leu Glu Trp Ile
        35                  40                  45

Gly Met Ile Asp Pro Ser Tyr Ser Glu Thr Arg Leu Asn Gln Lys Phe
    50                  55                  60

Lys Asp Lys Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Leu Tyr Gly Asn Tyr Phe Asp Tyr Trp Gly Gln Gly Thr Thr Leu
            100                 105                 110

Thr Val Ser Ser
        115

<210> SEQ ID NO 125
<211> LENGTH: 11
<212> TYPE: PRT
<213> ORGANISM: Artificial Sequence
<220> FEATURE:
<223> OTHER INFORMATION: IC17L L_CDR1

<400> SEQUENCE: 125

Lys Ala Ser Glu Asp Ile Tyr Asn Arg Leu Ala
1               5                   10

<210> SEQ ID NO 126
<211> LENGTH: 7
<212> TYPE: PRT
<213> ORGANISM: Artificial Sequence
```

<220> FEATURE:
<223> OTHER INFORMATION: IC17L L_CDR2

<400> SEQUENCE: 126

Gly Ala Thr Ser Leu Glu Thr
1               5

<210> SEQ ID NO 127
<211> LENGTH: 9
<212> TYPE: PRT
<213> ORGANISM: Artificial Sequence
<220> FEATURE:
<223> OTHER INFORMATION: IC17L L_CDR3

<400> SEQUENCE: 127

Gln Gln Tyr Trp Ser Thr Pro Tyr Thr
1               5

<210> SEQ ID NO 128
<211> LENGTH: 107
<212> TYPE: PRT
<213> ORGANISM: Artificial Sequence
<220> FEATURE:
<223> OTHER INFORMATION: IC17L

<400> SEQUENCE: 128

Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
                20                  25                  30

Leu Ala Trp Tyr Gln Gln Lys Pro Gly Asn Ala Pro Arg Leu Leu Ile
            35                  40                  45

Ser Gly Ala Thr Ser Leu Glu Thr Gly Val Pro Ser Arg Phe Ser Gly
        50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Tyr
                85                  90                  95

Thr Phe Gly Gly Gly Thr Lys Leu Glu Val Lys
            100                 105

<210> SEQ ID NO 129
<211> LENGTH: 6
<212> TYPE: PRT
<213> ORGANISM: Artificial Sequence
<220> FEATURE:
<223> OTHER INFORMATION: DQN0344H0976 H_CDR1

<400> SEQUENCE: 129

Ser Ala Tyr Trp Met Val
1               5

<210> SEQ ID NO 130
<211> LENGTH: 17
<212> TYPE: PRT
<213> ORGANISM: Artificial Sequence
<220> FEATURE:
<223> OTHER INFORMATION: DQN0344H0976 H_CDR2

<400> SEQUENCE: 130

Ala Val Tyr Gly Gly Ser Asp Thr Thr Tyr Tyr Ala Lys Trp Thr Glu
1               5                   10                  15

Gly

```
<210> SEQ ID NO 131
<211> LENGTH: 13
<212> TYPE: PRT
<213> ORGANISM: Artificial Sequence
<220> FEATURE:
<223> OTHER INFORMATION: DQN0344H0976 H_CDR3

<400> SEQUENCE: 131

Glu Pro Leu Asn Tyr Tyr Tyr Tyr Gly Glu Leu Asn Leu
1               5                   10

<210> SEQ ID NO 132
<211> LENGTH: 11
<212> TYPE: PRT
<213> ORGANISM: Artificial Sequence
<220> FEATURE:
<223> OTHER INFORMATION: DQN0344L0591 L_CDR1

<400> SEQUENCE: 132

Gln Ala Thr Glu Glu Ile Tyr Ser Gly Leu Ala
1               5                   10

<210> SEQ ID NO 133
<211> LENGTH: 7
<212> TYPE: PRT
<213> ORGANISM: Artificial Sequence
<220> FEATURE:
<223> OTHER INFORMATION: DQN0344L0591 L_CDR2

<400> SEQUENCE: 133

Tyr Val Ser Thr Leu Tyr Glu
1               5

<210> SEQ ID NO 134
<211> LENGTH: 10
<212> TYPE: PRT
<213> ORGANISM: Artificial Sequence
<220> FEATURE:
<223> OTHER INFORMATION: DQN0344L0591 L_CDR3

<400> SEQUENCE: 134

Gln Thr Tyr Glu Asp Val Ser Ala Val Thr
1               5                   10

<210> SEQ ID NO 135
<211> LENGTH: 6
<212> TYPE: PRT
<213> ORGANISM: Artificial Sequence
<220> FEATURE:
<223> OTHER INFORMATION: DQN0385H1270 H_CDR1

<400> SEQUENCE: 135

Glu Trp Tyr Phe Met Ser
1               5

<210> SEQ ID NO 136
<211> LENGTH: 17
<212> TYPE: PRT
<213> ORGANISM: Artificial Sequence
<220> FEATURE:
<223> OTHER INFORMATION: DQN0385H1270 H_CDR2

<400> SEQUENCE: 136

Ser Ile Asp Thr Gly Ser Gly Ser Ile Asp Tyr Ala Glu Trp Val Glu
1               5                   10                  15
```

Gly

```
<210> SEQ ID NO 137
<211> LENGTH: 8
<212> TYPE: PRT
<213> ORGANISM: Artificial Sequence
<220> FEATURE:
<223> OTHER INFORMATION: DQN0385H1270 H_CDR3

<400> SEQUENCE: 137

Asp Ile Gly Ile Asp Tyr Asn Phe
1               5

<210> SEQ ID NO 138
<211> LENGTH: 11
<212> TYPE: PRT
<213> ORGANISM: Artificial Sequence
<220> FEATURE:
<223> OTHER INFORMATION: DQN0385L0722 L_CDR1

<400> SEQUENCE: 138

Gln Thr Thr Gln Ser Ile Ser Ser Tyr Leu Asn
1               5                   10

<210> SEQ ID NO 139
<211> LENGTH: 7
<212> TYPE: PRT
<213> ORGANISM: Artificial Sequence
<220> FEATURE:
<223> OTHER INFORMATION: DQN0385L0722 L_CDR2

<400> SEQUENCE: 139

Tyr Ala Ser Thr Lys Ala Glu
1               5

<210> SEQ ID NO 140
<211> LENGTH: 8
<212> TYPE: PRT
<213> ORGANISM: Artificial Sequence
<220> FEATURE:
<223> OTHER INFORMATION: DQN0385L0722 L_CDR3

<400> SEQUENCE: 140

His Tyr Gly Ile Ser Lys Val Ser
1               5

<210> SEQ ID NO 141
<211> LENGTH: 11
<212> TYPE: PRT
<213> ORGANISM: Artificial Sequence
<220> FEATURE:
<223> OTHER INFORMATION: DQN0385L0681 L_CDR1

<400> SEQUENCE: 141

Gln Thr Thr Gln Ser Ile Ser Ser Tyr Leu Asn
1               5                   10

<210> SEQ ID NO 142
<211> LENGTH: 7
<212> TYPE: PRT
<213> ORGANISM: Artificial Sequence
<220> FEATURE:
<223> OTHER INFORMATION: DQN0385L0681 L_CDR2

<400> SEQUENCE: 142

Tyr Ala Ser Thr Lys Ala Glu
1               5
```

```
<210> SEQ ID NO 143
<211> LENGTH: 8
<212> TYPE: PRT
<213> ORGANISM: Artificial Sequence
<220> FEATURE:
<223> OTHER INFORMATION: DQN0385L0681 L_CDR3

<400> SEQUENCE: 143

His Tyr Gly Ile Ser Lys Val Ser
1               5

<210> SEQ ID NO 144
<211> LENGTH: 6
<212> TYPE: PRT
<213> ORGANISM: Artificial Sequence
<220> FEATURE:
<223> OTHER INFORMATION: DQN0385H1352 H_CDR1

<400> SEQUENCE: 144

Glu Trp Tyr Phe Met Ser
1               5

<210> SEQ ID NO 145
<211> LENGTH: 17
<212> TYPE: PRT
<213> ORGANISM: Artificial Sequence
<220> FEATURE:
<223> OTHER INFORMATION: DQN0385H1352 H_CDR2

<400> SEQUENCE: 145

Ser Ile Asp Thr Gly Ser Gly Ser Ile Asp Tyr Ala Glu Trp Val Glu
1               5                   10                  15

Gly

<210> SEQ ID NO 146
<211> LENGTH: 8
<212> TYPE: PRT
<213> ORGANISM: Artificial Sequence
<220> FEATURE:
<223> OTHER INFORMATION: DQN0385H1352 H_CDR3

<400> SEQUENCE: 146

Asp Ile Gly Ile Asp Tyr Asn Phe
1               5

<210> SEQ ID NO 147
<211> LENGTH: 6
<212> TYPE: PRT
<213> ORGANISM: Artificial Sequence
<220> FEATURE:
<223> OTHER INFORMATION: DQN0385H1527 H_CDR1

<400> SEQUENCE: 147

Ser Trp Tyr Phe Met Ser
1               5

<210> SEQ ID NO 148
<211> LENGTH: 17
<212> TYPE: PRT
<213> ORGANISM: Artificial Sequence
<220> FEATURE:
<223> OTHER INFORMATION: DQN0385H1527 H_CDR2

<400> SEQUENCE: 148

Ser Ile Asp Thr Gly Ser Gly Ser Ile Asp Tyr Ala Glu Trp Val Glu
```

```
1               5                  10                 15
Gly

<210> SEQ ID NO 149
<211> LENGTH: 8
<212> TYPE: PRT
<213> ORGANISM: Artificial Sequence
<220> FEATURE:
<223> OTHER INFORMATION: DQN0385H1527 H_CDR3

<400> SEQUENCE: 149

Asp Ile Gly Ile Asp Tyr Asn Phe
1               5

<210> SEQ ID NO 150
<211> LENGTH: 11
<212> TYPE: PRT
<213> ORGANISM: Artificial Sequence
<220> FEATURE:
<223> OTHER INFORMATION: DQN0385L0605 L_CDR1

<400> SEQUENCE: 150

Gln Thr Thr Gln Ser Ile Ser Ser Tyr Leu Asn
1               5                   10

<210> SEQ ID NO 151
<211> LENGTH: 7
<212> TYPE: PRT
<213> ORGANISM: Artificial Sequence
<220> FEATURE:
<223> OTHER INFORMATION: DQN0385L0605 L_CDR2

<400> SEQUENCE: 151

Tyr Ala Ser Thr Lys Ala Glu
1               5

<210> SEQ ID NO 152
<211> LENGTH: 8
<212> TYPE: PRT
<213> ORGANISM: Artificial Sequence
<220> FEATURE:
<223> OTHER INFORMATION: DQN0385L0605 L_CDR3

<400> SEQUENCE: 152

His Tyr Gly Ile Ser Lys Val Ser
1               5

<210> SEQ ID NO 153
<211> LENGTH: 6
<212> TYPE: PRT
<213> ORGANISM: Artificial Sequence
<220> FEATURE:
<223> OTHER INFORMATION: DQN0385H1255 H_CDR1

<400> SEQUENCE: 153

Glu Trp Tyr Phe Met Ser
1               5

<210> SEQ ID NO 154
<211> LENGTH: 17
<212> TYPE: PRT
<213> ORGANISM: Artificial Sequence
<220> FEATURE:
<223> OTHER INFORMATION: DQN0385H1255 H_CDR2

<400> SEQUENCE: 154
```

Ser Ile Asp Thr Gly Ser Gly Ser Ile Asp Tyr Ala Gly Trp Val Glu
1               5                   10                  15

Glu

<210> SEQ ID NO 155
<211> LENGTH: 8
<212> TYPE: PRT
<213> ORGANISM: Artificial Sequence
<220> FEATURE:
<223> OTHER INFORMATION: DQN0385H1255 H_CDR3

<400> SEQUENCE: 155

Asp Ile Gly Ile Asp Tyr Asn Phe
1               5

<210> SEQ ID NO 156
<211> LENGTH: 6
<212> TYPE: PRT
<213> ORGANISM: Artificial Sequence
<220> FEATURE:
<223> OTHER INFORMATION: DQN0385H1521 H_CDR1

<400> SEQUENCE: 156

Ser Trp Tyr Phe Met Ser
1               5

<210> SEQ ID NO 157
<211> LENGTH: 17
<212> TYPE: PRT
<213> ORGANISM: Artificial Sequence
<220> FEATURE:
<223> OTHER INFORMATION: DQN0385H1521 H_CDR2

<400> SEQUENCE: 157

Ser Ile Asp Thr Gly Ser Gly Ser Ile Asp Tyr Ala Glu Trp Val Glu
1               5                   10                  15

Gly

<210> SEQ ID NO 158
<211> LENGTH: 8
<212> TYPE: PRT
<213> ORGANISM: Artificial Sequence
<220> FEATURE:
<223> OTHER INFORMATION: DQN0385H1521 H_CDR3

<400> SEQUENCE: 158

Asp Ile Gly Ile Asp Tyr Asn Phe
1               5

<210> SEQ ID NO 159
<211> LENGTH: 6
<212> TYPE: PRT
<213> ORGANISM: Artificial Sequence
<220> FEATURE:
<223> OTHER INFORMATION: DQN0385H1353 H_CDR1

<400> SEQUENCE: 159

Glu Trp Tyr Phe Met Ser
1               5

<210> SEQ ID NO 160
<211> LENGTH: 17
<212> TYPE: PRT
<213> ORGANISM: Artificial Sequence
<220> FEATURE:
<223> OTHER INFORMATION: DQN0385H1353 H_CDR2

<400> SEQUENCE: 160

Ser Ile Asp Thr Gly Ser Gly Ser Ile Asp Tyr Ala Glu Trp Val Glu
1               5                   10                  15

Gly

<210> SEQ ID NO 161
<211> LENGTH: 8
<212> TYPE: PRT
<213> ORGANISM: Artificial Sequence
<220> FEATURE:
<223> OTHER INFORMATION: DQN0385H1353 H_CDR3

<400> SEQUENCE: 161

Asp Ile Gly Ile Asp Tyr Asn Phe
1               5

<210> SEQ ID NO 162
<211> LENGTH: 328
<212> TYPE: PRT
<213> ORGANISM: Artificial Sequence
<220> FEATURE:
<223> OTHER INFORMATION: SG1399.A5

<400> SEQUENCE: 162

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Lys Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Arg Arg Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

```
Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Glu Gly Asn
        290                 295                 300

Val Phe Ser Cys Ser Val Leu His Glu Ala Leu His Ala His Tyr Thr
305                 310                 315                 320

Arg Glu Glu Leu Ser Leu Ser Pro
                325

<210> SEQ ID NO 163
<211> LENGTH: 328
<212> TYPE: PRT
<213> ORGANISM: Artificial Sequence
<220> FEATURE:
<223> OTHER INFORMATION: SG1398.A5

<400> SEQUENCE: 163

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Glu Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Glu Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Arg Arg Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Ser Arg Lys Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
            290                 295                 300

Val Phe Ser Cys Ser Val Leu His Glu Ala Leu His Ala His Tyr Thr
305                 310                 315                 320

Arg Lys Glu Leu Ser Leu Ser Pro
                325

<210> SEQ ID NO 164
<211> LENGTH: 6
<212> TYPE: PRT
<213> ORGANISM: Artificial Sequence
<220> FEATURE:
<223> OTHER INFORMATION: DQN0344H1013 H_CDR1

<400> SEQUENCE: 164

Ser Ala Tyr Trp Met Val
1               5

<210> SEQ ID NO 165
<211> LENGTH: 17
<212> TYPE: PRT
<213> ORGANISM: Artificial Sequence
<220> FEATURE:
<223> OTHER INFORMATION: DQN0344H1013 H_CDR2

<400> SEQUENCE: 165

Ala Val Tyr Gly Gly Ser Asp Thr Thr Tyr Tyr Ala Lys Trp Thr Glu
1               5                   10                  15

Gly

<210> SEQ ID NO 166
<211> LENGTH: 13
<212> TYPE: PRT
<213> ORGANISM: Artificial Sequence
<220> FEATURE:
<223> OTHER INFORMATION: DQN0344H1013 H_CDR3

<400> SEQUENCE: 166

Glu Pro Leu Asn Tyr Tyr Tyr Tyr Gly Glu Leu Asn Val
1               5                   10

<210> SEQ ID NO 167
<211> LENGTH: 11
<212> TYPE: PRT
<213> ORGANISM: Artificial Sequence
<220> FEATURE:
<223> OTHER INFORMATION: DQN0344L0620 L_CDR1

<400> SEQUENCE: 167

Gln Ala Thr Glu Asn Ile Tyr Ser Gly Leu Ala
1               5                   10

<210> SEQ ID NO 168
<211> LENGTH: 7
<212> TYPE: PRT
<213> ORGANISM: Artificial Sequence
<220> FEATURE:
<223> OTHER INFORMATION: DQN0344L0620 L_CDR2

<400> SEQUENCE: 168

Tyr Val Ser Thr Leu Ala Tyr
1               5

<210> SEQ ID NO 169
<211> LENGTH: 10

```
<212> TYPE: PRT
<213> ORGANISM: Artificial Sequence
<220> FEATURE:
<223> OTHER INFORMATION: DQN0344L0620 L_CDR3

<400> SEQUENCE: 169

Gln Thr Tyr Glu Asp Val Ser Ala Val Thr
1               5                   10

<210> SEQ ID NO 170
<211> LENGTH: 19
<212> TYPE: PRT
<213> ORGANISM: Artificial Sequence
<220> FEATURE:
<223> OTHER INFORMATION: CAMPATH-1H signal sequence

<400> SEQUENCE: 170

Met Gly Trp Ser Cys Ile Ile Leu Phe Leu Val Ala Thr Ala Thr Gly
1               5                   10                  15

Val His Ser

<210> SEQ ID NO 171
<211> LENGTH: 4
<212> TYPE: PRT
<213> ORGANISM: Artificial Sequence
<220> FEATURE:
<223> OTHER INFORMATION: GGGG linker

<400> SEQUENCE: 171

Gly Gly Gly Gly
1

<210> SEQ ID NO 172
<211> LENGTH: 33
<212> TYPE: PRT
<213> ORGANISM: Artificial Sequence
<220> FEATURE:
<223> OTHER INFORMATION: 33-mer gliadin peptide

<400> SEQUENCE: 172

Leu Gln Leu Gln Pro Phe Pro Gln Pro Glu Leu Pro Tyr Pro Gln Pro
1               5                   10                  15

Glu Leu Pro Tyr Pro Gln Pro Glu Leu Pro Tyr Pro Gln Pro Gln Pro
            20                  25                  30

Phe

<210> SEQ ID NO 173
<211> LENGTH: 5
<212> TYPE: PRT
<213> ORGANISM: Artificial Sequence
<220> FEATURE:
<223> OTHER INFORMATION: GGGGG linker

<400> SEQUENCE: 173

Gly Gly Gly Gly Gly
1               5

<210> SEQ ID NO 174
<211> LENGTH: 8
<212> TYPE: PRT
<213> ORGANISM: Artificial Sequence
<220> FEATURE:
<223> OTHER INFORMATION: 3C protease cleavage linker

<400> SEQUENCE: 174
```

```
Leu Glu Val Leu Phe Gln Gly Pro
1               5

<210> SEQ ID NO 175
<211> LENGTH: 11
<212> TYPE: PRT
<213> ORGANISM: Artificial Sequence
<220> FEATURE:
<223> OTHER INFORMATION: gamma 2 gliadin peptide

<400> SEQUENCE: 175

Ile Ile Gln Pro Glu Gln Pro Ala Gln Leu Pro
1               5                   10

<210> SEQ ID NO 176
<211> LENGTH: 17
<212> TYPE: PRT
<213> ORGANISM: Artificial Sequence
<220> FEATURE:
<223> OTHER INFORMATION: BC Hordein peptide

<400> SEQUENCE: 176

Glu Pro Glu Gln Pro Ile Pro Glu Gln Pro Gln Pro Tyr Pro Gln Gln
1               5                   10                  15

Pro

<210> SEQ ID NO 177
<211> LENGTH: 29
<212> TYPE: PRT
<213> ORGANISM: Artificial Sequence
<220> FEATURE:
<223> OTHER INFORMATION: CLIP peptide

<400> SEQUENCE: 177

Lys Leu Pro Lys Pro Pro Lys Pro Val Ser Lys Met Arg Met Ala Thr
1               5                   10                  15

Pro Leu Leu Met Gln Ala Leu Pro Met Gly Ala Leu Pro
            20                  25

<210> SEQ ID NO 178
<211> LENGTH: 15
<212> TYPE: PRT
<213> ORGANISM: Artificial Sequence
<220> FEATURE:
<223> OTHER INFORMATION: Hepatits B virus peptide

<400> SEQUENCE: 178

Pro Asp Arg Val His Phe Ala Ser Pro Leu His Val Ala Trp Arg
1               5                   10                  15

<210> SEQ ID NO 179
<211> LENGTH: 9
<212> TYPE: PRT
<213> ORGANISM: Artificial Sequence
<220> FEATURE:
<223> OTHER INFORMATION: Salmonella peptide

<400> SEQUENCE: 179

Met Met Ala Trp Arg Met Met Arg Tyr
1               5

<210> SEQ ID NO 180
<211> LENGTH: 16
<212> TYPE: PRT
<213> ORGANISM: Artificial Sequence
<220> FEATURE:
```

<223> OTHER INFORMATION: Thyroperoxidase peptide

<400> SEQUENCE: 180

Tyr Ile Asp Val Trp Leu Gly Gly Leu Ala Glu Asn Phe Leu Pro Tyr
1               5                   10                  15

<210> SEQ ID NO 181
<211> LENGTH: 14
<212> TYPE: PRT
<213> ORGANISM: Artificial Sequence
<220> FEATURE:
<223> OTHER INFORMATION: Mycobacterium bovis peptide

<400> SEQUENCE: 181

Lys Pro Leu Leu Ile Ile Ala Glu Asp Val Glu Gly Glu Tyr
1               5                   10

<210> SEQ ID NO 182
<211> LENGTH: 11
<212> TYPE: PRT
<213> ORGANISM: Artificial Sequence
<220> FEATURE:
<223> OTHER INFORMATION: alpha 1 gliadin peptide

<400> SEQUENCE: 182

Gln Pro Phe Pro Gln Pro Glu Leu Pro Tyr Pro
1 5 10

<210> SEQ ID NO 183
<211> LENGTH: 11
<212> TYPE: PRT
<213> ORGANISM: Artificial Sequence
<220> FEATURE:
<223> OTHER INFORMATION: alpha 2 gliadin peptide

<400> SEQUENCE: 183

Phe Pro Gln Pro Glu Leu Pro Tyr Pro Gln Pro
1 5 10

<210> SEQ ID NO 184
<211> LENGTH: 11
<212> TYPE: PRT
<213> ORGANISM: Artificial Sequence
<220> FEATURE:
<223> OTHER INFORMATION: gamma 1 gliadin peptide

<400> SEQUENCE: 184

Gln Pro Gln Gln Ser Phe Pro Glu Gln Gln Gln
1 5 10

<210> SEQ ID NO 185
<211> LENGTH: 12
<212> TYPE: PRT
<213> ORGANISM: Artificial Sequence
<220> FEATURE:
<223> OTHER INFORMATION: gamma 2 gliadin peptide

<400> SEQUENCE: 185

Gly Ile Ile Gln Pro Glu Gln Pro Ala Gln Leu Pro
1 5 10

<210> SEQ ID NO 186
<211> LENGTH: 11
<212> TYPE: PRT
<213> ORGANISM: Artificial Sequence
<220> FEATURE:
<223> OTHER INFORMATION: omega 1 gliadin peptide

```
<400> SEQUENCE: 186

Gln Pro Phe Pro Gln Pro Glu Gln Pro Phe Pro
1               5                   10

<210> SEQ ID NO 187
<211> LENGTH: 11
<212> TYPE: PRT
<213> ORGANISM: Artificial Sequence
<220> FEATURE:
<223> OTHER INFORMATION: omega 2 gliadin peptide

<400> SEQUENCE: 187

Phe Pro Gln Pro Glu Gln Pro Phe Pro Trp Gln
1               5                   10

<210> SEQ ID NO 188
<211> LENGTH: 16
<212> TYPE: PRT
<213> ORGANISM: Artificial Sequence
<220> FEATURE:
<223> OTHER INFORMATION: BC hordein peptide

<400> SEQUENCE: 188

Pro Gln Gln Pro Ile Pro Glu Gln Pro Gln Pro Tyr Pro Gln Gln Pro
1               5                   10                  15

<210> SEQ ID NO 189
<211> LENGTH: 11
<212> TYPE: PRT
<213> ORGANISM: Artificial Sequence
<220> FEATURE:
<223> OTHER INFORMATION: alpha 3 gliadin peptide

<400> SEQUENCE: 189

Pro Phe Arg Pro Glu Gln Pro Tyr Pro Gln Pro
1               5                   10

<210> SEQ ID NO 190
<211> LENGTH: 11
<212> TYPE: PRT
<213> ORGANISM: Artificial Sequence
<220> FEATURE:
<223> OTHER INFORMATION: alpha 1b gliadin peptide

<400> SEQUENCE: 190

Leu Pro Tyr Pro Gln Pro Glu Leu Pro Tyr Pro
1               5                   10

<210> SEQ ID NO 191
<211> LENGTH: 11
<212> TYPE: PRT
<213> ORGANISM: Artificial Sequence
<220> FEATURE:
<223> OTHER INFORMATION: gamma 4a gliadin peptide

<400> SEQUENCE: 191

Phe Ser Gln Pro Glu Gln Glu Phe Pro Gln Pro
1               5                   10

<210> SEQ ID NO 192
<211> LENGTH: 11
<212> TYPE: PRT
<213> ORGANISM: Artificial Sequence
<220> FEATURE:
<223> OTHER INFORMATION: gamma 4b gliadin peptide
```

```
<400> SEQUENCE: 192

Phe Pro Gln Pro Glu Gln Glu Phe Pro Gln Pro
1               5                   10

<210> SEQ ID NO 193
<211> LENGTH: 11
<212> TYPE: PRT
<213> ORGANISM: Artificial Sequence
<220> FEATURE:
<223> OTHER INFORMATION: avenin 1 peptide

<400> SEQUENCE: 193

Gln Pro Tyr Pro Glu Gln Glu Glu Pro Phe Val
1               5                   10

<210> SEQ ID NO 194
<211> LENGTH: 11
<212> TYPE: PRT
<213> ORGANISM: Artificial Sequence
<220> FEATURE:
<223> OTHER INFORMATION: avenin 2 peptide

<400> SEQUENCE: 194

Gln Pro Tyr Pro Glu Gln Glu Gln Pro Phe Val
1               5                   10

<210> SEQ ID NO 195
<211> LENGTH: 11
<212> TYPE: PRT
<213> ORGANISM: Artificial Sequence
<220> FEATURE:
<223> OTHER INFORMATION: avenin 3 peptide

<400> SEQUENCE: 195

Gln Pro Tyr Pro Glu Gln Glu Gln Pro Ile Leu
1               5                   10

<210> SEQ ID NO 196
<211> LENGTH: 14
<212> TYPE: PRT
<213> ORGANISM: Artificial Sequence
<220> FEATURE:
<223> OTHER INFORMATION: hordein 1 peptide

<400> SEQUENCE: 196

Pro Gln Gln Pro Phe Pro Gln Pro Glu Gln Pro Phe Arg Gln
1               5                   10

<210> SEQ ID NO 197
<211> LENGTH: 14
<212> TYPE: PRT
<213> ORGANISM: Artificial Sequence
<220> FEATURE:
<223> OTHER INFORMATION: hordein 2 peptide

<400> SEQUENCE: 197

Gln Glu Phe Pro Gln Pro Glu Gln Pro Phe Pro Gln Gln Pro
1               5                   10

<210> SEQ ID NO 198
<211> LENGTH: 14
<212> TYPE: PRT
<213> ORGANISM: Artificial Sequence
<220> FEATURE:
<223> OTHER INFORMATION: secalin 1 peptide

<400> SEQUENCE: 198
```

Pro Glu Gln Pro Phe Pro Gln Pro Glu Gln Pro Phe Pro Gln
1               5                   10

<210> SEQ ID NO 199
<211> LENGTH: 14
<212> TYPE: PRT
<213> ORGANISM: Artificial Sequence
<220> FEATURE:
<223> OTHER INFORMATION: secalin 2 peptide

<400> SEQUENCE: 199

Gln Pro Phe Pro Gln Pro Glu Gln Pro Phe Pro Gln Ser Gln
1               5                   10

<210> SEQ ID NO 200
<211> LENGTH: 15
<212> TYPE: PRT
<213> ORGANISM: Artificial Sequence
<220> FEATURE:
<223> OTHER INFORMATION: 14mer 1 gliadin peptide

<400> SEQUENCE: 200

Pro Gln Gln Gln Thr Leu Gln Pro Glu Gln Pro Ala Gln Leu Pro
1               5                   10                  15

<210> SEQ ID NO 201
<211> LENGTH: 33
<212> TYPE: PRT
<213> ORGANISM: Artificial Sequence
<220> FEATURE:
<223> OTHER INFORMATION: 33mer gliadin peptide

<400> SEQUENCE: 201

Leu Gln Leu Gln Pro Phe Pro Gln Pro Glu Leu Pro Tyr Pro Gln Pro
1               5                   10                  15

Glu Leu Pro Tyr Pro Gln Pro Glu Leu Pro Tyr Pro Gln Pro Gln Pro
            20                  25                  30

Phe

<210> SEQ ID NO 202
<211> LENGTH: 26
<212> TYPE: PRT
<213> ORGANISM: Artificial Sequence
<220> FEATURE:
<223> OTHER INFORMATION: 26mer gliadin peptide

<400> SEQUENCE: 202

Phe Leu Gln Pro Glu Gln Pro Phe Pro Glu Gln Pro Glu Gln Pro Tyr
1               5                   10                  15

Pro Glu Gln Pro Glu Gln Pro Phe Pro Gln
            20                  25

<210> SEQ ID NO 203
<211> LENGTH: 22
<212> TYPE: PRT
<213> ORGANISM: Artificial Sequence
<220> FEATURE:
<223> OTHER INFORMATION: P2A

<400> SEQUENCE: 203

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 204
<211> LENGTH: 15
<212> TYPE: PRT
<213> ORGANISM: Artificial Sequence
<220> FEATURE:
<223> OTHER INFORMATION: omega1/2 gliadin peptide

<400> SEQUENCE: 204

Glu Gln Pro Phe Pro Gln Pro Glu Gln Pro Phe Pro Trp Gln Pro
1               5                   10                  15

<210> SEQ ID NO 205
<211> LENGTH: 16
<212> TYPE: PRT
<213> ORGANISM: Artificial Sequence
<220> FEATURE:
<223> OTHER INFORMATION: BC hordein peptide

<400> SEQUENCE: 205

Glu Pro Glu Gln Pro Ile Pro Glu Gln Pro Gln Pro Tyr Pro Gln Gln
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: gamma 1 gliadin peptide

<400> SEQUENCE: 206

Pro Gln Gln Pro Gln Gln Ser Phe Pro Glu Gln Glu Gln Pro Ala
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: gamma 2 gliadin peptide

<400> SEQUENCE: 207

Gly Gln Gly Ile Ile Gln Pro Glu Gln Pro Ala Gln Leu Ile Arg
1               5                   10                  15

<210> SEQ ID NO 208
<211> LENGTH: 23
<212> TYPE: PRT
<213> ORGANISM: Artificial Sequence
<220> FEATURE:
<223> OTHER INFORMATION: gamma 3 gliadin peptide

<400> SEQUENCE: 208

Glu Gln Pro Phe Pro Glu Gln Pro Glu Gln Pro Tyr Pro Glu Gln Pro
1               5                   10                  15

Glu Gln Pro Phe Pro Gln Pro
            20

<210> SEQ ID NO 209
<211> LENGTH: 12
<212> TYPE: PRT
<213> ORGANISM: Artificial Sequence
<220> FEATURE:
<223> OTHER INFORMATION: gamma 4a gliadin peptide

<400> SEQUENCE: 209

```
Phe Ser Gln Pro Glu Gln Glu Phe Pro Gln Pro Gln
1               5                   10

<210> SEQ ID NO 210
<211> LENGTH: 20
<212> TYPE: PRT
<213> ORGANISM: Artificial Sequence
<220> FEATURE:
<223> OTHER INFORMATION: gamma 4d gliadin peptide

<400> SEQUENCE: 210

Trp Pro Gln Gln Gln Pro Phe Pro Gln Pro Glu Gln Pro Phe Cys Glu
1               5                   10                  15

Gln Pro Gln Arg
            20
```

ANTI-HLA-DQ2.5 ANTIBODY AND ITS USE FOR THE TREATMENT OF CELIAC DISEASE

CROSS-REFERENCE TO RELATED APPLICATION

This application claims the benefit of Japanese Application No. 2020-157873, filed Sep. 18, 2020.

SEQUENCE LISTING

This application contains a Sequence Listing that has been submitted electronically as an ASCII text file named SequenceListing.txt. The ASCII text file, updated on Oct. 8, 2021, is 191 kilobytes in size. The material in the ASCII text file is hereby incorporated by reference in its entirety.

TECHNICAL FIELD

The present invention relates to anti-HLA-DQ2.5 antibodies and their use for the treatment of celiac disease.

BACKGROUND ART

Celiac (coeliac) disease is an autoimmune disorder in which the ingestion of gluten causes damage to the small intestine in genetically-sensitive patients (NPL 1 to 5). About 1% of the Western population, i.e., 8 million people in the United States and the European Union are thought to suffer from celiac disease; however, no remarkable therapeutic advances have been achieved since the disease was recognized in 1940s. Human leukocyte antigens (HLAs) belonging to Major Histocompatibility Complex (MHC) class II include HLA-DR, HLA-DP and HLA-DQ molecules such as the HLA-DQ2.5 isoform (hereinafter referred to as "HLA-DQ2.5"), which form heterodimers composed of alpha and beta chains on the cell surface. A majority (>90%) of the celiac disease patients have an HLA-DQ2.5 haplotype allele (NPL 6). The isoform is thought to have stronger affinity towards gluten peptides. As with other isoforms, HLA-DQ2.5 presents processed antigens derived from exogenous sources to a T cell receptor (TCR) on T cells. As a result of digestion of gluten-rich food such as bread in celiac disease patients, immunogenic gluten peptides such as gliadin peptides are formed (NPL 2). The peptides are transported through the small intestine epithelium into lamina propria and deamidated by tissue transglutaminase such as transglutaminase 2 (TG2). The deamidated gliadin peptides are processed by antigen-presenting cells (APCs) which load them on HLA-DQ2.5. The loaded peptides are presented to HLA-DQ2.5-restricted T cells, and activate innate and adaptive immune responses. This causes inflammatory injury of the small intestinal mucosa and symptoms including various types of gastrointestinal disturbance, nutritional deficiencies, and systemic symptoms (NPL8, 9, and 10). It is reported that an anti-HLA DQ neutralizing antibody inhibits gluten peptides dependent activation of T cells from celiac patients. (NPL7) The currently practicable treatment of celiac disease is lifelong adherence to a gluten-free diet (GFD). However, in reality, it is difficult to completely eliminate gluten exposure even with GFD. The tolerable gluten dose for these patients is only about 10 to 50 mg/day (NPL 11). Cross contamination can widely occur in GFD production, and a trace amount of gluten can cause celiac disease symptoms even in patients with good compliance to GFD. In the presence of such a risk of unintentional gluten exposure, there is a need for adjunctive therapy to GFD.

CITATION LIST

Non Patent Literature

[NPL 1] N Engl J Med 2007; 357:1731-1743
[NPL 2] J Biomed Sci. 2012; 19(1): 88
[NPL 3] N Engl J Med 2003; 348:2517-2524
[NPL 4] Gut 2003; 52:960-965
[NPL 5] Dig Dis Sci 2004; 49:1479-1484
[NPL 6] Gastroenterology 2011; 141:610-620
[NPL 7] Gut 2005; 54:1217-1223
[NPL 8] Gastroenterology 2014; 146:1649-58
[NPL 9] Nutrients 2013 Oct. 5(10): 3975-3992
[NPL 10] J Clin Invest. 2007; 117(1):41-49
[NPL 11] Am J Clin Nutr 2007; 85: 160-6

SUMMARY OF INVENTION

Technical Problem

Under the above-mentioned circumstances with the need for adjunctive therapy, the present invention provides anti-HLA-DQ2.5 antigen-binding molecules.

Solution to Problem

The antigen-binding molecules of the present invention have been altered and can bind to two or more complexes formed by HLA-DQ2.5 and a gluten peptide.

More specifically, the present invention provides the following.

[1] A multispecific antigen-binding molecule comprising:
 (i) a first antigen-binding moiety that has binding activity to HLA-DQ2.5 in the form of a complex with a gluten peptide; and
 (ii) a second antigen-binding moiety that has binding activity to HLA-DQ2.5 in the form of a complex with a gluten peptide;
 wherein the antigen-binding molecule binds to two or more complexes of HLA-DQ2.5 and gluten peptides,
 wherein at least one of the gluten peptides in the complexes bound by the first antigen-binding moiety is different from at least one of the gluten peptides in the complexes bound by the second antigen-binding moiety; and
 wherein the antigen-binding molecule has substantially no binding activity to either or both of a HLA-DQ2.5 positive PBMC B cell and a Ba/F3 cell that expresses HLA-DQ2.5,
 wherein the antigen-binding molecule is humanized, and
 wherein one or more amino acids in a heavy chain and/or a light chain of the first antigen-binding moiety and/or second antigen-binding moiety in the multispecific antigen-binding molecule are altered.

[1a] The multispecific antigen-binding molecule of [1], wherein the antigen-binding molecule has substantially no binding activity to a Ba/F3 cell that expresses HLA-DQ2.2.

[1-1] The multispecific antigen-binding molecule of [1] or [1a], wherein one or more amino acids in a heavy chain and/or a light chain of the first antigen-binding moiety and/or second antigen-binding moiety in the multispecific antigen-binding molecule are substituted.

[1-2] The multispecific antigen-binding molecule of [1-1], which comprises at least one amino acid substitution in a variable region of the heavy chain; at least one amino acid substitution in a constant region of the heavy chain; at least one amino acid substitution in a variable region of the light chain; and at least one amino acid substitution in a constant region of the light chain.

[2] The multispecific antigen-binding molecule of any one of [1] to [1-2], wherein the gluten peptide is an immune dominant peptide related to celiac disease.

[3] The multispecific antigen-binding molecule of any one of [1] to [2], wherein the gluten peptide is selected from the group consisting of 33mer gliadin peptide, alpha 1 gliadin peptide, alpha 2 gliadin peptide, gamma 1 gliadin peptide, gamma 2 gliadin peptide, omega 1 gliadin peptide, omega 2 gliadin peptide, BC Hordein peptide, alpha 3 gliadin peptide, alpha 1b gliadin peptide, gamma 4a gliadin peptide, gamma 4b gliadin peptide, avenin 1 peptide, avenin 2 peptide, avenin 3 peptide, hordein 1 peptide, hordein 2 peptide, secalin 1 peptide, secalin 2 peptide, and 26mer gliadin peptide.

[3-1] The multispecific antigen-binding molecule of any one of [1] to [2], wherein the gluten peptide(s) is/are one, two, three, four, five, six, seven, eight, nine, ten, eleven, twelve, 13, 14, 15, 16, 17, 18, 19 or all of: 33mer gliadin peptide, alpha 1 gliadin peptide, alpha 2 gliadin peptide, gamma 1 gliadin peptide, gamma 2 gliadin peptide, omega 1 gliadin peptide, omega 2 gliadin peptide, BC Hordein peptide, alpha 3 gliadin peptide, alpha 1b gliadin peptide, gamma 4a gliadin peptide, gamma 4b gliadin peptide, avenin 1 peptide, avenin 2 peptide, avenin 3 peptide, hordein 1 peptide, hordein 2 peptide, secalin 1 peptide, secalin 2 peptide, and 26mer gliadin peptide.

[3-2] The multispecific antigen-binding molecule of any one of [1] to [2], wherein the gluten peptide is selected from the group consisting of 33mer gliadin peptide, alpha 1 gliadin peptide, alpha 2 gliadin peptide, gamma 1 gliadin peptide, omega 1 gliadin peptide, omega 2 gliadin peptide, BC Hordein peptide, alpha 3 gliadin peptide, alpha 1b gliadin peptide, gamma 4a gliadin peptide, gamma 4b gliadin peptide, avenin 1 peptide, avenin 2 peptide, avenin 3 peptide, hordein 1 peptide, hordein 2 peptide, secalin 1 peptide, secalin 2 peptide, and 26mer gliadin peptide.

[3-3] The multispecific antigen-binding molecule of any one of [1] to [2], wherein the gluten peptide(s) is/are one, two, three, four, five, six, seven, eight, nine, ten, eleven, twelve, 13, 14, 15, 16, 17, 18 or all of: 33mer gliadin peptide, alpha 1 gliadin peptide, alpha 2 gliadin peptide, gamma 1 gliadin peptide, omega 1 gliadin peptide, omega 2 gliadin peptide, BC Hordein peptide, alpha 3 gliadin peptide, alpha 1b gliadin peptide, gamma 4a gliadin peptide, gamma 4b gliadin peptide, avenin 1 peptide, avenin 2 peptide, avenin 3 peptide, hordein 1 peptide, hordein 2 peptide, secalin 1 peptide, secalin 2 peptide, and 26mer gliadin peptide.

[4] The multispecific antigen-binding molecule of any one of [1] to [3-3], which has substantially no binding activity to HLA-DQ2.5 in the form of a complex with an irrelevant peptide, wherein the irrelevant peptide is at least one peptide selected from the group consisting of: CLIP peptide, Hepatitis B virus 1 peptide, *Salmonella* peptide, *Mycobacterium bovis* peptide, and thyroperoxidase peptide.

[4-1] The multispecific antigen-binding molecule of any one of [1] to [3-3], which has substantially no binding activity to HLA-DQ2.5 in the form of complexes with irrelevant peptides, wherein the irrelevant peptides are all of: CLIP peptide, Hepatitis B virus 1 peptide, *Salmonella* peptide, *Mycobacterium bovis* peptide, and thyroperoxidase peptide.

[5] The multispecific antigen-binding molecule of any one of [1] to [4-1], which has substantially no binding activity to HLA-DP, HLA-DR, HLA-DQ5.1, HLA-DQ6.3, HLA-DQ7.3, HLA-DQ7.5, and HLA-DQ8.

[6] The multispecific antigen-binding molecule of any one of [1] to [5], which blocks (i) the interaction between HLA-DQ2.5/gluten peptide complex and HLA-DQ2.5/gluten peptide-restricted CD4+ T cell; and/or (ii) the interaction between HLA-DQ2.2/gluten peptide complex and HLA-DQ2.2/gluten peptide-restricted CD4+ T cell.

[6-2] The multispecific antigen-binding molecule of [6], wherein the gluten peptide is selected from the group consisting of alpha 1 gliadin peptide, alpha 1b gliadin peptide, alpha 2 gliadin peptide, omega 1 gliadin peptide, omega 2 gliadin peptide, gamma 1 gliadin peptide, gamma 2 gliadin peptide, gamma 3 gliadin peptide, gamma 4a gliadin peptide, gamma 4d gliadin peptide, and BC Hordein peptide.

[7] The multispecific antigen-binding molecule of any one of [1] to [6-2], wherein the antigen-binding molecule has enhanced binding activity to the complex formed by HLA-DQ2.5 and the gluten peptide, compared to before said humanization and alteration.

[8] The multispecific antigen-binding molecule of any one of [1] to [7], wherein the antigen-binding molecule has enhanced cross reactivity towards gluten peptides, compared to before said humanization and alteration.

[8-1] The multispecific antigen-binding molecule of [8], wherein the gluten peptides are omega 2 gliadin peptide, BC hordein peptide, gamma 1 gliadin peptide, gamma 2 gliadin peptide, gamma 4a gliadin peptide, and gamma 4d gliadin peptide.

[9] The multispecific antigen-binding molecule of any one of [1] to [8-1], wherein one, two, three or all sets of amino acid residues selected from the group consisting of the sets of amino acid residues shown in (a) to (d) below in the heavy chain and the light chain of the antigen-binding molecule are amino acid residues which electrostatically repel each other:

(a) an amino acid residue in a heavy chain constant region (CH1) which is at position 175 according to EU numbering, and an amino acid residue in a light chain constant region (CL) which is at position 131 according to Kabat numbering, (b) an amino acid residue in CH1 which is at position 175 according to EU numbering, and an amino acid residue in CL which is at position 160 according to Kabat numbering, (c) amino acid residue in CH1 which is at position 175 according to EU numbering, and amino acid residues in CL which are at positions 131 and 160 according to Kabat numbering, (d) amino acid residues in CH1 which are at positions 147 and 175 according to EU numbering, and amino acid residues in CL which are at positions 131 and 160 according to Kabat numbering.

[10] The multispecific antigen-binding molecule of [9], further wherein two or more amino acid residues that form an interface between a heavy chain variable region and a light chain variable region are amino acid residues which electrostatically repel each other.

[11] The multispecific antigen-binding molecule of [10], wherein the amino acid residues which electrostatically repel each other are one or two sets of amino acid residues selected from the group consisting of the sets of amino acid residues of (a) and (b) below:

(a) an amino acid residue in the heavy chain variable region which is at position 39 according to Kabat numbering, and an amino acid residue in the light chain variable region which is at position 38 according to Kabat numbering, (b) an amino acid residue in the heavy chain variable region which is at position 45 according to Kabat numbering, and an amino acid residue in the light chain variable region which is at position 44 according to Kabat numbering.

[12] The multispecific antigen-binding molecule of any one of [9] to [11], wherein the amino acid residues which electrostatically repel each other are selected from the amino acid residues included in either set of (X) or (Y) below:

(X) glutamic acid (E), aspartic acid (D), (Y) lysine (K), arginine (R), histidine (H).

[13] The multispecific antigen-binding molecule of any one of [9] to [12], which further comprises an Fc domain that exhibits reduced binding affinity to human Fc gamma receptor, as compared to a native human IgG1 Fc domain.

[14] The multispecific antigen-binding molecule of [13], wherein the Fc domain comprises Arg at position 235 and Arg at position 236, wherein the amino acid positions are numbered according to EU numbering.

[15] The multispecific antigen-binding molecule of [13] or [14], wherein the Fc domain is composed of a first Fc-region subunit and a second Fc-region subunit that are capable of stable association.

[16] The multispecific antigen-binding molecule of [15], wherein the Fc domain comprises (e1) or (e2) below:

(e1) the first Fc-region subunit comprising Cys at position 349, Ser at position 366, Ala at position 368 and Val at position 407, and the second Fc-region comprising Cys at position 354 and Trp at position 366;

(e2) the first Fc-region subunit comprising Glu at position 439, and the second Fc-region comprising Lys at position 356, wherein the amino acid positions are numbered according to EU numbering.

[17] The multispecific antigen-binding molecule of any one of [13] to [16], wherein the Fc domain further exhibits stronger FcRn binding affinity to human FcRn, as compared to a native human IgG1 Fc domain.

[18] The multispecific antigen-binding molecule of [16], wherein the first and/or second Fc-region subunit comprises Leu at position 428, Ala at position 434, Arg at position 438, and Glu at position 440, wherein the amino acid positions are numbered according to EU numbering.

[19] The multispecific antigen-binding molecule of any one of [1] to [8], wherein the multispecific antigen-binding molecule comprises one or more of the amino acid residues of (i) to (xii) below:

(i) glutamic acid or lysine at position 175 (EU numbering) in the heavy-chain constant region;

(ii) glutamic acid at position 147 (EU numbering) in the heavy-chain constant region;

(iii) glutamic acid or lysine at position 131 (Kabat numbering) in the light-chain constant region;

(iv) glutamic acid or lysine at position 160 (Kabat numbering) in the light-chain constant region;

(v) arginine at position 235 (EU numbering) in the heavy-chain constant region;

(vi) arginine at position 236 (EU numbering) in the heavy-chain constant region;

(vii) lysine at position 356 (EU numbering) in the heavy-chain constant region;

(viii) leucine at position 428 (EU numbering) in the heavy-chain constant region;

(ix) alanine at position 434 (EU numbering) in the heavy-chain constant region;

(x) arginine at position 438 (EU numbering) in the heavy-chain constant region;

(xi) glutamic acid at position 439 (EU numbering) in the heavy-chain constant region;

(xii) glutamic acid at position 440 (EU numbering) in the heavy-chain constant region.

[19-1] The multispecific antigen-binding molecule of [19], which is a bispecific antibody comprising:

a first heavy chain comprising lysine at position 175 (EU numbering), arginine at position 235 (EU numbering), arginine at position 236 (EU numbering), leucine at position 428 (EU numbering), alanine at position 434 (EU numbering), arginine at position 438 (EU numbering), glutamic acid at position 439 (EU numbering), and glutamic acid at position 440 (EU numbering);

a first light chain comprising glutamic acid at position 131 (Kabat numbering) and glutamic acid at position 160 (Kabat numbering);

a second heavy chain comprising glutamic acid at position 147 (EU numbering), glutamic acid at position 175 (EU numbering), arginine at position 235 (EU numbering), arginine at position 236 (EU numbering), lysine at position 356 (EU numbering), leucine at position 428 (EU numbering), alanine at position 434 (EU numbering), arginine at position 438 (EU numbering), and glutamic acid at position 440 (EU numbering); and a second light chain comprising lysine at position 131 (Kabat numbering) and lysine at position 160 (Kabat numbering).

[19-2] The multispecific antigen-binding molecule of [19-1], wherein:

the first heavy chain further comprises glutamic acid at position 419 (EU numbering), and proline at position 445 (EU numbering), and an amino acid deletion at positions 446 and 447 (EU numbering); and the second heavy chain further comprises lysine at position 196 (EU numbering), proline at position 445 (EU numbering), and an amino acid deletion at positions 446 and 447 (EU numbering).

[19-3] The multispecific antigen-binding molecule of [19-1] or [19-2], wherein:

the first heavy chain further comprises glycine at position 16 (Kabat numbering), alanine at position 32 (Kabat numbering), lysine at position 61 (Kabat numbering), valine at position 35a (Kabat numbering), alanine at position 50 (Kabat numbering), glutamic acid at position 64 (Kabat numbering), threonine at position 73 (Kabat numbering), glutamic acid at position 95 (Kabat numbering), and valine at position 102 (Kabat numbering);

the first light chain further comprises glutamic acid at position 28 (Kabat numbering), tyrosine at position 55 (Kabat numbering), glutamic acid or tyrosine at position 56 (Kabat numbering), glutamic acid at position 92 (Kabat numbering), valine at position 94 (Kabat numbering), and alanine at position 95a (Kabat numbering);

the second heavy chain further comprises glutamic acid at position 28 (Kabat numbering), alanine or glutamic acid at position 30 (Kabat numbering), glutamic acid at position 31 (Kabat numbering), tryptophan at position 32 (Kabat numbering), phenylalanine at position 34 (Kabat numbering), methionine at position 35 (Kabat numbering), serine at position 35a (Kabat numbering), serine at position 50 (Kabat numbering), glutamic acid or glycine at position 61 (Kabat numbering), glutamic acid at position 64 (Kabat numbering), and glutamic acid at position 65 (Kabat numbering); and the second light chain further comprises threonine at position 25 (Kabat numbering), lysine at position 54 (Kabat numbering), glutamic acid at position 56 (Kabat numbering), leucine at position 67 (Kabat numbering), glutamine at position 79 (Kabat numbering), and lysine at position 94 (Kabat numbering).

[19a] The multispecific antigen-binding molecule of any one of [1] to [19-3], wherein the multispecific antigen-binding molecule has substantially no binding activity to the gluten peptide itself.

[20] A multispecific antigen-binding molecule comprising a first antigen-binding moiety and a second antigen-binding moiety;

wherein the first antigen-binding moiety comprises any one of (a1) to (a3) below:

(a1) a first antibody variable region comprising the complementarity determining region (CDR) 1 of SEQ ID NO: 129, the CDR 2 of SEQ ID NO: 130, the CDR 3 of SEQ ID NO: 131, and a second antibody variable region comprising the CDR 1 of SEQ ID NO: 132, the CDR 2 of SEQ ID NO: 133, the CDR 3 of SEQ ID NO: 134;

(a2) a first antibody variable region comprising the complementarity determining region (CDR) 1 of SEQ ID NO: 164, the CDR 2 of SEQ ID NO: 165, the CDR 3 of SEQ ID NO: 166, and a second antibody variable region comprising the CDR 1 of SEQ ID NO: 167, the CDR 2 of SEQ ID NO: 168, the CDR 3 of SEQ ID NO: 169; and (a3) a first amino acid sequence that has at least 70%, 75%, 80%, 85%, 90%, or 95% sequence identity to the first antibody variable region recited in (a1) or (a2), and a second amino acid sequence that has at least 70%, 75% 80%, 85%, 90%, or 95% sequence identity to the second antibody variable region recited in (a1) or (a2).

[21] The multispecific antigen-binding molecule of [20], wherein the second antigen-binding moiety comprises any one of (b1) to (b8) below:

(b1) a third antibody variable region comprising the complementarity determining region (CDR) 1 of SEQ ID NO: 135, the CDR 2 of SEQ ID NO: 136, the CDR 3 of SEQ ID NO: 137 and a fourth antibody variable region comprising the CDR 1 of SEQ ID NO: 138, the CDR 2 of SEQ ID NO: 139, the CDR 3 of SEQ ID NO: 140;

(b2) a third antibody variable region comprising the complementarity determining region (CDR) 1 of SEQ ID NO: 135, the CDR 2 of SEQ ID NO: 136, the CDR 3 of SEQ ID NO: 137, and a fourth antibody variable region comprising the CDR 1 of SEQ ID NO: 141, the CDR 2 of SEQ ID NO: 142, the CDR 3 of SEQ ID NO: 143;

(b3) a third antibody variable region comprising the complementarity determining region (CDR) 1 of SEQ ID NO: 144, the CDR 2 of SEQ ID NO: 145, the CDR 3 of SEQ ID NO: 146, and a fourth antibody variable region comprising the CDR 1 of SEQ ID NO: 141, the CDR 2 of SEQ ID NO: 142, the CDR 3 of SEQ ID NO: 143;

(b4) a third antibody variable region comprising the complementarity determining region (CDR) 1 of SEQ ID NO: 147, the CDR 2 of SEQ ID NO: 148, the CDR 3 of SEQ ID NO: 149, and a fourth antibody variable region comprising the CDR 1 of SEQ ID NO: 150, the CDR 2 of SEQ ID NO: 151, the CDR 3 of SEQ ID NO: 152;

(b5) a third antibody variable region comprising the complementarity determining region (CDR) 1 of SEQ ID NO: 153, the CDR 2 of SEQ ID NO: 154, the CDR 3 of SEQ ID NO: 155, and a fourth antibody variable region comprising the CDR 1 of SEQ ID NO: 150, the CDR 2 of SEQ ID NO: 151, the CDR 3 of SEQ ID NO: 152;

(b6) a third antibody variable region comprising the complementarity determining region (CDR) 1 of SEQ ID NO: 156, the CDR 2 of SEQ ID NO: 157, the CDR 3 of SEQ ID NO: 158, and a fourth antibody variable region comprising the CDR 1 of SEQ ID NO: 150, the CDR 2 of SEQ ID NO: 151, the CDR 3 of SEQ ID NO: 152;

(b7) a third antibody variable region comprising the complementarity determining region (CDR) 1 of SEQ ID NO: 159, the CDR 2 of SEQ ID NO: 160, the CDR 3 of SEQ ID NO: 161, and a fourth antibody variable region comprising the CDR 1 of SEQ ID NO: 141, the CDR 2 of SEQ ID NO: 142, the CDR 3 of SEQ ID NO: 143; and (b8) a third amino acid sequence that has at least 70%, 75%, 80%, 85%, 90%, or 95% sequence identity to the third antibody variable region recited in any one of (b1) to (b7), and a fourth amino acid sequence that has at least 70%, 75%, 80%, 85%, 90%, or 95% sequence identity to the fourth antibody variable region recited in any one of (b1) to (b7).

[21-2] A multispecific antigen-binding molecule comprising a first antigen-binding moiety and a second antigen-binding moiety, wherein the second antigen-binding moiety comprises any one of (b1) to (b8) below:

(b1) a first antibody variable region comprising the complementarity determining region (CDR) 1 of SEQ ID NO: 135, the CDR 2 of SEQ ID NO: 136, the CDR 3 of SEQ ID NO: 137 and a second antibody variable region comprising the CDR 1 of SEQ ID NO: 138, the CDR 2 of SEQ ID NO: 139, the CDR 3 of SEQ ID NO: 140;

(b2) a first antibody variable region comprising the complementarity determining region (CDR) 1 of SEQ ID NO: 135, the CDR 2 of SEQ ID NO: 136, the CDR 3 of SEQ ID NO: 137, and a second antibody variable region comprising the CDR 1 of SEQ ID NO: 141, the CDR 2 of SEQ ID NO: 142, the CDR 3 of SEQ ID NO: 143;

(b3) a first antibody variable region comprising the complementarity determining region (CDR) 1 of SEQ ID NO: 144, the CDR 2 of SEQ ID NO: 145, the CDR 3 of SEQ ID NO: 146, and a second antibody variable region comprising the CDR 1 of SEQ ID NO: 141, the CDR 2 of SEQ ID NO: 142, the CDR 3 of SEQ ID NO: 143;

(b4) a first antibody variable region comprising the complementarity determining region (CDR) 1 of SEQ ID NO: 147, the CDR 2 of SEQ ID NO: 148, the CDR 3 of SEQ ID NO: 149, and a second antibody variable region comprising the CDR 1 of SEQ ID NO: 150, the CDR 2 of SEQ ID NO: 151, the CDR 3 of SEQ ID NO: 152;

(b5) a first antibody variable region comprising the complementarity determining region (CDR) 1 of SEQ ID NO: 153, the CDR 2 of SEQ ID NO: 154, the CDR 3 of SEQ ID NO: 155, and a second antibody variable region comprising the CDR 1 of SEQ ID NO: 150, the CDR 2 of SEQ ID NO: 151, the CDR 3 of SEQ ID NO: 152;

(b6) a first antibody variable region comprising the complementarity determining region (CDR) 1 of SEQ ID NO: 156, the CDR 2 of SEQ ID NO: 157, the CDR 3 of SEQ ID NO: 158, and a second antibody variable region comprising the CDR 1 of SEQ ID NO: 150, the CDR 2 of SEQ ID NO: 151, the CDR 3 of SEQ ID NO: 152;

(b7) a first antibody variable region comprising the complementarity determining region (CDR) 1 of SEQ ID NO: 159, the CDR 2 of SEQ ID NO: 160, the CDR 3 of SEQ ID NO: 161, and a second antibody variable region comprising the CDR 1 of SEQ ID NO: 141, the CDR 2 of SEQ ID NO: 142, the CDR 3 of SEQ ID NO: 143; and (b8) a first amino acid sequence that has at least 70%, 75%, 80%, 85%, 90%, or 95% sequence identity to the first antibody variable region recited in any one of (b1) to (b7), and a second amino acid sequence that has at least 70%, 75%, 80%, 85%, 90%, or 95% sequence identity to the second antibody variable region recited in any one of (b1) to (b7).

[22] A multispecific antigen-binding molecule comprising a first antigen-binding moiety and a second antigen-binding moiety;

wherein the first antigen-binding moiety comprises any one of (c1) to (c3) below:

(c1) a first antibody variable region comprising the complementarity determining region (CDR) 1 of SEQ ID NO: 129, the CDR 2 of SEQ ID NO: 130, the CDR 3 of SEQ ID NO: 131, and a second antibody variable region comprising the CDR 1 of SEQ ID NO: 132, the CDR 2 of SEQ ID NO: 133, the CDR 3 of SEQ ID NO: 134;

(c2) a first antibody variable region comprising the complementarity determining region (CDR) 1 of SEQ ID NO: 164, the CDR 2 of SEQ ID NO: 165, the CDR 3 of SEQ ID NO: 166, and a second antibody variable region comprising the CDR 1 of SEQ ID NO: 167, the CDR 2 of SEQ ID NO: 168, the CDR 3 of SEQ ID NO: 169; and (c3) a first amino acid sequence that has at least 70%, 75%, 80%, 85%, 90%, or 95% sequence identity to the first antibody variable region recited in (c1) or (c2), and a second amino acid sequence that has at least 70%, 75%, 80%, 85%, 90%, or 95% sequence identity to the second antibody variable region recited in (c1) or (c2), wherein the second antigen-binding moiety comprises any one of (d1) to (d8) below:

(d1) a third antibody variable region comprising the complementarity determining region (CDR) 1 of SEQ ID NO: 135, the CDR 2 of SEQ ID NO: 136, the CDR 3 of SEQ ID NO: 137 and a fourth antibody variable region comprising the CDR 1 of SEQ ID NO: 138, the CDR 2 of SEQ ID NO: 139, the CDR 3 of SEQ ID NO: 140;

(d2) a third antibody variable region comprising the complementarity determining region (CDR) 1 of SEQ ID NO: 135, the CDR 2 of SEQ ID NO: 136, the CDR 3 of SEQ ID NO: 137, and a fourth antibody variable region comprising the CDR 1 of SEQ ID NO: 141, the CDR 2 of SEQ ID NO: 142, the CDR 3 of SEQ ID NO: 143;

(d3) a third antibody variable region comprising the complementarity determining region (CDR) 1 of SEQ ID NO: 144, the CDR 2 of SEQ ID NO: 145, the CDR 3 of SEQ ID NO: 146, and a fourth antibody variable region comprising the CDR 1 of SEQ ID NO: 141, the CDR 2 of SEQ ID NO: 142, the CDR 3 of SEQ ID NO: 143;

(d4) a third antibody variable region comprising the complementarity determining region (CDR) 1 of SEQ ID NO: 147, the CDR 2 of SEQ ID NO: 148, the CDR 3 of SEQ ID NO: 149, and a fourth antibody variable region comprising the CDR 1 of SEQ ID NO: 150, the CDR 2 of SEQ ID NO: 151, the CDR 3 of SEQ ID NO: 152;

(d5) a third antibody variable region comprising the complementarity determining region (CDR) 1 of SEQ ID NO: 153, the CDR 2 of SEQ ID NO: 154, the CDR 3 of SEQ ID NO: 155, and a fourth antibody variable region comprising the CDR 1 of SEQ ID NO: 150, the CDR 2 of SEQ ID NO: 151, the CDR 3 of SEQ ID NO: 152;

(d6) a third antibody variable region comprising the complementarity determining region (CDR) 1 of SEQ ID NO: 156, the CDR 2 of SEQ ID NO: 157, the CDR 3 of SEQ ID NO: 158, and a fourth antibody variable region comprising the CDR 1 of SEQ ID NO: 150, the CDR 2 of SEQ ID NO: 151, the CDR 3 of SEQ ID NO: 152;

(d7) a third antibody variable region comprising the complementarity determining region (CDR) 1 of SEQ ID NO: 159, the CDR 2 of SEQ ID NO: 160, the CDR 3 of SEQ ID NO: 161, and a fourth antibody variable region comprising the CDR 1 of SEQ ID NO: 141, the CDR 2 of SEQ ID NO: 142, the CDR 3 of SEQ ID NO: 143; and (d8) a third amino acid sequence that has at least 70%, 75%, 80%, 85%, 90%, or 95% sequence identity to the third antibody variable region recited in any one of (d1) to (d7), and a fourth amino acid sequence that has at least 70%, 75%, 80%, 85%, 90%, or 95% sequence identity to the fourth antibody variable region recited in any one of (d1) to (d7).

[22-2] A multispecific antigen-binding that comprises a first antigen-binding moiety comprising first and second antibody variable regions and a second antigen-binding moiety comprising third and fourth antibody variable regions, wherein the multispecific antigen-binding molecule comprises any one of (1) to (15) below:

(1) a first antibody variable region comprising the complementarity determining region (CDR) 1 of SEQ ID NO: 129, the CDR 2 of SEQ ID NO: 130, the CDR 3 of SEQ ID NO: 131; a second antibody variable region comprising the CDR 1 of SEQ ID NO: 132, the CDR 2 of SEQ ID NO: 133, the CDR 3 of SEQ ID NO: 134; a third antibody variable region comprising the complementarity determining region (CDR) 1 of SEQ ID NO: 135, the CDR 2 of SEQ ID NO: 136, the CDR 3 of SEQ ID NO: 137; and a fourth antibody variable region comprising the CDR 1 of SEQ ID NO: 138, the CDR 2 of SEQ ID NO: 139, the CDR 3 of SEQ ID NO: 140;

(2) a first antibody variable region comprising the complementarity determining region (CDR) 1 of SEQ ID NO: 129, the CDR 2 of SEQ ID NO: 130, the CDR 3 of SEQ ID NO: 131; a second antibody variable region comprising the CDR 1 of SEQ ID NO: 132, the CDR 2 of SEQ ID NO: 133, the CDR 3 of SEQ ID NO:

134; a third antibody variable region comprising the complementarity determining region (CDR) 1 of SEQ ID NO: 135, the CDR 2 of SEQ ID NO: 136, the CDR 3 of SEQ ID NO: 137; and a fourth antibody variable region comprising the CDR 1 of SEQ ID NO: 141, the CDR 2 of SEQ ID NO: 142, the CDR 3 of SEQ ID NO: 143;

(3) a first antibody variable region comprising the complementarity determining region (CDR) 1 of SEQ ID NO: 129, the CDR 2 of SEQ ID NO: 130, the CDR 3 of SEQ ID NO: 131; a second antibody variable region comprising the CDR 1 of SEQ ID NO: 132, the CDR 2 of SEQ ID NO: 133, the CDR 3 of SEQ ID NO: 134; a third antibody variable region comprising the complementarity determining region (CDR) 1 of SEQ ID NO: 144, the CDR 2 of SEQ ID NO: 145, the CDR 3 of SEQ ID NO: 146; and a fourth antibody variable region comprising the CDR 1 of SEQ ID NO: 141, the CDR 2 of SEQ ID NO: 142, the CDR 3 of SEQ ID NO: 143;

(4) a first antibody variable region comprising the complementarity determining region (CDR) 1 of SEQ ID NO: 129, the CDR 2 of SEQ ID NO: 130, the CDR 3 of SEQ ID NO: 131; a second antibody variable region comprising the CDR 1 of SEQ ID NO: 132, the CDR 2 of SEQ ID NO: 133, the CDR 3 of SEQ ID NO: 134; a third antibody variable region comprising the complementarity determining region (CDR) 1 of SEQ ID NO: 147, the CDR 2 of SEQ ID NO: 148, the CDR 3 of SEQ ID NO: 149; and a fourth antibody variable region comprising the CDR 1 of SEQ ID NO: 150, the CDR 2 of SEQ ID NO: 151, the CDR 3 of SEQ ID NO: 152;

(5) a first antibody variable region comprising the complementarity determining region (CDR) 1 of SEQ ID NO: 129, the CDR 2 of SEQ ID NO: 130, the CDR 3 of SEQ ID NO: 131; a second antibody variable region comprising the CDR 1 of SEQ ID NO: 132, the CDR 2 of SEQ ID NO: 133, the CDR 3 of SEQ ID NO: 134; a third antibody variable region comprising the complementarity determining region (CDR) 1 of SEQ ID NO: 153, the CDR 2 of SEQ ID NO: 154, the CDR 3 of SEQ ID NO: 155; and a fourth antibody variable region comprising the CDR 1 of SEQ ID NO: 150, the CDR 2 of SEQ ID NO: 151, the CDR 3 of SEQ ID NO: 152;

(6) a first antibody variable region comprising the complementarity determining region (CDR) 1 of SEQ ID NO: 129, the CDR 2 of SEQ ID NO: 130, the CDR 3 of SEQ ID NO: 131; a second antibody variable region comprising the CDR 1 of SEQ ID NO: 132, the CDR 2 of SEQ ID NO: 133, the CDR 3 of SEQ ID NO: 134; a third antibody variable region comprising the complementarity determining region (CDR) 1 of SEQ ID NO: 156, the CDR 2 of SEQ ID NO: 157, the CDR 3 of SEQ ID NO: 158; and a fourth antibody variable region comprising the CDR 1 of SEQ ID NO: 150, the CDR 2 of SEQ ID NO: 151, the CDR 3 of SEQ ID NO: 152;

(7) a first antibody variable region comprising the complementarity determining region (CDR) 1 of SEQ ID NO: 129, the CDR 2 of SEQ ID NO: 130, the CDR 3 of SEQ ID NO: 131; a second antibody variable region comprising the CDR 1 of SEQ ID NO: 132, the CDR 2 of SEQ ID NO: 133, the CDR 3 of SEQ ID NO: 134; a third antibody variable region comprising the complementarity determining region (CDR) 1 of SEQ ID NO: 159, the CDR 2 of SEQ ID NO: 160, the CDR 3 of SEQ ID NO: 161; and a fourth antibody variable region comprising the CDR 1 of SEQ ID NO: 141, the CDR 2 of SEQ ID NO: 142, the CDR 3 of SEQ ID NO: 143; and (8) a first antibody variable region comprising the complementarity determining region (CDR) 1 of SEQ ID NO: 164, the CDR 2 of SEQ ID NO: 165, the CDR 3 of SEQ ID NO: 166; a second antibody variable region comprising the CDR 1 of SEQ ID NO: 167, the CDR 2 of SEQ ID NO: 168, the CDR 3 of SEQ ID NO: 169; a third antibody variable region comprising the complementarity determining region (CDR) 1 of SEQ ID NO: 135, the CDR 2 of SEQ ID NO: 136, the CDR 3 of SEQ ID NO: 137; and a fourth antibody variable region comprising the CDR 1 of SEQ ID NO: 138, the CDR 2 of SEQ ID NO: 139, the CDR 3 of SEQ ID NO: 140;

(9) a first antibody variable region comprising the complementarity determining region (CDR) 1 of SEQ ID NO: 164, the CDR 2 of SEQ ID NO: 165, the CDR 3 of SEQ ID NO: 166; a second antibody variable region comprising the CDR 1 of SEQ ID NO: 167, the CDR 2 of SEQ ID NO: 168, the CDR 3 of SEQ ID NO: 169; a third antibody variable region comprising the complementarity determining region (CDR) 1 of SEQ ID NO: 135, the CDR 2 of SEQ ID NO: 136, the CDR 3 of SEQ ID NO: 137; and a fourth antibody variable region comprising the CDR 1 of SEQ ID NO: 141, the CDR 2 of SEQ ID NO: 142, the CDR 3 of SEQ ID NO: 143;

(10) a first antibody variable region comprising the complementarity determining region (CDR) 1 of SEQ ID NO: 164, the CDR 2 of SEQ ID NO: 165, the CDR 3 of SEQ ID NO: 166; a second antibody variable region comprising the CDR 1 of SEQ ID NO: 167, the CDR 2 of SEQ ID NO: 168, the CDR 3 of SEQ ID NO: 169; a third antibody variable region comprising the complementarity determining region (CDR) 1 of SEQ ID NO: 144, the CDR 2 of SEQ ID NO: 145, the CDR 3 of SEQ ID NO: 146; and a fourth antibody variable region comprising the CDR 1 of SEQ ID NO: 141, the CDR 2 of SEQ ID NO: 142, the CDR 3 of SEQ ID NO: 143;

(11) a first antibody variable region comprising the complementarity determining region (CDR) 1 of SEQ ID NO: 164, the CDR 2 of SEQ ID NO: 165, the CDR 3 of SEQ ID NO: 166; a second antibody variable region comprising the CDR 1 of SEQ ID NO: 167, the CDR 2 of SEQ ID NO: 168, the CDR 3 of SEQ ID NO: 169; a third antibody variable region comprising the complementarity determining region (CDR) 1 of SEQ ID NO: 147, the CDR 2 of SEQ ID NO: 148, the CDR 3 of SEQ ID NO: 149; and a fourth antibody variable region comprising the CDR 1 of SEQ ID NO: 150, the CDR 2 of SEQ ID NO: 151, the CDR 3 of SEQ ID NO: 152;

(12) a first antibody variable region comprising the complementarity determining region (CDR) 1 of SEQ ID NO: 164, the CDR 2 of SEQ ID NO: 165, the CDR 3 of SEQ ID NO: 166; a second antibody variable region comprising the CDR 1 of SEQ ID NO: 167, the CDR 2 of SEQ ID NO: 168, the CDR 3 of SEQ ID NO: 169; a third antibody variable region comprising the complementarity determining region (CDR) 1 of SEQ ID NO: 153, the CDR 2 of SEQ ID NO: 154, the CDR 3 of SEQ ID NO: 155; and a fourth antibody variable region comprising the CDR 1 of SEQ ID NO: 150, the CDR 2 of SEQ ID NO: 151, the CDR 3 of SEQ ID NO: 152;

(13) a first antibody variable region comprising the complementarity determining region (CDR) 1 of SEQ ID NO: 164, the CDR 2 of SEQ ID NO: 165, the CDR 3 of SEQ ID NO: 166; a second antibody variable region comprising the CDR 1 of SEQ ID NO: 167, the CDR 2 of SEQ ID NO: 168, the CDR 3 of SEQ ID NO: 169; a third antibody variable region comprising the complementarity determining region (CDR) 1 of SEQ ID NO: 156, the CDR 2 of SEQ ID NO: 157, the CDR 3 of SEQ ID NO: 158; and a fourth antibody variable region comprising the CDR 1 of SEQ ID NO: 150, the CDR 2 of SEQ ID NO: 151, the CDR 3 of SEQ ID NO: 152;

(14) a first antibody variable region comprising the complementarity determining region (CDR) 1 of SEQ ID NO: 164, the CDR 2 of SEQ ID NO: 165, the CDR 3 of SEQ ID NO: 166; a second antibody variable region comprising the CDR 1 of SEQ ID NO: 167, the CDR 2 of SEQ ID NO: 168, the CDR 3 of SEQ ID NO: 169; a third antibody variable region comprising the complementarity determining region (CDR) 1 of SEQ ID NO: 159, the CDR 2 of SEQ ID NO: 160, the CDR 3 of SEQ ID NO: 161; and a fourth antibody variable region comprising the CDR 1 of SEQ ID NO: 141, the CDR 2 of SEQ ID NO: 142, the CDR 3 of SEQ ID NO: 143; and

(15) a first amino acid sequence that has at least 70%, 75%, 80%, 85%, 90%, or 95% sequence identity to the first antibody variable region recited in any one of (1) to (14); a second amino acid sequence that has at least 70%, 75%, 80%, 85%, 90%, or 95% sequence identity to the second antibody variable region recited in any one of (1) to (14); a third amino acid sequence that has at least 70%, 75%, 80%, 85%, 90%, or 95% sequence identity to the third antibody variable region recited in any one of (1) to (14); and a fourth amino acid sequence that has at least 70%, 75%, 80%, 85%, 90%, or 95% sequence identity to the fourth antibody variable region recited in any one of (1) to (14).

[23] The multispecific antigen-binding molecule of any one of [20] to [22-2], wherein the antibody variable region comprised in the first and/or second antigen-binding moiety comprises human antibody frameworks or humanized antibody frameworks.

[24] A multispecific antigen-binding molecule comprising a first antigen-binding moiety and a second antigen-binding moiety;
wherein the first antigen-binding moiety comprises any one of (e1) to (e3) below:
(e1) a first antibody variable region comprising the amino acid sequence of SEQ ID NO: 88, and a second antibody variable region comprising the amino acid sequence of SEQ ID NO: 90;
(e2) a first antibody variable region comprising the amino acid sequence of SEQ ID NO: 89, and a second antibody variable region comprising the amino acid sequence of SEQ ID NO: 91; and
(e3) a first amino acid sequence that has at least 70%, 75%, 80%, 85%, 90%, or 95% sequence identity to the first antibody variable region recited in (e1) or (e2), and a second amino acid sequence that has at least 70%, 75%, 80%, 85%, 90%, or 95% sequence identity to the second antibody variable region recited in (e1) or (e2).

[25] The multispecific antigen-binding molecule of [24], wherein the second antigen-binding moiety comprises any one of (f1) to (f8) below:
(f1) a third antibody variable region comprising the amino acid sequence of SEQ ID NO: 92, and a fourth antibody variable region comprising the amino acid sequence of SEQ ID NO: 98;
(f2) a third antibody variable region comprising the amino acid sequence of SEQ ID NO: 92, and a fourth antibody variable region comprising the amino acid sequence of SEQ ID NO: 99;
(f3) a third antibody variable region comprising the amino acid sequence of SEQ ID NO: 93, and a fourth antibody variable region comprising the amino acid sequence of SEQ ID NO: 99;
(f4) a third antibody variable region comprising the amino acid sequence of SEQ ID NO: 94, and a fourth antibody variable region comprising the amino acid sequence of SEQ ID NO: 100;
(f5) a third antibody variable region comprising the amino acid sequence of SEQ ID NO: 95, and a fourth antibody variable region comprising the amino acid sequence of SEQ ID NO: 100;
(f6) a third antibody variable region comprising the amino acid sequence of SEQ ID NO: 96, and a fourth antibody variable region comprising the amino acid sequence of SEQ ID NO: 100;
(f7) a third antibody variable region comprising the amino acid sequence of SEQ ID NO: 97, and a fourth antibody variable region comprising the amino acid sequence of SEQ ID NO: 99; and
(f8) a third amino acid sequence that has at least 70%, 75%, 80%, 85%, 90%, or 95% sequence identity to the third antibody variable region recited in any one of (f1) to (f7), and a fourth amino acid sequence that has at least 70%, 75%, 80%, 85%, 90%, or 95% sequence identity to the fourth antibody variable region recited in any one of (f1) to (f7).

[26] A multispecific antigen-binding molecule comprising a first antigen-binding moiety and a second antigen-binding moiety;
wherein the first antigen-binding moiety comprises any one of (e1) to (e3) below:
(e1) a first antibody variable region comprising the amino acid sequence of SEQ ID NO: 88, and a second antibody variable region comprising the amino acid sequence of SEQ ID NO: 90;
(e2) a first antibody variable region comprising the amino acid sequence of SEQ ID NO: 89, and a second antibody variable region comprising the amino acid sequence of SEQ ID NO: 91; and
(e3) a first amino acid sequence that has at least 70%, 75%, 80%, 85%, 90%, or 95% sequence identity to the first antibody variable region recited in (e1) or (e2), and a second amino acid sequence that has at least 70%, 75%, 80%, 85%, 90%, or 95% sequence identity to the second antibody variable region recited in (e1) or (e2), and
wherein the second antigen-binding moiety comprises any one of (f1) to (f8) below:
(f1) a third antibody variable region comprising the amino acid sequence of SEQ ID NO: 92, and a fourth antibody variable region comprising the amino acid sequence of SEQ ID NO: 98;

(f2) a third antibody variable region comprising the amino acid sequence of SEQ ID NO: 92, and a fourth antibody variable region comprising the amino acid sequence of SEQ ID NO: 99;
(f3) a third antibody variable region comprising the amino acid sequence of SEQ ID NO: 93, and a fourth antibody variable region comprising the amino acid sequence of SEQ ID NO: 99;
(f4) a third antibody variable region comprising the amino acid sequence of SEQ ID NO: 94, and a fourth antibody variable region comprising the amino acid sequence of SEQ ID NO: 100;
(f5) a third antibody variable region comprising the amino acid sequence of SEQ ID NO: 95, and a fourth antibody variable region comprising the amino acid sequence of SEQ ID NO: 100;
(f6) a third antibody variable region comprising the amino acid sequence of SEQ ID NO: 96, and a fourth antibody variable region comprising the amino acid sequence of SEQ ID NO: 100;
(f7) a third antibody variable region comprising the amino acid sequence of SEQ ID NO: 97, and a fourth antibody variable region comprising the amino acid sequence of SEQ ID NO: 99; and
(f8) a third amino acid sequence that has at least 70%, 75%, 80%, 85%, 90%, or 95% sequence identity to the third antibody variable region recited in any one of (f1) to (f7), and a fourth amino acid sequence that has at least 70%, 75%, 80%, 85%, 90%, or 95% sequence identity to the fourth antibody variable region recited in any one of (f1) to (f7).

[26-2] A multispecific antigen-binding molecule that comprises a first antigen-binding moiety comprising first and second antibody variable regions and a second antigen-binding moiety comprising third and fourth antibody variable regions, wherein the multispecific antigen-binding molecule comprises any one of (1) to (15) below:
(1) a first antibody variable region comprising the amino acid sequence of SEQ ID NO: 88; a second antibody variable region comprising the amino acid sequence of SEQ ID NO: 90; a third antibody variable region comprising the amino acid sequence of SEQ ID NO: 92; and a fourth antibody variable region comprising the amino acid sequence of SEQ ID NO: 98;
(2) a first antibody variable region comprising the amino acid sequence of SEQ ID NO: 88; and a second antibody variable region comprising the amino acid sequence of SEQ ID NO: 90; a third antibody variable region comprising the amino acid sequence of SEQ ID NO: 92; and a fourth antibody variable region comprising the amino acid sequence of SEQ ID NO: 99;
(3) a first antibody variable region comprising the amino acid sequence of SEQ ID NO: 88; a second antibody variable region comprising the amino acid sequence of SEQ ID NO: 90; a third antibody variable region comprising the amino acid sequence of SEQ ID NO: 93; and a fourth antibody variable region comprising the amino acid sequence of SEQ ID NO: 99;
(4) a first antibody variable region comprising the amino acid sequence of SEQ ID NO: 88; a second antibody variable region comprising the amino acid sequence of SEQ ID NO: 90; a third antibody variable region comprising the amino acid sequence of SEQ ID NO: 94; and a fourth antibody variable region comprising the amino acid sequence of SEQ ID NO: 100;
(5) a first antibody variable region comprising the amino acid sequence of SEQ ID NO: 88; a second antibody variable region comprising the amino acid sequence of SEQ ID NO: 90; a third antibody variable region comprising the amino acid sequence of SEQ ID NO: 95; and a fourth antibody variable region comprising the amino acid sequence of SEQ ID NO: 100;
(6) a first antibody variable region comprising the amino acid sequence of SEQ ID NO: 88; a second antibody variable region comprising the amino acid sequence of SEQ ID NO: 90; a third antibody variable region comprising the amino acid sequence of SEQ ID NO: 96; a fourth antibody variable region comprising the amino acid sequence of SEQ ID NO: 100;
(7) a first antibody variable region comprising the amino acid sequence of SEQ ID NO: 88; a second antibody variable region comprising the amino acid sequence of SEQ ID NO: 90; a third antibody variable region comprising the amino acid sequence of SEQ ID NO: 97; and a fourth antibody variable region comprising the amino acid sequence of SEQ ID NO: 99;
(8) a first antibody variable region comprising the amino acid sequence of SEQ ID NO: 89; a second antibody variable region comprising the amino acid sequence of SEQ ID NO: 91; a third antibody variable region comprising the amino acid sequence of SEQ ID NO: 92; and a fourth antibody variable region comprising the amino acid sequence of SEQ ID NO: 98;
(9) a first antibody variable region comprising the amino acid sequence of SEQ ID NO: 89; and a second antibody variable region comprising the amino acid sequence of SEQ ID NO: 91; a third antibody variable region comprising the amino acid sequence of SEQ ID NO: 92; and a fourth antibody variable region comprising the amino acid sequence of SEQ ID NO: 99;
(10) a first antibody variable region comprising the amino acid sequence of SEQ ID NO: 89; a second antibody variable region comprising the amino acid sequence of SEQ ID NO: 91; a third antibody variable region comprising the amino acid sequence of SEQ ID NO: 93; and a fourth antibody variable region comprising the amino acid sequence of SEQ ID NO: 99;
(11) a first antibody variable region comprising the amino acid sequence of SEQ ID NO: 89; a second antibody variable region comprising the amino acid sequence of SEQ ID NO: 91; a third antibody variable region comprising the amino acid sequence of SEQ ID NO: 94; and a fourth antibody variable region comprising the amino acid sequence of SEQ ID NO: 100;
(12) a first antibody variable region comprising the amino acid sequence of SEQ ID NO: 89; a second antibody variable region comprising the amino acid sequence of SEQ ID NO: 91; a third antibody variable region comprising the amino acid sequence of SEQ ID NO: 95; and a fourth antibody variable region comprising the amino acid sequence of SEQ ID NO: 100;
(13) a first antibody variable region comprising the amino acid sequence of SEQ ID NO: 89; a second antibody variable region comprising the amino acid sequence of SEQ ID NO: 91; a third antibody variable region comprising the amino acid sequence of SEQ ID NO: 96; and a fourth antibody variable region comprising the amino acid sequence of SEQ ID NO: 100;
(14) a first antibody variable region comprising the amino acid sequence of SEQ ID NO: 89; a second antibody variable region comprising the amino acid sequence of SEQ ID NO: 91; a third antibody variable region comprising the amino acid sequence of SEQ ID NO:

97; and a fourth antibody variable region comprising the amino acid sequence of SEQ ID NO: 99;

(15) a first amino acid sequence that has at least 70%, 75%, 80%, 85%, 90%, or 95% sequence identity to the first antibody variable region recited in any one of (1) to (14); a second amino acid sequence that has at least 70%, 75%, 80%, 85%, 90%, or 95% sequence identity to the second antibody variable region recited in any one of (1) to (14); a third amino acid sequence that has at least 70%, 75%, 80%, 85%, 90%, or 95% sequence identity to the third antibody variable region recited in any one of (1) to (14); and a fourth amino acid sequence that has at least 70%, 75%, 80%, 85%, 90%, or 95% sequence identity to the fourth antibody variable region recited in any one of (1) to (14).

[27] A multispecific antigen-binding molecule comprising a combination of two polypeptide chains selected from the group consisting of (A1) to (A3) below:

(A1) a first heavy chain comprising amino acid sequence of SEQ ID NO: 42 and a first light chain comprising amino acid sequence of SEQ ID NO: 43;

(A2) a first heavy chain comprising amino acid sequence of SEQ ID NO: 45 and a first light chain comprising amino acid sequence of SEQ ID NO: 46; and (A3) a first amino acid sequence that has at least 70%, 75%, 80%, 85%, 90%, or 95% sequence identity to the first heavy chain sequence recited in (A1) or (A2), and a second amino acid sequence that has at least 70%, 75%, 80%, 85%, 90%, or 95% sequence identity to the first light chain sequence recited in (A1) or (A2).

[27-2] A multispecific antigen-binding molecule comprising a combination of two polypeptide chains selected from the group consisting of (A1) to (A3) below:

(A1) a first heavy chain comprising amino acid sequence of SEQ ID NO: 41 and a first light chain comprising amino acid sequence of SEQ ID NO: 43;

(A2) a first heavy chain comprising amino acid sequence of SEQ ID NO: 44 and a first light chain comprising amino acid sequence of SEQ ID NO: 46; and (A3) a first amino acid sequence that has at least 70%, 75%, 80%, 85%, 90%, or 95% sequence identity to the first heavy chain sequence recited in (A1) or (A2), and a second amino acid sequence that has at least 70%, 75%, 80%, 85%, 90%, or 95% sequence identity to the first light chain sequence recited in (A1) or (A2).

[28] The multispecific antigen-binding molecule of [27] or [27-2], further comprising a combination of two polypeptide chains selected from the group consisting of (B1) to (B8) below:

(B1) a second heavy chain comprising amino acid sequence of SEQ ID NO: 54 and a second light chain comprising amino acid sequence of SEQ ID NO: 55;

(B2) a second heavy chain comprising amino acid sequence of SEQ ID NO: 54 and a second light chain comprising amino acid sequence of SEQ ID NO: 56;

(B3) a second heavy chain comprising amino acid sequence of SEQ ID NO: 58 and a second light chain comprising amino acid sequence of SEQ ID NO: 56;

(B4) a second heavy chain comprising amino acid sequence of SEQ ID NO: 60 and a second light chain comprising amino acid sequence of SEQ ID NO: 61;

(B5) a second heavy chain comprising amino acid sequence of SEQ ID NO: 63 and a second light chain comprising amino acid sequence of SEQ ID NO: 61;

(B6) a second heavy chain comprising amino acid sequence of SEQ ID NO: 65 and a second light chain comprising amino acid sequence of SEQ ID NO: 61;

(B7) a second heavy chain comprising amino acid sequence of SEQ ID NO: 67 and a second light chain comprising amino acid sequence of SEQ ID NO: 56; and (B8) a third amino acid sequence that has at least 70%, 75%, 80%, 85%, 90%, or 95% sequence identity to the second heavy chain sequence recited in any one of (B1) to (B7), and a fourth amino acid sequence that has at least 70%, 75%, 80%, 85%, 90%, or 95% sequence identity to the second light chain sequence recited in any one of (B1) to (B7).

[28-2] The multispecific antigen-binding molecule of [27] or [27-2], further comprising a combination of two polypeptide chains selected from the group consisting of (B1) to (B8) below:

(B1) a second heavy chain comprising amino acid sequence of SEQ ID NO: 53 and a second light chain comprising amino acid sequence of SEQ ID NO: 55;

(B2) a second heavy chain comprising amino acid sequence of SEQ ID NO: 53 and a second light chain comprising amino acid sequence of SEQ ID NO: 56;

(B3) a second heavy chain comprising amino acid sequence of SEQ ID NO: 57 and a second light chain comprising amino acid sequence of SEQ ID NO: 56;

(B4) a second heavy chain comprising amino acid sequence of SEQ ID NO: 59 and a second light chain comprising amino acid sequence of SEQ ID NO: 61;

(B5) a second heavy chain comprising amino acid sequence of SEQ ID NO: 62 and a second light chain comprising amino acid sequence of SEQ ID NO: 61;

(B6) a second heavy chain comprising amino acid sequence of SEQ ID NO: 64 and a second light chain comprising amino acid sequence of SEQ ID NO: 61;

(B7) a second heavy chain comprising amino acid sequence of SEQ ID NO: 66 and a second light chain comprising amino acid sequence of SEQ ID NO: 56; and (B8) a third amino acid sequence that has at least 70%, 75%, 80%, 85%, 90%, or 95% sequence identity to the second heavy chain sequence recited in any one of (B1) to (B7), and a fourth amino acid sequence that has at least 70%, 75%, 80%, 85%, 90%, or 95% sequence identity to the second light chain sequence recited in any one of (B1) to (B7).

[29] A multispecific antigen-binding molecule comprising a combination of four polypeptide chains selected from the group consisting of (1) to (15) below:

(1) a first heavy chain comprising amino acid sequence of SEQ ID NO: 42 and a first light chain comprising amino acid sequence of SEQ ID NO: 43, and a second heavy chain comprising amino acid sequence of SEQ ID NO: 54 and a second light chain comprising amino acid sequence of SEQ ID NO: 55;

(2) a first heavy chain comprising amino acid sequence of SEQ ID NO: 42 and a first light chain comprising amino acid sequence of SEQ ID NO: 43, and a second heavy chain comprising amino acid sequence of SEQ ID NO: 54 and a second light chain comprising amino acid sequence of SEQ ID NO: 56;

(3) a first heavy chain comprising amino acid sequence of SEQ ID NO: 42 and a first light chain comprising amino acid sequence of SEQ ID NO: 43, and a second heavy chain comprising amino acid sequence of SEQ ID NO: 58 and a second light chain comprising amino acid sequence of SEQ ID NO: 56;

(4) a first heavy chain comprising amino acid sequence of SEQ ID NO: 42 and a first light chain comprising amino acid sequence of SEQ ID NO: 43, and a second heavy chain comprising amino acid sequence of SEQ ID NO: 60 and a second light chain comprising amino acid sequence of SEQ ID NO: 61;

(5) a first heavy chain comprising amino acid sequence of SEQ ID NO: 42 and a first light chain comprising amino acid sequence of SEQ ID NO: 43, and a second heavy chain comprising amino acid sequence of SEQ ID NO: 63 and a second light chain comprising amino acid sequence of SEQ ID NO: 61;

(6) a first heavy chain comprising amino acid sequence of SEQ ID NO: 45 and a first light chain comprising amino acid sequence of SEQ ID NO: 46, and a second heavy chain comprising amino acid sequence of SEQ ID NO: 54 and a second light chain comprising amino acid sequence of SEQ ID NO: 55;

(7) a first heavy chain comprising amino acid sequence of SEQ ID NO: 45 and a first light chain comprising amino acid sequence of SEQ ID NO: 46, and a second heavy chain comprising amino acid sequence of SEQ ID NO: 65 and a second light chain comprising amino acid sequence of SEQ ID NO: 61;

(8) a first heavy chain comprising amino acid sequence of SEQ ID NO: 45 and a first light chain comprising amino acid sequence of SEQ ID NO: 46, and a second heavy chain comprising amino acid sequence of SEQ ID NO: 54 and a second light chain comprising amino acid sequence of SEQ ID NO: 56;

(9) a first heavy chain comprising amino acid sequence of SEQ ID NO: 45 and a first light chain comprising amino acid sequence of SEQ ID NO: 46, and a second heavy chain comprising amino acid sequence of SEQ ID NO: 58 and a second light chain comprising amino acid sequence of SEQ ID NO: 56;

(10) a first heavy chain comprising amino acid sequence of SEQ ID NO: 45 and a first light chain comprising amino acid sequence of SEQ ID NO: 46, and a second heavy chain comprising amino acid sequence of SEQ ID NO: 67 and a second light chain comprising amino acid sequence of SEQ ID NO: 56;

(11) a first heavy chain comprising amino acid sequence of SEQ ID NO: 42 and a first light chain comprising amino acid sequence of SEQ ID NO: 43, and a second heavy chain comprising amino acid sequence of SEQ ID NO: 65 and a second light chain comprising amino acid sequence of SEQ ID NO: 61;

(12) a first heavy chain comprising amino acid sequence of SEQ ID NO: 42 and a first light chain comprising amino acid sequence of SEQ ID NO: 43, and a second heavy chain comprising amino acid sequence of SEQ ID NO: 67 and a second light chain comprising amino acid sequence of SEQ ID NO: 56;

(13) a first heavy chain comprising amino acid sequence of SEQ ID NO: 45 and a first light chain comprising amino acid sequence of SEQ ID NO: 46, and a second heavy chain comprising amino acid sequence of SEQ ID NO: 63 and a second light chain comprising amino acid sequence of SEQ ID NO: 61;

(14) a first heavy chain comprising amino acid sequence of SEQ ID NO: 45 and a first light chain comprising amino acid sequence of SEQ ID NO: 46, and a second heavy chain comprising amino acid sequence of SEQ ID NO: 60 and a second light chain comprising amino acid sequence of SEQ ID NO: 61; and

(15) a first amino acid sequence that has at least 70%, 75%, 80%, 85%, 90%, or 95% sequence identity to the first heavy chain sequence recited in any one of (1) to (14); a second amino acid sequence that has at least 70%, 75%, 80%, 85%, 90%, or 95% sequence identity to the first light chain sequence recited in any one of (1) to (14); a third amino acid sequence that has at least 70%, 75%, 80%, 85%, 90%, or 95% sequence identity to the second heavy chain sequence recited in any one of (1) to (14); and a fourth amino acid sequence that has at least 70%, 75%, 80%, 85%, 90%, or 95% sequence identity to the second light chain sequence recited in any one of (1) to (14).

[29-2] A multispecific antigen-binding molecule comprising a combination of four polypeptide chains selected from the group consisting of (1) to (15) below:

(1) a first heavy chain comprising amino acid sequence of SEQ ID NO: 41 and a first light chain comprising amino acid sequence of SEQ ID NO: 43, and a second heavy chain comprising amino acid sequence of SEQ ID NO: 53 and a second light chain comprising amino acid sequence of SEQ ID NO: 55;

(2) a first heavy chain comprising amino acid sequence of SEQ ID NO: 41 and a first light chain comprising amino acid sequence of SEQ ID NO: 43, and a second heavy chain comprising amino acid sequence of SEQ ID NO: 53 and a second light chain comprising amino acid sequence of SEQ ID NO: 56;

(3) a first heavy chain comprising amino acid sequence of SEQ ID NO: 41 and a first light chain comprising amino acid sequence of SEQ ID NO: 43, and a second heavy chain comprising amino acid sequence of SEQ ID NO: 57 and a second light chain comprising amino acid sequence of SEQ ID NO: 56;

(4) a first heavy chain comprising amino acid sequence of SEQ ID NO: 41 and a first light chain comprising amino acid sequence of SEQ ID NO: 43, and a second heavy chain comprising amino acid sequence of SEQ ID NO: 59 and a second light chain comprising amino acid sequence of SEQ ID NO: 61;

(5) a first heavy chain comprising amino acid sequence of SEQ ID NO: 41 and a first light chain comprising amino acid sequence of SEQ ID NO: 43, and a second heavy chain comprising amino acid sequence of SEQ ID NO: 62 and a second light chain comprising amino acid sequence of SEQ ID NO: 61;

(6) a first heavy chain comprising amino acid sequence of SEQ ID NO: 44 and a first light chain comprising amino acid sequence of SEQ ID NO: 46, and a second heavy chain comprising amino acid sequence of SEQ ID NO: 53 and a second light chain comprising amino acid sequence of SEQ ID NO: 55;

(7) a first heavy chain comprising amino acid sequence of SEQ ID NO: 44 and a first light chain comprising amino acid sequence of SEQ ID NO: 46, and a second heavy chain comprising amino acid sequence of SEQ ID NO: 64 and a second light chain comprising amino acid sequence of SEQ ID NO: 61;

(8) a first heavy chain comprising amino acid sequence of SEQ ID NO: 44 and a first light chain comprising amino acid sequence of SEQ ID NO: 46, and a second heavy chain comprising amino acid sequence of SEQ ID NO: 53 and a second light chain comprising amino acid sequence of SEQ ID NO: 56;

(9) a first heavy chain comprising amino acid sequence of SEQ ID NO: 44 and a first light chain comprising amino acid sequence of SEQ ID NO: 46, and a second heavy chain comprising amino acid sequence of SEQ ID NO: 57 and a second light chain comprising amino acid sequence of SEQ ID NO: 56;

(10) a first heavy chain comprising amino acid sequence of SEQ ID NO: 44 and a first light chain comprising amino acid sequence of SEQ ID NO: 46, and a second heavy chain comprising amino acid sequence of SEQ ID NO: 66 and a second light chain comprising amino acid sequence of SEQ ID NO: 56;

(11) a first heavy chain comprising amino acid sequence of SEQ ID NO: 41 and a first light chain comprising amino acid sequence of SEQ ID NO: 43, and a second heavy chain comprising amino acid sequence of SEQ ID NO: 64 and a second light chain comprising amino acid sequence of SEQ ID NO: 61;

(12) a first heavy chain comprising amino acid sequence of SEQ ID NO: 41 and a first light chain comprising amino acid sequence of SEQ ID NO: 43, and a second heavy chain comprising amino acid sequence of SEQ ID NO: 66 and a second light chain comprising amino acid sequence of SEQ ID NO: 56;

(13) a first heavy chain comprising amino acid sequence of SEQ ID NO: 44 and a first light chain comprising amino acid sequence of SEQ ID NO: 46, and a second heavy chain comprising amino acid sequence of SEQ ID NO: 62 and a second light chain comprising amino acid sequence of SEQ ID NO: 61;

(14) a first heavy chain comprising amino acid sequence of SEQ ID NO: 44 and a first light chain comprising amino acid sequence of SEQ ID NO: 46, and a second heavy chain comprising amino acid sequence of SEQ ID NO: 59 and a second light chain comprising amino acid sequence of SEQ ID NO: 61; and

(15) a first amino acid sequence that has at least 70%, 75%, 80%, 85%, 90%, or 95% sequence identity to the first heavy chain sequence recited in any one of (1) to (14); a second amino acid sequence that has at least 70%, 75%, 80%, 85%, 90%, or 95% sequence identity to the first light chain sequence recited in any one of (1) to (14); a third amino acid sequence that has at least 70%, 75%, 80%, 85%, 90%, or 95% sequence identity to the second heavy chain sequence recited in any one of (1) to (14); and a fourth amino acid sequence that has at least 70%, 75%, 80%, 85%, 90%, or 95% sequence identity to the second light chain sequence recited in any one of (1) to (14).

[29a] A combination of any one of (i) to (iii) below:
(i) a multispecific antigen-binding molecule comprising the sequences recited in any one of (a1) to (a3) of [20], and a multispecific antigen-binding molecule comprising the sequences recited in any one of (bi) to (b8) of [21];
(ii) a multispecific antigen-binding molecule comprising the sequences recited in any one of (e1) to (e3) of [24], and a multispecific antigen-binding molecule comprising the sequences recited in any one of (f1) to (f8) of [25]; and
(iii) a multispecific antigen-binding molecule comprising the sequences recited in any one of (A1) to (A3) of [27] or [27-2], and a multispecific antigen-binding molecule comprising the sequences recited in any one of (B1) to (B8) of [28] or [28-2].

[30] A nucleic acid encoding the multispecific antigen-binding molecule of any one of [1] to [29].

[31] A vector comprising the nucleic acid of [30].

[32] A cell comprising the nucleic acid of [30] or the vector of [31].

[33] A method of producing a multispecific antigen-binding molecule comprising culturing the cell of [32] so that the multispecific antigen-binding molecule is produced.

[34] The method of [33], further comprising recovering the multispecific antigen-binding molecule from the culture of the cell.

[35] A pharmaceutical composition comprising the multispecific antigen-binding molecule of any one of [1] to [29] or the combination of [29a], and a pharmaceutically acceptable carrier.

[36] The composition of [35], which is a pharmaceutical composition for use in the treatment and/or prevention of celiac disease.

[37] Use of the multispecific antigen-binding molecule of any one of [1] to [29] or the combination of [29a] in the manufacture of a medicament.

[38] The use of [37], wherein the medicament is a medicament for treatment and/or prevention of celiac disease.

[39] A method of treating an individual having celiac disease comprising administering to the individual an effective amount of the multispecific antigen-binding molecule of any one of [1] to [29] or the combination of [29a].

[40] A kit for use in the treatment and/or prevention of celiac disease, which comprising at least the multispecific antigen-binding molecule of any one of [1] to [29] or the combination of [29a], and instructions for use.

BRIEF DESCRIPTION OF DRAWINGS

FIG. 1-1 shows the results of anti-HLA-DQ antibody (variant DQN0344H0976/L0591//DQN0385H1270/L0722-F6) binding against Ba/F3 cell lines expressing HLA class II (all antibodies were tested at 0.05 microgram (micro g)/mL, and control DQN0139bb (DQN0139bb-SG181) (WO2018/155692) and IC17dK were tested at 1 micro g/mL). In the indicated names of the gluten peptides, "a", "g" and "w" mean "alpha", "gamma" and "omega", respectively.

FIG. 1-2 shows the results of anti-HLA-DQ antibody (variant DQN0344H0976/L0591//DQN0385H1270/L0681-F6) binding against Ba/F3 cell lines expressing HLA class II (all antibodies were tested at 0.05 micro g/mL, and control DQN0139bb and IC17dK were tested at 1 micro g/mL).

FIG. 1-3 shows the results of anti-HLA-DQ antibody (variant DQN0344H0976/L0591//DQN0385H1352/L0681-F6) binding against Ba/F3 cell lines expressing HLA class II (all antibodies were tested at 0.05 micro g/mL, and control DQN0139bb and IC17dK were tested at 1 micro g/mL).

FIG. 1-4 shows the results of anti-HLA-DQ antibody (variant DQN0344H0976/L0591//DQN0385H1527/L0605-F6) binding against Ba/F3 cell lines expressing HLA class II (all antibodies were tested at 0.05 micro g/mL, and control DQN0139bb and IC17dK were tested at 1 micro g/mL).

FIG. 1-5 shows the results of Anti-HLA-DQ antibody (variant DQN0344H0976/L0591//DQN0385H1255/L0605-F6) binding against Ba/F3 cell lines expressing HLA class II (all antibodies were tested at 0.05 micro g/mL, and control DQN0139bb and IC17dK were tested at 1 micro g/mL).

FIG. 1-6 shows the results of anti-HLA-DQ antibody (variant DQN0344H1013/L0620//DQN0385H1270/L0722-F6) binding against Ba/F3 cell lines expressing HLA class II (all antibodies were tested at 0.05 micro g/mL, and control DQN0139bb and IC17dK were tested at 1 micro g/mL).

FIG. 1-7 shows the results of anti-HLA-DQ antibody (variant DQN0344H1013/L0620//DQN0385H1521/L0605-F6) binding against Ba/F3 cell lines expressing HLA class II (all antibodies were tested at 0.05 micro g/mL, and control DQN0139bb and IC17dK were tested at 1 micro g/mL).

FIG. 1-8 shows the results of anti-HLA-DQ antibody (variant DQN0344H1013/L0620//DQN0385H1270/L0681-

F6) binding against Ba/F3 cell lines expressing HLA class II (all antibodies were tested at 0.05 micro g/mL, and control DQN0139bb and IC17dK were tested at 1 micro g/mL).

FIG. 1-9 shows the results of anti-HLA-DQ antibody (variant DQN0344H1013/L0620//DQN0385H1352/L0681-F6) binding against Ba/F3 cell lines expressing HLA class II (all antibodies were tested at 0.05 micro g/mL, and control DQN0139bb and IC17dK were tested at 1 micro g/mL).

FIG. 1-10 shows the results of anti-HLA-DQ antibody (variant DQN0344H1013/L0620//DQN0385H1353/L0681-F6) binding against Ba/F3 cell lines expressing HLA class II (all antibodies were tested at 0.05 micro g/mL, and control DQN0139bb and IC17dK were tested at 1 micro g/mL).

FIG. 1-11 shows the results of anti-HLA-DQ antibody (variant DQN0344H0976/L0591//DQN0385H1521/L0605-F6) binding against Ba/F3 cell lines expressing HLA class II (antibodies were tested at 0.05 micro g/mL, and control DQN0139bb and IC17dK were tested at 1 micro g/mL; (#) for HLA-DQ2.5 and HLA-DQ2.5/hCLIP, antibodies were tested at 0.313 micro g/mL, and control DQN0139bb and IC17dK were tested at 20 micro g/mL).

FIG. 1-12 shows the results of anti-HLA-DQ antibody (variant DQN0344H0976/L0591//DQN0385H1353/L0681-F6) binding against Ba/F3 cell lines expressing HLA class II (antibodies were tested at 0.05 micro g/mL, and control DQN0139bb and IC17dK were tested at 1 micro g/mL; (#) for HLA-DQ2.5 and HLA-DQ2.5/hCLIP, antibodies were tested at 0.313 micro g/mL, and control DQN0139bb and IC17dK were tested at 20 micro g/mL).

FIG. 1-13 shows the results of anti-HLA-DQ antibody (variant DQN0344H1013/L0620//DQN0385H1255/L0605-F6) binding against Ba/F3 cell lines expressing HLA class II (antibodies were tested at 0.05 micro g/mL, and control DQN0139bb and IC17dK were tested at 1 micro g/mL; (#) for HLA-DQ2.5 and HLA-DQ2.5/hCLIP, antibodies were tested at 0.313 micro g/mL, and control DQN0139bb and IC17dK were tested at 20 micro g/mL).

FIG. 1-14 shows the results of anti-HLA-DQ antibody (variant) binding to HLA-DP, DR, DQ5.1, and DQ6.3 (all antibodies were tested at 0.05 micro g/mL, and control DQN0139bb and IC17dK were tested at 1 micro g/mL).

FIG. 1-15 shows the results of DQN0139bb binding against Ba/F3 cell lines expressing HLA class II (control DQN0139bb was tested at 1 micro g/mL).

FIG. 1-16 shows the results of IC17dK against Ba/F3 cell lines expressing HLA class II (control IC17dK was tested at 1 micro g/mL).

FIG. 2 shows the results of antibody binding to PBMC-derived, CD19+ B cells (antibodies were tested at 0.05 micro g/mL, and control DQN0139bb and IC17dK were tested at 1 microg/mL; (#) for HLA-DQ2.5 and HLA-DQ2.5-CLIP, antibodies were tested at 0.313 micro g/mL; and control DQN0139bb and IC17dK were tested at 20 ug/mL).

FIG. 3-1 shows the inhibitory effect of anti-HLA DQ antibodies on HLA-DQ2.5/alpha 1 gliadin dependent Jurkat T cell activation.

FIG. 3-2 shows the inhibitory effect of anti-HLA DQ antibodies on HLA-DQ2.5/alpha 2 gliadin dependent Jurkat T cell activation.

FIG. 3-3 shows the inhibitory effect of anti-HLA DQ antibodies on HLA-DQ2.5/alpha 1b gliadin dependent Jurkat T cell activation FIG. 3-4 shows the inhibitory effect of anti-HLA DQ antibodies on HLA-DQ2.5/omega 1 gliadin dependent Jurkat T cell activation.

FIG. 3-5 shows the inhibitory effect of anti-HLA DQ antibodies on HLA-DQ2.5/omega 2 gliadin dependent Jurkat T cell activation FIG. 3-6 shows the inhibitory effect of anti-HLA DQ antibodies on HLA-DQ2.5/BC hordein dependent Jurkat T cell activation.

FIG. 3-7 shows the inhibitory effect of anti-HLA DQ antibodies on HLA-DQ2.5/gamma 1 gliadin dependent Jurkat T cell activation FIG. 3-8 shows the inhibitory effect of anti-HLA DQ antibodies on HLA-DQ2.5/gamma 2 gliadin dependent Jurkat T cell activation.

FIG. 3-9 shows the inhibitory effect of anti-HLA DQ antibodies on HLA-DQ2.5/gamma 3 gliadin dependent Jurkat T cell activation.

FIG. 3-10 shows the inhibitory effect of anti-HLA DQ antibodies on HLA-DQ2.5/gamma 4a gliadin dependent Jurkat T cell activation.

FIG. 4-1 shows the inhibitory effect of anti-HLA DQ antibodies on HLA-DQ2.5/alpha 1 gliadin dependent Jurkat T cell activation.

FIG. 4-2 shows the inhibitory effect of anti-HLA DQ antibodies on HLA-DQ2.5/alpha 2 gliadin dependent Jurkat T cell activation.

FIG. 4-3 shows the inhibitory effect of anti-HLA DQ antibodies on HLA-DQ2.5/alpha 1b gliadin dependent Jurkat T cell activation.

FIG. 4-4 shows the inhibitory effect of anti-HLA DQ antibodies on HLA-DQ2.5/omega 1 gliadin dependent Jurkat T cell activation.

FIG. 4-5 shows the inhibitory effect of anti-HLA DQ antibodies on HLA-DQ2.5/omega 2 gliadin dependent Jurkat T cell activation.

FIG. 4-6 shows the inhibitory effect of anti-HLA DQ antibodies on HLA-DQ2.5/BC hordein dependent Jurkat T cell activation.

FIG. 4-7 shows the inhibitory effect of anti-HLA DQ antibodies on HLA-DQ2.5/gamma 1 gliadin dependent Jurkat T cell activation.

FIG. 4-8 shows the inhibitory effect of anti-HLA DQ antibodies on HLA-DQ2.5/gamma 2 gliadin dependent Jurkat T cell activation.

FIG. 4-9 shows the inhibitory effect of anti-HLA DQ antibodies on HLA-DQ2.5/gamma 3 gliadin dependent Jurkat T cell activation.

FIG. 4-10 shows the inhibitory effect of anti-HLA DQ antibodies on HLA-DQ2.5/gamma 4a gliadin dependent Jurkat T cell activation.

FIG. 5-1 shows the 33mer gliadin mediated HLA-DQ2.2/alpha 1a gliadin dependent Jurkat T cell activation.

FIG. 5-2 shows the 33mer gliadin mediated HLA-DQ2.2/alpha 2 gliadin dependent Jurkat T cell activation.

FIG. 5-3 shows the inhibitory effect of anti-HLA DQ antibodies on HLA-DQ2.2/alpha 1a gliadin dependent Jurkat T cell activation.

FIG. 5-4 shows the inhibitory effect of anti-HLA DQ antibodies on HLA-DQ2.2/alpha 2 gliadin dependent Jurkat T cell activation.

DESCRIPTION OF EMBODIMENTS

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3d edition (2001) Cold Spring Harbor Laboratory Press, Cold Spring Harbor, N.Y.; Current Protocols in Molecular Biology (F. M. Ausubel, et al. eds., (2003)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, A Laboratory Manual, and Animal Cell Culture (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J.

Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "antigen-binding moiety" or "antigen-binding domain" refers to the part of an antibody that comprises the area which specifically binds to and is complementary to part or all of an antigen. An antigen-binding moiety/domain may be provided by, for example, one or more antibody variable domains (also called antibody variable regions). Preferably, the antigen-binding moieties/domains contain both the antibody light chain variable region (VL) and antibody heavy chain variable region (VH).

The term "anti-HLA-DQ2.5 antigen-binding molecule (antibody)" refers to an antigen-binding molecule (antibody) that is capable of binding to HLA-DQ2.5 or one or more complexes formed by HLA-DQ2.5 and a gluten peptide with sufficient affinity such that the antibody is useful as a diagnostic and/or therapeutic agent in targeting HLA-DQ2.5. In one embodiment, the extent of binding of an anti-HLA-DQ2.5 antigen-binding molecule (antibody) to an unrelated antigen is less than about 10% of the binding of the antibody to HLA-DQ2.5 or the HLA-DQ2.5/gluten peptide complex as measured, e.g., by a radioimmunoassay (RIA). In certain embodiments, an antibody which has "binding activity" to HLA-DQ2.5 or the HLA-DQ2.5/gluten peptide complex has a dissociation constant (Kd) of 1 micromolar (micro M) or less, 100 nM or less, 10 nM or less, 1 nM or less, 0.1 nM or less, 0.01 nM or less, or 0.001 nM or less (e.g. $10^{-8}$ M or less, e.g. from $10^{-8}$ M to $10^{-13}$ M, e.g., from $10^{-9}$ M to $10^{-13}$ M).

The term "antigen-binding molecule", as used herein, refers to any molecule that comprises an antigen-binding site or any molecule that has binding activity to an antigen, and may further refers to molecules such as a peptide or protein having a length of about five amino acids or more. The peptide and protein are not limited to those derived from a living organism, and for example, they may be a polypeptide produced from an artificially designed sequence. They may also be any of a naturally-occurring polypeptide, synthetic polypeptide, recombinant polypeptide, and such. Scaffold molecules comprising known stable conformational structure such as alpha/beta barrel as scaffold, and in which part of the molecule is made into antigen-binding site, is also one embodiment of the antigen binding molecule described herein. In some embodiments, the "antigen-binding molecule" is an antibody. The terms "antigen-binding molecule" and "antibody" herein are used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. In some embodiments, the antibody is a multispecific antibody. In some embodiments, the multispecific antibody is a bispecific antibody.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

"Autoimmune disease" refers to a non-malignant disease or disorder arising from and directed against an individual's own tissues. The autoimmune diseases herein specifically exclude malignant or cancerous diseases or conditions, especially excluding B cell lymphoma, acute lymphoblastic leukemia (ALL), chronic lymphocytic leukemia (CLL), Hairy cell leukemia and chronic myeloblastic leukemia. Examples of autoimmune diseases or disorders include, but are not limited to, celiac disease, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE) (including but not limited to lupus nephritis, cutaneous lupus); diabetes mellitus (e.g. Type I diabetes mellitus or insulin dependent diabetes mellitus); multiple sclerosis; Reynaud's syndrome; autoimmune thyroiditis; Hashimoto's thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobulinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia.

The term "celiac (coeliac) disease" refers to a hereditary autoimmune disease caused by damages in the small intestine upon ingestion of gluten contained in food. Symptoms of celiac disease include, but are not limited to, gastrointestinal disturbance such as abdominal pain, diarrhea, and gastroesophageal reflux, vitamin deficiency, mineral deficiency, central nervous system (CNS) symptoms such as fatigue and anxiety depression, bone symptoms such as osteomalacia and osteoporosis, skin symptoms such as skin inflammation, blood symptoms such as anemia and lymphocytopenia, and other symptoms such as infertility, hypogonadism, and children's failure to thrive and short stature.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called alpha, delta, epsilon, gamma, and mu, respectively.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) or glycine-lysine (residues 446-447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

Herein, the term "gluten" collectively refers to a composite of storage proteins called prolamins found in wheat and other related grains. In the gut lumen, gluten is degraded into so-called gluten peptides. Gluten peptides include, but are not limited to, gliadin from wheat, hordein from barley, and secalin from rye, and avenin from oat.

In celiac disease, gluten peptides are antigenic peptides recognized by T cells that cause the disease. Meanwhile, immune dominance is the phenomenon where immune response is mainly triggered by a relatively small number of antigenic peptides. Such antigenic peptides may be called "immune dominant peptides". In celiac disease, such immune dominant peptides include, for example, alpha 1 gliadin (which may also be called "alpha T a gliadin") and alpha 2 gliadin (both of which are included in the sequence of 33mer gliadin), and omega 1 gliadin, omega 2 gliadin, and BC hordein (five peptides in total) (Science Translational Medicine 21 Jul. 2010: Vol. 2, Issue 41, pp. 41ra51). Alternatively, the immune dominant peptides include alpha 1 gliadin, alpha 2 gliadin, omega 1 gliadin, omega 2 gliadin, BC hordein, gamma 1 gliadin, and gamma 2 gliadin (seven peptides in total), but are not limited thereto. Herein, such immune dominant peptides may be called "immune dominant peptides related to celiac disease". As long as they are dominantly related to celiac disease, the types and total number of the peptides are not particularly limited.

The phrase "substantially no binding activity", as used herein, refers to activity of an antibody to bind to an antigen of no interest at a level of binding that includes non-specific or background binding but does not include specific binding. In other words, such an antibody has "no specific/significant binding activity" towards the antigen of no interest. The specificity can be measured by any methods mentioned in this specification or known in the art. The above-mentioned level of non-specific or background binding may be zero, or may not be zero but near zero, or may be very low enough to be technically neglected by those skilled in the art. For example, when a skilled person cannot detect or observe any significant (or relatively strong) signal for binding between the antibody and the antigen of no interest in a suitable binding assay, it can be said that the antibody has "substantially no binding activity" or "no specific/significant binding activity" towards the antigen of no interest. Alternatively, "substantially no binding activity" or "no specific/significant binding activity" can be rephrased as "not specifically/ significantly/substantially bind" (to the antigen of no interest). Sometimes, the phrase "no binding activity" has substantially the same meaning as the phrase "substantially no binding activity" or "no specific/significant binding activity" in the art.

Herein, "HLA-DR/DP" means "HLA-DR and HLA-DP" or "HLA-DR or HLA-DP". These HLAs are MHC class II molecules encoded by the corresponding haplotype alleles on the MHC class II locus in human. "HLA-DQ" collectively refers to HLA-DQ isoforms including HLA-DQ2.5, HLA-DQ7.5, HLA-DQ5.1, HLA-DQ6.3, HLA-DQ7.3, and HLA-DQ8. In the present invention, in addition to HLA-DQ2.5, HLA-DQ molecules include, but are not limited to, HLA-DQ molecules of known subtypes (isoforms) such as HLA-DQ2.2, HLA-DQ2.3, HLA-DQ4.3, HLA-DQ4.4, HLA-DQ5.1, HLA-DQ5.2, HLA-DQ5.3, HLA-DQ5.4, HLA-DQ6.1, HLA-DQ6.2, HLA-DQ6.3, HLA-DQ6.4, HLA-DQ6.9, HLA-DQ7.2, HLA-DQ7.3, HLA-DQ7.4, HLA-DQ7.5, HLA-DQ7.6, HLA-DQ8, HLA-DQ9.2, and HLA-DQ9.3. Similarly, "HLA-DR (DP)" refers to HLA-DR (DP) isoforms.

The terms "host cell," "host cell line," and "host cell culture" are used interchangeably and refer to "cells" into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. The term "human antibody framework" may also be used to refer to the framework. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

In one embodiment, HVR residues comprise those identified in the specification.]] Unless otherwise indicated, HVR residues and other residues in the variable domain (e.g., FR residues) are numbered herein according to Kabat et al., supra.

An "immunoconjugate" is an antibody conjugated to one or more heterologous molecule(s).

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

In the present invention, a CLIP peptide may be used together with a suitable HLA-DQ molecule mentioned above when evaluating the binding of the anti-HLA-DQ2.5 antibodies to these HLA-DQ molecules.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-HLA-DQ2.5 antigen-binding molecule (antibody)" (also simply called "nucleic acid encoding an anti-HLA-DQ2.5 antigen-binding molecule (antibody)") refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies composing the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa and lambda, based on the amino acid sequence of its constant domain.

The term "nucleic acid molecule" or "polynucleotide" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both, sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g., Stadler ert al, Nature Medicine 2017, published online 12 Jun. 2017, doi:10.1038/nm.4356 or EP 2 101 823 B1).

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR) software, or GENETYX (registered trademark) software (Genetyx Co., Ltd.). Those skilled in the art can determine appropriate parameters for aligning sequences, including any algorithms needed to achieve maximal alignment over the full length of the sequences being compared.

The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" or "pharmaceutical composition" refers to a preparation which is in such form as to permit the biological activity of an active ingredient contained therein to be effective, and which contains no additional components which are unacceptably toxic to a subject to which the formulation/composition would be administered.

A "pharmaceutically acceptable carrier" refers to an ingredient in a pharmaceutical formulation/composition, other than an active ingredient, which is nontoxic to a subject. A pharmaceutically acceptable carrier includes, but is not limited to, a buffer, excipient, stabilizer, or preservative.

The term "HLA-DQ2.5," as used herein, refers to any native HLA-DQ2.5 from any vertebrate source, including mammals such as primates (e.g. humans) and rodents (e.g., mice and rats), unless otherwise indicated. The term encompasses "full-length" unprocessed HLA-DQ2.5 as well as any form of HLA-DQ2.5 that results from processing in the cell. The term also encompasses naturally occurring variants of HLA-DQ2.5, e.g., splice variants or allelic variants. The amino acid sequence of exemplary HLA-DQ2.5 is publicly available in Research Collaboratory for Structural Bioinformatics (RCSB) Protein Data Bank (PDB) accession code 4OZG and IPD-IMGT/HLA Database.

Herein, "TCR" means "T-cell receptor" which is a membrane protein located on the surface of T cells (such as HLA-DQ2.5-restricted CD4+ T cells), and recognizes an antigen fragment (such as a gluten peptide) presented on MHC molecules including HLA-DQ2.5.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

Amino Acid Modifications

An antigen-binding molecule (or antibody) of the invention may comprise one or more modifications. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

An antigen-binding molecule (or antibody) of the invention may comprise amino acid substitutions. Conservative substitutions are shown in Table 1-1 under the heading of "preferred substitutions." More substantial changes are provided in Table 1-1 under the heading of "exemplary substitutions," and as further described below in reference to amino acid side chain classes. Amino acid substitutions may be introduced into an antibody of interest and the products screened for a desired activity, e.g., antigen-binding.

TABLE 1-1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Herein, as an expression showing alteration of amino acids, an expression that shows before and after a number indicating a specific position, one-letter or three-letter codes for amino acids before and after alteration, respectively, may be used appropriately. For example, the alteration N100bL or Asn100bLeu used when substituting an amino acid contained in an antibody variable region indicates substitution of Asn at position 100b (according to Kabat numbering) with Leu. That is, the number shows the amino acid position according to Kabat numbering, the one-letter or three-letter amino-acid code written before the number shows the amino acid before substitution, and the one-letter or three-letter amino-acid code written after the number shows the amino acid after substitution. Similarly, the alteration P238D or Pro238Asp used when substituting an amino acid of the Fc region contained in an antibody constant region indicates substitution of Pro at position 238 (according to EU numbering) with Asp. That is, the number shows the amino acid position according to EU numbering, the one-letter or three-letter amino-acid code written before the number shows the amino acid before substitution, and the one-letter or three-letter amino-acid code written after the number shows the amino acid after substitution.

Multispecific Antigen-Binding Molecules/Antibodies

The term "multispecific antigen-binding molecule (antibody)" refers to an antigen-binding molecule (antibody) that binds specifically to more than one antigen (e.g., a peptide)

or epitope. In some embodiments, the antigen-binding molecule (antibody) has at least a first antigen-binding moiety/domain that can bind to one or more antigens (e.g., peptides) and a second antigen-binding moiety/domain that can bind to one or more antigens (e.g., peptides). Some or all of the antigens bound by the first antigen-binding moiety/domain may be different from some or all of the antigens bound by the second antigen-binding moiety/domain. Alternatively, some of the antigens bound by the first antigen-binding moiety/domain may be identical to some of the antigens bound by the second antigen-binding moiety/domain.

In the context of the present invention, the "multispecific antigen-binding molecule (antibody)" may bind specifically to different types of antigens or epitopes. More specifically, multispecific antigen-binding molecules (antibodies) are those having specificity to at least two different types of antigens or epitopes, and, in addition to molecules/antibodies recognizing different antigens, molecules/antibodies recognizing different epitopes on the same antigen are also included. For example, ordinarily, such molecules bind to two antigens or epitopes ("bispecific antigen-binding molecules (antibodies)"; used in the present description to have the same meaning as "dual-specific antigen-binding molecules (antibodies)"), but they may even have specificity toward more antigens or epitopes (for example, three or more types of antigens).

Herein, the terms such as "multispecific" and "bispecific" mean that the specificity of an antigen-binding domain/region is different from the specificity of another antigen-binding domain/region. That is, the terms mean that there are two or more specificities in an antigen-binding molecule. For example, in a "bispecific" antigen-binding molecule (antibody), a first antigen-binding moiety/domain may bind to a first group of complexes formed by HLA-DQ2.5 and a gluten peptide, and the second antigen-binding moiety/domain may bind to a second group of complexes formed by HLA-DQ2.5 and a gluten peptide. The members (i.e., complexes) of the two groups may overlap but may not be identical. That is, some complexes may be included in both of the groups. The terms such as "multispecific" and "bispecific" can cover this situation. The same applies to first and second groups of complexes that are not bound by the first/second antigen-binding moiety/domain.

The term "bispecific" means that the antigen binding molecule is able to specifically bind to at least two distinct antigenic determinants. Examples of a preferred embodiment of the "multispecific antigen-binding molecule" of the present invention include multispecific antibodies. When an Fc region with reduced Fcγ receptor-binding activity is used as the multispecific antibody Fc region, an Fc region derived from the multispecific antibody may be used appropriately. Bispecific antibodies are particularly preferred as the multispecific antibodies of the present invention. In this case, a bispecific antibody is an antibody having two different specificities. IgG-type bispecific antibodies can be secreted from a hybrid hybridoma (quadroma) produced by fusing two types of hybridomas that produce IgG antibodies (Milstein et al., Nature (1983) 305, 537-540).

A multispecific antigen-binding molecule (antibody) may comprise at least two antigen-binding moieties/domains. A bispecific antigen-binding molecule (antibody) may comprise a first antigen-binding moiety/domain and a second antigen-binding moiety/domain.

A bispecific antigen-binding molecule (or bispecific antibody) may comprise a first antigen-binding moiety/domain and a second antigen-binding moiety/domain. The first antigen-binding moiety/domain may comprise a first antibody variable region and a second antibody variable region. The first antibody variable region associates with the second antibody variable region. The association between the first antibody variable region and the second antibody variable region allows binding of the first antigen-binding moiety/domain to a first antigen/epitope. Similarly, the second antigen-binding moiety/domain may comprise a third antibody variable region and a fourth antibody variable region. The third antibody variable region associates with the fourth antibody variable region. The association between the third antibody variable region and the fourth antibody variable region allows binding of the second antigen-binding moiety/domain to a second antigen/epitope. In some embodiments, the first antibody variable region is a heavy-chain (H-chain) variable region (VH) (which may be called "a first heavy-chain (H-chain) variable region (VH)"), and the second antibody variable region is a light-chain (L-chain) variable region (VL) (which may be called "a first light-chain (L-chain) variable region (VL)"). In some embodiments, the third antibody variable region is a heavy-chain (H-chain) variable region (VH) (which may be called "a second heavy-chain (H-chain) variable region (VH)"), and the fourth antibody variable region is a light-chain (L-chain) variable region (VL) (which may be called "a second light-chain (L-chain) variable region (VL)"). The first heavy-chain (H-chain) variable region (VH) associates with the first light-chain (L-chain) variable region (VL) for binding to the first antigen/epitope. The second heavy-chain (H-chain) variable region (VH) associates with the second light-chain (L-chain) variable region (VL) for binding to the second antigen/epitope. The association (alternatively referred to as "interaction") between the variable regions (i.e., between VH and VL) relies on the structure (e.g., amino acid residues) on the VH/VL interface as known in the art. In the present invention, preferably, a bispecific antigen-binding molecule (antibody) can bind to two or more gluten peptides (or complexes formed by HLA-DQ2.5 and gluten peptides). In some embodiments, a bispecific antigen-binding molecule (antibody) comprises a first antigen-binding moiety/domain (comprising a first antibody variable region and a second antibody variable region (supra.)) which binds to one or more complexes formed by HLA-DQ2.5 and a gluten peptide, and a second antigen-binding moiety/domain (comprising a third antibody variable region and a fourth antibody variable region (supra.)) which binds to one or more complexes formed by HLA-DQ2.5 and a gluten peptide. In this context, preferably, at least one gluten peptide in the complexes bound by the first antigen-binding moiety/domain is different from at least one gluten peptide in the complexes bound by the second antigen-binding moiety/domain. In other words, the members of the gluten peptides in the complexes bound by the first antigen-binding moiety/domain and the members of the gluten peptides in the complexes bound by the second antigen-binding moiety/domain may overlap but not be completely identical. The gluten peptides in the complexes bound by the first/second antigen-binding moiety/domain may be selected from any gluten peptides described herein. Preferably, the first/second antigen-binding moiety/domain is capable of binding to one type of gluten peptide, or two or more types of gluten peptides.

In the context of the present disclosure, for simplicity, the term "antibody" may be used rather than also referring to "antigen-binding molecule". However, a skilled person can understand that the term "antibody" may be replaced with "antigen-binding molecule" where applicable.

In one aspect, the invention is based, in part, on the binding of an anti-HLA-DQ2.5 antigen-binding molecule (antibody) to HLA-DQ2.5 that presents a gluten peptide to T cells. In certain embodiments, antibodies that bind to HLA-DQ2.5 are provided.

In one aspect, the invention provides antigen-binding molecules or antibodies that has binding activity to HLA-DQ2.5 or one or more complexes formed by HLA-DQ2.5 and a gluten peptide. In certain embodiments, the anti-HLA-DQ2.5 antigen-binding molecule (antibody) has the functions/characteristics mentioned below.

The anti-HLA-DQ2.5 antigen-binding molecule (antibody) has binding activity to HLA-DQ2.5 in the form of a complex with a gluten peptide (i.e., HLA-DQ2.5/gluten peptide complex). More preferably, the anti-HLA-DQ2.5 antigen-binding molecule (antibody) has specific binding activity to HLA-DQ2.5 in the form of a complex with a gluten peptide (i.e., HLA-DQ2.5/gluten peptide complex).

The anti-HLA-DQ2.5 antigen-binding molecule (antibody) has substantially no binding activity to an antigen of no interest, such as HLA-DQ5.1/DQ6.3/DQ7.3/DQ7.5/DQ8/DR/DP, i.e., the anti-HLA-DQ2.5 antigen-binding molecule (antibody) does not substantially bind to the antigen of no interest. For example, the anti-HLA-DQ2.5 antigen-binding molecule (antibody) has no specific binding activity to HLA-DR/DP or no significant binding activity to HLA-DR/DP. That is, the antibody does not specifically bind to HLA-DR/DP or significantly bind to HLA-DR/DP. Similarly, the anti-HLA-DQ2.5 antigen-binding molecule (antibody) has substantially no binding activity to an HLA-DQ molecule such as HLA-DQ7.5, HLA-DQ8, HLA-DQ5.1, HLA-DQ6.3, and HLA-DQ7.3, i.e., the anti-HLA-DQ2.5 antigen-binding molecule (antibody) does not substantially bind to an HLA-DQ molecule such as HLA-DQ7.5, HLA-DQ8, HLA-DQ5.1, HLA-DQ6.3, and HLA-DQ7.3. In other words, the anti-HLA-DQ2.5 antigen-binding molecule (antibody) has no specific/significant binding activity to an HLA-DQ molecule such as HLA-DQ7.5, HLA-DQ8, HLA-DQ5.1, HLA-DQ6.3, and HLA-DQ7.3. That is, the anti-HLA-DQ2.5 antigen-binding molecule (antibody) does not specifically/significantly bind to an HLA-DQ molecule such as HLA-DQ7.5, HLA-DQ8, HLA-DQ5.1, HLA-DQ6.3, and HLA-DQ7.3.

To prevent any substantial inhibitory effects on these non-target MHC class II molecules, and to improve antibody PK for the celiac disease patients who have HLA-DQ2.5, these characteristics ("substantially no binding activity") are preferable. The feature of the "substantially no binding activity" can be defined, for example, using the FACS results described herein. The anti-HLA-DQ2.5 antigen-binding molecule (antibody) having "substantially no binding activity" to a specific antigen may have an MFI (Mean Fluorescence Intensity) value that is 250% or less, preferably 200% or less, more preferably 150% or less of the MFI value of the negative control under the measurement conditions described herein.

In an aspect, for a bispecific antigen-binding molecule (antibody), the anti-HLA-DQ2.5 antigen-binding molecule (antibody) having "substantially no binding activity" to a specific antigen has an MFI value that is 2% or less, more preferably 1% or less when taking a MFI value of the IC17dK as 0% and a MFI value of DQN0139bb as 100% under the measurement conditions described herein. DQN0139bb is disclosed in, e.g., WO2018/155692.

The anti-HLA-DQ2.5 antigen-binding molecule (antibody) has binding activity to HLA-DQ2.5 that is in complex with a gluten peptide described herein. Herein, a complex formed between an HLA-DQ2.5 molecule and a gluten peptide is referred to as "a complex formed by HLA-DQ2.5 and a gluten peptide", "an HLA-DQ2.5/gluten peptide complex", or "HLA-DQ2.5/gluten peptide". It may also be rephrased as, for example, "HLA-DQ2.5 loaded with a gluten peptide", "gluten peptide-loaded HLA-DQ2.5", "HLA-DQ2.5 bound by a gluten peptide", "HLA-DQ2.5 in the form of a complex with a gluten peptide", and "a complex of HLA-DQ2.5 and a gluten peptide". The above wording (e.g., "a complex formed by HLA-DQ2.5 and . . . [peptide]") also apply to peptides such as 33mer gliadin peptide, alpha 1 gliadin peptide (which may also be called "alpha 1a gliadin peptide"), alpha 2 gliadin peptide, gamma 1 gliadin peptide, gamma 2 gliadin peptide, omega 1 gliadin peptide, omega 2 gliadin peptide, BC Hordein peptide, alpha 3 gliadin peptide, alpha 1b gliadin peptide, gamma 4a gliadin peptide, gamma 4b gliadin peptide, avenin 1 peptide, avenin 2 peptide, avenin 3 peptide, hordein 1 peptide, hordein 2 peptide, secalin 1 peptide, secalin 2 peptide, and 26mer gliadin peptide, 14 mer 1 peptide, CLIP (hCLIP) peptide, Hepatitis B virus 1 (HBV1) peptide, *Salmonella* peptide, *Mycobacterium bovis* (*M. bovis*) peptide, thyroperoxidase (TPO) peptide, etc.

Meanwhile, the anti-HLA-DQ2.5 antigen-binding molecule (antibody) has substantially no binding activity to an "irrelevant" peptide. Herein, "irrelevant" peptides include those that have been reported to be able to be presented on HLA-DQ2.5 but are irrelevant to celiac disease or irrelevant to the present invention, i.e., those which are not the above-mentioned gluten peptides of interest. For example, the irrelevant peptides include, but are not limited to, CLIP (hCLIP) peptide, Hepatitis B virus 1 (HBV1) peptide, *Salmonella* peptide, *Mycobacterium bovis* (*M. bovis*) peptide, thyroperoxidase (TPO) peptide, etc.

To prevent any substantial inhibitory effects on these non-target MHC class II molecules and HLA-DQ2.5 in the form of a complex with irrelevant peptide, and to improve antibody PK for the celiac disease patients, these characteristics ("substantially no binding activity") are preferable.

The feature of the "binding activity" can be defined, for example, using the FACS results described herein. The anti-HLA-DQ2.5 antigen-binding molecule (antibody) having "binding activity" to a specific antigen may have an MFI (Mean Fluorescence Intensity) value that is 300% or above, preferably 500% or above, more preferably 1000% or above of the MFI value of the negative control under the measurement conditions described herein.

In an aspect, for a bispecific antigen-binding molecule (antibody), the anti-HLA-DQ2.5 antigen-binding molecule (antibody) having "binding activity" to a specific antigen has an MFI value that is 3% or above, preferably 6% or above, preferably 10% or above, more preferably 20% or above when taking a MFI value of the IC17dK as 0% and a MFI value of DQN0139bb as 100% under the measurement conditions described herein.

When particularly referring to the specificity of binding, "binding activity" can be rephrased as "specific binding activity".

Anti-HLA-DQ2.5 antigen-binding molecules (antibodies) of the invention have a dissociation constant (Kd) of $5\times10^{-7}$ M or less, preferably $4\times10^{-7}$ M or less, preferably $3\times10^{-7}$ M or less, preferably $2\times10^{-7}$ M or less, preferably $1\times10^{-7}$ M or less, preferably $9\times10^{-8}$ M or less, preferably $8\times10^{-8}$ M or less, preferably $7\times10^{-8}$ M or less, preferably $6\times10^{-8}$ M or less, preferably $5\times10^{-8}$ M or less, preferably $4\times10^{-8}$ M or less, preferably $3\times10^{-8}$ M or less, preferably $2\times10^{-8}$ M or less, preferably $1\times10^{-8}$ M or less, preferably $9\times10^{-9}$ M or less, preferably $8 \times 10^{-9}$ M or less, preferably $7 \times 10^{-9}$ M or less, preferably $6 \times 10^{-9}$ M or less, preferably $5 \times 10^{-9}$ M or less, preferably $4 \times 10^{-9}$ M or less, preferably $3 \times 10^{-9}$ M or less, preferably $2 \times 10^{-9}$ M or less, for binding to one or more complexes formed by HLA-DQ2.5 and a gluten peptide described herein.

An appropriate multispecific antigen-binding molecule of the present invention comprises (1) a moiety/domain comprising an antibody variable region having binding activity to HLA-DQ2.5 in the form of a complex(es) with a gluten peptide(s);

(2) a moiety/domain comprising an antibody variable region having binding activity to HLA-DQ2.5 in the form of a complex(es) with a gluten peptide(s); and (3) a moiety/domain comprising an Fc region with reduced Fcγ receptor-binding activity mentioned above, without limitation to its structure.

In the present invention, each of the above-mentioned domains can be linked directly by peptide bonds. For example, when using $F(ab')_2$ as the domain comprising an antibody variable region of (1) and (2), and these Fc regions as the domain comprising an Fc region with reduced Fcγ receptor-binding activity of (3), the polypeptides formed by linking the antibody variable region-containing domains of (1) and (2) and the Fc region-containing domain of (3) by peptide bonds will form an antibody structure. Such antibodies can be produced by purification from the above-mentioned hybridoma culture medium, and also by purifying antibodies from the culture medium of desired host cells that stably carry polynucleotides encoding the polypeptides constituting the antibody.

Examples of a preferred antibody H-chain variable region of the present invention contained in the antibody variable region having binding activity to HLA-DQ2.5 in the form of a complex(es) with a gluten peptide(s), comprises any of the antibody H-chain variable regions described herein, or antibody H-chain variable regions having CDR sequences whose CDR1, CDR2, and CDR3 amino acid sequences are the same as the CDR1, CDR2, and CDR3 amino acid sequences contained in the H-chain variable regions described herein, or antibody H-chain variable regions which are functionally equivalent to the above-mentioned variable regions.

Examples of a preferred antibody variable region having T-cell receptor complex-binding activity of the present invention include antibody variable regions having binding activity to HLA-DQ2.5 in the form of a complex(es) with a gluten peptide(s). Examples of an antibody H-chain variable region contained in such antibody variable regions include the antibody H-chain variable regions described herein, antibody H-chain variable regions having CDR sequences whose CDR1, CDR2, and CDR3 amino acid sequences are the same as the CDR1, CDR2, and CDR3 amino acid sequences contained in the antibody H-chain variable regions described herein, and antibody H-chain variable regions that are functionally equivalent to the above-mentioned variable regions.

In the present invention, the phrase "functionally equivalent" means that the binding affinities for an antigen are equivalent, or alternatively, it means that the neutralization activities against cells expressing HLA-DQ2.5/gluten peptide (or tissues containing these cells) are equivalent when it is used as a multispecific antigen-binding molecule. The binding affinity and neutralizing activity can be measured based on the description herein. The cells used for measurement of the activity may be the desired expressing HLA-DQ2.5/gluten peptide (or a desired tissue containing these cells), and any suitable cell lines can be used. Regarding the antibody constant regions, the phrase may mean that the decreases in Fcγ receptor-binding activity are equivalent.

For example, an antibody H-chain variable region functionally equivalent to the antibody H chain variable region described herein (i.e., the original H chain variable region) means that this region has the same binding affinity when it is combined with the antibody L-chain variable region described herein which forms a pair with the original H chain, or alternatively that the region has the same neutralizing activity towards cells expressing HLA-DQ2.5/gluten peptide (or a tissue containing these cells) when used for a multispecific antigen-binding molecule. Furthermore, an antibody L-chain variable region functionally equivalent to the antibody L-chain variable region described herein (i.e., the original L-chain variable region) means that this region has the same binding affinity when it is combined with the antibody H-chain variable region described herein which forms a pair with the original L chain, or alternatively that the region has the same neutralizing activity towards cells expressing HLA-DQ2.5/gluten peptide (or a tissue containing these cells) when used for a multispecific antigen-binding molecule.

The term "equivalent" does not necessarily have to mean the same degree of activity, and the activity may be enhanced. Specifically, for antigen-binding affinity, examples include the case where the value (KD value/parent KD value) obtained by comparison to the binding affinity of the antibody variable region serving as the control (parent KD value) is 1.5 or less. The value of KD value/parent KD value is preferably 1.3 or less, more preferably 1.2 or less, 1.1 or less, 1.0 or less, 0.9 or less, 0.8 or less, 0.7 or less, 0.6 or less, or 0.5 or less. While there is no lower limit, examples include $10^{-1}$, $10^{-2}$, $10^{-3}$, $10^{-4}$, $10^{-5}$, or $10^{-6}$. More specifically, in the present invention, the value of KD value/parent KD value is preferably $10^{-6}$ to $1.5 \times 10^{-0}$, more preferably $10^{-6}$ to $10^{-1}$, even more preferably $10^{-6}$ to $10^{-2}$, and yet even more preferably $10^{-6}$ to $10^{-1}$.

Regarding the moiety/domain comprising an antibody variable region having binding activity to HLA-DQ2.5/gluten peptide, the KD value towards HLA-DQ2.5/gluten peptide may be, for example, $2 \times 10^{-8}$ M or less, $1 \times 10^{-8}$ M or less, $9 \times 10^{-9}$ M or less, $8 \times 10^{-9}$ M or less, $7 \times 10^{-9}$ M or less, $6 \times 10^{-9}$ M or less, $5 \times 10^{-9}$ M or less, $4 \times 10^{-9}$ M or less, $3 \times 10^{-9}$ M or less, $2 \times 10^{-9}$ M or less, or $1 \times 10^{-9}$ M or less.

In the present invention, antibody variable regions that are "functionally equivalent" are not particularly limited as long as they are antibody H-chain and/or antibody L-chain variable regions that satisfy the above-described conditions. Examples of such antibody variable regions include regions produced by introducing substitution, deletion, addition, and/or insertion of one or more amino acids (for example, 1, 2, 3, 4, 5, or 10 amino acids) into the amino acid sequences of the variable regions of Tables 1 to 3 mentioned above. A method well known to those skilled in the art for introducing one or more amino-acid substitutions, deletions, additions, and/or insertions into an amino acid sequence is a method of introducing mutations into proteins. For example, those skilled in the art can prepare variable regions that are functionally equivalent to the antibody variable regions having the above-mentioned functions by appropriately introducing mutations into amino acid sequences using methods such as site-directed mutagenesis (Hashimoto-Gotoh, T., Mizuno, T., Ogasahara, Y., and Nakagawa, M. (1995) An oligodeoxyribonucleotide-directed dual amber method for site-directed mutagenesis. Gene 152, 271-275; Zoller, M. J., and Smith, M. (1983) Oligonucleotide-directed mutagenesis of DNA fragments cloned into M13 vectors. Methods Enzymol. 100, 468-500; Kramer, W., Drutsa, V., Jansen, H. W., Kramer, B., Pflugfelder, M., and Fritz, H. J. (1984) The gapped duplex DNA approach to oligonucleotide-directed mutation construction. Nucleic Acids Res. 12, 9441-9456; Kramer, W., and Fritz, H. J. (1987) Oligonucleotide-directed construction of mutations via gapped duplex DNA. Methods Enzymol. 154, 350-367; and Kunkel, T. A. (1985) Rapid and efficient site-specific mutagenesis without phenotypic selection. Proc. Natl. Acad. Sci. USA 82, 488-492).

When an amino acid residue is altered, the amino acid is preferably mutated into a different amino acid(s) that conserves the properties of the amino acid side-chain. Examples of amino-acid side chain properties are: hydrophobic amino acids (A, I, L, M, F, P, W, Y, and V), hydrophilic amino acids (R, D, N, C, E, Q, G, H, K, S, and T), amino acids containing aliphatic side chains (G, A, V, L, I, and P), amino acids containing hydroxyl group-containing side chains (S, T, and Y), amino acids containing sulfur atom-containing side chains (C and M), amino acids containing carboxylic acid- and amide-containing side chains (D, N, E, and Q), amino acids containing basic side chains (R, K, and H), and amino acids containing aromatic side chains (H, F, Y, and W) (amino acids are represented by one-letter codes in parentheses). Amino acid substitutions within each of these groups are called conservative substitutions. It is already known that a polypeptide containing a modified amino acid sequence in which one or more amino acid residues in a given amino acid sequence are deleted, added, and/or substituted with other amino acids can retain the original biological activity (Mark, D. F. et al., Proc. Natl. Acad. Sci. USA; (1984) 81: 5662-6; Zoller, M. J. and Smith, M., Nucleic Acids Res. (1982) 10: 6487-500; Wang, A. et al., Science (1984) 224: 1431-3; Dalbadie-McFarland, G. et al., Proc. Natl. Acad. Sci. USA (1982) 79: 6409-13). Variable regions of the present invention containing such amino acid modifications have an amino acid sequence identity of at least 70%, more preferably at least 75%, even more preferably at least 80%, still more preferably at least 85%, yet more preferably at least 90%, and most preferably at least 95%, with the amino acid sequence of the CDR sequences, FR sequences, or whole variable regions of the variable region prior to modification. Herein, sequence identity is defined as the percentage of residues identical to those in the original amino acid sequence of the H-chain variable region or L-chain variable region determined after the sequences are aligned, and gaps are appropriately introduced to maximize the sequence identity as necessary. The identity of amino acid sequences can be determined by the method described below.

Furthermore, a "functionally equivalent antibody variable region" can be obtained, for example, from nucleic acids that hybridize under stringent conditions with nucleic acids comprising a nucleotide sequence encoding the amino acid sequence of a variable region in Tables 1 to 3 mentioned above. Stringent hybridization conditions for isolating a nucleic acid that hybridizes under stringent conditions with a nucleic acid comprising a nucleotide sequence encoding the amino acid sequence of a variable region include, for example, the conditions of 6 M urea, 0.4% SDS, 0.5×SSC, and 37° C., or hybridization conditions with a stringency equivalent thereto. Isolation of nucleic acids with a much higher homology can be expected with more stringent conditions, for example, the conditions of 6 M urea, 0.4% SDS, 0.1×SSC, and 42° C. The washing conditions following the hybridization are, for example, washing using 0.5× SSC (1×SSC is 0.15 M NaCl and 0.015 M sodium citrate at pH7.0) and 0.1% SDS at 60° C., more preferably washing using 0.2×SSC and 0.1% SDS at 60° C., even more preferably washing using 0.2×SSC and 0.1% SDS at 62° C., yet even more preferably washing using 0.2×SSC and 0.1% SDS at 65° C., and still more preferably washing using 0.1×SSC and 0.1% SDS at 65° C. The sequences of the isolated nucleic acids can be determined by the known methods described below. The overall nucleotide sequence homology of the isolated nucleic acid is at least 50% or higher, preferably 70% or higher, and more preferably 90% or higher (for example, 95%, 96%, 97%, 98%, 99%, or higher) sequence identity.

Nucleic acids that hybridize under stringent conditions to a nucleic acid comprising a nucleotide sequence encoding the amino acid sequence of a variable region can also be isolated by using, instead of the above-described methods using hybridization techniques, gene amplification methods such as polymerase chain reaction (PCR) that uses primers synthesized based on information of the nucleotide sequence encoding the variable-region amino acid sequence.

The identity of one nucleotide sequence or amino acid sequence to another can be determined using the algorithm BLAST, by Karlin and Altschul (Proc. Natl. Acad. Sci. USA (1993) 90: 5873-7). Programs called BLASTN and BLASTX were developed based on this algorithm (Altschul et al., J. Mol. Biol. (1990) 215: 403-10). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST).

The Fc region comprised in the multispecific antigen-binding molecule of the present invention is not particularly limited as long as it is an Fc region having reduced Fcγ receptor-binding activity, examples of a preferred Fc region of the present invention include combinations of the Fc-region portions described herein.

Examples of a preferred multispecific antigen-binding molecule of the present invention include bispecific antibodies comprising a first antibody variable region having binding activity to HLA-DQ2.5 in the form of a complex(es) with a gluten peptide(s) and a second antibody variable region having binding activity to HLA-DQ2.5 in the form of a complex(es) with a gluten peptide(s). Examples of such bispecific antibodies include bispecific antibodies comprising H and L chains described herein, and bispecific antibodies that bind to an epitope overlapping with an epitope bound by the above antibodies, and which contain an Fc region with reduced Fcγ receptor-binding activity.

Whether an antibody recognizes an epitope that overlaps with an epitope recognized by another antibody can be confirmed by the competition between the two antibodies against the epitope. Competition between the antibodies can be evaluated by competitive binding assays using means such as enzyme-linked immunosorbent assay (ELISA), fluorescence energy transfer method (FRET), and fluorometric microvolume assay technology (FMAT (Registered trademark)). The amount of an antibody bound to an antigen indirectly correlates with the binding ability of a candidate competitor antibody (a test antibody) that competitively binds to the overlapping epitope. In other words, as the amount or affinity of a test antibody against the overlapping epitope increases, the amount of the antibody bound to the antigen decreases, and the amount of the antigen-bound test antibody increases. Specifically, the appropriately labeled antibody and antibody to be evaluated are simultaneously added to the antigen, and the antibody bound as a result are detected using the label. The amount of the antigen-bound antibody can be easily determined by labeling the antibody beforehand. This label is not particularly limited, and the labeling method is selected according to the assay technique used. Specifically, the labeling method includes fluorescent labeling, radiolabeling, enzymatic labeling, and such.

For example, the fluorescently labeled antibody and the unlabeled antibody or test antibody are simultaneously added to beads immobilized with HLA-DQ2.5/gluten peptide, and the labeled antibody is detected by fluorometric microvolume assay technology.

Herein, the "antibody that binds to the overlapping epitope" refers to a test antibody that can reduce the amount of the bound labeled antibody by at least 50% at a concentration that is usually 100 times higher, preferably 80 times higher, more preferably 50 times higher, even more preferably 30 times higher, and still more preferably 10 times higher than the concentration at which the non-labeled antibody reduces 50% of the amount of the labeled antibody bound ($IC_{50}$).

Multispecific antigen-binding molecules, which have the antigen-binding sites of antibodies that bind to epitopes overlapping with epitopes bound by the above-mentioned antibodies, can yield excellent binding activity or neutralizing activity.

The multispecific antigen-binding molecules of the present invention are produced by the same technique as the method for producing recombinant antibodies mentioned herein.

In certain embodiments, any one or more amino acids of an anti-HLA-DQ2.5 antigen-binding molecule (antibody) as provided above are substituted in any of the heavy-chain and/or light-chain constant and/or variable regions or domains.

In certain embodiments, the substitutions are conservative substitutions, as provided herein.

Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HUMAB (registered trademark) technology; U.S. Pat. No. 7,041,870 describing K-M MOUSE (registered trademark) technology, and U.S. Patent Application Publication No. US 2007/0061900, describing VELOCIMOUSE (registered trademark) technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boemer et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Chimeric and Humanized Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Natl. Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

In any of the above embodiments, an anti-HLA-DQ2.5 antigen-binding molecule (antibody) is humanized. In one embodiment, an anti-HLA-DQ2.5 antigen-binding molecule (antibody) comprises HVRs as in any of the above embodiments, and further comprises an acceptor human framework, e.g., a human immunoglobulin framework or a human consensus framework. In another embodiment, an anti-HLA-DQ2.5 antigen-binding molecule (antibody) comprises HVRs as in any of the above embodiments, and further comprises the FR1, FR2, FR3, or FR4 sequence shown herein. Herein, "human framework" may also be called "humanized framework" focusing on the fact that the antibody is humanized.

In some embodiments, a multispecific antigen-binding molecule of the invention comprises:
(i) a first antigen-binding moiety that has binding activity to HLA-DQ2.5 in the form of a complex with a gluten peptide; and
(ii) a second antigen-binding moiety that has binding activity to HLA-DQ2.5 in the form of a complex with a gluten peptide;
wherein the antigen-binding molecule binds to two or more complexes of HLA-DQ2.5 and gluten peptides,
wherein at least one of the gluten peptides in the complexes bound by the first antigen-binding moiety is different from at least one of the gluten peptides in the complexes bound by the second antigen-binding moiety; and
wherein the antigen-binding molecule has substantially no binding activity to either or both of a HLA-DQ2.5 positive PBMC B cell and a Ba/F3 cell that expresses HLA-DQ2.5 or HLA-DQ2.2,
wherein the antigen-binding molecule is humanized, and
wherein one or more amino acids in a heavy-chain and/or light-chain constant and/or variable region in the first antigen-binding moiety and/or second antigen-binding moiety in the multispecific antigen-binding molecule are altered.

In some embodiments, in the multispecific antigen-binding molecule, one or more amino acids in a heavy chain and/or a light chain of the first antigen-binding moiety and/or second antigen-binding moiety in the multispecific antigen-binding molecule are substituted.

In some embodiments, the multispecific antigen-binding molecule comprises at least one amino acid substitution in a variable region of the heavy chain; at least one amino acid substitution in a constant region of the heavy chain; at least one amino acid substitution in a variable region of the light chain; and at least one amino acid substitution in a constant region of the light chain.

In some embodiments, the gluten peptide is an immune dominant peptide related to celiac disease.

In some embodiments, the gluten peptide is selected from the group consisting of 33mer gliadin peptide, alpha 1 gliadin peptide, alpha 2 gliadin peptide, gamma 1 gliadin peptide, gamma 2 gliadin peptide, omega 1 gliadin peptide, omega 2 gliadin peptide, BC Hordein peptide, alpha 3 gliadin peptide, alpha 1b gliadin peptide, gamma 4a gliadin peptide, gamma 4b gliadin peptide, avenin 1 peptide, avenin 2 peptide, avenin 3 peptide, hordein 1 peptide, hordein 2 peptide, secalin 1 peptide, secalin 2 peptide, and 26mer gliadin peptide.

In some embodiments, the gluten peptide(s) is/are one, two, three, four, five, six, seven, eight, nine, ten, eleven, twelve, 13, 14, 15, 16, 17, 18, 19 or all of 33mer gliadin peptide, alpha 1 gliadin peptide, alpha 2 gliadin peptide, gamma 1 gliadin peptide, gamma 2 gliadin peptide, omega 1 gliadin peptide, omega 2 gliadin peptide, BC Hordein peptide, alpha 3 gliadin peptide, alpha 1b gliadin peptide, gamma 4a gliadin peptide, gamma 4b gliadin peptide, avenin 1 peptide, avenin 2 peptide, avenin 3 peptide, hordein 1 peptide, hordein 2 peptide, secalin 1 peptide, secalin 2 peptide, and 26mer gliadin peptide.

In some embodiments, the gluten peptide is selected from the group consisting of 33mer gliadin peptide, alpha 1 gliadin peptide, alpha 2 gliadin peptide, gamma 1 gliadin peptide, omega 1 gliadin peptide, omega 2 gliadin peptide, BC Hordein peptide, alpha 3 gliadin peptide, alpha 1b gliadin peptide, gamma 4a gliadin peptide, gamma 4b gliadin peptide, avenin 1 peptide, avenin 2 peptide, avenin 3 peptide, hordein 1 peptide, hordein 2 peptide, secalin 1 peptide, secalin 2 peptide, and 26mer gliadin peptide.

In some embodiments, the gluten peptide(s) is/are one, two, three, four, five, six, seven, eight, nine, ten, eleven, twelve, 13, 14, 15, 16, 17, 18, or all of 33mer gliadin peptide, alpha 1 gliadin peptide, alpha 2 gliadin peptide, gamma 1 gliadin peptide, omega 1 gliadin peptide, omega 2 gliadin peptide, BC Hordein peptide, alpha 3 gliadin peptide, alpha 1b gliadin peptide, gamma 4a gliadin peptide, gamma 4b gliadin peptide, avenin 1 peptide, avenin 2 peptide, avenin 3 peptide, hordein 1 peptide, hordein 2 peptide, secalin 1 peptide, secalin 2 peptide, and 26mer gliadin peptide.

In some embodiments, the multispecific antigen-binding molecule has substantially no binding activity to the gluten peptide itself or the gluten peptides themselves. In this context, the terms "itself" and "themselves" refer to a state where the gluten peptide(s) do(es) not form a complex with HLA-DQ2.5.

In some embodiments, the multispecific antigen-binding molecule has substantially no binding activity to HLA-DQ2.5 in the form of a complex with an irrelevant peptide, wherein the irrelevant peptide is at least one peptide selected from the group consisting of: CLIP (hCLIP) peptide, Hepatitis B virus 1 peptide, *Salmonella* peptide, *Mycobacterium bovis* peptide, and thyroperoxidase peptide.

In some embodiments, the multispecific antigen-binding molecule has substantially no binding activity to HLA-DQ2.5 in the form of complexes with irrelevant peptides, wherein the irrelevant peptides are all of CLIP (hCLIP) peptide, Hepatitis B virus 1 peptide, *Salmonella* peptide, *Mycobacterium bovis* peptide, and thyroperoxidase peptide. In some embodiments, the antigen-binding molecule has enhanced binding activity to the complex formed by HLA-DQ2.5 and the gluten peptide, compared to before said humanization and alteration. In this context, "enhanced binding activity" means that the antigen-binding molecule binds to the complex formed by HLA-DQ2.5 and the gluten peptide stronger than the prior antibody before the modifications, i.e., humanization and alteration.

In some embodiments, the antigen-binding molecule has enhanced cross reactivity towards gluten peptides, compared to before said humanization and alteration. In some embodiments, the gluten peptides are omega 2 gliadin peptide, BC hordein peptide, gamma 1 gliadin peptide, gamma 2 gliadin peptide, gamma 4a gliadin peptide, and gamma 4d gliadin peptide. In this context, "enhanced cross reactivity towards gluten peptides" means that the antigen-binding molecule binds to or shows neutralizing activities towards more gluten peptides than the prior antibody before the modifications, i.e., humanization and alteration.

In another aspect, an anti-HLA-DQ2.5 antigen-binding molecule (antibody) comprises a heavy-chain variable domain (VH) sequence having at least 90%, 91%, 92%, 93%, 94%, 95%, 96%, 97%, 98%, 99%, or 100% sequence identity to the amino acid sequence of the heavy-chain variable domain (VH) sequence disclosed herein. In certain embodiments, a VH sequence having at least 90%, 91%, 92%, 93%, 94%, 95%, 96%, 97%, 98%, or 99% identity comprises substitutions (e.g., conservative substitutions), insertions, or deletions relative to the reference (i.e., original) sequence, but an anti-HLA-DQ2.5 antigen-binding molecule (antibody) comprising that sequence retains the ability to bind to HLA-DQ2.5. In certain embodiments, a total of 1 to 10 amino acids have been substituted, inserted and/or deleted relative to the reference (i.e., original) sequence. In certain embodiments, substitutions, insertions, or deletions occur in regions outside the HVRs (i.e., in the FRs). Optionally, the anti-HLA-DQ2.5 antigen-binding molecule (antibody) comprises a VH sequence disclosed herein or a sequence comprising a post-translational modification thereof. In a particular embodiment, the VH comprises one, two or three HVRs selected from: (a) HVR-H1 disclosed herein, (b) HVR-H2 disclosed herein, and (c) HVR-H3 disclosed herein. Post-translational modifications include but are not limited to a modification of glutamine or glutamate at the N terminus of the heavy chain or light chain to pyroglutamic acid by pyroglutamylation.

Amino acids contained in the amino acid sequences of the present invention may be post-translationally modified (for example, the modification of an N-terminal glutamine into a pyroglutamic acid by pyroglutamylation is well-known to those skilled in the art). Naturally, such post-translationally modified amino acids are included in the amino acid sequences in the present invention.

In another aspect, an anti-HLA-DQ2.5 antigen-binding molecule (antibody) is provided, wherein the molecule/antibody comprises a light-chain variable domain (VL) having at least 90%, 91%, 92%, 93%, 94%, 95%, 96%, 97%, 98%, 99%, or 100% sequence identity to the amino acid sequence of the light-chain variable domain (VL) disclosed herein. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference (i.e., original) sequence, but an anti-HLA-DQ2.5 antigen-binding molecule (antibody) comprising that sequence retains the ability to bind to HLA-DQ2.5. In certain embodiments, a total of 1 to 10 amino acids have been substituted, inserted and/or deleted in relative to the reference (i.e., original) sequence. In certain embodiments, the substitutions, insertions, or deletions occur in regions outside the HVRs (i.e., in the FRs). Optionally, the anti-HLA-DQ2.5 antigen-binding molecule (antibody) comprises the VL sequence disclosed herein or a sequence comprising a post-translational modification thereof. In a particular embodiment, the VL comprises one, two or three HVRs selected from (a) HVR-L1 disclosed herein; (b) HVR-L2 disclosed herein; and (c) HVR-L3 disclosed herein. Post-translational modifications include but are not limited to a modification of glutamine or glutamate at the N terminus of the heavy chain or light chain to pyroglutamic acid by pyroglutamylation.

In another aspect, an anti-HLA-DQ2.5 antigen-binding molecule (antibody) is provided, wherein the molecule/antibody comprises a VH as in any of the embodiments provided above, and a VL as in any of the embodiments provided above. In one embodiment, the molecule/antibody comprises the VH sequence disclosed herein or a sequence comprising a post-translational modification thereof, and the VL sequence disclosed herein or a sequence comprising a post-translational modification thereof. Post-translational modifications include but are not limited to a modification of glutamine or glutamate at the N terminus of the heavy chain or light chain to pyroglutamic acid by pyroglutamylation.

In a further aspect, the invention provides an antigen-binding molecule (antibody) that binds to the same epitope as an anti-HLA-DQ2.5 antigen-binding molecule (antibody) provided herein. For example, in certain embodiments, a molecule/antibody is provided that binds to the same epitope as any of the molecules/antibodies described herein. In certain embodiments, a molecule/antibody is provided that binds to an epitope within a fragment of HLA-DQ2.5 consisting of about 8 to 17 amino acids, or within a complex formed by HLA-DQ2.5 and a gluten peptide. In this context, the gluten peptide may be any of the gluten peptides described herein.

In a further aspect, the invention provides an antigen-binding molecule (antibody) that competes with another antigen-binding molecule (antibody) for binding to HLA-DQ2.5 or a complex formed by HLA-DQ2.5 and a gluten peptide. For example, in certain embodiments, a molecule/antibody is provided that competes with any of the molecules/antibodies described herein for binding to HLA-DQ2.5 or a complex formed by HLA-DQ2.5 and a gluten peptide. In this context, the gluten peptide may be any of the gluten peptides described herein.

In a further aspect of the invention, an anti-HLA-DQ2.5 antigen-binding molecule (antibody) according to any of the above embodiments is a monoclonal antigen-binding molecule (antibody), including a chimeric, humanized or human antigen-binding molecule (antibody). In preferred embodiments, the anti-HLA-DQ2.5 antigen-binding molecule (antibody) of the invention is a humanized antigen-binding molecule (antibody). In one embodiment, an anti-HLA-DQ2.5 antigen-binding molecule (antibody) is an antibody fragment, e.g., a Fv, Fab, Fab', scFv, diabody, or F(ab')$_2$ fragment. In another embodiment, the antibody is a full-length antibody, e.g., an intact IgG$_1$ antibody or other antibody class or isotype as defined herein.

In a further aspect, an anti-HLA-DQ2.5 antigen-binding molecule (antibody) according to any of the above embodiments may incorporate any of the features described below, whether singly or in combination:

Antibody Affinity

In certain embodiments, an antibody provided herein has a dissociation constant (Kd) of 1 micromolar (micro M) or less, 100 nM or less, 10 nM or less, 1 nM or less, 0.1 nM or less, 0.01 nM or less, or 0.001 nM or less (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881(1999)). To establish conditions for the assay, MICROTITER (registered trademark) multi-well plates (Thermo Scientific) are coated overnight with 5 microgram (micro g)/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23 degrees C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20 (registered trademark)) in PBS. When the plates have dried, 150 microliter (micro L)/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE (registered trademark) surface plasmon resonance assay. For example, an assay using a BIACORE (registered trademark)-2000 or a BIACORE(registered trademark)-3000 apparatus (BIAcore, Inc., Piscataway, N.J.) is performed at 25 degrees C. with immobilized antigen CM5 chips at approximately 10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 micro g/ml (approximately 0.2 micro M) before injection at a flow rate of 5 micro L/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25 degrees C. at a flow rate of approximately 25 micro L/min. Association rates ($k_{on}$) and dissociation rates ($k_{off}$) are calculated using a simple one-to-one Langmuir binding model (BIACORE (registered trademark) Evaluation Software version 3.2) by simultaneously fitting the association and dissociation sensorgrams. The equilibrium dissociation constant (Kd) is calculated as the ratio $k_{off}/k_{on}$. See, e.g., Chen et al., J. Mol. Biol. 293:865-881 (1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25 degrees C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. Nat. Med. 9:129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

Antibodies with increased half-lives and increased binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which increase binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, Nature 322:738-40 (1988); U.S. Pat. Nos. 5,648,260; 5,624,821; and WO 94/29351 concerning other examples of Fc region variants.

Fc Region

The term "Fc region" or "Fc domain" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) or glycine-lysine (residues 446-447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

Fc Receptor

The term "Fc receptor" or "FcR" refers to a receptor that binds to the Fc region of an antibody. In some embodiments, an FcR is a native human FcR. In some embodiments, an FcR is one which binds an IgG antibody (a gamma receptor) and includes receptors of the Fc gamma RI, Fc gamma RII, and Fc gamma RIII subclasses, including allelic variants and alternatively spliced forms of those receptors. Fc gamma RII receptors include Fc gamma RIIA (an "activating receptor") and Fc gamma RIIB (an "inhibiting receptor"), which have similar amino acid sequences that differ primarily in the cytoplasmic domains thereof. Activating receptor Fc gamma RIIA contains an immunoreceptor tyrosine-based activation motif (ITAM) in its cytoplasmic domain. Inhibiting receptor Fc gamma RIIB contains an immunoreceptor tyrosine-based inhibition motif (ITIM) in its cytoplasmic domain. (see, e.g., Daeron, Annu. Rev. Immunol. 15:203-234 (1997)). FcRs are reviewed, for example, in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., J. Immunol. 117:587 (1976) and Kim et al., J. Immunol. 24:249 (1994)) and regulation of homeostasis of immunoglobulins. Methods of measuring binding to FcRn are known (see, e.g., Ghetie and Ward., Immunol. Today 18(12):592-598 (1997); Ghetie et al., Nature Biotechnology, 15(7):637-640 (1997); Hinton et al., J. Biol. Chem. 279(8):6213-6216 (2004); WO 2004/92219 (Hinton et al.).

Binding to human FcRn in vivo and plasma half-life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with increased or decreased binding to FcRs. See also, e.g., Shields et al. J. Biol. Chem. 9(2):6591-6604 (2001).

Fc Gamma Receptor

Fc gamma receptor refers to a receptor capable of binding to the Fc domain of monoclonal IgG1, IgG2, IgG3, or IgG4 antibodies, and includes all members belonging to the family of proteins substantially encoded by an Fc gamma receptor gene. In human, the family includes Fc gamma RI (CD64) including isoforms Fc gamma RIa, Fc gamma RIb and Fc gamma RIc; Fc gamma RII (CD32) including isoforms Fc gamma RIIa (including allotype H131 and R131), Fc gamma RIIb (including Fc gamma RIIb-1 and Fc gamma RIIb-2), and Fc gamma RIIc; and Fc gamma RIII (CD16) including isoform Fc gamma RIIIa (including allotype V158 and F158) and Fc gamma RIIIb (including allotype Fc gamma RIIIb-NA1 and Fc gamma RIIIb-NA2); as well as all unidentified human Fc gamma receptors, Fc gamma receptor isoforms, and allotypes thereof. However, Fc gamma receptor is not limited to these examples. Without being limited thereto, Fc gamma receptor includes those derived from humans, mice, rats, rabbits, and monkeys. Fc gamma receptor may be derived from any organisms. Mouse Fc gamma receptor includes, without being limited to, Fc gamma RI (CD64), Fc gamma RII (CD32), Fc gamma RIII (CD16), and Fc gamma RIII-2 (CD16-2), as well as all unidentified mouse Fc gamma receptors, Fc gamma receptor isoforms, and allotypes thereof. Such preferred Fc gamma receptors include, for example, human Fc gamma RI (CD64), Fc gamma RIIA (CD32), Fc gamma RIIB (CD32), Fc gamma RIIIA (CD16), and/or Fc gamma RIIIB (CD16). Whether an Fc gamma receptor has binding activity to the Fc domain of a monoclonal IgG1, IgG2, IgG3, or IgG4 antibody can be assessed by AlphaScreen™ (Amplified Luminescent Proximity Homogeneous Assay), surface plasmon resonance (SPR)-based BIACORE method, and others (Proc. Natl. Acad. Sci. USA (2006) 103(11), 4005-4010), in addition to the above-described FACS and ELISA formats.

Meanwhile, "Fc ligand" or "effector ligand" refers to a molecule and preferably a polypeptide that binds to an antibody Fc domain, forming an Fc/Fc ligand complex. The molecule may be derived from any organisms. The binding of an Fc ligand to Fc preferably induces one or more effector functions. Such Fc ligands include, but are not limited to, Fc receptors, Fc gamma receptor, Fc alpha receptor, Fc beta receptor, FcRn, C1q, and C3, mannan-binding lectin, mannose receptor, *Staphylococcus* Protein A, *Staphylococcus* Protein G, and viral Fc gamma receptors. The Fc ligands also include Fc receptor homologs (FcRH) (Davis et al., (2002) Immunological Reviews 190, 123-136), which are a family of Fc receptors homologous to Fc gamma receptor. The Fc ligands also include unidentified molecules that bind to Fc.

Fc Gamma Receptor-Binding Activity

The impaired binding activity of Fc domain to any of the Fc gamma receptors Fc gamma RI, Fc gamma RIIA, Fc gamma RIIB, Fc gamma RIIIA, and/or Fc gamma RIIIB can be assessed by using the above-described FACS and ELISA formats as well as AlphaScreen™ (Amplified Luminescent Proximity Homogeneous Assay) and surface plasmon resonance (SPR)-based BIACORE method (Proc. Natl. Acad. Sci. USA (2006) 103(11), 4005-4010).

AlphaScreen™ (Amplified Luminescent Proximity Homogeneous Assay) is performed by the ALPHA technology based on the principle described below using two types of beads: donor and acceptor beads. A luminescent signal is detected only when molecules linked to the donor beads interact biologically with molecules linked to the acceptor beads and when the two beads are located in close proximity. Excited by laser beam, the photosensitizer in a donor bead converts oxygen around the bead into excited singlet oxygen. When the singlet oxygen diffuses around the donor beads and reaches the acceptor beads located in close proximity, a chemiluminescent reaction within the acceptor beads is induced. This reaction ultimately results in light emission. If molecules linked to the donor beads do not interact with molecules linked to the acceptor beads, the singlet oxygen produced by donor beads do not reach the acceptor beads and chemiluminescent reaction does not occur.

For example, a biotin-labeled antigen-binding molecule or antibody is immobilized to the donor beads and glutathione S-transferase (GST)-tagged Fc gamma receptor is immobilized to the acceptor beads. In the absence of an antigen-binding molecule or antibody comprising a competitive mutant Fc domain, Fc gamma receptor interacts with an antigen-binding molecule or antibody comprising a wild-type Fc domain, inducing a signal of 520 to 620 nm as a result. The antigen-binding molecule or antibody having a non-tagged mutant Fc domain competes with the antigen-binding molecule or antibody comprising a wild-type Fc domain for the interaction with Fc gamma receptor. The relative binding affinity can be determined by quantifying the reduction of fluorescence as a result of competition. Methods for biotinylating the antigen-binding molecules or antibodies such as antibodies using Sulfo-NHS-biotin or the like are known. Appropriate methods for adding the GST tag to an Fc gamma receptor include methods that involve fusing polypeptides encoding Fc gamma receptor and GST in-frame, expressing the fused gene using cells introduced with a vector carrying the gene, and then purifying using a glutathione column. The induced signal can be preferably analyzed, for example, by fitting to a one-site competition model based on nonlinear regression analysis using software such as GRAPHPAD PRISM (GraphPad; San Diego).

One of the substances for observing their interaction is immobilized as a ligand onto the gold thin layer of a sensor chip. When light is shed on the rear surface of the sensor chip so that total reflection occurs at the interface between the gold thin layer and glass, the intensity of reflected light is partially reduced at a certain site (SPR signal). The other substance for observing their interaction is injected as an analyte onto the surface of the sensor chip. The mass of immobilized ligand molecule increases when the analyte binds to the ligand. This alters the refraction index of solvent on the surface of the sensor chip.

The change in refraction index causes a positional shift of SPR signal (conversely, the dissociation shifts the signal back to the original position). In the BIACORE (registered trademark) system, the amount of shift described above (i.e., the change of mass on the sensor chip surface) is plotted on the vertical axis, and thus the change of mass over time is shown as measured data (sensorgram). Kinetic parameters (association rate constant (ka) and dissociation rate constant (kd)) are determined from the curve of sensorgram, and affinity (KD) is determined from the ratio between these two constants. Inhibition assay is preferably used in the BIACORE methods. Examples of such inhibition assay are described in Proc. Natl. Acad. Sci. USA (2006) 103(11), 4005-4010.

Fc Region with a Reduced Fc Gamma Receptor-Binding Activity

Herein, "a reduced Fc gamma receptor-binding activity" means, for example, that based on the above-described analysis method the competitive activity of a test antigen-binding molecule or antibody is 50% or less, preferably 45% or less, 40% or less, 35% or less, 30% or less, 20% or less, or 15% or less, and particularly preferably 10% or less, 9% or less, 8% or less, 7% or less, 6% or less, 5% or less, 4% or less, 3% or less, 2% or less, or 1% or less than the competitive activity of a control antigen-binding molecule or antibody.

Antigen-binding molecules or antibodies comprising the Fc domain of a monoclonal IgG1, IgG2, IgG3, or IgG4 antibody can be appropriately used as control antigen-binding molecules or antibodies. The Fc domain structures are shown in RefSeq accession number AAC82527.1, RefSeq accession number AAB59393.1, RefSeq accession number CAA27268.1, and RefSeq accession number AAB59394.1. Furthermore, when an antigen-binding molecule or antibody comprising an Fc domain mutant of an antibody of a particular isotype is used as a test substance, the effect of the mutation of the mutant on the Fc gamma receptor-binding activity is assessed using as a control an antigen-binding molecule or antibody comprising an Fc domain of the same isotype. As described above, antigen-binding molecules or antibodies comprising an Fc domain mutant whose Fc gamma receptor-binding activity has been judged to be reduced are appropriately prepared.

Such known mutants include, for example, mutants having a deletion of amino acids 231A-238S (EU numbering) (WO 2009/011941), as well as mutants C226S, C229S, P238S, (C220S) (J. Rheumatol (2007) 34, 11); C226S and C229S (Hum. Antibod. Hybridomas (1990) 1(1), 47-54); C226S, C229S, E233P, L234V, and L235A (Blood (2007) 109, 1185-1192).

Specifically, the preferred antigen-binding molecules or antibodies include those comprising an Fc domain with a mutation (such as substitution) of at least one amino acid selected from the following amino acid positions: 220, 226, 229, 231, 232, 233, 234, 235, 236, 237, 238, 239, 240, 264, 265, 266, 267, 269, 270, 295, 296, 297, 298, 299, 300, 325, 327, 328, 329, 330, 331, or 332 (EU numbering), in the amino acids forming the Fc domain of an antibody of a particular isotype. The isotype of antibody from which the Fc domain originates is not particularly limited, and it is possible to use an appropriate Fc domain derived from a monoclonal IgG1, IgG2, IgG3, or IgG4 antibody. It is preferable to use Fc domains derived from IgG1 antibodies.

In the present invention, SG181 may be used as a Fc gamma receptor silenced Fc which attenuates Fc binding against Fc gamma receptors. In some embodiments, SG181.S3n (SEQ ID NO: 101) and SG181.S3p (SEQ ID NO: 102) may be used as heavy chain constant regions sequences. These heavy chain constant regions sequences may be included in the antigen-binding molecules or antibodies of the present invention for reduced Fc gamma receptor binding.

The other preferred antigen-binding molecules or antibodies include, for example, those comprising an Fc domain in which any amino acid at position 233, 234, 235, 236, 237, 327, 330, or 331 (EU numbering) in the amino acids forming the Fc domain of an IgG1 antibody is substituted with an amino acid of the corresponding position in EU numbering in the corresponding IgG2 or IgG4.

In some embodiments, the multispecific antigen-binding molecule of the invention further comprises an Fc domain that exhibits reduced binding affinity to human Fc gamma receptor, as compared to a native human IgG1 Fc domain.

In some embodiments, in the multispecific antigen-binding molecule of the invention, the Fc domain comprises Arg at position 235 and Arg at position 236, wherein the amino acid positions are numbered according to EU numbering.

Regulation of H-Chain/L-Chain Association and Other Features

Another embodiment of the present invention relates to an antigen-binding molecule in which the association of the heavy chain and light chain is regulated, a method of manufacturing an antigen-binding molecule in which the association of the heavy chain and light chain is regulated, and a method of regulating the association of the heavy chain and light chain in an antigen-binding molecule.

The antigen-binding molecule of the present invention relates to an antigen-binding molecule in which the association of the heavy chain and light chain is regulated, in which the heavy chain and light chain constituting the antigen-binding molecule are a combination of heavy chain and light chain of interest, and in which the amino acid residues at given locations in the constant region of the heavy chain (CH1) and the constant region of the light chain (CL) are mutually electrically repelling amino acid residues (having the same charge).

In the present invention, by making amino acid residues at given locations in CH1 and CL of an undesired combination of heavy chain and light chain into amino acid residues that mutually repel electrically (i.e., that have the same charge), the formation of undesired combinations of heavy chain and light chain can be prevented by utilizing this charge repulsion, and as a result, the desired combination of heavy chain and light chain can be formed.

In the present invention, the phrases "to regulate association" and "association is regulated" refer to regulating to achieve a desired association condition, and more specifically refers to regulating so that undesirable associations are not formed between the heavy chain and light chain.

In the present invention, the term "interface" generally refers to the association surface that results from association (interaction), and amino acid residues that form the interface are ordinarily one or more amino acid residues included in the polypeptide regions which participate in the association, and are more preferably amino acid residues that approach each other during association and are involved in the interaction. More specifically, this interaction includes, for example, instances where the amino acid residues come close during the association to form hydrogen bonds, electrostatic interactions, or salt bridges with each other.

In the present invention, the phrase, "amino acid residues forming an interface" more specifically refers to amino acid residues included in the polypeptide region that constitutes the interface. For example, polypeptide regions constituting the interface refer to polypeptide regions responsible for selective binding between molecules such as in antigen-binding molecules (e.g., antibodies), ligands, receptors, or substrates. More specifically, in antigen-binding molecules, such examples include heavy chain constant regions, heavy chain variable regions, light chain constant regions, and light chain variable regions.

In a preferred embodiment of the antigen-binding molecule of the present invention, the antigen-binding molecule has amino acid residues at given locations in CH1 and CL of an undesired combination of heavy chain and light chain before association regulation which electrically repel (which have the same charge).

By modifying amino acid residues in the aforementioned antigen-binding molecule into amino acid residues that mutually repel electrically (have the same charge), association of these amino acid residues is thought to be inhibited by the repulsive force of electrical charges.

Thus, in the aforementioned antigen-binding molecule, the modified amino acid residues are preferably amino acid residues that approach each other at association, in the polypeptide regions forming the interface.

The amino acid residues that approach during association can be determined by, for example, analyzing the three-dimensional structure of a polypeptide, and investigating the amino acid sequences of the polypeptide regions that form an interface during polypeptide association. Amino acid residues at the interface that mutually approach each other are preferable targets of "modification" in the antigen-binding molecule of the present invention.

Some amino acids are known to be electrically charged. In general, lysine (K), arginine (R) and histidine (H) are known to be amino acids having a positive charge (positively charged amino acids). Aspartic acid (D), glutamic acid (E), and such are known to be amino acids having a negative charge (negatively charged amino acids). In addition, alanine (A), asparagine (N), cysteine (C), glutamine (Q), glycine (G), isoleucine (I), leucine (L), methionine (M), phenylalanine (F), proline (P), serine (S), threonine (T), tryptophan (W), tyrosine (Y), valine (V), and the like are known to be amino acids that do not have a charge, or nonpolar amino acids.

Thus, amino acids that mutually repel electrically (have the same charge) in the present invention refer to:

(1) amino acids in which one of the amino acids is a positively charged amino acid and the other amino acid is also a positively charged amino acid, and (2) amino acids in which one of the amino acids is a negatively charged amino acid and the other amino acid is also a negatively charged amino acid.

Examples of amino acid modifications include modification of an uncharged amino acid or a nonpolar amino acid into a positively charged amino acid, modification of an uncharged amino acid or a nonpolar amino acid into a negatively charged amino acid, modification of a positively charged amino acid into a negatively charged amino acid, and modification of a negatively charged amino acid into a positively charged amino acid. Furthermore, modification of an uncharged amino acid or a nonpolar amino acid into a different uncharged or nonpolar amino acid, modification of a positively charged amino acid into a different positively charged amino acid, and modification of a negatively charged amino acid into a different negatively charged amino acid are also included in the amino acid modifications of the present invention.

Modifying amino acids in the present invention includes making one modification in each of the heavy and light chain, or making multiple modifications to each of the heavy and light chain. In addition, the number of modifications added to the heavy chain and light chain may be the same or different.

Modifying amino acids in the present invention includes making multiple modifications into positively charged amino acids on either the heavy chain or light chain, and making multiple modifications into negatively charged amino acids on the other chain. Moreover, multiple modifications into positively charged amino acids as well as multiple modifications into negatively charged amino acids may be made on the same heavy chain or light chain. In these modifications, modifications into uncharged amino acids or nonpolar amino acids as well as modifications of uncharged amino acids or nonpolar amino acids may also be suitably combined.

In the modifications of the present invention, for example, the amino acids on one of the chains can be used as they are without being modified, and in such cases, the heavy chain and light chain do not need to be both modified, and only one of the chains may be modified.

The light chain constant region of the antigen-binding molecule of the present invention is preferably a human light chain constant region. Examples of antibody light chain constant region include IgK (Kappa), IgL1, IgL2, IgL3, IgL6 and IgL7 (Lambda) type constant regions. The light chain constant region of the antigen-binding molecule of the present invention is not particularly limited; when using multiple types of light chains, the light chains may be different types of light chains, for example, Kappa and Lambda. Several allotype sequences obtained by genetic polymorphism are described in Sequences of Proteins of Immunological Interest, NIH Publication No. 91-3242 as human IgK (Kappa) constant region and human IgL7 (Lambda) constant region, and any of these may be used in the present invention.

Antibody constant regions, in particular, heavy chain constant regions, may be modified as necessary in order to improve the function or stability of an antigen-binding molecule. Examples of modifications for improving the function of an antigen-binding molecule include modifications that strengthen or weaken the binding between an antigen-binding molecule and an Fc gamma receptor ("Fc gamma R"), modifications that strengthen or weaken the binding between an antigen-binding molecule and FcRn, modifications that strengthen or weaken the cytotoxic activity (such as ADCC activity and CDC activity) of an antigen-binding molecule, and such. In addition, modifications that improve the heterogeneity of an antigen-binding molecule and modifications that improve the non-immunogenicity and/or pharmacokinetics may also be included.

Moreover, as the heterogeneity of the heavy chain C-terminal sequence of the IgG antibody, amidation of the C-terminal carboxyl group by deletion of the C-terminal amino acid, lysine residue, or by deletion of the two C-terminal amino acids, glycine and lysine, has been reported the (Anal. Biochem. 2007 Jan. 1:360(1):75-83). Thus, in the present invention, to lower heterogeneity of the heavy chain C terminus, it is preferable to use an IgG in which the C-terminal lysine or the C-terminal lysine and glycine have been deleted.

Since their antigenicity in the human body has been attenuated, chimeric and humanized antibodies using human-derived sequences are expected to be useful when administered to humans for therapeutic purposes or such.

A preferred example of the antigen-binding molecule of the present invention is a heteromeric multimer having two or more types of CH1 and two or more types of CL. This heteromeric multimer preferably binds to two or more types of epitopes, and an example thereof is a multispecific antibody.

A preferred example of a multispecific antibody of the present invention is a bispecific antibody. Thus, an example of a preferred embodiment of the antigen-binding molecule of the present invention is a bispecific antibody composed of two types of heavy chains (a first heavy chain and a second heavy chain) and two types of light chains (a first light chain and a second light chain).

Describing the "bispecific antibodies" of the preferred embodiments of the antigen-binding molecules of the present invention more precisely, the above-mentioned "first heavy chain" refers to one of the two heavy chains (H chains) forming the antibody, and the "second H chain" refers to the other H chain that is different from the first H chain.

That is, of the two H chains, one of them can be arbitrarily defined as the first H chain and the other can be defined as the second H chain. Similarly, the "first light chain" refers to one of the two light chains (L chains) forming the bispecific antibody, and the "second L chain" refers to the other L chain that is different from the first L chain. Of the two L chains, one of them can be arbitrarily defined as the first L chain and the other can be defined as the second L chain. Ordinarily, the first L chain and the first H chain are derived from a same antibody that binds to a certain antigen (or epitope), and the second L chain and the second H chain are also derived from a same antibody that binds to a certain antigen (or epitope). Herein, the L chain-H chain pair formed by the first H chain and L chain is called the first pair, and the L chain-H chain pair formed by the second H chain and L chain is called the second pair. The antigen (or epitope) used to produce the antibody from which the second pair derives is preferably different from the antigen used to produce the antibody from which the first pair derives. More specifically, antigens recognized by the first pair and the second pair may be the same, but preferably, the pairs bind to different antigens (or epitopes). In this case, the H chains and L chains of the first pair and second pair preferably have amino acid sequences that differ from each other. When the first pair and the second pair bind to different epitopes, the first pair and the second pair may recognize a completely different antigen, or they may recognize different sites (different epitopes) on the same antigen. Furthermore, one of them may recognize an antigen such as a protein, peptide, gene, or sugar, and the other may recognize cytotoxic substances such as radioactive substances, chemotherapeutic agents, or cell-derived toxins. However, when one wishes to produce an antibody having pairs formed by specific combinations of H chains and L chains, those specific H chains and L chains may be arbitrary determined to be the first pair and second pair.

A more detailed explanation is provided below on the case of an IgG-type bispecific antibody having two types of heavy chain constant regions CH1 (CH1-A and CH1-B) and two types of light chain constant regions (CL-A and CL-B); however, the present invention can be similarly applied to other antibodies as well.

When one wishes to obtain a bispecific antibody that would recognize one epitope by the first CH1-A and the first CL-A, and bind to another epitope by the second CH1-B and the second CL-B, theoretically there is the possibility that 10 types of antibody molecules may be produced when each of the four types of chains is expressed for producing that antibody.

In this case, desired antibody molecules can be preferentially acquired if, for example, the association is regulated so that association of CH1-A and CL-B and/or between CH1-B and CL-A is inhibited.

An example is modifying amino acid residues forming an interface between CH1-A and CL-B into positively charged amino acid residues and modifying amino acid residues forming an interface between CH1-B and CL-A into negatively charged amino acid residues. As a result of these modifications, unintended association between CH1-A and CL-B is inhibited since the amino acid residues forming the interface are both positively charged, and association between CH1-B and CL-A is also inhibited since the amino acid residues forming the interface are both negatively charged. Thus, the unintended association between CH1-A and CL-B and association between CH1-B and CL-A are inhibited because the amino acid residues forming the interfaces mutually have the same charge. As a result, antibodies having the intended association between CH1-A and CL-A, and the intended association between CH1-B and CL-B can be acquired efficiently. Moreover, the intended association between CH1-A and CL-A is promoted since the amino acid residues forming the interface have different types of charges from each other; and the intended association between CH1-B and CL-B is also promoted since the amino acid residues forming the interface have different types of charges from each other. Consequently, antibodies with intended association can be efficiently obtained.

Another example is modifying the amino acid residues forming the interface between CH1-A and CL-B into positively charged amino acid residues, when the amino acid residues forming the interface between CL-A and CH1-B are mutually uncharged or nonpolar amino acids. As a result of this modification, the unintended association between CH1-A and CL-B is inhibited because the amino acid residues forming the interface are both positively charged. On the other hand, since the amino acid residues forming the interfaces are amino acids that do not mutually repel electrically, the intended association between CH1-A and CL-A, and the intended association between CH1-B and CL-B will occur more easily than in the case where the amino acids repel electrically. Consequently, antibodies having the intended association between CH1-A and CL-A, and the intended association between CH1-B and CL-B can be efficiently obtained. Meanwhile, in this example, in the case that the amino acid residues forming the interface between CL-A and CH1-B are not mutually uncharged or nonpolar amino acids, they may be modified so as to become mutually uncharged or nonpolar amino acids.

Moreover, in another example, when the amino acid residues forming the interface between CL-B and CH1-B are uncharged or nonpolar amino acids in CH1-B, one of the amino acid residues forming the interface between CH1-A and CL-A is modified into a positively charged amino acid residue while the other is modified into a negatively charged amino acid residue; and amino acid residues forming the interface between CL-B and CH1-B in CL-B are modified so as to have the same charge as the modification made to CH1-A. As a result of this modification, while the intended association between CH1-A and CL-A is promoted because the amino acid residues forming the interface are a combination of positive charge and negative charge, the intended association between CH1-B and CL-B is not inhibited because the amino acid residues forming the interface are amino acids that do not mutually repel electrically. As a result, one can efficiently obtain an antibody having intended association between CH1-A and CL-A, and intended association between CH1-B and CL-B. Meanwhile, in this example, when the amino acid residues forming the interface between CL-B and CH1-B are not uncharged or nonpolar amino acids in CH1-B, they may be modified so as to become uncharged or nonpolar amino acids.

In addition, use of the association regulation of the present invention makes it possible to suppress association between CH1s (CH1-A and CH1-B), or association between CLs (CL-A and CL-B).

Those skilled in the art would be able to suitably determine the types of amino acid residues that come close during association at the CH1 and CL interface in a desired polypeptide for which regulation of association by the present invention is desired.

Further, those skilled in the art can also suitably acquire sequences that can be used as CH1 or CL of an antibody in an organism such as a human, monkey, mouse, rabbit, and the like by using a public database and such. More specifically, the amino acid sequence information of CH1 or CL can be acquired by means described in the Examples described below.

For example, with respect to the bispecific antibodies described in the Examples below, specific examples of amino acid residues that come close (that face or are in contact) at the interface of CH1 and CL upon association include the combinations shown below:

glutamine (Q) at position 175 according to EU numbering in CH1 and the facing (contacting) glutamine (Q) or glutamic acid (E) at position 160 according to Kabat numbering in CL;

glutamine (Q) at position 175 according to EU numbering in CH1 and the facing (contacting) threonine (T) or serine (S) at position 131 according to Kabat numbering in CL;

glutamine (Q) at position 175 according to EU numbering in CH1 and the facing (contacting) serine (S) or threonine (T) at position 131 and glutamine (Q) or glutamic acid (E) at position 160 according to Kabat numbering in CL; and, lysine (K) at position 147 and glutamine (Q) at position 175 according to EU numbering in CH1 and the facing (contacting) serine (S) or threonine (T) at position 131 and glutamine (Q) or glutamic acid (E) at position 160 according to Kabat numbering in CL.

The numbers described in EU numbering in the present invention are indicated in accordance with EU numbering (Sequences of proteins of immunological interest, NIH Publication No. 91-3242). In the present invention, the phrases "an amino acid residue at position X according to EU numbering" and "an amino acid at position X according to EU numbering" (where X is an arbitrary number) can also be read as "an amino acid residue that corresponds to position X according to EU numbering" and "an amino acid that corresponds to position X according to EU numbering". As indicated in the Examples described below, desired antigen-binding molecules can be preferentially acquired by modifying these amino acid residues and carrying out the methods of the present invention.

In an embodiment, the present invention provides an antigen-binding molecule in which association of the heavy chain and light chain is regulated, wherein one or two or more sets of amino acid residues selected from the group consisting of the sets of amino acid residues shown in (a) to (c) below in the heavy chain and light chain of the antigen-binding molecule are amino acid residues that mutually repel electrically:

(a) the amino acid residue contained in CH1 at position 175 according to EU numbering, and the amino acid residue contained in CL at position 160 according to Kabat numbering;

(b) the amino acid residue contained in CH1 at position 175 according to EU numbering, and the amino acid residue contained in CL at position 131 according to Kabat numbering;

(c) the amino acid residues contained in CH1 at positions 147 and 175 according to EU numbering, and the amino acid residues contained in CL at positions 131 and 160 according to Kabat numbering; and (d) the amino acid residue contained in CH1 at position 175 according to EU numbering, and the amino acid residues contained in CL at positions 131 and 160 according to Kabat numbering.

In the aforementioned antigen-binding molecule, the "amino acid residues that mutually repel electrically" or "amino acid residues having the same charge" are preferably selected from amino acid residues contained in, for example, either of the set of (X) or (Y) below:

(X) glutamic acid (E) or aspartic acid (D); or
(Y) lysine (K), arginine (R), or histidine (H).

In the aforementioned antigen-binding molecule, specific examples of the sets of the amino acid residues that mutually repel electrically include the sets of the amino acid residues below:

(a) the amino acid residue contained in CH1 at position 175 according to EU numbering, and the amino acid residue contained in CL at position 160 according to EU numbering;

(b) the amino acid residue contained in CH1 at position 175 according to EU numbering, and the amino acid residue contained in CL at position 131 according to Kabat numbering;

(c) the amino acid residues contained in CH1 at positions 147 and 175 according to EU numbering, and the amino acid residues contained in CL at positions 131 and 160 according to Kabat numbering;

(d) the amino acid residue contained in CH1 at position 175 according to EU numbering, and the amino acid residues contained in CL at positions 131 and 160 according to Kabat numbering.

In some embodiments, in the multispecific antigen-binding molecule, one, two, three or all sets of amino acid residues selected from the group consisting of the sets of amino acid residues shown in (a) to (d) below in the heavy chain and the light chain of the antigen-binding molecule are amino acid residues which electrostatically repel each other:

(a) an amino acid residue in a heavy chain constant region (CH1) which is at position 175 according to EU numbering, and an amino acid residue in a light chain constant region (CL) which is at position 131 according to Kabat numbering, (b) an amino acid residue in CH1 which is at position 175 according to EU numbering, and an amino acid residue in CL which is at position 160 according to Kabat numbering, (c) amino acid residue in CH1 which is at position 175 according to EU numbering, and amino acid residues in CL which are at positions 131 and 160 according to Kabat numbering, (d) amino acid residues in CH1 which are at positions 147 and 175 according to EU numbering, and amino acid residues in CL which are at positions 131 and 160 according to Kabat numbering.

The present invention provides an antigen-binding molecule in which one or two or more sets of amino acid residues selected from the group consisting of the sets of amino acid residues shown in (a1) to (c2) below in the heavy chain and light chain of the antigen-binding molecule are amino acid residues that mutually repel electrically:

(a1) the amino acid residue contained in CH1 at position 175 according to EU numbering which is glutamic acid (E) or aspartic acid (D), and the amino acid residue contained in CL at position 160 according to EU numbering which is glutamic acid (E) or aspartic acid (D);

(a2) the amino acid residue contained in CH1 at position 175 according to EU numbering which is lysine (K), histidine (H), or arginine (R), and the amino acid residue contained in CL at position 160 according to EU numbering which is lysine (K), histidine (H), or arginine (R);

(b1) the amino acid residue contained in CH1 at position 175 according to EU numbering which is glutamic acid (E) or aspartic acid (D), and the amino acid residue contained in CL at position 131 according to EU numbering which is glutamic acid (E) or aspartic acid (D);

(b2) the amino acid residue contained in CH1 at position 175 according to EU numbering which is lysine (K), histidine (H), or arginine (R), and the amino acid residue contained in CL at position 131 according to EU numbering which is lysine (K), histidine (H), or arginine (R);

(c1) the amino acid residues contained in CH1 at positions 147 and 175 according to EU numbering which are each glutamic acid (E) or aspartic acid (D), and the amino acid residues contained in CL at positions 131 and 160 according to EU numbering which are each glutamic acid (E) or aspartic acid (D);

(c2) the amino acid residues contained in CH1 at positions 147 and 175 according to EU numbering which are each lysine (K), histidine (H), or arginine (R), and the amino acid residues contained in CL at positions 131 and 160 according to EU numbering which are each lysine (K), histidine (H), or arginine (R).

In the aforementioned antigen-binding molecule, specific examples of amino acid residues that mutually repel electrically include the amino acid residues below:

(a1) the amino acid residue contained in CH1 at position 175 according to EU numbering which is glutamic acid (E) or aspartic acid (D), and the amino acid residue contained in CL at position 160 according to EU numbering which is glutamic acid (E) or aspartic acid (D);

(a2) the amino acid residue contained in CH1 at position 175 according to EU numbering which is lysine (K), histidine (H), or arginine (R), and the amino acid residue contained in CL at position 160 according to EU numbering which is lysine (K), histidine (H), or arginine (R);

(b1) the amino acid residue contained in CH1 at position 175 according to EU numbering which is glutamic acid (E) or aspartic acid (D), and the amino acid residue contained in CL at position 131 according to EU numbering which is glutamic acid (E) or aspartic acid (D);

(b2) the amino acid residue contained in CH1 at position 175 according to EU numbering which is lysine (K), histidine (H), or arginine (R), and the amino acid residue contained in CL at position 131 according to EU numbering which is lysine (K), histidine (H), or arginine (R);

(c1) the amino acid residues contained in CH1 at positions 147 and 175 according to EU numbering which are each glutamic acid (E) or aspartic acid (D), and the amino acid residues contained in CL at positions 131 and 160 according to EU numbering which are each glutamic acid (E) or aspartic acid (D);

(c2) the amino acid residues contained in CH1 at positions 147 and 175 according to EU numbering which are each lysine (K), histidine (H), or arginine (R), and the amino acid residues contained in CL at positions 131 and 160 according to EU numbering which are each lysine (K), histidine (H), or arginine (R);

(d1) the amino acid residue contained in CH1 at position 175 according to EU numbering which is glutamic acid (E) or aspartic acid (D), and the amino acid residues contained in CL at positions 131 and 160 according to EU numbering which are each glutamic acid (E) or aspartic acid (D);

(d2) the amino acid residue contained in CH1 at position 175 according to EU numbering which is lysine (K), histidine (H), or arginine (R), and the amino acid residues contained in CL at positions 131 and 160 according to EU numbering which are each lysine (K), histidine (H), or arginine (R).

In addition to the above, the technique for inhibiting the CH1/CL associated of no interest by introducing electric charge repulsion on the interface between CH1 and CL (WO 2013/065708) can be further applied to the antigen-binding molecule of the present invention. More specifically, the present invention provides an antigen-binding molecule having CH1 and CL, wherein one or two or more sets of amino acid residues selected from the group consisting of the sets of amino acid residues shown in (a) to (d) below mutually repel electrically:

(a) the amino acid residue contained in the heavy chain constant region (CH1) at position 147 according to EU numbering, and the amino acid residue contained in the light chain constant region (CL) at position 160 according to EU numbering;

(b) the amino acid residue contained in CH1 at position 147 according to EU numbering, and the amino acid residue contained in CL at position 131 according to EU numbering;

(c) the amino acid residue contained in CH1 at position 175 according to EU numbering, and the amino acid residue contained in CL at position 160 according to EU numbering;

(d) the amino acid residue contained in CH1 at position 213 according to EU numbering, and the amino acid residue contained in CL at position 123 according to EU numbering.

A technique for introducing electrical repulsion into the interface of the second constant region of the heavy chain (CH2) or the third constant region of the heavy chain (CH3) to suppress undesired association between heavy chains, a technique for introducing electrical repulsion into the interface of the heavy chain variable region and light chain variable region to suppress unintended association between the heavy chain and light chain, or a technique for modifying amino acid residues forming a hydrophobic core present at the interface of the heavy chain variable region and light chain variable region into polar amino acids having an electrical charge to suppress unintended association between the heavy chain and light chain can be further applied to the antigen-binding molecules of the present invention (see WO 2006/106905).

In the technique that suppresses unintended association between heavy chains by introducing electrical repulsion at the interface of CH2 or CH3, examples of amino acid residues that are in contact at the interface of other constant regions of the heavy chain include regions corresponding to position 356 (EU numbering) and position 439 (EU numbering), position 357 (EU numbering) and position 370 (EU numbering), and position 399 (EU numbering) and position 409 (EU numbering) in the CH3 region. For the numbering of the antibody constant regions, one may refer to the publication by Kabat et al. (Kabat, E. A., et al., 1991, Sequences of Proteins of Immunological Interest, NIH); and for the numbering of the heavy chain constant regions, the EU numbering are shown.

More specifically, for example, in an antigen-binding molecule containing two types of heavy chain CH3 regions, one to three sets of amino acid residues in the first heavy chain CH3 region, which are selected from the sets of amino acid residues of (1) to (3) below, may be made to mutually repel electrically:

(1) the amino acid residues contained in the heavy chain CH3 region at position 356 and position 439 according to EU numbering;

(2) the amino acid residues contained in the heavy chain CH3 region at position 357 and position 370 according to EU numbering; and (3) the amino acid residues contained in the heavy chain CH3 region at position 399 and position 409 according to EU numbering.

Moreover, the antibody can be an antibody having a set of amino acid residues in the second heavy chain CH3 region distinct from the aforementioned first heavy chain CH3 region, wherein the set of amino acid residues is selected from the sets of amino acid residues shown in (1) to (3) above, and wherein the one to three sets of amino acid residues that correspond to the sets of amino acid residues shown in (1) to (3) above, which mutually repel electrically in the first heavy chain CH3 region, do not electrically repel from the corresponding amino acid residues in the first heavy chain CH3 region.

The amino acid residues described in (1) to (3) above approach each other upon association. Those skilled in the art would be able to find sites corresponding to the amino acid residues described in (1) to (3) mentioned above for a desired heavy chain CH3 region or heavy chain constant region by homology modeling and such using commercially available software, and to suitably modify the amino acid residues at those sites.

In the aforementioned antigen-binding molecule, "electrically repelling", "having a same charge", or "carrying the same charge" means that, for example, any two or more amino acid residues have amino acid residues that are contained in either one group of (X) and (Y) mentioned herein.

In a preferred embodiment of the aforementioned antigen-binding molecule, the first heavy chain CH3 region and the second heavy chain CH3 region may be cross-linked by disulfide bonds.

In the present invention, an amino acid residue subjected to "modification" is not limited to an amino acid residue of the antigen-binding molecule variable region or antibody constant region mentioned above. Those skilled in the art would be able to find amino acid residues that form an interface in a polypeptide variant or heteromeric multimer by homology modeling and the like using commercially available software, and to modify amino acid residues at those sites so as to regulate association.

Homology modeling is a technique for predicting the three-dimensional structure of a protein using commercially available software. When constructing the structure of a protein with unknown three-dimensional structure, one first searches for a protein that has been determined to have a highly homologous three-dimensional structure to the protein. Next, using this three-dimensional structure as a template, one constructs the structure of the protein with unknown structure, and the structure is further optimized by molecular dynamics methods and the like to predict the three-dimensional structure of the unknown protein.

In the technique for introducing electrical repulsion into the interface of the heavy chain variable region and light chain variable region to suppress undesired association of the heavy chain and light chain, examples of amino acid residues that are in contact at the interface of the heavy chain variable region (VH) and light chain variable region (VL) include glutamine (Q) at position 39 according to Kabat numbering in the VH (FR2 region) and the facing (contacting) glutamine (Q) at position 38 according to Kabat numbering in the VL (FR2 region). Moreover, a preferable example is leucine (L) at position 45 according to the Kabat numbering in the VH (FR2) and the facing proline (P) at position 44 according to the Kabat numbering in the VL (FR2). The publication by Kabat, et al. (Kabat, E. A., et al., 1991, Sequence of Proteins of Immunological Interest, NIH) was referred to for the numbering of these sites.

Since these amino acid residues are known to be highly conserved in humans and mice (J. Mol. Recognit. 2003; 16: 113-120), association of the variable regions of antigen-binding molecules can be regulated for VH-VL association of antigen-binding molecules other than those indicated in the Examples by modifying amino acid residues corresponding to the above-mentioned amino acid residues.

In some embodiments, in the multispecific antigen-binding molecule, further, two or more amino acid residues that form an interface between a heavy chain variable region and a light chain variable region are amino acid residues which electrostatically repel each other.

A specific example is an antigen-binding molecule in which two or more amino acid residues forming the interface of the VH and VL are amino acid residues that mutually repel electrically. More specifically, examples include an antigen-binding molecule with one set or two sets of amino acid residues selected from the group consisting of the sets of amino acid residues shown in (a) or (b) below:

(a) the amino acid residue contained in the VH at position 39 according to Kabat numbering and, the amino acid residue contained in the VL at position 38 according to Kabat numbering; or (b) the amino acid residue contained in the VH at position 45 according to Kabat numbering, and the amino acid residue contained in the VL at position 44 according to Kabat numbering.

In some embodiments, in the multispecific antigen-binding molecule, the amino acid residues which electrostatically repel each other are one or two sets of amino acid residues selected from the group consisting of the sets of amino acid residues of (a) and (b) below:

(a) an amino acid residue in the heavy chain variable region which is at position 39 according to Kabat numbering, and an amino acid residue in the light chain variable region which is at position 38 according to Kabat numbering, (b) an amino acid residue in the heavy chain variable region which is at position 45 according to Kabat numbering, and an amino acid residue in the light chain variable region which is at position 44 according to Kabat numbering.

Each of the amino acid residues described in the aforementioned (a) or (b) approaches each other upon association. Those skilled in the art would be able to find sites that correspond to the amino acid residues described in the aforementioned (a) or (b) in a desired VH or VL by homology modeling and the like using commercially available software, and to suitably modify the amino acid residues at those sites.

In some embodiments, in the multispecific antigen-binding molecule, the amino acid residues which electrostatically repel each other are selected from the amino acid residues included in either set of (X) or (Y) below:

(X) glutamic acid (E), aspartic acid (D),
(Y) lysine (K), arginine (R), histidine (H).

In the technique for modifying amino acid residues forming a hydrophobic core present at the interface of the VH and VL into polar amino acids having an electrical charge to suppress unintended association of the heavy chain and light chain, preferable examples of amino acid residues which are able to form a hydrophobic core at the interface of the VH and VL include leucine (L) at position 45 according to Kabat numbering in the VH (FR2), and the facing proline (P) at position 44 according to Kabat numbering in the VL (FR2). For the numbering of these sites, Kabat, et al. (Kabat, E. A., et al., 1991, Sequences of Proteins of Immunological Interest, NIH) was used as a reference.

In general, the term "hydrophobic core" refers to a part that is formed by an assembly of hydrophobic amino acid side chains at the interior of associated polypeptides.

Examples of hydrophobic amino acids include alanine, isoleucine, leucine, methionine, phenylalanine, proline, tryptophan, and valine. Furthermore, amino acid residues other than hydrophobic amino acids (for example tyrosine) may be involved in the formation of a hydrophobic core. This hydrophobic core together with a hydrophilic surface, in which hydrophilic amino acid side chains are exposed to the exterior, becomes a driving force for promoting association of water-soluble polypeptides. When hydrophobic amino acids of two different domains are present on a molecular surface and are exposed to water molecules, the entropy will increase and the free energy will increase. Accordingly, the two domains will associate with each other to decrease the free energy and become stable, and hydrophobic amino acids at the interface will be buried into the interior of the molecule to form a hydrophobic core.

It is thought that when polypeptide association occurs, formation of a hydrophobic core is inhibited by modifying hydrophobic amino acids forming the hydrophobic core to polar amino acids having an electrical charge; and consequently, polypeptide association is thought to be inhibited.

Those skilled in the art would be able to recognize the presence or absence of a hydrophobic core, the formation site (region), and the like by analyzing amino acid sequences for a desired antigen-binding molecule. Namely, the antigen-binding molecule of the present invention is an antigen-binding molecule characterized in that amino acid residues capable of forming a hydrophobic core at an interface are modified to amino acid residues having an electrical charge. More specifically, examples include an antigen-binding molecule in which the amino acid residues shown in either (1) or (2) below are amino acid residues having an electrical charge. Side chains of the amino acid residues shown in (1) and (2) below are adjacent to each other, and can form a hydrophobic core:

(1) the amino acid residue contained in the VH at position 45 according to Kabat numbering; and
(2) the amino acid residue contained in the VL at position 44 according to Kabat numbering.

Preferable examples of amino acid residues having an electrical charge in the aforementioned antigen-binding molecule include glutamic acid (E), aspartic acid (D), lysine (K), arginine (R) and histidine (H). More preferable examples include glutamic acid (E) and lysine (K).

Generally, the amino acid residues described in the aforementioned (1) and (2) in humans and mice are respectively:

(1) leucine (L), and
(2) proline (P).

Thus, in a preferred embodiment of the present invention, these amino acid residues are subjected to modification (such as substitution with amino acids having an electrical charge). Furthermore, the types of the aforementioned amino acid residues of (1) and (2) are not necessarily limited to the aforementioned amino acid residues, but may also be other amino acids equivalent to these amino acid residues.

Other known techniques can be applied to the antigen-binding molecules of the present invention. For example, in order to promote association of the first VH (VH1) and the first VL (VL1) and/or the second VH (VH2) and the second VL (VL2), an amino acid side chain present in the variable region of one of the H chains can be substituted with a larger side chain (knob), and an amino acid side chain present in the opposing variable region of the other H chain can be substituted with a smaller side chain (hole), so that the knob may be arranged in the hole, and association of VH1 and VL1 and/or VH2 and VL2 is promoted; and consequently, association of VH1 and VL2 and/or VH2 and VL1 can be further suppressed.

For example, in the case of human IgG1, in order to make an amino acid side chain in the CH3 region of one H chain a larger side chain (knob), the modifications of Y349C and T366W are made, and in order to make an amino acid side chain in the CH3 region of the other H chain a smaller side chain, the modifications of D356C, T336S, L368A and Y407V are made.

In some embodiments, in the multispecific antigen-binding molecule, an Fc domain is composed of a first Fc-region subunit and a second Fc-region subunit that are capable of stable association.

In some embodiments, in the multispecific antigen-binding molecule, the Fc domain comprises (e1) or (e2) below:

(e1) the first Fc-region subunit comprising Cys at position 349, Ser at position 366, Ala at position 368 and Val at position 407, and the second Fc-region comprising Cys at position 354 and Trp at position 366;

(e2) the first Fc-region subunit comprising Glu at position 439, and the second Fc-region comprising Lys at position 356, wherein the amino acid positions are numbered according to EU numbering.

For example, the knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Still other known techniques can be applied to the antigen-binding molecules of the present invention. A target antigen-binding molecule can be efficiently prepared by complementary association of CH3 using strand-exchange engineered domain CH3, in which a portion of CH3 of one H chain of an antigen-binding molecule is changed to a sequence derived from IgA corresponding to that portion, and a complementary portion of CH3 of the other H chain is introduced with a sequence derived from IgA corresponding to that portion (Protein Engineering Design & Selection, 23: 195-202, 2010).

Still other known techniques can be applied to the antigen-binding molecules of the present invention. When producing bispecific antibodies, a target bispecific antibody can be prepared by, for example, imparting a difference in isoelectric point by making different amino acid modifications to each of the variable regions of the two types of H chains, and utilizing that difference in isoelectric point for purification by ion exchange chromatography (WO 2007/114325).

The technique of modifying the amino acid residue at position 435 according to EU numbering, which is a site related to binding between IgG and Protein A, to an amino acid having a different binding strength toward Protein A, such as Arg, may also be used on the antigen-binding molecule of the present invention in combination with the aforementioned techniques. By using this technique, the interaction between the H chain and Protein A can be changed, and only heterodimeric antigen-binding molecules can be efficiently purified using a Protein A column. This technique can also be used independently without combining with the aforementioned techniques.

The modifications of the present invention can be used on antigen-binding molecules such as the one below, for example, an antigen-binding molecule having a structure in which, to promote association of a first VH (VH1) and a first VL (VL1) and/or a second VH (VH2) and a second VL (VL2), VH1 is linked to an Fc region through a first CH1 and VL1 is linked to a first CL, and VH2 is linked to another Fc region through a second CL and VL2 is linked to a second CH1 (WO 09/80254).

A plurality, for example, two or more of the aforementioned known techniques can be used in combination for the antigen-binding molecule of the present invention.

Furthermore, the antigen-binding molecule of the present invention may be prepared based on an antibody to which modifications of the aforementioned known techniques have been made.

In addition, the present invention provides a method for producing an antigen-binding molecule in which association between a heavy chain and a light chain is regulated. A preferred embodiment of the production method of the present invention is a method for producing an antigen-binding molecule in which association between a heavy chain and a light chain is regulated, comprising:

(1) modifying nucleic acids encoding CH1 and CL such that one set or two or more sets of amino acid residues selected from the group consisting of the sets of amino acid residues shown in (a) to (c) below are amino acid residues that electrostatically repel each other:

(a) an amino acid residue in a heavy chain constant region (CH1) which is at position 175 according to EU numbering, and an amino acid residue in a light chain constant region (CL) which is at position 131 according to Kabat numbering, (b) an amino acid residue in CH1 which is at position 175 according to EU numbering, and an amino acid residue in CL which is at position 160 according to Kabat numbering, (c) amino acid residues in CH1 which are at positions 175 according to EU numbering, and amino acid residues in CL which are at positions 131 and 160 according to Kabat numbering.

(d) amino acid residues in CH1 which are at positions 147 and 175 according to EU numbering, and amino acid residues in CL which are at positions 131 and 160 according to Kabat numbering.

(2) introducing the modified nucleic acids into a host cell and culturing the host cell such that the nucleic acids are expressed; and (3) collecting an antigen-binding molecule from a cell culture of the host cell.

In addition, the present invention relates to a production method comprising, in the aforementioned step (1), modifying the nucleic acids so that the amino acid residues that electrically repel each other are selected from among the amino acid residues contained in either of the groups of the aforementioned (X) and (Y).

Moreover, the present invention relates to a production method comprising in the aforementioned step (1), modifying the nucleic acids so that two or more amino acid residues that form the interface of the VH and VL are amino acid residues that electrically repel each other. Preferably, the amino acid residues that electrically repel each other are any set of amino acid residues selected from the group consisting of, for example, the sets of amino acid residues shown in (a) and (b) below:

(a) the amino acid residue contained in the VH at position 39 according to Kabat numbering, and the amino acid residue contained in the VL at position 38 according to Kabat numbering; or (b) the amino acid residue contained in the VH at position 45 according to Kabat numbering, and the amino acid residue contained in the VL at position 44 according to Kabat numbering.

The aforementioned amino acid residues which electrically repel each other are preferably selected from the amino acid residues contained in either set of the aforementioned (X) and (Y).

In addition, the present invention provides a method for regulating association of heavy and light chains of an antigen-binding molecule. A preferred embodiment of the method for regulating association of the present invention is a method for regulating association of heavy and light chains of an antigen-binding molecule, comprising modifying nucleic acids such that one set or two or more sets of amino acid residues selected from the group consisting of the sets of amino acid residues shown in (a) to (c) below are amino acid residues that electrostatically repel each other:

(a) an amino acid residue in a heavy chain constant region (CH1) which is at position 175 according to EU numbering, and an amino acid residue in a light chain constant region (CL) which is at position 131 according to EU numbering, (b) an amino acid residue in CH1 which is at position 175 according to EU numbering, and an amino acid residue in CL which is at position 160 according to EU numbering, (c) amino acid residues in CH1 which are at positions 175 according to EU numbering, and amino acid residues in CL which are at positions 131 and 160 according to EU numbering.

(d) amino acid residues in CH1 which are at positions 147 and 175 according to EU numbering, and amino acid residues in CL which are at positions 131 and 160 according to EU numbering.

In addition, the present invention relates to a method for regulating association comprising, in the aforementioned step (1), modifying the nucleic acids such that the amino acid residues that electrostatically repel each other are selected from the amino acid residues included in the aforementioned group of either (X) or (Y).

Moreover, the present invention relates to a method for regulating association comprising, in the aforementioned step (1), modifying the nucleic acids such that two or more amino acid residues that form a VH-VL interface are amino acid residues that electrostatically repel each other. Here, the amino acid residues that electrostatically repel each other are preferably any one set of amino acid residues selected from the group consisting of, for example, the sets of amino acid residues shown in (a) and (b) below:

(a) an amino acid residue in VH that is at position 39 according to Kabat numbering, and an amino acid residue in VL that is at position 38 according to Kabat numbering, (b) an amino acid residue in VH that is at position 45 according to Kabat numbering, and an amino acid residue in VL that is at position 44 according to Kabat numbering.

According to the method for regulating association of the present invention, a desired bispecific antibody can be obtained preferentially and efficiently as previously described. Namely, a desired heteromeric multimer in the form of a bispecific antibody can be efficiently formed from a monomer mixture.

The phrase "modify nucleic acids" in the above-mentioned methods of the present invention refers to modifying nucleic acids so that they correspond to amino acid residues introduced by the "modifications" of the present invention. More specifically, it refers to modifying the nucleic acids encoding the original (pre-modified) amino acid residues to the nucleic acids encoding the amino acid residues that are to be introduced by the modification. Ordinarily, it means performing gene manipulations or mutation treatment that would result in at least one nucleotide insertion, deletion, or substitution to the original nucleic acid so that codons encoding amino acid residues of interest is formed. More specifically, codons encoding the original amino acid residues are substituted with codons encoding the amino acid residues that are to be introduced by the modification. Such nucleic acid modification can be performed suitably by those skilled in the art using known techniques such as site-specific mutagenesis and PCR mutagenesis. In addition, the present invention provides nucleic acids that encode an antigen-binding molecule of the present invention. Moreover, vectors carrying the nucleic acids are also included in the present invention.

In some embodiments, the Fc domain of the multispecific antigen-binding molecule consists of a pair of polypeptide chains comprising heavy chain domains of an immunoglobulin molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other. In one embodiment the multispecific antigen-binding molecule described herein comprises not more than one Fc domain.

In one embodiment described herein, the Fc domain of the multispecific-antigen binding molecule is an IgG Fc domain. In a particular embodiment, the Fc domain is an IgG1 Fc domain. In another embodiment, the Fc domain is an IgG1 Fc domain. In a further particular embodiment, the Fc domain is a human IgG1 Fc region.

In some embodiments, the present disclosure provides a multispecific antigen-binding molecule further comprising an Fc domain which exhibits reduced binding affinity to human Fc gamma receptor, as compared to a native human IgG1 Fc domain, wherein the Fc domain further exhibits stronger FcRn binding affinity to human FcRn, as compared to a native human IgG1 Fc domain.

In some embodiments, the present disclosure provides a multispecific antigen-binding molecule further comprising an Fc domain which exhibits reduced binding affinity to human Fc gamma receptor, as compared to a native human IgG1 Fc domain, wherein the first and/or second Fc region subunit comprised in the Fc domain comprises Leu at position 428, Ala at position 434, Arg at position 438, and Glu at position 440, wherein the amino acid positions are numbered according to EU numbering.

In some embodiments, in the multispecific antigen-binding molecule, the Fc domain further exhibits stronger FcRn binding affinity to human FcRn, as compared to a native human IgG1 Fc domain.

In some embodiments, in the multispecific antigen-binding molecule, the first and/or second Fc-region subunit comprises Leu at position 428, Ala at position 434, Arg at position 438, and Glu at position 440, wherein the amino acid positions are numbered according to EU numbering.

IgG-type bispecific antibodies are secreted by introducing the genes of L chains and H chains constituting the two types of IgGs of interest, i.e. a total of four genes, into cells, and co-expressing them. However, the number of combinations of H and L chains of IgG that can be produced by these methods is theoretically ten combinations. Accordingly, it is difficult to purify an IgG comprising the desired combination of H and L chains from ten types of IgGs. Furthermore, theoretically the amount of secretion of the IgG having the desired combination will decrease remarkably, and therefore large-scale culturing will be necessary, and production costs will increase further.

Therefore, techniques for promoting the association among H chains and between L and H chains having the desired combinations can be applied to the multispecific antigen-binding molecules of the present invention.

For example, techniques for suppressing undesired H-chain association by introducing electrostatic repulsion at the interface of the second constant region or the third constant region of the antibody H chain (CH2 or CH3) can be applied to multispecific antibody association (WO2006/106905).

In the present invention, amino acid residues subjected to modification are not limited to the above-mentioned amino acid residues of the antibody variable regions or the antibody constant regions. Those skilled in the art can identify the amino acid residues that form an interface in mutant polypeptides or heteromultimers by homology modeling and such using commercially available software; and amino acid residues of these positions can then be subjected to modification so as to regulate the association.

Other known techniques can also be used for the association of multispecific antibodies of the present invention. Fc region-containing polypeptides comprising different amino acids can be efficiently associated with each other by substituting an amino acid side chain present in one of the H-chain Fc regions of the antibody with a larger side chain (knob), and substituting an amino acid side chain present in the corresponding Fc region of the other H chain with a smaller side chain (hole) to allow placement of the knob within the hole. The knob(s)-into-hole(s) method is discussed elsewhere herein.

In addition, other known techniques can also be used for formation of multispecific antibodies of the present invention. Association of polypeptides having different sequences can be induced efficiently by complementary association of CH3 using a strand-exchange engineered domain CH3 produced by changing part of one of the H-chain CH3s of an antibody to a corresponding IgA-derived sequence and introducing a corresponding IgA-derived sequence into the complementary portion of the other H-chain CH3 (Protein Engineering Design & Selection, 23; 195-202, 2010). This known technique can also be used to efficiently form multispecific antibodies of interest.

In addition, technologies for antibody production using association of antibody CH1 and CL and association of VH and VL as described in WO 2011/028952, WO2014/018572, and Nat Biotechnol. 2014 February; 32(2):191-8; technologies for producing bispecific antibodies using separately prepared monoclonal antibodies in combination (Fab Arm Exchange) as described in WO2008/119353 and WO2011/131746; technologies for regulating association between antibody heavy-chain CH3s as described in WO2012/058768 and WO2013/063702; technologies for producing bispecific antibodies composed of two types of light chains and one type of heavy chain as described in WO2012/023053; technologies for producing bispecific antibodies using two bacterial cell strains that individually express one of the chains of an antibody comprising a single H chain and a single L chain as described by Christoph et al. (Nature Biotechnology Vol. 31, p 753-758 (2013)); and such may be used for the formation of multispecific antibodies.

Alternatively, even when a multispecific antibody of interest cannot be formed efficiently, a multispecific antibody of the present invention can be obtained by separating and purifying the multispecific antibody of interest from the produced antibodies. For example, a method for enabling purification of two types of homomeric forms and the heteromeric antibody of interest by ion-exchange chromatography by imparting a difference in isoelectric points by introducing amino acid substitutions into the variable regions of the two types of H chains has been reported (WO2007114325). To date, as a method for purifying heteromeric antibodies, methods using Protein A to purify a heterodimeric antibody comprising a mouse IgG2a H chain that binds to Protein A and a rat IgG2b H chain that does not bind to Protein A have been reported (WO98050431 and WO95033844). Furthermore, a heterodimeric antibody can be purified efficiently on its own by using H chains comprising substitution of amino acid residues at EU numbering positions 435 and 436, which is the IgG-Protein A binding site, with Tyr, His, or such which are amino acids that yield a different Protein A affinity, or using H chains with a different protein A affinity obtained according to the method of Reference Example 5, to change the interaction of each of the H chains with Protein A, and then using a Protein A column.

Furthermore, an Fc region whose Fc region C-terminal heterogeneity has been improved can be appropriately used as an Fc region of the present invention. More specifically, the present invention provides Fc regions produced by deleting glycine at position 446 and lysine at position 447 as specified by EU numbering from the amino acid sequences of two polypeptides constituting an Fc region derived from IgG1, IgG2, IgG3, or IgG4.

A plurality, such as two or more, of these technologies can be used in combination. Furthermore, these technologies can be appropriately and separately applied to the two H chains to be associated. Furthermore, these techniques can be used in combination with the above-mentioned Fc region which has reduced binding activity to an Fcγ receptor. Furthermore, an antigen-binding molecule of the present invention may be a molecule produced separately so that it has the same amino acid sequence, based on the antigen-binding molecule subjected to the above-described modifications.

In some embodiments, the multispecific antigen-binding molecule comprises one or more of the amino acid residues of (i) to (xii) below:

(i) glutamic acid or lysine at position 175 (EU numbering) in the heavy-chain constant region;

(ii) glutamic acid at position 147 (EU numbering) in the heavy-chain constant region;

(iii) glutamic acid or lysine at position 131 (Kabat numbering) in the light-chain constant region;

(iv) glutamic acid or lysine at position 160 (Kabat numbering) in the light-chain constant region;

(v) arginine at position 235 (EU numbering) in the heavy-chain constant region;

(vi) arginine at position 236 (EU numbering) in the heavy-chain constant region;

(vii) lysine at position 356 (EU numbering) in the heavy-chain constant region;

(viii) leucine at position 428 (EU numbering) in the heavy-chain constant region;

(ix) alanine at position 434 (EU numbering) in the heavy-chain constant region;

(x) arginine at position 438 (EU numbering) in the heavy-chain constant region;

(xi) glutamic acid at position 439 (EU numbering) in the heavy-chain constant region;

(xii) glutamic acid at position 440 (EU numbering) in the heavy-chain constant region.

In some embodiments, the multispecific antigen-binding molecule is a bispecific antibody comprising:
  a first heavy chain comprising lysine at position 175 (EU numbering), arginine at position 235 (EU numbering), arginine at position 236 (EU numbering), leucine at position 428 (EU numbering), alanine at position 434 (EU numbering), arginine at position 438 (EU numbering), glutamic acid at position 439 (EU numbering), and glutamic acid at position 440 (EU numbering);
  a first light chain comprising glutamic acid at position 131 (Kabat numbering) and glutamic acid at position 160 (Kabat numbering);
  a second heavy chain comprising glutamic acid at position 147 (EU numbering), glutamic acid at position 175 (EU numbering), arginine at position 235 (EU numbering), arginine at position 236 (EU numbering), lysine at position 356 (EU numbering), leucine at position 428 (EU numbering), alanine at position 434 (EU numbering), arginine at position 438 (EU numbering), and glutamic acid at position 440 (EU numbering); and a second light chain comprising lysine acid at position 131 (Kabat numbering) and lysine at position 160 (Kabat numbering).

In some embodiments, in the multispecific antigen-binding molecule:

the first heavy chain further comprises glutamic acid at position 419 (EU numbering), and proline at position 445 (EU numbering), and an amino acid deletion at positions 446 and 447 (EU numbering); and the second heavy chain further comprises lysine at position 196 (EU numbering), proline at position 445 (EU numbering), and an amino acid deletion at positions 446 and 447 (EU numbering).

In some embodiments, in the multispecific antigen-binding molecule:

the first heavy chain further comprises glycine at position 16 (Kabat numbering), alanine at position 32 (Kabat numbering), valine at position 35a (Kabat numbering), alanine at position 50 (Kabat numbering), lysine at position 61 (Kabat numbering), glutamic acid at position 64 (Kabat numbering), threonine at position 73 (Kabat numbering), glutamic acid at position 95 (Kabat numbering), and valine at position 102 (Kabat numbering);

the first light chain further comprises glutamic acid at position 28 (Kabat numbering), tyrosine at position 55 (Kabat numbering), glutamic acid or tyrosine at position 56 (Kabat numbering), glutamic acid at position 92 (Kabat numbering), valine at position 94 (Kabat numbering), and alanine at position 95a (Kabat numbering);

the second heavy chain further comprises glutamic acid at position 28 (Kabat numbering), alanine or glutamic acid at position 30 (Kabat numbering), glutamic acid at position 31 (Kabat numbering), tryptophan at position 32 (Kabat numbering), phenylalanine at position 34 (Kabat numbering), and methionine at position 35 (Kabat numbering), serine at position 35a (Kabat numbering), serine at position 50 (Kabat numbering), glutamic acid or glycine at position 61 (Kabat numbering), glutamic acid at position 64 (Kabat numbering), and glutamic acid at position 65 (Kabat numbering); and the second light chain further comprises threonine at position 25 (Kabat numbering), lysine at position 54 (Kabat numbering), glutamic acid at position 56 (Kabat numbering), leucine at position 67 (Kabat numbering), glutamine at position 79 (Kabat numbering), and lysine at position 94 (Kabat numbering).

Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178: 1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about +/−3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249: 533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

In a preferred embodiment, the antibodies mentioned above may have their first H-chain CH3 region and second H-chain CH3 region crosslinked by disulfide bonds.

Multispecific antigen-binding molecules prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purincation an antibody, ligand, receptor or antigen can be used to which the multispecific antigen-binding molecule binds. For example, for affinity chromatography purincation of multispecific antigen-binding molecules of the invention, a matrix with protein A or protein G may be used. Sequential Protein A or G affinity chromatography and size exclusion chromatography can be used to isolate a multispecific antigen-binding molecule. The purity of the multispecific antigen-binding molecule can be determined by any of a variety of well-known analytical methods including gel electrophoresis, high pressure liquid chromatography, and the like.

Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Recombinant Methods and Compositions

Antibodies may be produced using recombinant methods and compositions, e.g., as described in U.S. Pat. No. 4,816, 567. In one embodiment, isolated nucleic acid encoding an anti-HLA-DQ2.5 antigen-binding molecule (antibody) described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp2/0 cell). In one embodiment, a method of making an anti-HLA-DQ2.5 antigen-binding molecule (antibody) is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-HLA-DQ2.5 antigen-binding molecule (antibody), nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gemgross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR⁻ CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

Assays

Anti-HLA-DQ2.5 antigen-binding molecules (antibodies) provided herein may be identified, screened for, or characterized for their physical/chemical properties and/or biological activities by various assays known in the art.

Binding Assays and Other Assays

In one aspect, an antibody of the invention is tested for its antigen binding activity, e.g., by known methods such as ELISA, Western blot, etc.

In another aspect, competition assays may be used to identify an antibody that competes with, for example, any of the above-mentioned antibodies for binding to HLA-DQ2.5 (or HLA-DQ2.5/gluten peptide complex). In certain embodiments, such a competing antibody binds to the same epitope (e.g., a linear or a conformational epitope) that is bound by the above-mentioned antibodies. Detailed exemplary methods for mapping an epitope to which an antibody binds are provided in Morris (1996) "Epitope Mapping Protocols," in Methods in Molecular Biology vol. 66 (Humana Press, Totowa, N.J.).

In an exemplary competition assay, immobilized HLA-DQ2.5 (or HLA-DQ2.5/gluten peptide complex) is incubated in a solution comprising a first labeled antibody that binds to HLA-DQ2.5 (or HLA-DQ2.5/gluten peptide complex) and a second unlabeled antibody that is being tested for its ability to compete with the first antibody for binding to HLA-DQ2.5 (or HLA-DQ2.5/gluten peptide complex). The second antibody may be present in a hybridoma supernatant. As a control, immobilized HLA-DQ2.5 (or HLA-DQ2.5/gluten peptide complex) is incubated in a solution comprising the first labeled antibody but not the second unlabeled antibody. After incubation under conditions permissive for binding of the first antibody to HLA-DQ2.5 (or HLA-DQ2.5/gluten peptide complex), excess unbound antibody is removed, and the amount of label associated with immobilized HLA-DQ2.5 (or HLA-DQ2.5/gluten peptide complex) is measured. If the amount of label associated with immobilized HLA-DQ2.5 (or HLA-DQ2.5/gluten peptide complex) is substantially reduced in the test sample relative to the control sample, then that indicates that the second antibody is competing with the first antibody for binding to HLA-DQ2.5 (or HLA-DQ2.5/gluten peptide complex). See Harlow and Lane (1988) Antibodies: A Laboratory Manual ch. 14 (Cold Spring Harbor Laboratory, Cold Spring Harbor, N.Y.).

Animals such as rabbits, mice, rats, and other animals suitable for immunization are immunized with an antigen (e.g., HLA-DQ2.5 or HLA-DQ2.5/gluten peptide complex). The antigen may be prepared as a recombinant protein using any methods, for example, as mentioned herein. Antibody-containing samples such as the blood and spleen are collected from the immunized animals. For B cell selection, for example, a biotinylated antigen is prepared, and antigen-binding B cells are bound by the biotinylated antigen, and the cells are subjected to cell sorting and culturing for selection. Specific binding of the cells to the antigen may be evaluated by any suitable method such as the ELISA method. This method may also be used for assessing the absence of cross-reactivity towards antigens of no interest. To isolate or determine the sequence of the selected antibody, for example, RNAs are purified from the cells, and DNAs encoding regions of the antibody are prepared by reverse transcription of the RNAs and PCR amplification. Furthermore, cloned antibody genes may be expressed in suitable cells, and the antibody may be purified from the culture supernatants for further analysis.

To test whether an anti-HLA-DQ2.5 antigen-binding molecule (antibody) binds to an antigen of interest (e.g., a complex formed by HLA-DQ2.5 and a gluten peptide such as those described herein), any methods for assessing the binding can be used. For example, when an FACS-based cell sorting method is used, cells expressing the antigen are incubated with the tested antibody, and then a suitable secondary antibody against the tested (i.e., primary) antibody is added and incubated. The binding between the antigen and the tested antibody is detected by FACS analysis using, for example, a chromogenic/fluorescent label attached to the secondary antibody (for example, as mentioned herein). Alternatively, any of the measurement methods mentioned in "Antibody Affinity" in this specification can be utilized. For example, the measurement of Kd by a BIACORE (registered trademark) surface plasmon resonance assay can be used for assessing the binding between the tested antibody and the antigen of interest mentioned herein).

In certain embodiments, the method of the present invention further comprises: testing whether the antibody has neutralizing activity against the binding between HLA-DQ2.5 (or HLA-DQ2.5/gluten peptide complex) and TCR (or the interaction between HLA-DQ2.5 (or HLA-DQ2.5/gluten peptide complex) and HLA-DQ2.5-restricted CD4+ T cells); and selecting the antibody that has the neutralizing activity. In certain embodiments, the method of the present invention further comprises: testing whether the antibody has neutralizing activity against the binding between HLA-DQ2.2 (or HLA-DQ2.2/gluten peptide complex) and TCR (or the interaction between HLA-DQ2.2 (or HLA-DQ2.2/gluten peptide complex) and HLA-DQ2.2-restricted CD4+ T cells); and selecting the antibody that has the neutralizing activity. These steps can be performed in the presence of a gluten peptide such as those described herein, i.e., using HLA-DQ2.5 or HLA-DQ2.2 bound by the peptide. The neutralizing activity can be assessed, for example, as mentioned herein. Briefly, beads such as streptavidin-coated yellow particles are appropriately prepared, and soluble HLA-DQ bound by a peptide is added to the beads for immobilization on a plate. The plate is washed and blocked, and the antibody is added thereto and incubated. When the binding between HLA-DQ2.5 (or HLA-DQ2.5/gluten peptide complex) and TCR is assessed, for example, D2 TCR tetramer-PE may be added and incubated. Binding between the two may be evaluated based on the chromogenic/fluorescent label of TCR bound by HLA-DQ2.5 (or HLA-DQ2.5/gluten peptide complex).

In some embodiments, the multispecific antigen-binding molecule blocks the interaction between HLA-DQ2.5/gluten peptide complex and HLA-DQ2.5/gluten peptide-restricted CD4+ T cell. In some embodiments, the multispecific antigen-binding molecule blocks the interaction between HLA-DQ2.2/gluten peptide complex and HLA-DQ2.2/gluten peptide-restricted CD4+ T cell. In this context, the gluten peptide is the peptide in the complex bound by any of the antigen-binding molecules/domains described above.

In some embodiments, the gluten peptide is selected from the group consisting of alpha 1 gliadin peptide, alpha 1b gliadin peptide, alpha 2 gliadin peptide, omega 1 gliadin peptide, omega 2 gliadin peptide, gamma 1 gliadin peptide, gamma 2 gliadin peptide, gamma 3 gliadin peptide, gamma 4a gliadin peptide, gamma 4d gliadin peptide, and BC Hordein peptide.

In some embodiments, the multispecific antigen-binding molecule has substantially no binding activity to HLA-DP, HLA-DR, HLA-DQ5.1, HLA-DQ6.3, HLA-DQ7.3, HLA-DQ7.5, and HLA-DQ8.

In some embodiments, the antigen-binding molecule of the invention has enhanced binding activity to a complex formed by HLA-DQ2.5 and a gluten peptide. In this context, the gluten peptide may be any of the gluten peptides described above. The degree of enhancement may be determined as compared to the binding activity to a complex formed by HLA-DQ2.5 and an irrelevant peptide, or to a cell without the complex of interest, e.g., a HLA-DQ2.5 positive PBMC B cell and/or a Ba/F3 cell that expresses HLA-DQ2.5 or HLA-DQ2.2.

The bispecific antibody of the invention comprises a heavy chain and a light chain of a first arm/half-antibody and a heavy chain and a light chain of a second arm/half-antibody. The term "arm" or "half-antibody" refers to a portion of an antibody comprising one heavy chain and one light chain. In some embodiments, the bispecific antibody comprises VH (heavy-chain variable region) and VL (light-chain variable region) of a first arm/half-antibody and VH and VL of a second arm/half-antibody. In some embodiments, the bispecific antibody comprises HCDR1, HCDR2, HCDR3, LCDR1, LCDR2, and LCDR3 of a first arm/half-antibody and HCDR1, HCDR2, HCDR3, LCDR1, LCDR2, and LCDR3 of a second arm/half-antibody.

In some embodiments, for bispecific antibodies of the invention, the first arm/half-antibody is derived from the DQN0344xx (DQN0344Hx/DQN0344Lx) described herein and the second arm/half-antibody is derived from DQN0385ee (DQN0385He/DQN0385Le) described herein. The sequence ID numbers (SEQ ID NOs) of VH, VL, HCDR1, HCDR2, HCDR3, LCDR1, LCDR2, LCDR3, and full-length heavy (H) and light (L) chains of the bispecific antibodies of the invention are shown in Tables 2-3 to 2-6 (below).

In some embodiments, the antibody of the invention comprises: HCDR1 comprising the sequence of SEQ ID NO: 129 or 164; HCDR2 comprising the sequence of SEQ ID NO: 130 or 165; and HCDR3 comprising the sequence of SEQ ID NO: 131 or 166.

In some embodiments, the antibody of the invention comprises: LCDR1 comprising the sequence of SEQ ID NO: 132 or 167; LCDR2 comprising the sequence of SEQ ID NO: 133 or 168; and LCDR3 comprising the sequence of SEQ ID NO: 134 or 169.

In some embodiments, the antibody of the invention comprises a heavy chain variable region comprising the sequence of SEQ ID NO: 88 or 89.

In some embodiments, the antibody of the invention comprises a heavy chain constant region comprising the sequence of SEQ ID NO: 105 or 162.

In some embodiments, the antibody of the invention comprises a light chain variable region comprising the sequence of SEQ ID NO: 90 or 91.

In some embodiments, the antibody of the invention comprises a light chain constant region comprising the sequence of SEQ ID NO: 106.

In some embodiments, the antibody of the invention comprises: a (full-length) heavy chain comprising the sequence of SEQ ID NO: 41, 42, 44, or 45.

In some embodiments, the antibody of the invention comprises: a (full-length) light chain comprising the sequence of SEQ ID NO: 43 or 46.

In some embodiments, the antibody of the invention comprises: HCDR1 comprising the sequence of SEQ ID NO: 135, 144, 147, 153, 156, or 159; HCDR2 comprising the sequence of SEQ ID NO: 136, 145, 148, 154, 157, or 160; and HCDR3 comprising the sequence of SEQ ID NO: 137, 146, 149, 155, 158, or 161.

In some embodiments, the antibody of the invention comprises: LCDR1 comprising the sequence of SEQ ID NO: 138, 141, or 150; LCDR2 comprising the sequence of SEQ ID NO: 139, 142, or 151; and LCDR3 comprising the sequence of SEQ ID NO: 140, 143, or 152.

In some embodiments, the antibody of the invention comprises a heavy chain variable region comprising the sequence of SEQ ID NO: 92, 93, 94, 95, 96, or 97.

In some embodiments, the antibody of the invention comprises a heavy chain constant region comprising the sequence of SEQ ID NO: 104 or 163.

In some embodiments, the antibody of the invention comprises a light chain variable region comprising the sequence of SEQ ID NO: 98, 99, or 100.

In some embodiments, the antibody of the invention comprises a light chain constant region comprising the sequence of SEQ ID NO: 107.

In some embodiments, the antibody of the invention comprises: a (full-length) heavy chain comprising the sequence of SEQ ID NO: 53, 54, 57, 58, 59, 60, 62, 63, 64, 65, 66, or 67.

In some embodiments, the antibody of the invention comprises: a (full-length) light chain comprising the sequence of SEQ ID NO: 55, 56, or 61.

Specific sequences of the full-length H and L chains for the arms/half-antibodies (comprised in the bispecific antibodies of the invention) are shown in Table 1-2.

TABLE 1-2

Full-length H and L chains for the bispecific antibodies
The H (or L) chains comprise, from the N-terminus to C-terminus, HCDR1, HCDR2, and HCDR3 (or LCDR1, LCDR2, and LCDR3) which are underlined in this table.

| SEQ ID NO: | H/L Chain; Arm | Sequence |
|---|---|---|
| 41 | H chain for DQN0344H0976/ L0591 | QVQLVESGGGVVQPGGSLRLSCAASGFTFS<u>SAYWMVW</u> VRQAPGQGLEWMG<u>AVYGGSDTTYYAKWTEG</u>RFTISRD TSKNTLYLQMNSLRAEDTAVYYCAR<u>EPLNYYYYGELNL</u> WGQGTLVTVSSASTKGPSVFPLAPSSKSTSGGTAALGC LVKDYFPEPVTVSWNSGALTSGVHTFPAVLKSSGLYSLS SVVTVPSSSLGTQTYICNVNHKPSNTKVDKRVEPKSCDK THTCPPCPAPELRRGPSVFLFPPKPKDTLMISRTPEVTC VVVDVSHEDPEVKFNVVYVDGVEVHNAKTKPREEQYNS TYRWSVLTVLHQDWLNGKEYKCKVSNKALPAPIEKTISK AKGQPREPQVYTLPPSREEMTKNQVSLTCLVKGFYPSDI AVEWESNGQPENNYKTTPPVLDSDGSFFLYSKLTVDKS RWQEGNVFSCSVLHEALHAHYTREELSLSP |
| 42 | H chain for DQN0344H0976/ L0591 | QVQLVESGGGVVQPGGSLRLSCAASGFTFS<u>SAYWMVW</u> VRQAPGQGLEWMG<u>AVYGGSDTTYYAKWTEG</u>RFTISRD TSKNTLYLQMNSLRAEDTAVYYCAREPLNYYYYGELNL WGQGTLVTVSSASTKGPSVFPLAPSSKSTSGGTAALGC LVKDYFPEPVTVSWNSGALTSGVHTFPAVLKSSGLYSLS SVVTVPSSSLGTQTYICNVNHKPSNTKVDKRVEPKSCDK THTCPPCPAPELRRGPSVFLFPPKPKDTLMISRTPEVTC VVVDVSHEDPEVKFNINYVDGVEVHNAKTKPREEQYNS TYRVVSVLTVLHQDWLNGKEYKCKVSNKALPAPIEKTISK AKGQPREPQVYTLPPSREEMTKNQVSLTCLVKGFYPSDI AVEWESNGQPENNYKTTPPVLDSDGSFFLYSKLTVDKS RWQEGNVFSCSVLHEALHAHYTREELSLSP |
| 43 | L chain for DQN0344H0976/ L0591 | DIQMTQSPSSLSASVGDRVTITCQ<u>ATEEIYSGLA</u>WYQQK PGKAPKLLIY<u>YVSTLYE</u>GIPARFSGSGSGTDFTLTISSLEP EDFAVYYCQ<u>TYEDVSAVT</u>FGQGTKVEIKRTVAAPSVFIFP PSDEQLKSGTAEVVCLLNNFYPREAKVQWKVDNALQSG NSEESVTEQDSKDSTYSLSSTLTLSKADYEKHKVYACEV THQGLSSPVTKSFNRGEC |
| 44 | H chain for DQN0344H1013/ L0620 | QVQLVESGGGVVQPGRSLRLSCAASGFTFS<u>SAYWMVW</u> VRQAPGQGLEWMG<u>AVYGGSDTTYYAKWTEG</u>RFTISRD TSKNTLYLQMNSLRAEDTAVYYCAREP<u>LNYYYYGELNV</u> WGQGTLVTVSSASTKGPSVFPLAPSSKSTSGGTAALGC LVKDYFPEPVTVSWNSGALTSGVHTFPAVLKSSGLYSLS SVVTVPSSSLGTQTYICNVNHKPSNTKVDKRVEPKSCDK THTCPPCPAPELRRGPSVFLFPPKPKDTLMISRTPEVTC VVVDVSHEDPEVKFNVVYVDGVEVHNAKTKPREEQYNS TYRVVSVLTVLHQDWLNGKEYKCKVSNKALPAPIEKTISK AKGQPREPQVYTLPPSREEMTKNQVSLTCLVKGFYPSDI AVEWESNGQPENNYKTTPPVLDSDGSFFLYSKLTVDKS RWQEGNVFSCSVLHEALHAHYTREELSLSP |

TABLE 1-2-continued

Full-length H and L chains for the bispecific antibodies
The H (or L) chains comprise, from the N-terminus to C-terminus, HCDR1, HCDR2,
and HCDR3 (or LCDR1, LCDR2, and LCDR3) which are underlined in this table.

| SEQ ID NO: | H/L Chain; Arm | Sequence |
| --- | --- | --- |
| 45 | H chain for DQN0344H1013/ L0620 | QVQLVESGGGVVQPGRSLRLSCAASGFTFS<u>SAYWMVW</u>VRQAPGQGLEWMG<u>AVYGGSDTTYYAKWTEG</u>RFTISRDTSKNTLYLQMNSLRAEDTAVYYCAR<u>EPLNYYYGELNV</u>WGQGTLVTVSSASTKGPSVFPLAPSSKSTSGGTAALGCLVKDYFPEPVTVSWNSGALTSGVHTFPAVLKSSGLYSLSSVVTVPSSSLGTQTYICNVNHKPSNTKVDKRVEPKSCDKTHTCPPCPAPELRRGPSVFLFPPKPKDTLMISRTPEVTCVVVDVSHEDPEVKFNVVYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQEGNVFSCSVLHEALHAHYTREELSLSP |
| 46 | L chain for DQN0344H1013/ L0620 | DIQMTQSPSSLSASVGDRVTITC<u>QATENIYSGLA</u>VVYQQKPGKAPKLLIY<u>YVSTLAYG</u>IPARFSGSGSGTDFTLTISSLEPEDFAVYYC<u>QTYEDVSAVT</u>FGQGTKVEIKRTVAAPSVFIFPPSDEQLKSGTAEVVCLLNNFYPREAKVQWKVDNALQSGNSEESVTEQDSKDSTYSLSSTLTLSKADYEKHKVYACEVTHQGLSSPVTKSFNRGEC |
| 53 | H chain for DQN0385H1270/ L0722 and DQN0385H1270/ L0681 | QVQLVESGGGVVQPGRSLRLSCAASGFTFS<u>EWYFMSW</u>VRQAPGKGLEWVA<u>SIDTGSGSIDYAEWVEG</u>RFTISRDNSKNTLYLQMNSLRAEDTAVYYCAR<u>DIGIDYNF</u>WGPGTLVTVSSASTKGPSVFPLAPSSKSTSGGTAALGCLVEDYFPEPVTVSWNSGALTSGVHTFPAVLESSGLYSLSSVVTVPSSSLGTKTYICNVNHKPSNTKVDKRVEPKSCDKTHTCPPCPAPELRRGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRKEMTKNQVSLTCLVKGFYPSDIAVEWESNGQPENNYKTTPPVLDSDGSFFLYSKLTVDKSRWQQGNVFSCSVLHEALHAHYTRKELSLSP |
| 54 | H chain for DQN0385H1270/ L0722 and DQN0385H1270/ L0681 | QVQLVESGGGVVQPGRSLRLSCAASGFTFS<u>EWYFMSW</u>VRQAPGKGLWNVA<u>SIDTGSGSIDYAEWVEG</u>RFTISRDNSKNTLYLQMNSLRAEDTAVYYCAR<u>DIGIDYNF</u>WGPGTLVTVSSASTKGPSVFPLAPSSKSTSGGTAALGCLVEDYFPEPVTVSWNSGALTSGVHTFPAVLESSGLYSLSSVVTVPSSSLGTKTYICNVNHKPSNTKVDKRVEPKSCDKTHTCPPCPAPELRRGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRKEMTKNQVSLTCLVKGFYPSDIAVEWESNGQPENNYKTTPPVLDSDGSFFLYSKLTVDKSRWQQGNVFSCSVLHEALHAHYTRKELSLSP |
| 55 | L chain for DQN0385H1270/ L0722 | DIQMTQSPSSLSASVGDRVTITC<u>QTTQSISSYLN</u>WYQQKPGQPPKLLIY<u>YASTKAEG</u>IPARFSGSGLGTDFTLTISSLQPEDFAVYYC<u>HYGISKVS</u>FGQGTKVEIKRTVAAPSVFIFPPSDEQLKSGTAKVVCLLNNFYPREAKVQWKVDNALQSGNSKESVTEQDSKDSTYSLSSTLTLSKADYEKHKVYACEVTHQGLSSPVTKSFNRGEC |
| 56 | L chain for DQN0385H1270/ L0681 and DQN0385H1352/ L0681 | DIQMTQSPSSLSASVGDRVTITC<u>QTTQSISSYLN</u>WYQQKPGQPPKLLIY<u>YASTKAEG</u>IPARFSGSGLGTDFTLTISSLEPEDFAVYYC<u>HYGISKVS</u>FGQGTKVEIKRTVAAPSVFIFPPSDEQLKSGTAKVVCLLNNFYPREAKVQWKVDNALQSGNSKESVTEQDSKDSTYSLSSTLTLSKADYEKHKVYACEVTHQGLSSPVTKSFNRGEC |
| 57 | H chain for DQN0385H1352/ L0681 | QVQLVESGGGVVQPGRSLRLSCAASGFEFS<u>EWYFMSW</u>VRQAPGKGLEWVA<u>SIDTGSGSIDYAEWVEG</u>RFTISRDNSKNTLYLQMNSLRAEDTAVYYCAR<u>DIGIDYNF</u>WGPGTLVTVSSASTKGPSVFPLAPSSKSTSGGTAALGCLVEDYFPEPVTVSWNSGALTSGVHTFPAVLESSGLYSLSSVVTVPSSSLGTKTYICNVNHKPSNTKVDKRVEPKSCDKTHTCPPCPAPELRRGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREP |

TABLE 1-2-continued

Full-length H and L chains for the bispecific antibodies
The H (or L) chains comprise, from the N-terminus to C-terminus, HCDR1, HCDR2,
and HCDR3 (or LCDR1, LCDR2, and LCDR3) which are underlined in this table.

| SEQ ID NO: | H/L Chain; Arm | Sequence |
|---|---|---|
| | | QVYTLPPSREKMTKNQVSLTCLVKGFYPSDIAVEWESN GQPENNYKTTPPVLDSDGSFFLYSKLTVDKSRWQQGNV FSCSVLHEALHAHYTRKELSLSP |
| 58 | H chain for DQN0385H1352/ L0681 | QVQLVESGGGVVQPGRSLRLSCAASGFEFS<u>EWYFMSW</u> VRQAPGKGLWNVA<u>SIDTGSGSIDYAEWVEG</u>RFTISRDN SKNTLYLQMNSLRAEDTAVYYCAR<u>DIGIDYNF</u>WGPGTLV TVSSASTKGPSVFPLAPSSKSTSGGTAALGCLVEDYFPE PVTVSWNSGALTSGVHTFPAVLESSGLYSLSSVVTVPSS SLGTKTYICNVNHKPSNTKVDKRVEPKSCDKTHTCPPCP APELRRGPSVFLFPPKPKDTLMISRTPEVTCVVVDVSHE DPEVKFNWYVDGVEVHNAKTKPREEQYNSTYRVVSVLT VLHQDWLNGKEYKCKVSNKALPAPIEKTISKAKGQPREP QVYTLPPSREKMTKNQVSLTCLVKGFYPSDIAVEWESN GQPENNYKTTPPVLDSDGSFFLYSKLTVDKSRWQQGNV FSCSVLHEALHAHYTRKELSLSP |
| 59 | H chain for DQN0385H1527/ L0605 | QVQLVESGGGVVQPGRSLRLSCAASGFTFA<u>SWYFMSW</u> VRQAPGKGLEWVA<u>SIDTGSGSIDYAEWVEG</u>RFTISRDN SKNTLYLQMNSLRAEDTAVYYCAR<u>DIGIDYNF</u>WGPGTLV TVSSASTKGPSVFPLAPSSKSTSGGTAALGCLVEDYFPE PVTVSWNSGALTSGVHTFPAVLESSGLYSLSSVVTVPSS SLGTKTYICNVNHKPSNTKVDKRVEPKSCDKTHTCPPCP APELRRGPSVFLFPPKPKDTLMISRTPEVTCVVVDVSHE DPEVKFNWYVDGVEVHNAKTKPREEQYNSTYRVVSVLT VLHQDWLNGKEYKCKVSNKALPAPIEKTISKAKGQPREP QVYTLPPSREKMTKNQVSLTCLVKGFYPSDIAVEWESN GQPENNYKTTPPVLDSDGSFFLYSKLTVDKSRWQQGNV FSCSVLHEALHAHYTRKELSLSP |
| 60 | H chain for DQN0385H1527/ L0605 | QVQLVESGGGVVQPGRSLRLSCAASGFTFA<u>SWYFMSW</u> VRQAPGKGLEWVA<u>SIDTGSGSIDYAEWVEG</u>RFTISRDN SKNTLYLQMNSLRAEDTAVYYCAR<u>DIGIDYNF</u>WGPGTLV TVSSASTKGPSVFPLAPSSKSTSGGTAALGCLVEDYFPE PVTVSWNSGALTSGVHTFPAVLESSGLYSLSSVVTVPSS SLGTKTYICNVNHKPSNTKVDKRVEPKSCDKTHTCPPCP APELRRGPSVFLFPPKPKDTLMISRTPEVTCVVVDVSHE DPEVKFNWYVDGVEVHNAKTKPREEQYNSTYRVVSVLT VLHQDWLNGKEYKCKVSNKALPAPIEKTISKAKGQPREP QVYTLPPSREKMTKNQVSLTCLVKGFYPSDIAVEWESN GQPENNYKTTPPVLDSDGSFFLYSKLTVDKSRWQQGNV FSCSVLHEALHAHYTRKELSLSP |
| 61 | L chain for DQN0385H1527/ L0605 and DQN0385H1255/ L0605 | DIQMTQSPSSLSASVGDRVTITC<u>QTTQSISSYLN</u>WYQQK PGQPPKLLIY<u>YASTKAEG</u>IPARFSGSGSGTDFTLTISSLE PEDFAVYYC<u>HYGISKVSF</u>GQGTKVEIKRTVAAPSVFIFPP SDEQLKSGTAKVVCLLNNFYPREAKVQWKVDNALQSGN SKESVTEQDSKDSTYSLSSTLTLSKADYEKHKVYACEVT HQGLSSPVTKSFNRGEC |
| 62 | H chain for DQN0385H1255/ L0605 | QVQLVESGGGVVQPGRSLRLSCAASGFTF<u>SEWYFMSW</u> VRQAPGKGLEWVA<u>SIDTGSGSIDYAGWVEER</u>FTISRDN SKNTLYLQMNSLRAEDTAVYYCAR<u>DIGIDYNF</u>WGPGTLV TVSSASTKGPSVFPLAPSSKSTSGGTAALGCLVEDYFPE PVTVSWNSGALTSGVHTFPAVLESSGLYSLSSVVTVPSS SLGTKTYICNVNHKPSNTKVDKRVEPKSCDKTHTCPPCP APELRRGPSVFLFPPKPKDTLMISRTPEVTCVVVDVSHE DPEVKFNWYVDGVEVHNAKTKPREEQYNSTYRVVSVLT VLHQDWLNGKEYKCKVSNKALPAPIEKTISKAKGQPREP QVYTLPPSREKMTKNQVSLTCLVKGFYPSDIAVEWESN GQPENNYKTTPPVLDSDGSFFLYSKLTVDKSRWQQGNV FSCSVLHEALHAHYTRKELSLSP |
| 63 | H chain for DQN0385H1255/ L0605 | QVQLVESGGGVVQPGRSLRLSCAASGFTF<u>SEWYFMSW</u> VRQAPGKGLEWVA<u>SIDTGSGSIDYAGWVEER</u>FTISRDN SKNTLYLQMNSLRAEDTAVYYCAR<u>DIGIDYNF</u>WGPGTLV TVSSASTKGPSVFPLAPSSKSTSGGTAALGCLVEDYFPE PVTVSWNSGALTSGVHTFPAVLESSGLYSLSSVVTVPSS SLGTKTYICNVNHKPSNTKVDKRVEPKSCDKTHTCPPCP APELRRGPSVFLFPPKPKDTLMISRTPEVTCVVVDVSHE DPEVKFNWYVDGVEVHNAKTKPREEQYNSTYRVVSVLT VLHQDWLNGKEYKCKVSNKALPAPIEKTISKAKGQPREP |

TABLE 1-2-continued

Full-length H and L chains for the bispecific antibodies
The H (or L) chains comprise, from the N-terminus to C-terminus, HCDR1, HCDR2,
and HCDR3 (or LCDR1, LCDR2, and LCDR3) which are underlined in this table.

| SEQ ID NO: | H/L Chain; Arm | Sequence |
|---|---|---|
| | | QVYTLPPSREKMTKNQVSLTCLVKGFYPSDIAVEWESN GQPENNYKTTPPVLDSDGSFFLYSKLTVDKSRWQQGNV FSCSVLHEALHAHYTRKELSLSP |
| 64 | H chain for DQN0385H1521/ L0605 | QVQLVESGGGVVQPGRSLRLSCAASGFTFE<u>SWYFMSW</u> VRQAPGKGLEWVA<u>SIDTGSGSIDYAEWVEG</u>RFTISRDN SKNTLYLQMNSLRAEDTAVYYCAR<u>DIGIDYNF</u>WGPGTLV TVSSASTKGPSVFPLAPSSKSTSGGTAALGCLVEDYFPE PVTVSWNSGALTSGVHTFPAVLESSGLYSLSSVVTVPSS SLGTKTYICNVNHKPSNTKVDKRVEPKSCDKTHTCPPCP APELRRGPSVFLFPPKPKDTLMISRTPEVTCVVVDVSHE DPEVKFNWYVDGVEVHNAKTKPREEQYNSTYRVVSVLT VLHQDWLNGKEYKCKVSNKALPAPIEKTISKAKGQPREP QVYTLPPSREKMTKNQVSLTCLVKGFYPSDIAVEWESN GQPENNYKTTPPYLDSDGSFFLYSKLTVDKSRWQQGNV FSCSVLHEALHAHYTRKELSLSP |
| 65 | H chain for DQN0385H1521/ L0605 | QVQLVESGGGVVQPGRSLRLSCAASGFTFE<u>SWYFMSW</u> VRQAPGKGLEWVA<u>SIDTGSGSIDYAEWVEG</u>RFTISRDN SKNTLYLQMNSLRAEDTAVYYCAR<u>DIGIDYNF</u>WGPGTLV TVSSASTKGPSVFPLAPSSKSTSGGTAALGCLVEDYFPE PVTVSWNSGALTSGVHTFPAVLESSGLYSLSSVVTVPSS SLGTKTYICNVNHKPSNTKVDKRVEPKSCDKTHTCPPCP APELRRGPSVFLFPPKPKDTLMISRTPEVTCVVVDVSHE DPEVKFNWYVDGVEVHNAKTKPREEQYNSTYRVVSVLT VLHQDWLNGKEYKCKVSNKALPAPIEKTISKAKGQPREP QVYTLPPSREKMTKNQVSLTCLVKGFYPSDIAVEWESN GQPENNYKTTPPVLDSDGSFFLYSKLTVDKSRWQQGNV FSCSVLHEALHAHYTRKELSLSP |
| 66 | H chain for DQN0385H1353/ L0681 | QVQLVESGGGVVQPGRSLRLSCAASGFTFA<u>EWYFMSW</u> VRQAPGKGLEWVA<u>SIDTGSGSIDYAEWVEG</u>RFTISRDN SKNTLYLQMNSLRAEDTAVYYCAR<u>DIGIDYNF</u>WGPGTLV TVSSASTKGPSVFPLAPSSKSTSGGTAALGCLVEDYFPE PVTVSWNSGALTSGVHTFPAVLESSGLYSLSSVVTVPSS SLGTKTYICNVNHKPSNTKVDKRVEPKSCDKTHTCPPCP APELRRGPSVFLFPPKPKDTLMISRTPEVTCVVVDVSHE DPEVKFNWYVDGVEVHNAKTKPREEQYNSTYRVVSVLT VLHQDWLNGKEYKCKVSNKALPAPIEKTISKAKGQPREP QVYTLPPSREKMTKNQVSLTCLVKGFYPSDIAVEWESN GQPENNYKTTPPYLDSDGSFFLYSKLTVDKSRWQQGNV FSCSVLHEALHAHYTRKELSLSP |
| 67 | H chain for DQN0385H1353/ L0681 | QVQLVESGGGVVQPGRSLRLSCAASGFTFA<u>EWYFMSW</u> VRQAPGKGLEWVA<u>SIDTGSGSIDYAEWVEG</u>RFTISRDN SKNTLYLQMNSLRAEDTAVYYCAR<u>DIGIDYNF</u>WGPGTLV TVSSASTKGPSVFPLAPSSKSTSGGTAALGCLVEDYFPE PVTVSWNSGALTSGVHTFPAVLESSGLYSLSSVVTVPSS SLGTKTYICNVNHKPSNTKVDKRVEPKSCDKTHTCPPCP APELRRGPSVFLFPPKPKDTLMISRTPEVTCVVVDVSHE DPEVKFNWYVDGVEVHNAKTKPREEQYNSTYRVVSVLT VLHQDWLNGKEYKCKVSNKALPAPIEKTISKAKGQPREP QVYTLPPSREKMTKNQVSLTCLVKGFYPSDIAVEWESN GQPENNYKTTPPVLDSDGSFFLYSKLTVDKSRWQQGNV FSCSVLHEALHAHYTRKELSLSP |

In some embodiments, the present disclosure provides a multispecific antigen-binding molecule comprising a first antigen-binding moiety and a second antigen-binding moiety;
wherein the first antigen-binding moiety comprises any one of (a1) to (a3) below:
(a1) a first antibody variable region comprising the complementarity determining region (CDR) 1 of SEQ ID NO: 129, the CDR 2 of SEQ ID NO: 130, the CDR 3 of SEQ ID NO: 131, and a second antibody variable region comprising the CDR 1 of SEQ ID NO: 132, the CDR 2 of SEQ ID NO: 133, the CDR 3 of SEQ ID NO: 134;
(a2) a first antibody variable region comprising the complementarity determining region (CDR) 1 of SEQ ID NO: 164, the CDR 2 of SEQ ID NO: 165, the CDR 3 of SEQ ID NO: 166, and a second antibody variable region comprising the CDR 1 of SEQ ID NO: 167, the CDR 2 of SEQ ID NO: 168, the CDR 3 of SEQ ID NO: 169; and
(a3) a first amino acid sequence that has at least 70%, 75%, 80%, 85%, 90%, or 95% sequence identity to the first antibody variable region recited in (a1) or (a2), and a second amino acid sequence that has at least 70%, 75% 80%, 85%, 90%, or 95% sequence identity to the second antibody variable region recited in (a1) or (a2).

In some embodiments, in the multispecific antigen-binding molecule comprising, the second antigen-binding moiety comprises any one of (b1) to (b8) below:
- (b1) a third antibody variable region comprising the complementarity determining region (CDR) 1 of SEQ ID NO: 135, the CDR 2 of SEQ ID NO: 136, the CDR 3 of SEQ ID NO: 137 and a fourth antibody variable region comprising the CDR 1 of SEQ ID NO: 138, the CDR 2 of SEQ ID NO: 139, the CDR 3 of SEQ ID NO: 140;
- (b2) a third antibody variable region comprising the complementarity determining region (CDR) 1 of SEQ ID NO: 135, the CDR 2 of SEQ ID NO: 136, the CDR 3 of SEQ ID NO: 137, and a fourth antibody variable region comprising the CDR 1 of SEQ ID NO: 141, the CDR 2 of SEQ ID NO: 142, the CDR 3 of SEQ ID NO: 143;
- (b3) a third antibody variable region comprising the complementarity determining region (CDR) 1 of SEQ ID NO: 144, the CDR 2 of SEQ ID NO: 145, the CDR 3 of SEQ ID NO: 146, and a fourth antibody variable region comprising the CDR 1 of SEQ ID NO: 141, the CDR 2 of SEQ ID NO: 142, the CDR 3 of SEQ ID NO: 143;
- (b4) a third antibody variable region comprising the complementarity determining region (CDR) 1 of SEQ ID NO: 147, the CDR 2 of SEQ ID NO: 148, the CDR 3 of SEQ ID NO: 149, and a fourth antibody variable region comprising the CDR 1 of SEQ ID NO: 150, the CDR 2 of SEQ ID NO: 151, the CDR 3 of SEQ ID NO: 152;
- (b5) a third antibody variable region comprising the complementarity determining region (CDR) 1 of SEQ ID NO: 153, the CDR 2 of SEQ ID NO: 154, the CDR 3 of SEQ ID NO: 155, and a fourth antibody variable region comprising the CDR 1 of SEQ ID NO: 150, the CDR 2 of SEQ ID NO: 151, the CDR 3 of SEQ ID NO: 152;
- (b6) a third antibody variable region comprising the complementarity determining region (CDR) 1 of SEQ ID NO: 156, the CDR 2 of SEQ ID NO: 157, the CDR 3 of SEQ ID NO: 158, and a fourth antibody variable region comprising the CDR 1 of SEQ ID NO: 150, the CDR 2 of SEQ ID NO: 151, the CDR 3 of SEQ ID NO: 152;
- (b7) a third antibody variable region comprising the complementarity determining region (CDR) 1 of SEQ ID NO: 159, the CDR 2 of SEQ ID NO: 160, the CDR 3 of SEQ ID NO: 161, and a fourth antibody variable region comprising the CDR 1 of SEQ ID NO: 141, the CDR 2 of SEQ ID NO: 142, the CDR 3 of SEQ ID NO: 143; and
- (b8) a third amino acid sequence that has at least 70%, 75%, 80%, 85%, 90%, or 95% sequence identity to the third antibody variable region recited in any one of (b1) to (b7), and a fourth amino acid sequence that has at least 70%, 75%, 80%, 85%, 90%, or 95% sequence identity to the fourth antibody variable region recited in any one of (b1) to (b7).

In some embodiments, the present disclosure provides a multispecific antigen-binding molecule comprising a first antigen-binding moiety and a second antigen-binding moiety;
wherein the first antigen-binding moiety comprises any one of (c1) to (c3) below:
- (c1) a first antibody variable region comprising the complementarity determining region (CDR) 1 of SEQ ID NO: 129, the CDR 2 of SEQ ID NO: 130, the CDR 3 of SEQ ID NO: 131, and a second antibody variable region comprising the CDR 1 of SEQ ID NO: 132, the CDR 2 of SEQ ID NO: 133, the CDR 3 of SEQ ID NO: 134;
- (c2) a first antibody variable region comprising the complementarity determining region (CDR) 1 of SEQ ID NO: 164, the CDR 2 of SEQ ID NO: 165, the CDR 3 of SEQ ID NO: 166, and a second antibody variable region comprising the CDR 1 of SEQ ID NO: 167, the CDR 2 of SEQ ID NO: 168, the CDR 3 of SEQ ID NO: 169; and
- (c3) a first amino acid sequence that has at least 70%, 75%, 80%, 85%, 90%, or 95% sequence identity to the first antibody variable region recited in (c1) or (c2), and a second amino acid sequence that has at least 70%, 75%, 80%, 85%, 90%, or 95% sequence identity to the second antibody variable region recited in (c1) or (c2), wherein the second antigen-binding moiety comprises any one of (d1) to (d8) below:
- (d1) a third antibody variable region comprising the complementarity determining region (CDR) 1 of SEQ ID NO: 135, the CDR 2 of SEQ ID NO: 136, the CDR 3 of SEQ ID NO: 137 and a fourth antibody variable region comprising the CDR 1 of SEQ ID NO: 138, the CDR 2 of SEQ ID NO: 139, the CDR 3 of SEQ ID NO: 140;
- (d2) a third antibody variable region comprising the complementarity determining region (CDR) 1 of SEQ ID NO: 135, the CDR 2 of SEQ ID NO: 136, the CDR 3 of SEQ ID NO: 137, and a fourth antibody variable region comprising the CDR 1 of SEQ ID NO: 141, the CDR 2 of SEQ ID NO: 142, the CDR 3 of SEQ ID NO: 143;
- (d3) a third antibody variable region comprising the complementarity determining region (CDR) 1 of SEQ ID NO: 144, the CDR 2 of SEQ ID NO: 145, the CDR 3 of SEQ ID NO: 146, and a fourth antibody variable region comprising the CDR 1 of SEQ ID NO: 141, the CDR 2 of SEQ ID NO: 142, the CDR 3 of SEQ ID NO: 143;
- (d4) a third antibody variable region comprising the complementarity determining region (CDR) 1 of SEQ ID NO: 147, the CDR 2 of SEQ ID NO: 148, the CDR 3 of SEQ ID NO: 149, and a fourth antibody variable region comprising the CDR 1 of SEQ ID NO: 150, the CDR 2 of SEQ ID NO: 151, the CDR 3 of SEQ ID NO: 152;
- (d5) a third antibody variable region comprising the complementarity determining region (CDR) 1 of SEQ ID NO: 153, the CDR 2 of SEQ ID NO: 154, the CDR 3 of SEQ ID NO: 155, and a fourth antibody variable region comprising the CDR 1 of SEQ ID NO: 150, the CDR 2 of SEQ ID NO: 151, the CDR 3 of SEQ ID NO: 152;
- (d6) a third antibody variable region comprising the complementarity determining region (CDR) 1 of SEQ ID NO: 156, the CDR 2 of SEQ ID NO: 157, the CDR 3 of SEQ ID NO: 158, and a fourth antibody variable region comprising the CDR 1 of SEQ ID NO: 150, the CDR 2 of SEQ ID NO: 151, the CDR 3 of SEQ ID NO: 152;
- (d7) a third antibody variable region comprising the complementarity determining region (CDR) 1 of SEQ ID NO: 159, the CDR 2 of SEQ ID NO: 160, the CDR 3 of SEQ ID NO: 161, and a fourth antibody variable region comprising the CDR 1 of SEQ ID NO: 141, the CDR 2 of SEQ ID NO: 142, the CDR 3 of SEQ ID NO: 143; and (d8) a third amino acid sequence that has at least 70%, 75%, 80%, 85%, 90%, or 95% sequence identity to the third antibody variable region recited in any one of (d1) to (d7), and a fourth amino acid sequence that has at least 70%, 75%, 80%, 85%, 90%, or 95% sequence identity to the fourth antibody variable region recited in any one of (d1) to (d7).

In some embodiments, the present disclosure provides a multispecific antigen-binding molecule that comprises a first antigen-binding moiety comprising first and second antibody variable regions and a second antigen-binding moiety comprising third and fourth antibody variable regions, wherein the multispecific antigen-binding molecule comprises any one of (1) to (15) below:

(1) a first antibody variable region comprising the complementarity determining region (CDR) 1 of SEQ ID NO: 129, the CDR 2 of SEQ ID NO: 130, the CDR 3 of SEQ ID NO: 131, and a second antibody variable region comprising the CDR 1 of SEQ ID NO: 132, the CDR 2 of SEQ ID NO: 133, the CDR 3 of SEQ ID NO: 134; a third antibody variable region comprising the complementarity determining region (CDR) 1 of SEQ ID NO: 135, the CDR 2 of SEQ ID NO: 136, the CDR 3 of SEQ ID NO: 137 and a fourth antibody variable region comprising the CDR 1 of SEQ ID NO: 138, the CDR 2 of SEQ ID NO: 139, the CDR 3 of SEQ ID NO: 140;

(2) a first antibody variable region comprising the complementarity determining region (CDR) 1 of SEQ ID NO: 129, the CDR 2 of SEQ ID NO: 130, the CDR 3 of SEQ ID NO: 131, and a second antibody variable region comprising the CDR 1 of SEQ ID NO: 132, the CDR 2 of SEQ ID NO: 133, the CDR 3 of SEQ ID NO: 134; a third antibody variable region comprising the complementarity determining region (CDR) 1 of SEQ ID NO: 135, the CDR 2 of SEQ ID NO: 136, the CDR 3 of SEQ ID NO: 137, and a fourth antibody variable region comprising the CDR 1 of SEQ ID NO: 141, the CDR 2 of SEQ ID NO: 142, the CDR 3 of SEQ ID NO: 143;

(3) a first antibody variable region comprising the complementarity determining region (CDR) 1 of SEQ ID NO: 129, the CDR 2 of SEQ ID NO: 130, the CDR 3 of SEQ ID NO: 131, and a second antibody variable region comprising the CDR 1 of SEQ ID NO: 132, the CDR 2 of SEQ ID NO: 133, the CDR 3 of SEQ ID NO: 134; a third antibody variable region comprising the complementarity determining region (CDR) 1 of SEQ ID NO: 144, the CDR 2 of SEQ ID NO: 145, the CDR 3 of SEQ ID NO: 146, and a fourth antibody variable region comprising the CDR 1 of SEQ ID NO: 141, the CDR 2 of SEQ ID NO: 142, the CDR 3 of SEQ ID NO: 143;

(4) a first antibody variable region comprising the complementarity determining region (CDR) 1 of SEQ ID NO: 129, the CDR 2 of SEQ ID NO: 130, the CDR 3 of SEQ ID NO: 131, and a second antibody variable region comprising the CDR 1 of SEQ ID NO: 132, the CDR 2 of SEQ ID NO: 133, the CDR 3 of SEQ ID NO: 134; a third antibody variable region comprising the complementarity determining region (CDR) 1 of SEQ ID NO: 147, the CDR 2 of SEQ ID NO: 148, the CDR 3 of SEQ ID NO: 149, and a fourth antibody variable region comprising the CDR 1 of SEQ ID NO: 150, the CDR 2 of SEQ ID NO: 151, the CDR 3 of SEQ ID NO: 152;

(5) a first antibody variable region comprising the complementarity determining region (CDR) 1 of SEQ ID NO: 129, the CDR 2 of SEQ ID NO: 130, the CDR 3 of SEQ ID NO: 131, and a second antibody variable region comprising the CDR 1 of SEQ ID NO: 132, the CDR 2 of SEQ ID NO: 133, the CDR 3 of SEQ ID NO: 134; a third antibody variable region comprising the complementarity determining region (CDR) 1 of SEQ ID NO: 153, the CDR 2 of SEQ ID NO: 154, the CDR 3 of SEQ ID NO: 155, and a fourth antibody variable region comprising the CDR 1 of SEQ ID NO: 150, the CDR 2 of SEQ ID NO: 151, the CDR 3 of SEQ ID NO: 152;

(6) a first antibody variable region comprising the complementarity determining region (CDR) 1 of SEQ ID NO: 129, the CDR 2 of SEQ ID NO: 130, the CDR 3 of SEQ ID NO: 131, and a second antibody variable region comprising the CDR 1 of SEQ ID NO: 132, the CDR 2 of SEQ ID NO: 133, the CDR 3 of SEQ ID NO: 134; a third antibody variable region comprising the complementarity determining region (CDR) 1 of SEQ ID NO: 156, the CDR 2 of SEQ ID NO: 157, the CDR 3 of SEQ ID NO: 158, and a fourth antibody variable region comprising the CDR 1 of SEQ ID NO: 150, the CDR 2 of SEQ ID NO: 151, the CDR 3 of SEQ ID NO: 152;

(7) a first antibody variable region comprising the complementarity determining region (CDR) 1 of SEQ ID NO: 129, the CDR 2 of SEQ ID NO: 130, the CDR 3 of SEQ ID NO: 131, and a second antibody variable region comprising the CDR 1 of SEQ ID NO: 132, the CDR 2 of SEQ ID NO: 133, the CDR 3 of SEQ ID NO: 134; a third antibody variable region comprising the complementarity determining region (CDR) 1 of SEQ ID NO: 159, the CDR 2 of SEQ ID NO: 160, the CDR 3 of SEQ ID NO: 161, and a fourth antibody variable region comprising the CDR 1 of SEQ ID NO: 141, the CDR 2 of SEQ ID NO: 142, the CDR 3 of SEQ ID NO: 143; and (8) a first antibody variable region comprising the complementarity determining region (CDR) 1 of SEQ ID NO: 164, the CDR 2 of SEQ ID NO: 165, the CDR 3 of SEQ ID NO: 166, and a second antibody variable region comprising the CDR 1 of SEQ ID NO: 167, the CDR 2 of SEQ ID NO: 168, the CDR 3 of SEQ ID NO: 169; a third antibody variable region comprising the complementarity determining region (CDR) 1 of SEQ ID NO: 135, the CDR 2 of SEQ ID NO: 136, the CDR 3 of SEQ ID NO: 137 and a fourth antibody variable region comprising the CDR 1 of SEQ ID NO: 138, the CDR 2 of SEQ ID NO: 139, the CDR 3 of SEQ ID NO: 140;

(9) a first antibody variable region comprising the complementarity determining region (CDR) 1 of SEQ ID NO: 164, the CDR 2 of SEQ ID NO: 165, the CDR 3 of SEQ ID NO: 166, and a second antibody variable region comprising the CDR 1 of SEQ ID NO: 167, the CDR 2 of SEQ ID NO: 168, the CDR 3 of SEQ ID NO: 169; a third antibody variable region comprising the complementarity determining region (CDR) 1 of SEQ ID NO: 135, the CDR 2 of SEQ ID NO: 136, the CDR 3 of SEQ ID NO: 137, and a fourth antibody variable region comprising the CDR 1 of SEQ ID NO: 141, the CDR 2 of SEQ ID NO: 142, the CDR 3 of SEQ ID NO: 143;

(10) a first antibody variable region comprising the complementarity determining region (CDR) 1 of SEQ ID NO: 164, the CDR 2 of SEQ ID NO: 165, the CDR 3 of SEQ ID NO: 166, and a second antibody variable region comprising the CDR 1 of SEQ ID NO: 167, the CDR 2 of SEQ ID NO: 168, the CDR 3 of SEQ ID NO: 169; a third antibody variable region comprising the complementarity determining region (CDR) 1 of SEQ ID NO: 144, the CDR 2 of SEQ ID NO: 145, the CDR 3 of SEQ ID NO: 146, and a fourth antibody variable region comprising the CDR 1 of SEQ ID NO: 141, the CDR 2 of SEQ ID NO: 142, the CDR 3 of SEQ ID NO: 143;

(11) a first antibody variable region comprising the complementarity determining region (CDR) 1 of SEQ ID NO: 164, the CDR 2 of SEQ ID NO: 165, the CDR 3 of SEQ ID NO: 166, and a second antibody variable region comprising the CDR 1 of SEQ ID NO: 167, the CDR 2 of SEQ ID NO: 168, the CDR 3 of SEQ ID NO: 169; a third antibody variable region comprising the complementarity determining region (CDR) 1 of SEQ ID NO: 147, the CDR 2 of SEQ ID NO: 148, the CDR 3 of SEQ ID NO: 149, and a fourth antibody variable region comprising the CDR 1 of SEQ ID NO: 150, the CDR 2 of SEQ ID NO: 151, the CDR 3 of SEQ ID NO: 152;

(12) a first antibody variable region comprising the complementarity determining region (CDR) 1 of SEQ ID NO: 164, the CDR 2 of SEQ ID NO: 165, the CDR 3 of SEQ ID NO: 166, and a second antibody variable region comprising the CDR 1 of SEQ ID NO: 167, the CDR 2 of SEQ ID NO: 168, the CDR 3 of SEQ ID NO: 169; a third antibody variable region comprising the complementarity determining region (CDR) 1 of SEQ ID NO: 153, the CDR 2 of SEQ ID NO: 154, the CDR 3 of SEQ ID NO: 155, and a fourth antibody variable region comprising the CDR 1 of SEQ ID NO: 150, the CDR 2 of SEQ ID NO: 151, the CDR 3 of SEQ ID NO: 152;

(13) a first antibody variable region comprising the complementarity determining region (CDR) 1 of SEQ ID NO: 164, the CDR 2 of SEQ ID NO: 165, the CDR 3 of SEQ ID NO: 166, and a second antibody variable region comprising the CDR 1 of SEQ ID NO: 167, the CDR 2 of SEQ ID NO: 168, the CDR 3 of SEQ ID NO: 169; a third antibody variable region comprising the complementarity determining region (CDR) 1 of SEQ ID NO: 156, the CDR 2 of SEQ ID NO: 157, the CDR 3 of SEQ ID NO: 158, and a fourth antibody variable region comprising the CDR 1 of SEQ ID NO: 150, the CDR 2 of SEQ ID NO: 151, the CDR 3 of SEQ ID NO: 152;

(14) a first antibody variable region comprising the complementarity determining region (CDR) 1 of SEQ ID NO: 164, the CDR 2 of SEQ ID NO: 165, the CDR 3 of SEQ ID NO: 166, and a second antibody variable region comprising the CDR 1 of SEQ ID NO: 167, the CDR 2 of SEQ ID NO: 168, the CDR 3 of SEQ ID NO: 169; a third antibody variable region comprising the complementarity determining region (CDR) 1 of SEQ ID NO: 159, the CDR 2 of SEQ ID NO: 160, the CDR 3 of SEQ ID NO: 161, and a fourth antibody variable region comprising the CDR 1 of SEQ ID NO: 141, the CDR 2 of SEQ ID NO: 142, the CDR 3 of SEQ ID NO: 143; and

(15) a first amino acid sequence that has at least 70%, 75%, 80%, 85%, 90%, or 95% sequence identity to the first antibody variable region recited in any one of (1) to (14), a second amino acid sequence that has at least 70%, 75%, 80%, 85%, 90%, or 95% sequence identity to the second antibody variable region recited in any one of (1) to (14), a third amino acid sequence that has at least 70%, 75%, 80%, 85%, 90%, or 95% sequence identity to the third antibody variable region recited in any one of (1) to (14), and a fourth amino acid sequence that has at least 70%, 75%, 80%, 85%, 90%, or 95% sequence identity to the fourth antibody variable region recited in any one of (1) to (14).

In some embodiments, in the multispecific antigen-binding molecule, the antibody variable region comprised in the first and/or second antigen-binding moiety comprises human antibody frameworks or humanized antibody frameworks.

In some embodiments, the present disclosure provides a multispecific antigen-binding molecule comprising a first antigen-binding moiety and a second antigen-binding moiety;

wherein the first antigen-binding moiety comprises any one of (e1) to (e3) below:

(e1) a first antibody variable region comprising the amino acid sequence of SEQ ID NO: 88, and a second antibody variable region comprising the amino acid sequence of SEQ ID NO: 90;

(e2) a first antibody variable region comprising the amino acid sequence of SEQ ID NO: 89, and a second antibody variable region comprising the amino acid sequence of SEQ ID NO: 91; and (e3) a first amino acid sequence that has at least 70%, 75%, 80%, 85%, 90%, or 95% sequence identity to the first antibody variable region recited in (e1) or (e2), and a second amino acid sequence that has at least 70%, 75% 80%, 85%, 90%, or 95% sequence identity to the second antibody variable region recited in (e1) or (e2).

In some embodiments, in the multispecific antigen-binding molecule, the second antigen-binding moiety comprises any one of (f1) to (f8) below:

(f1) a third antibody variable region comprising the amino acid sequence of SEQ ID NO: 92, and a fourth antibody variable region comprising the amino acid sequence of SEQ ID NO: 98;

(f2) a third antibody variable region comprising the amino acid sequence of SEQ ID NO: 92, and a fourth antibody variable region comprising the amino acid sequence of SEQ ID NO: 99;

(f3) a third antibody variable region comprising the amino acid sequence of SEQ ID NO: 93, and a fourth antibody variable region comprising the amino acid sequence of SEQ ID NO: 99;

(f4) a third antibody variable region comprising the amino acid sequence of SEQ ID NO: 94, and a fourth antibody variable region comprising the amino acid sequence of SEQ ID NO: 100;

(f5) a third antibody variable region comprising the amino acid sequence of SEQ ID NO: 95, and a fourth antibody variable region comprising the amino acid sequence of SEQ ID NO: 100;

(f6) a third antibody variable region comprising the amino acid sequence of SEQ ID NO: 96, and a fourth antibody variable region comprising the amino acid sequence of SEQ ID NO: 100;

(f7) a third antibody variable region comprising the amino acid sequence of SEQ ID NO: 97, and a fourth antibody variable region comprising the amino acid sequence of SEQ ID NO: 99; and (f8) a third amino acid sequence that has at least 70%, 75%, 80%, 85%, 90%, or 95% sequence identity to the third antibody variable region recited in any one of (f1) to (f7), and a fourth amino acid sequence that has at least 70%, 75%, 80%, 85%, 90%, or 95% sequence identity to the fourth antibody variable region recited in any one of (f1) to (f7).

In some embodiments, the present disclosure provides a multispecific antigen-binding molecule comprising a first antigen-binding moiety and a second antigen-binding moiety;

wherein the first antigen-binding moiety comprises any one of (e1) to (e3) below:

(e1) a first antibody variable region comprising the amino acid sequence of SEQ ID NO: 88, and a second antibody variable region comprising the amino acid sequence of SEQ ID NO: 90;

(e2) a first antibody variable region comprising the amino acid sequence of SEQ ID NO: 89, and a second antibody variable region comprising the amino acid sequence of SEQ ID NO: 91; and (e3) a first amino acid sequence that has at least 70%, 75%, 80%, 85%, 90%, or 95% sequence identity to the first antibody variable region recited in (e1) or (e2), and a second amino acid sequence that has at least 70%, 75%, 80%, 85%, 90%, or 95% sequence identity to the second antibody variable region recited in (e1) or (e2), and wherein the second antigen-binding moiety comprises any one of (f1) to (f8) below:

(f1) a third antibody variable region comprising the amino acid sequence of SEQ ID NO: 92, and a fourth antibody variable region comprising the amino acid sequence of SEQ ID NO: 98;

(f2) a third antibody variable region comprising the amino acid sequence of SEQ ID NO: 92, and a fourth antibody variable region comprising the amino acid sequence of SEQ ID NO: 99;

(f3) a third antibody variable region comprising the amino acid sequence of SEQ ID NO: 93, and a fourth antibody variable region comprising the amino acid sequence of SEQ ID NO: 99;

(f4) a third antibody variable region comprising the amino acid sequence of SEQ ID NO: 94, and a fourth antibody variable region comprising the amino acid sequence of SEQ ID NO: 100;

(f5) a third antibody variable region comprising the amino acid sequence of SEQ ID NO: 95, and a fourth antibody variable region comprising the amino acid sequence of SEQ ID NO: 100;

(f6) a third antibody variable region comprising the amino acid sequence of SEQ ID NO: 96, and a fourth antibody variable region comprising the amino acid sequence of SEQ ID NO: 100;

(f7) a third antibody variable region comprising the amino acid sequence of SEQ ID NO: 97, and a fourth antibody variable region comprising the amino acid sequence of SEQ ID NO: 99; and (f8) a third amino acid sequence that has at least 70%, 75%, 80%, 85%, 90%, or 95% sequence identity to the third antibody variable region recited in any one of (f1) to (f7), and a fourth amino acid sequence that has at least 70%, 75%, 80%, 85%, 90%, or 95% sequence identity to the fourth antibody variable region recited in any one of (f1) to (f7).

In some embodiments, the present disclosure provides a multispecific antigen-binding molecule that comprises a first antigen-binding moiety comprising first and second antibody variable regions and a second antigen-binding moiety comprising third and fourth antibody variable regions, wherein the multispecific antigen-binding molecule comprises any one of (1) to (15) below:

(1) a first antibody variable region comprising the amino acid sequence of SEQ ID NO: 88; a second antibody variable region comprising the amino acid sequence of SEQ ID NO: 90; a third antibody variable region comprising the amino acid sequence of SEQ ID NO: 92; and a fourth antibody variable region comprising the amino acid sequence of SEQ ID NO: 98;

(2) a first antibody variable region comprising the amino acid sequence of SEQ ID NO: 88; and a second antibody variable region comprising the amino acid sequence of SEQ ID NO: 90; a third antibody variable region comprising the amino acid sequence of SEQ ID NO: 92; and a fourth antibody variable region comprising the amino acid sequence of SEQ ID NO: 99;

(3) a first antibody variable region comprising the amino acid sequence of SEQ ID NO: 88; a second antibody variable region comprising the amino acid sequence of SEQ ID NO: 90; a third antibody variable region comprising the amino acid sequence of SEQ ID NO: 93; and a fourth antibody variable region comprising the amino acid sequence of SEQ ID NO: 99;

(4) a first antibody variable region comprising the amino acid sequence of SEQ ID NO: 88; a second antibody variable region comprising the amino acid sequence of SEQ ID NO: 90; a third antibody variable region comprising the amino acid sequence of SEQ ID NO: 94; and a fourth antibody variable region comprising the amino acid sequence of SEQ ID NO: 100;

(5) a first antibody variable region comprising the amino acid sequence of SEQ ID NO: 88; a second antibody variable region comprising the amino acid sequence of SEQ ID NO: 90; a third antibody variable region comprising the amino acid sequence of SEQ ID NO: 95; and a fourth antibody variable region comprising the amino acid sequence of SEQ ID NO: 100;

(6) a first antibody variable region comprising the amino acid sequence of SEQ ID NO: 88; a second antibody variable region comprising the amino acid sequence of SEQ ID NO: 90; a third antibody variable region comprising the amino acid sequence of SEQ ID NO: 96; a fourth antibody variable region comprising the amino acid sequence of SEQ ID NO: 100;

(7) a first antibody variable region comprising the amino acid sequence of SEQ ID NO: 88; a second antibody variable region comprising the amino acid sequence of SEQ ID NO: 90; a third antibody variable region comprising the amino acid sequence of SEQ ID NO: 97; and a fourth antibody variable region comprising the amino acid sequence of SEQ ID NO: 99;

(8) a first antibody variable region comprising the amino acid sequence of SEQ ID NO: 89; a second antibody variable region comprising the amino acid sequence of SEQ ID NO: 91; a third antibody variable region comprising the amino acid sequence of SEQ ID NO: 92; and a fourth antibody variable region comprising the amino acid sequence of SEQ ID NO: 98;

(9) a first antibody variable region comprising the amino acid sequence of SEQ ID NO: 89; and a second antibody variable region comprising the amino acid sequence of SEQ ID NO: 91; a third antibody variable region comprising the amino acid sequence of SEQ ID NO: 92; and a fourth antibody variable region comprising the amino acid sequence of SEQ ID NO: 99;

(10) a first antibody variable region comprising the amino acid sequence of SEQ ID NO: 89; a second antibody variable region comprising the amino acid sequence of SEQ ID NO: 91; a third antibody variable region comprising the amino acid sequence of SEQ ID NO: 93; and a fourth antibody variable region comprising the amino acid sequence of SEQ ID NO: 99;

(11) a first antibody variable region comprising the amino acid sequence of SEQ ID NO: 89; a second antibody variable region comprising the amino acid sequence of SEQ ID NO: 91; a third antibody variable region comprising the amino acid sequence of SEQ ID NO: 94; and a fourth antibody variable region comprising the amino acid sequence of SEQ ID NO: 100;

(12) a first antibody variable region comprising the amino acid sequence of SEQ ID NO: 89; a second antibody variable region comprising the amino acid sequence of SEQ ID NO: 91; a third antibody variable region comprising the amino acid sequence of SEQ ID NO: 95; and a fourth antibody variable region comprising the amino acid sequence of SEQ ID NO: 100;

(13) a first antibody variable region comprising the amino acid sequence of SEQ ID NO: 89; a second antibody variable region comprising the amino acid sequence of SEQ ID NO: 91; a third antibody variable region comprising the amino acid sequence of SEQ ID NO: 96; and a fourth antibody variable region comprising the amino acid sequence of SEQ ID NO: 100;

(14) a first antibody variable region comprising the amino acid sequence of SEQ ID NO: 89; a second antibody variable region comprising the amino acid sequence of SEQ ID NO: 91; a third antibody variable region comprising the amino acid sequence of SEQ ID NO: 97; and a fourth antibody variable region comprising the amino acid sequence of SEQ ID NO: 99;

(15) a first amino acid sequence that has at least 70%, 75%, 80%, 85%, 90%, or 95% sequence identity to the first antibody variable region recited in any one of (1) to (14); a second amino acid sequence that has at least 70%, 75%, 80%, 85%, 90%, or 95% sequence identity to the second antibody variable region recited in any one of (1) to (14); a third amino acid sequence that has at least 70%, 75%, 80%, 85%, 90%, or 95% sequence identity to the third antibody variable region recited in any one of (1) to (14); and a fourth amino acid sequence that has at least 70%, 75%, 80%, 85%, 90%, or 95% sequence identity to the fourth antibody variable region recited in any one of (1) to (14).

In some embodiments, the present disclosure provides a multispecific antigen-binding molecule comprising a combination of two polypeptide chains selected from the group consisting of (A1) to (A3) below:

(A1) a first heavy chain comprising amino acid sequence of SEQ ID NO: 42 and a first light chain comprising amino acid sequence of SEQ ID NO: 43;

(A2) a first heavy chain comprising amino acid sequence of SEQ ID NO: 45 and a first light chain comprising amino acid sequence of SEQ ID NO: 46; and (A3) a first amino acid sequence that has at least 70%, 75%, 80%, 85%, 90%, or 95% sequence identity to the first heavy chain sequence recited in (A1) or (A2), and a second amino acid sequence that has at least 70%, 75%, 80%, 85%, 90%, or 95% sequence identity to the first light chain sequence recited in (A1) or (A2).

In some embodiments, the multispecific antigen-binding molecule further comprises a combination of two polypeptide chains selected from the group consisting of (B1) to (B8) below:

(B1) a second heavy chain comprising amino acid sequence of SEQ ID NO: 54 and a second light chain comprising amino acid sequence of SEQ ID NO: 55;

(B2) a second heavy chain comprising amino acid sequence of SEQ ID NO: 54 and a second light chain comprising amino acid sequence of SEQ ID NO: 56;

(B3) a second heavy chain comprising amino acid sequence of SEQ ID NO: 58 and a second light chain comprising amino acid sequence of SEQ ID NO: 56;

(B4) a second heavy chain comprising amino acid sequence of SEQ ID NO: 60 and a second light chain comprising amino acid sequence of SEQ ID NO: 61;

(B5) a second heavy chain comprising amino acid sequence of SEQ ID NO: 63 and a second light chain comprising amino acid sequence of SEQ ID NO: 61;

(B6) a second heavy chain comprising amino acid sequence of SEQ ID NO: 65 and a second light chain comprising amino acid sequence of SEQ ID NO: 61;

(B7) a second heavy chain comprising amino acid sequence of SEQ ID NO: 67 and a second light chain comprising amino acid sequence of SEQ ID NO: 56; and (B8) a third amino acid sequence that has at least 70%, 75%, 80%, 85%, 90%, or 95% sequence identity to the second heavy chain sequence recited in any one of (B1) to (B7), and a fourth amino acid sequence that has at least 70%, 75%, 80%, 85%, 90%, or 95% sequence identity to the second light chain sequence recited in any one of (B1) to (B7).

In some embodiments, the multispecific antigen-binding molecule further comprises a combination of two polypeptide chains selected from the group consisting of (B1) to (B8) below:

(B1) a second heavy chain comprising amino acid sequence of SEQ ID NO: 53 and a second light chain comprising amino acid sequence of SEQ ID NO: 55;

(B2) a second heavy chain comprising amino acid sequence of SEQ ID NO: 53 and a second light chain comprising amino acid sequence of SEQ ID NO: 56;

(B3) a second heavy chain comprising amino acid sequence of SEQ ID NO: 57 and a second light chain comprising amino acid sequence of SEQ ID NO: 56;

(B4) a second heavy chain comprising amino acid sequence of SEQ ID NO: 59 and a second light chain comprising amino acid sequence of SEQ ID NO: 61;

(B5) a second heavy chain comprising amino acid sequence of SEQ ID NO: 62 and a second light chain comprising amino acid sequence of SEQ ID NO: 61;

(B6) a second heavy chain comprising amino acid sequence of SEQ ID NO: 64 and a second light chain comprising amino acid sequence of SEQ ID NO: 61;

(B7) a second heavy chain comprising amino acid sequence of SEQ ID NO: 66 and a second light chain comprising amino acid sequence of SEQ ID NO: 56; and (B8) a third amino acid sequence that has at least 70%, 75%, 80%, 85%, 90%, or 95% sequence identity to the second heavy chain sequence recited in any one of (B1) to (B7), and a fourth amino acid sequence that has at least 70%, 75%, 80%, 85%, 90%, or 95% sequence identity to the second light chain sequence recited in any one of (B1) to (B7).

In some embodiments, the present disclosure provides a multispecific antigen-binding molecule comprising a combination of four polypeptide chains selected from the group consisting of (1) to (15) below:

(1) a first heavy chain comprising amino acid sequence of SEQ ID NO: 42 and a first light chain comprising amino acid sequence of SEQ ID NO: 43, and a second heavy chain comprising amino acid sequence of SEQ ID NO: 54 and a second light chain comprising amino acid sequence of SEQ ID NO: 55;

(2) a first heavy chain comprising amino acid sequence of SEQ ID NO: 42 and a first light chain comprising amino acid sequence of SEQ ID NO: 43, and a second heavy chain comprising amino acid sequence of SEQ ID NO: 54 and a second light chain comprising amino acid sequence of SEQ ID NO: 56;

(3) a first heavy chain comprising amino acid sequence of SEQ ID NO: 42 and a first light chain comprising amino acid sequence of SEQ ID NO: 43, and a second heavy chain comprising amino acid sequence of SEQ ID NO: 58 and a second light chain comprising amino acid sequence of SEQ ID NO: 56;

(4) a first heavy chain comprising amino acid sequence of SEQ ID NO: 42 and a first light chain comprising amino acid sequence of SEQ ID NO: 43, and a second heavy chain comprising amino acid sequence of SEQ ID NO: 60 and a second light chain comprising amino acid sequence of SEQ ID NO: 61;

(5) a first heavy chain comprising amino acid sequence of SEQ ID NO: 42 and a first light chain comprising amino acid sequence of SEQ ID NO: 43, and a second heavy chain comprising amino acid sequence of SEQ ID NO: 63 and a second light chain comprising amino acid sequence of SEQ ID NO: 61;

(6) a first heavy chain comprising amino acid sequence of SEQ ID NO: 45 and a first light chain comprising amino acid sequence of SEQ ID NO: 46, and a second heavy chain comprising amino acid sequence of SEQ ID NO: 54 and a second light chain comprising amino acid sequence of SEQ ID NO: 55;

(7) a first heavy chain comprising amino acid sequence of SEQ ID NO: 45 and a first light chain comprising amino acid sequence of SEQ ID NO: 46, and a second heavy chain comprising amino acid sequence of SEQ ID NO: 65 and a second light chain comprising amino acid sequence of SEQ ID NO: 61;

(8) a first heavy chain comprising amino acid sequence of SEQ ID NO: 45 and a first light chain comprising amino acid sequence of SEQ ID NO: 46, and a second heavy chain comprising amino acid sequence of SEQ ID NO: 54 and a second light chain comprising amino acid sequence of SEQ ID NO: 56;

(9) a first heavy chain comprising amino acid sequence of SEQ ID NO: 45 and a first light chain comprising amino acid sequence of SEQ ID NO: 46, and a second heavy chain comprising amino acid sequence of SEQ ID NO: 58 and a second light chain comprising amino acid sequence of SEQ ID NO: 56;

(10) a first heavy chain comprising amino acid sequence of SEQ ID NO: 45 and a first light chain comprising amino acid sequence of SEQ ID NO: 46, and a second heavy chain comprising amino acid sequence of SEQ ID NO: 67 and a second light chain comprising amino acid sequence of SEQ ID NO: 56;

(11) a first heavy chain comprising amino acid sequence of SEQ ID NO: 42 and a first light chain comprising amino acid sequence of SEQ ID NO: 43, and a second heavy chain comprising amino acid sequence of SEQ ID NO: 65 and a second light chain comprising amino acid sequence of SEQ ID NO: 61;

(12) a first heavy chain comprising amino acid sequence of SEQ ID NO: 42 and a first light chain comprising amino acid sequence of SEQ ID NO: 43, and a second heavy chain comprising amino acid sequence of SEQ ID NO: 67 and a second light chain comprising amino acid sequence of SEQ ID NO: 56;

(13) a first heavy chain comprising amino acid sequence of SEQ ID NO: 45 and a first light chain comprising amino acid sequence of SEQ ID NO: 46, and a second heavy chain comprising amino acid sequence of SEQ ID NO: 63 and a second light chain comprising amino acid sequence of SEQ ID NO: 61;

(14) a first heavy chain comprising amino acid sequence of SEQ ID NO: 45 and a first light chain comprising amino acid sequence of SEQ ID NO: 46, and a second heavy chain comprising amino acid sequence of SEQ ID NO: 60 and a second light chain comprising amino acid sequence of SEQ ID NO: 61; and

(15) a first amino acid sequence that has at least 70%, 75%, 80%, 85%, 90%, or 95% sequence identity to the first heavy chain sequence recited in any one of (1) to (14); a second amino acid sequence that has at least 70%, 75%, 80%, 85%, 90%, or 95% sequence identity to the first light chain sequence recited in any one of (1) to (14); a third amino acid sequence that has at least 70%, 75%, 80%, 85%, 90%, or 95% sequence identity to the second heavy chain sequence recited in any one of (1) to (14); and a fourth amino acid sequence that has at least 70%, 75%, 80%, 85%, 90%, or 95% sequence identity to the second light chain sequence recited in any one of (1) to (14).

In some embodiments, the present disclosure provides a multispecific antigen-binding molecule comprising a combination of four polypeptide chains selected from the group consisting of (1) to (15) below:

(1) a first heavy chain comprising amino acid sequence of SEQ ID NO: 41 and a first light chain comprising amino acid sequence of SEQ ID NO: 43, and a second heavy chain comprising amino acid sequence of SEQ ID NO: 53 and a second light chain comprising amino acid sequence of SEQ ID NO: 55;

(2) a first heavy chain comprising amino acid sequence of SEQ ID NO: 41 and a first light chain comprising amino acid sequence of SEQ ID NO: 43, and a second heavy chain comprising amino acid sequence of SEQ ID NO: 53 and a second light chain comprising amino acid sequence of SEQ ID NO: 56;

(3) a first heavy chain comprising amino acid sequence of SEQ ID NO: 41 and a first light chain comprising amino acid sequence of SEQ ID NO: 43, and a second heavy chain comprising amino acid sequence of SEQ ID NO: 57 and a second light chain comprising amino acid sequence of SEQ ID NO: 56;

(4) a first heavy chain comprising amino acid sequence of SEQ ID NO: 41 and a first light chain comprising amino acid sequence of SEQ ID NO: 43, and a second heavy chain comprising amino acid sequence of SEQ ID NO: 59 and a second light chain comprising amino acid sequence of SEQ ID NO: 61;

(5) a first heavy chain comprising amino acid sequence of SEQ ID NO: 41 and a first light chain comprising amino acid sequence of SEQ ID NO: 43, and a second heavy chain comprising amino acid sequence of SEQ ID NO: 62 and a second light chain comprising amino acid sequence of SEQ ID NO: 61;

(6) a first heavy chain comprising amino acid sequence of SEQ ID NO: 44 and a first light chain comprising amino acid sequence of SEQ ID NO: 46, and a second heavy chain comprising amino acid sequence of SEQ ID NO: 53 and a second light chain comprising amino acid sequence of SEQ ID NO: 55;

(7) a first heavy chain comprising amino acid sequence of SEQ ID NO: 44 and a first light chain comprising amino acid sequence of SEQ ID NO: 46, and a second heavy chain comprising amino acid sequence of SEQ ID NO: 64 and a second light chain comprising amino acid sequence of SEQ ID NO: 61;

(8) a first heavy chain comprising amino acid sequence of SEQ ID NO: 44 and a first light chain comprising amino acid sequence of SEQ ID NO: 46, and a second heavy chain comprising amino acid sequence of SEQ ID NO: 53 and a second light chain comprising amino acid sequence of SEQ ID NO: 56;

(9) a first heavy chain comprising amino acid sequence of SEQ ID NO: 44 and a first light chain comprising amino acid sequence of SEQ ID NO: 46, and a second heavy chain comprising amino acid sequence of SEQ ID NO: 57 and a second light chain comprising amino acid sequence of SEQ ID NO: 56;

(10) a first heavy chain comprising amino acid sequence of SEQ ID NO: 44 and a first light chain comprising amino acid sequence of SEQ ID NO: 46, and a second heavy chain comprising amino acid sequence of SEQ ID NO: 66 and a second light chain comprising amino acid sequence of SEQ ID NO: 56;

(11) a first heavy chain comprising amino acid sequence of SEQ ID NO: 41 and a first light chain comprising amino acid sequence of SEQ ID NO: 43, and a second heavy chain comprising amino acid sequence of SEQ ID NO: 64 and a second light chain comprising amino acid sequence of SEQ ID NO: 61;

(12) a first heavy chain comprising amino acid sequence of SEQ ID NO: 41 and a first light chain comprising amino acid sequence of SEQ ID NO: 43, and a second heavy chain comprising amino acid sequence of SEQ ID NO: 66 and a second light chain comprising amino acid sequence of SEQ ID NO: 56;

(13) a first heavy chain comprising amino acid sequence of SEQ ID NO: 44 and a first light chain comprising amino acid sequence of SEQ ID NO: 46, and a second heavy chain comprising amino acid sequence of SEQ ID NO: 62 and a second light chain comprising amino acid sequence of SEQ ID NO: 61;

(14) a first heavy chain comprising amino acid sequence of SEQ ID NO: 44 and a first light chain comprising amino acid sequence of SEQ ID NO: 46, and a second heavy chain comprising amino acid sequence of SEQ ID NO: 59 and a second light chain comprising amino acid sequence of SEQ ID NO: 61; and

(15) a first amino acid sequence that has at least 70%, 75%, 80%, 85%, 90%, or 95% sequence identity to the first heavy chain sequence recited in any one of (1) to (14); a second amino acid sequence that has at least 70%, 75%, 80%, 85%, 90%, or 95% sequence identity to the first light chain sequence recited in any one of (1) to (14); a third amino acid sequence that has at least 70%, 75%, 80%, 85%, 90%, or 95% sequence identity to the second heavy chain sequence recited in any one of (1) to (14); and a fourth amino acid sequence that has at least 70%, 75%, 80%, 85%, 90%, or 95% sequence identity to the second light chain sequence recited in any one of (1) to (14).

In some embodiments, the present disclosure provides a combination of any one of (i) to (iii) below:

(i) a multispecific antigen-binding molecule comprising the sequences recited in any one of (a1) to (a3) above, and a multispecific antigen-binding molecule comprising the sequences recited in any one of (b1) to (b8) above;

(ii) a multispecific antigen-binding molecule comprising the sequences recited in any one of (e1) to (e3) above, and a multispecific antigen-binding molecule comprising the sequences recited in any one of (f1) to (f8) above; and (iii) a multispecific antigen-binding molecule comprising the sequences recited in any one of (A1) to (A3) above, and a multispecific antigen-binding molecule comprising the sequences recited in any one of (B1) to (B8) above.

In some embodiments, the antigen-binding molecule of the invention is a bispecific antigen-binding molecule.

In some embodiments, the bispecific antigen-binding molecule is a bispecific antibody.

In some embodiments, the present disclosure provides a nucleic acid encoding the antigen-binding molecule of the invention. In some embodiments, the nucleic acid is an isolated nucleic acid.

In some embodiments, the present disclosure provides a vector comprising the nucleic acid. In some embodiments, the present disclosure provides a vector into which the nucleic acid is introduced.

In some embodiments, the present disclosure provides a cell comprising the nucleic acid or the vector. In some embodiments, the cell is a host cell.

In some embodiments, the present disclosure provides a method of producing a multispecific antigen-binding molecule of the invention, comprising culturing the cell so that the multispecific antigen-binding molecule is produced. In some embodiments, the method further comprises recovering the multispecific antigen-binding molecule from the culture of the cell.

The nucleic acid, vector, cell, and method can be suitably made/performed in view of the present disclosure and technical knowledge in the art.

Immunoconjugates

The invention also provides immunoconjugates comprising an anti-HLA-DQ2.5 antigen-binding molecule (antibody) herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med.

Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $^{211}$At, $^{131}$I, $^{125}$I, $^{90}$Y, $^{186}$Re, $^{188}$Re, $^{153}$Sm, $^{212}$Bi, $^{32}$P, $^{212}$Pb and radioactive isotopes of Lu. When the radioconjugate is used for detection, it may comprise a radioactive atom for scintigraphic studies, for example Tc-99m or $^{123}$I, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionuclide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Pharmaceutical Compositions/Formulations

Pharmaceutical compositions/formulations of an anti-HLA-DQ2.5 antigen-binding molecule (antibody) as described herein are prepared by mixing such antibody having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX (registered trademark), Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The composition/formulation herein may also contain more than one active ingredients as necessary for the particular indication being treated, preferably those with complementary activities that do not adversely affect each other. For example, it may be desirable to further provide a drug that might be combined with the anti-HLA-DQ2.5 antigen-binding molecule (antibody). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The compositions/formulations to be used for in vivo administration are generally sterile. Sterility may be readily accomplished, e.g., by filtration through sterile filtration membranes.

Therapeutic Methods and Compositions

Any of the anti-HLA-DQ2.5 antigen-binding molecules (antibodies) provided herein may be used in therapeutic methods. In one aspect, an anti-HLA-DQ2.5 antigen-binding molecule (antibody) for use as a medicament is provided. In further aspects, an anti-HLA-DQ2.5 antigen-binding molecule (antibody) for use in treating celiac disease is provided. In certain embodiments, an anti-HLA-DQ2.5 antigen-binding molecule (antibody) for use in a method of treatment is provided. In certain embodiments, the invention provides an anti-HLA-DQ2.5 antigen-binding molecule (antibody) for use in a method of treating an individual having celiac disease comprising administering to the individual an effective amount of the anti-HLA-DQ2.5 antigen-binding molecule (antibody). In one such embodiment, the method further comprises administering to the individual an effective amount of at least one additional therapeutic agent, e.g., as described below.

In a further aspect, the invention provides for the use of an anti-HLA-DQ2.5 antigen-binding molecule (antibody) in the manufacture or preparation of a medicament. In one embodiment, the medicament is for treatment of celiac disease. In a further embodiment, the medicament is for use in a method of treating celiac disease comprising administering to an individual having celiac disease an effective amount of the medicament. In one such embodiment, the method further comprises administering to the individual an effective amount of at least one additional therapeutic agent, e.g., as described below.

In some embodiments, the present disclosure provides use of the multispecific antigen-binding molecule of the invention in the manufacture of a medicament. In some embodiments, the medicament is a medicament for treatment and/or prevention of celiac disease.

In a further aspect, the invention provides a method for treating a celiac disease. In one embodiment, the method comprises administering to an individual having celiac disease an effective amount of an anti-HLA-DQ2.5 antigen-binding molecule (antibody). In one such embodiment, the method further comprises administering to the individual an effective amount of at least one additional therapeutic agent, as described below. An "individual" according to any of the above embodiments may be a human.

In some embodiments, the present disclosure provides a method of treating an individual having celiac disease comprising administering to the individual an effective amount of the multispecific antigen-binding molecule of the invention. In some embodiments, the present disclosure provides use of the multispecific antigen-binding molecule of the invention for treating an individual having celiac disease.

In a further aspect, the invention provides a pharmaceutical composition/formulation comprising any of the anti-HLA-DQ2.5 antigen-binding molecules (antibodies) provided herein, e.g., for use in any of the above therapeutic methods for celiac disease. In one embodiment, a pharmaceutical composition/formulation comprises any of the anti-HLA-DQ2.5 antigen-binding molecules (antibodies) provided herein and a pharmaceutically acceptable carrier. In another embodiment, a pharmaceutical composition/formulation comprises any of the anti-HLA-DQ2.5 antigen-binding molecules (antibodies) provided herein and at least one additional therapeutic agent, e.g., as described below.

In some embodiments, the present disclosure provides a pharmaceutical composition/formulation comprising the multispecific antigen-binding molecule of the invention, and a pharmaceutically acceptable carrier. In some embodiments, the composition/formulation is a pharmaceutical composition/formulation for use in the treatment and/or prevention of celiac disease.

Antibodies of the invention can be used either alone or in combination with other agents in a therapy. For instance, an antibody of the invention may be co-administered with at least one additional therapeutic agent. In certain embodiments, an additional therapeutic agent is any agent which is suitable for co-administration and available to those skilled in the art.

An antibody of the invention can be used either alone or in combination with another antibody in a therapy. For instance, an antibody of the invention may be co-administered with at least one additional antibody of the invention. In certain embodiments, these antibodies are administered concurrently or simultaneously, or subsequently. In certain embodiments, a mixture, cocktail, or combination of these antibodies which is suitable for co-administration is administered. These antibodies may be any antibodies disclosed herein. In some embodiments, these antibodies are two or more homomeric antibodies disclosed herein, such as DQN0344xx and DQN0385ee or any optimized and/or humanized variants of DQN0344xx and DQN0385ee.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-HLA-DQ2.5 antigen-binding molecule (antibody) and administration of an additional therapeutic agent occur within about one month, or within about one, two or three weeks, or within about one, two, three, four, five, or six days, of each other.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Two or more of the antibodies of the invention (i.e., two or more therapeutic agents of the invention) may be administered in a course of treatment. They may be administered separately or simultaneously. They may be administered concomitantly. In concomitant administration, two or more antibodies may be administered simultaneously or separately. In some cases, a certain antibody/agent may be administered first; and the symptom may be monitored; and depending on the symptom, if necessary, another antibody/agent may be further administered. Alternatively, two or more antibodies of the invention may be contained in a combination drug/agent. Such a combination drug/agent may be administered as described herein. The dose/dosage of each antibody contained may be suitably determined as mentioned herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 micro g/kg to 15 mg/kg (e.g. 0.1 mg/kg-Omg/kg) of antibody can be an initial candidate dosage for administration to the patient, whether, for example, by one or more separate administrations, or by continuous infusion. One typical daily dosage might range from about 1 micro g/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. The progress of this therapy is easily monitored by conventional techniques and assays.

It is understood that any of the above formulations or therapeutic methods may be carried out using an immunoconjugate of the invention in place of or in addition to an anti-HLA-DQ2.5 antigen-binding molecule (antibody).

Kit/Articles of Manufacture

In another aspect of the invention, a kit or an article of manufacture containing materials useful for the treatment, prevention and/or diagnosis of the disorders described above is provided. The kit or article of manufacture comprises a container and a label on or a package insert associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active ingredient in the composition is an antibody of the invention. The label or package insert indicates that the composition is used for treating the condition of choice. Moreover, the kit or article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The kit or article of manufacture in this embodiment of the invention may further comprise a package insert indicating that the compositions can be used to treat a particular condition. Alternatively, or additionally, the kit or article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the kits or articles of manufacture may include an immunoconjugate of the invention in place of or in addition to an anti-HLA-DQ2.5 antigen-binding molecule (antibody).

In some embodiments, the present disclosure provides a kit for use in the treatment and/or prevention of celiac disease, which comprises at least the multispecific antigen-binding molecule of the invention, and instructions for use.

Methods of Using Antigen-Binding Molecules

The antigen-binding molecules of the present disclosure can be combined with techniques of various, preexisting medical use. Non-limiting examples of techniques that can be combined with the antigen-binding molecules of the present disclosure include methods of incorporating a nucleic acid encoding an antigen-binding molecule into the living body using a viral vector or such, and directly expressing the antigen-binding molecule. Examples of such viral vectors include, but not limited to, adenovirus. Alternatively, it is possible to directly incorporate a nucleic acid encoding an antigen-binding molecule into the living body by, for example, an electroporation method or a method of directly administering a nucleic acid, without using a viral vector. Alternatively, it is possible to administer a cell genetically modified to secrete/express the antigen-binding molecule to the living body, and allow the antigen-binding molecule to be continuously secreted in the living body.

Although the invention will be described in some detail by way of illustration and example for purposes of clarity of understanding, the descriptions and examples should not be construed as limiting the scope of the invention. The disclosures of all patent and scientific literature cited herein are expressly incorporated in their entirety by reference.

EXAMPLES

The following are examples of compositions of the invention. It is understood that various other embodiments may be practiced, given the general description provided above.

Example 1

Expression and Purification of Recombinant Proteins 1.1. Expression and Purification of Recombinant HLA-DQ2.5/33Mer Gliadin Peptide Complex, HLA-DQ2.5/Gamma 2 Gliadin Peptide Complex, and HLA-DQ2.5/BC Hordein Peptide Complex Expression and Purification of Recombinant HLA-DQ2.5/33Mer Gliadin Peptide Complex The sequences used for expression and purification are: HLA-DQA1*0501 (Protein Data Bank accession code 4OZG) and HLA-DQB1*0201 (Protein Data Bank accession code 4OZG), both of which have a CAMPATH-1H signal sequence: MGWSCIILFLVATATGVHS (SEQ ID NO: 170). HLA-DQA1*0501 has C47S mutation, GGGG linker (SEQ ID NO: 171) and c-fos leucine zipper sequence (PNAS, 1998 Sep. 29; 95(20): 11828-33) and a Flag-tag on the C-terminus of HLA-DQA1*0501. HLA-DQB1*0201 has 33-mer gliadin peptide sequence: LQLQPFPQPELPYPQPELPYPQPELPYPQPQPF (SEQ ID NO: 172), and factor X cleavage linker (Acta Crystallogr Sect F Struct Biol Cryst Commun. 2007 Dec. 1; 63(Pt 12): 1021-1025.) on the N-terminus of HLA-DQB1*0201, GGGGG linker (SEQ ID NO: 173) and c-jun leucine zipper sequence (Proc. Natl. Acad. Sci. USA, 1998 Sep. 29; 95(20): 11828-33), GGGGG linker (SEQ ID NO: 173), and BAP sequence (BMC Biotechnol. 2008; 8: 41), 8×His-tag on the C-terminus of HLA-DQB1*0201. A recombinant HLA-DQ2.5/33mer gliadin peptide complex was expressed transiently using FreeStyle™293-F cell line (Thermo Fisher). Conditioned media expressing the HLA-DQ2.5/33mer gliadin peptide complex was incubated with an immobilized metal affinity chromatography (IMAC) resin, followed by elution with imidazole. Fractions containing the HLA-DQ2.5/33mer gliadin peptide complex were collected and subsequently subjected to a SUPERDEX (registered trademark) 200 gel filtration column (GE healthcare) equilibrated with 1×PBS. Fractions containing the HLA-DQ2.5/33mer gliadin peptide complex were then pooled and stored at −80 degrees Celsius (C).

Expression and Purification of Recombinant HLA-DQ2.5/Gamma 2 Gliadin Peptide Complex The sequences used for expression and purification are: HLA-DQA1*0501 (Protein Data Bank accession code 4OZG) and HLA-DQB1*0201 (Protein Data Bank accession code 4OZG), both of which have a CAMPATH-1H signal sequence: MGWSCIILFLVATATGVHS (SEQ ID NO: 170). HLA-DQA1*0501 has C47S mutation, 3C protease cleavage linker: LEVLFQGP (SEQ ID NO: 174) and GGGG linker (SEQ ID NO: 171) and c-fos leucine zipper sequence (PNAS, 1998 Sep. 29; 95(20): 11828-33) and a Flag-tag on the C-terminus of HLA-DQA1*0501. HLA-DQB1*0201 has gamma 2 gliadin peptide sequence: IIQPEQPAQLP (SEQ ID NO: 175), and factor X cleavage linker (Acta Crystallogr Sect F Struct Biol Cryst Commun. 2007 Dec. 1; 63(Pt 12): 1021-1025.) on the N-terminus of HLA-DQB1*0201, 3C protease cleavage linker: LEVLFQGP (SEQ ID NO: 174) and c-jun leucine zipper sequence (Proc. Natl. Acad. Sci. USA, 1998 Sep. 29; 95(20): 11828-33), GGGGG linker (SEQ ID NO: 173), and BAP sequence (BMC Biotechnol. 2008; 8: 41), 8×His-tag on the C-terminus of HLA-DQB1*0201. A recombinant HLA-DQ2.5/gamma 2 gliadin peptide complex was expressed transiently using FreeStyle™293-F cell line. Conditioned media expressing the HLA-DQ2.5/gamma 2 gliadin peptide complex was incubated with an IMAC resin, followed by elution with imidazole. Fractions containing the HLA-DQ2.5/gamma 2 gliadin peptide complex were collected and subsequently subjected to a SUPERDEX (registered trademark) 200 gel filtration column equilibrated with 1×PBS. Fractions containing the HLA-DQ2.5/gamma 2 gliadin peptide complex were then pooled and stored at −80 degrees C.

Expression and purification of recombinant HLA-DQ2.5/BC Hordein peptide complex The sequences used for expression and purification are: HLA-DQA1*0501 (Protein Data Bank accession code 4OZG) and HLA-DQB1*0201 (Protein Data Bank accession code 4OZG), both of which have a CAMPATH-1H signal sequence: MGWSCIILFL-VATATGVHS (SEQ ID NO: 170). HLA-DQA1*0501 has C47S mutation, 3C protease cleavage linker: LEVLFQGP (SEQ ID NO: 174) and GGGG linker (SEQ ID NO: 171) and c-fos leucine zipper sequence (PNAS, 1998 Sep. 29; 95(20): 11828-33) and a Flag-tag on the C-terminus of HLA-DQA1*0501. HLA-DQB1*0201 has BC Hordein peptide sequence: EPEQPIPEQPQPYPQQP (SEQ ID NO: 176), and factor X cleavage linker (Acta Crystallogr Sect F Struct Biol Cryst Commun. 2007 Dec. 1; 63(Pt 12): 1021-1025.) on the N-terminus of HLA-DQB1*0201, 3C protease cleavage linker: LEVLFQGP (SEQ ID NO: 174) and c-jun leucine zipper sequence (Proc. Natl. Acad. Sci. USA, 1998 Sep. 29; 95(20): 11828-33), GGGGG linker (SEQ ID NO: 173), and BAP sequence (BMC Biotechnol. 2008; 8: 41), 8×His-tag on the C-terminus of HLA-DQB1*0201. A recombinant HLA-DQ2.5/BC Hordein peptide complex was expressed transiently using FreeStyle™293-F cell line. Conditioned media expressing the HLA-DQ2.5/BC Hordein peptide complex was incubated with an IMAC resin, followed by elution with imidazole. Fractions containing the HLA-DQ2.5/BC Hordein peptide complex were collected and subsequently subjected to a SUPERDEX (registered trademark) 200 gel filtration column equilibrated with 1×PBS. Fractions containing the HLA-DQ2.5/BC Hordein peptide complex were then pooled and stored at −80 degrees C.

Example 2

2.1 Establishment of Ba/F3 Cell Lines Expressing HLA-DQ2.5, HLA-DQ2.2, HLA-DQ7.5, HLA-DQ8, HLA-DQ5.1, HLA-DQ6.3, HLA-DQ7.3, HLA-DR, and HLA-DP HLA-DQA1*0501 cDNA (IMGT/HLA Accession No. HLA00613), HLA-DQA1*0201 cDNA (IMGT/HLA Accession No. HLA00607), HLA-DQA1*0505 cDNA (IMGT/HLA Accession No. HLA00619), HLA-DQA1*0301 cDNA (IMGT/HLA Accession No. HLA00608), HLA-DQA1*0101 cDNA (IMGT/HLA Accession No. HLA00601), HLA-DQA1*0103 cDNA (IMGT/HLA Accession No. HLA00604), HLA-DQA1*0303 cDNA (IMGT/HLA Accession No. HLA00611), HLA-DRA1*0101 cDNA (GenBank Accession No. NM_019111.4), or HLADPA1*0103 cDNA (IMGT/HLA Accession No. HLA00499), was Inserted into the Expression Vector pCXND3 (WO2008/156083)

HLA-DQB1*0201 cDNA (IMGT/HLA accession No. HLA00622), HLA-DQB1*0202 cDNA (IMGT/HLA accession No. HLA00623), HLA-DQB1*0301 cDNA (IMGT/HLA accession No. HLA00625), HLA-DQB1*0302 cDNA (IMGT/HLA accession No. HLA00627), HLA-DQB1*0501 cDNA (IMGT/HLA accession No. HLA00638), HLA- DQB1*0603 cDNA (IMGT/HLA accession No. HLA00647), HLA-DRB1*0301 cDNA (IMGT/HLA accession No. HLA00671), or HLA-DPB1*0401 cDNA (IMGT/HLA accession No. HLA00521) was inserted into the expression vector pCXZD1 (US/20090324589).

Each of the linearized HLA-DQA1*0501-pCXND3 and HLA-DQB1*0201-pCXZD1, and each of the linearized HLA-DQA1*0201-pCXND3 and HLA-DQB1*0202-pCXZD1, HLA-DQA1*0505-pCXND3 and HLA-DQB1*0301-pCXZD1, HLA-DQA1*0301-pCXND3 and HLA-DQB1*0302-pCXZD1, HLA-DQA1*0101-pCXND3 and HLA-DQB1*0501-pCXZD1, HLA-DQA1*0103-pCXND3 and HLA-DQB1*0603-pCXZD1, HLA-DQA1*0303-pCXND3 and HLA-DQB1*0301-pCXZD1, HLA-DRA1*0101-pCXND3 and HLA-DRB1*0301-pCXZD1, HLA-DPA1*0103-pCXND3 and HLA-DPB1*0401-pCXZD1, were simultaneously introduced into mouse IL-3-dependent pro-B cell-derived cell line Ba/F3 by electroporation (LONZA, the 4D-Nucleofector™ X apparatus). Transfected cells were then cultured in media containing the Geneticin™ and Zeocin™ media. Cultured and expanded cell was then checked the expression of HLA molecule and confirmed high expression of HLA.

Established each cell lines were named Ba/F3-HLA-DQ2.5 (HLA-DQA1*0501, HLA-DQB1*0201), Ba/F3-HLA-DQ2.2 (HLA-DQA1*0201, HLA-DQB1*0202), Ba/F3-HLA-DQ7.5 (HLA-DQA1*0505, HLA-DQB1*0301), Ba/F3-HLA-DQ8 (HLA-DQA1*0301, HLA-DQB1*0302), Ba/F3-HLA-DQ5.1 (HLA-DQA1*0101, HLA-DQB1*0501), Ba/F3-HLA-DQ6.3 (HLA-DQA1*0103, HLA-DQB1*0603), Ba/F3-HLA-DQ7.3 (HLA-DQA1*0303, HLA-DQB1*0301), Ba/F3-HLA-DR (HLA-DRA1*0101, HLA-DRB1*0301), Ba/F3-HLA-DP (HLA-DPA1*0103, HLA-DPB1*0401).

2.2 Establishment of Ba/F3 Cell Lines Expressing HLA-DQ2.5/CLIP Peptide, HLA-DQ2.5/Hepatitis B Virus Peptide, HLA-DQ2.5/*Salmonella* Peptide, HLA-DQ2.5/Thyroperoxidase Peptide, HLA-DQ2.5/*Mycobacterium bovis* Peptide, HLA-DQ2.5/Alpha 1 Gliadin Peptide, HLA-DQ2.5/Alpha 2 Gliadin Peptide, HLA-DQ2.5/Gamma 1 Gliadin Peptide, HLA-DQ2.5/Gamma2 Gliadin Peptide, HLA-DQ2.5/Omega 1 Gliadin Peptide, HLA-DQ2.5/Omega 2 Gliadin Peptide, HLA-DQ2.5/BC Hordein Peptide, HLA-DQ2.5/Alpha 3 Gliadin Peptide, HLA-DQ2.5/Alpha 1b Gliadin Peptide, HLA-DQ2.5/Gamma 4a Gliadin Peptide, HLA-DQ2.5/Gamma 4b Gliadin Peptide, HLA-DQ2.5/Avenin 1 Peptide, HLA-DQ2.5/Avenin 2 Peptide, HLA-DQ2.5/Avenin 3 Peptide, HLA-DQ2.5/Hordein 1 Peptide, HLA-DQ2.5/Hordein 2 Peptide, HLA-DQ2.5/Secalin 1 Peptide, HLA-DQ2.5/Secalin 2 Peptide, HLA-DQ2.5/33Mer Gliadin Peptide, HLA-DQ2.5/26Mer Gliadin Peptide HLA-DQA1*0501 cDNA (IMGT/HLA accession No. HLA00613) was inserted into the expression vector pCXND3 (WO2008/156083).

HLA-DQB1*0201 cDNA (IMGT/HLA accession No. HLA00622) was inserted into the expression vector pCXZD1 (US/20090324589). HLA-DQB1*0201 for the HLA-DQ2.5/each peptide complex has each peptide sequence and factor X cleavage linker: (Acta Crystallogr Sect F Struct Biol Cryst Commun. 2007 Dec. 1; 63(Pt 12): 1021-1025.) on the N-terminus of HLA-DQB1*0201. In particular of each peptide sequence, KLPKPPKPVSKMRMATPLLMQALPMGALP (SEQ ID NO: 177) was used for the CLIP (hCLIP) peptide sequence, PDRVHFASPLHVAWR (SEQ ID NO: 178) was used for the Hepatitis B virus peptide sequence, MMAWRMMRY (SEQ ID NO: 179) was used for the *Salmonella* peptide sequence, YIDVWLGGLAENFLPY (SEQ ID NO: 180) was used for the Thyroperoxidase peptide sequence, KPLLIIAEDVEGEY (SEQ ID NO: 181) was used for the *Mycobacterium bovis* peptide sequence, QPFPQPELPYP (SEQ ID NO: 182) was used for the alpha 1 gliadin peptide sequence, FPQPELPYPQP (SEQ ID NO: 183) was used for the alpha 2 gliadin peptide sequence, QPQQSFPEQQQ (SEQ ID NO: 184) was used for the gamma 1 gliadin peptide sequence, GIIQPEQPAQLP (SEQ ID NO: 185) was used for the gamma 2 gliadin peptide sequence, QPFPQPEQPFP (SEQ ID NO: 186) was used for the omega 1 gliadin peptide sequence, FPQPEQPFPWQ (SEQ ID NO: 187) was used for the omega 2 gliadin peptide sequence, PQQPIPEQPQPYPQQP (SEQ ID NO: 188) was used for the BC hordein peptide sequence, PFRPEQPYPQP (SEQ ID NO: 189) was used for the alpha 3 gliadin peptide sequence, LPYPQPELPYP (SEQ ID NO: 190) was used for the alpha 1b gliadin peptide sequence, FSQPEQEFPQP (SEQ ID NO: 191) was used for the gamma 4a gliadin peptide sequence, FPQPEQEFPQP (SEQ ID NO: 192) was used for the gamma 4b gliadin peptide sequence, QPYPEQEEPFV (SEQ ID NO: 193) was used for the avenin 1 peptide sequence, QPYPEQEQPFV (SEQ ID NO: 194) was used for the avenin 2 peptide sequence, QPYPEQEQPIL (SEQ ID NO: 195) was used for the avenin 3 peptide sequence, PQQPFPQPEQPFRQ (SEQ ID NO: 196) was used for the hordein 1 peptide sequence, QEFPQPEQPFPQQP (SEQ ID NO: 197) was used for the hordein 2 peptide sequence, PEQPFPQPEQPFPQ (SEQ ID NO: 198) was used for the secalin 1 peptide sequence, QPFPQPEQPFPQSQ (SEQ ID NO: 199) was used for the secalin 2 peptide sequence, PQQQTLQPEQPAQLP (SEQ ID NO: 200) was used for the 14mer 1 peptide sequence, LQLQPFPQPELPYPQPELPYPQPELPYPQPQPF (SEQ ID NO: 201) was used for the 33mer gliadin peptide sequence, FLQPEQPFPEQPEQPYPEQPEQPFPQ (SEQ ID NO: 202) was used for the 26mer gliadin peptide sequence.

Each of the linearized HLA-DQA1*0501-pCXND3 and HLA-DQB1*0201/each peptide-pCXZD1 were simultaneously introduced into mouse IL-3-dependent pro-B cell-derived cell line Ba/F3 by electroporation (LONZA, the 4D-Nucleofector™ X apparatus). Transfected cells were then cultured in media containing the Geneticin™ and Zeocin™ media.

Cultured and expanded cell was then checked the expression of HLA-DQ2.5 molecule and confirmed high expression of HLA-DQ2.5. Established each cell lines were named Ba/F3-HLA-DQ2.5/CLIP (HLA-DQA1*0501, HLA-DQB1*0201 for HLA-DQ2.5/CLIP peptide), Ba/F3-HLA-DQ2.5/HBV1 (HLA-DQA1*0501, HLA-DQB1*0201 for HLA-DQ2.5/Hepatitis B virus peptide), Ba/F3-HLA-DQ2.5/*Salmonella* (HLA-DQA1*0501, HLA-DQB1*0201 for HLA-DQ2.5/*Salmonella* peptide), Ba/F3-HLA-DQ2.5/TPO (HLA-DQA1*0501, HLA-DQB1*0201 for HLA-DQ2.5/Thyroperoxidase peptide), Ba/F3-HLA-DQ2.5/*M. bovis* (HLA-DQA1*0501, HLA-DQB1*0201 for HLA-DQ2.5/*Mycobacterium bovis* peptide), Ba/F3-HLA-DQ2.5/alpha 1 gliadin (HLA-DQA1*0501, HLA-DQB1*0201 for HLA-DQ2.5/alpha 1 gliadin peptide), Ba/F3-HLA-DQ2.5/alpha 2 gliadin (HLA-DQA1*0501, HLA-DQB1*0201 for HLA-DQ2.5/alpha 2 gliadin peptide), Ba/F3-HLA-DQ2.5/gamma 1 gliadin (HLA-DQA1*0501, HLA-DQB1*0201 for HLA-DQ2.5/gamma 1 gliadin peptide), Ba/F3-HLA-DQ2.5/gamma 2 gliadin (HLA-DQA1*0501, HLA-DQB1*0201 for HLA-DQ2.5/gamma 2 gliadin peptide), Ba/F3-HLA-DQ2.5/omega 1 gliadin (HLA-DQA1*0501, HLA-DQB1*0201 for HLA-DQ2.5/omega 1 gliadin peptide), Ba/F3-HLA-DQ2.5/omega 2 gliadin (HLA-DQA1*0501, HLA-DQB1*0201 for HLA-DQ2.5/omega 2 gliadin peptide), Ba/F3-HLA-DQ2.5/BC hordein (HLA-DQA1*0501, HLA-DQB1*0201 for HLA-DQ2.5/BC hordein peptide), Ba/F3-HLA-DQ2.5/alpha 3 gliadin(HLA-DQA1*0501, HLA-DQB1*0201 for HLA-DQ2.5/alpha 3 gliadin peptide), Ba/F3-HLA-DQ2.5/alpha 1b gliadin(HLA-DQA1*0501, HLA-DQB1*0201 for HLA-DQ2.5/alpha 1b gliadin peptide), Ba/F3-HLA-DQ2.5/gamma 4a gliadin (HLA-DQA1*0501, HLA-DQB1*0201 for HLA-DQ2.5/gamma 4a gliadin peptide), Ba/F3-HLA-DQ2.5/gamma 4b gliadin(HLA-DQA1*0501, HLA-DQB1*0201 for HLA-DQ2.5/gamma 4b gliadin peptide), Ba/F3-HLA-DQ2.5/avenin 1 (HLA-DQA1*0501, HLA-DQB1*0201 for HLA-DQ2.5/avenin 1 peptide), Ba/F3-HLA-DQ2.5/avenin 2 (HLA-DQA1*0501, HLA-DQB1*0201 for HLA-DQ2.5/avenin 2 peptide), Ba/F3-HLA-DQ2.5/avenin 3 (HLA-DQA1*0501, HLA-DQB1*0201 for HLA-DQ2.5/avenin 3 peptide), Ba/F3-HLA-DQ2.5/hordein 1 (HLA-DQA1*0501, HLA-DQB1*0201 for HLA-DQ2.5/hordein 1 peptide), Ba/F3-HLA-DQ2.5/hordein 2 (HLA-DQA1*0501, HLA-DQB1*0201 for HLA-DQ2.5/hordein 2 peptide), Ba/F3-HLA-DQ2.5/secalin 1 (HLA-DQA1*0501, HLA-DQB1*0201 for HLA-DQ2.5/secalin 1 peptide), Ba/F3-HLA-DQ2.5/secalin 2 (HLA-DQA1*0501, HLA-DQB1*0201 for HLA-DQ2.5/secalin 2 peptide), Ba/F3-HLA-DQ2.5/14mer 1 (HLA-DQA1*0501, HLA-DQB1*0201 for HLA-DQ2.5/14mer 1 peptide), Ba/F3-HLA-DQ2.5/33mer gliadin (HLA-DQA1*0501, HLA-DQB1*0201 for HLA-DQ2.5/33mer gliadin peptide), Ba/F3-HLA-DQ2.5/26mer gliadin (HLA-DQA1*0501, HLA-DQB1*0201 for HLA-DQ2.5/26mer gliadin peptide).

Example 3

Lead Antibodies Identification

Anti-DQ2.5 lead antibodies, DQN0344xx (heavy chain: DQN0344Hx, SEQ ID NO: 71 and light chain: DQN0344Lx, SEQ ID NO: 75) and DQN0385ee (heavy chain: DQN0385He, SEQ ID NO: 79 and light chain: DQN0385Le, SEQ ID NO: 83) were selected in accordance to the procedures described in WO2019069993.

Humanization

Although DQN0344xx and DQN0385ee showed favorable selectivity and cross-reactivity against HLA-DQ2.5/gluten peptides, the variable regions of these antibodies are in rabbit sequences, thus, it is not applicable for administration into patients due to immunogenicity issue. Therefore, humanization of the variable regions for these antibodies were performed.

49 types of VHs were designed by substituting the frameworks of DQN0344Hx and DQN0385He with human germline frameworks (SEQ ID NO: 1, 2, 3, 4, 5, 6 or 7 as FRI, SEQ ID NO: 9 for DNQ0344Hx and 10 for DQN0385He as FR2, SEQ ID NO: 11, 12, 13, 14, 15, 16 or 17 as FR3, SEQ ID NO: 18 for DNQ0344Hx and 19 for DQN0385He as FR4). 16 types of VLs were designed by substituting the frameworks of DQN0344Lx and DQN0385Le with human germline frameworks (SEQ ID NO: 20, 21, 22 or 23 as FR1, SEQ ID NO: 24 for DQN0344Lx and 34 for DQN0385Le as FR2, SEQ ID NO: 26, 27, 28, or 29 as FR3, SEQ ID NO: 30 as FR4). The polynucleotides encoding DQN0344Hx, DQN0385He and the designed VHs were cloned into expression vectors containing polynucleotides encoded for the heavy chain constant region SG1 (SEQ ID NO: 31) respectively. The polynucleotides encoding DQN0344Lx, DQN0385Le and the designed VLs were cloned into expression vectors containing polynucleotides encoded for the light chain constant region SKI (SEQ ID NO: 32), respectively. Thereafter, heavy chains comprising DQN0344Hx or DQN0385He, together with the respective designed VHs, were transiently expressed with their corresponding light chains, DQN0344Lx, DQN0385Le or the respective designed VLs, into Expi293™ expression system (Invitrogen) followed by Protein A purification.

Binding profiles of these antibodies against HLA-DQ2.5/multiple gluten peptides was evaluated by FCM analysis. Binding activities of each antibody is represented by the Mean Fluorescence Intensity values (MFI). Antibodies were incubated with HLA-DQ2.5-gluten peptide-Ba/F3 cells for 30 minutes at room temperature and washed with FACS buffer (2% FBS, 2 mM EDTA in PBS). Goat F(ab')2 anti-Human IgG, Mouse ads-PE (Southern Biotech, Cat. 2043-09) was then added and incubated for 20 minutes in the dark at 4° C. and subsequently washed. Data acquisition was performed on LSRFortessa™ X-20 cell analyzer (Becton Dickinson), followed by analysis using the FlowJo™ software (Tree Star) and Microsoft® Office Excel® 2013 software.

Among the 49 types of designed VHs and the 16 types of designed VLs, 25H and 09L (as shown in Table 2-1) were selected as framework region sequences in DQN0344xx based on the binding against HLA-DQ2.5/gluten peptides as well as antibody expression level, and named as DQN034425 (DQN034425H/09L (heavy chain SEQ ID NO: 84, light chain SEQ ID NO: 85)). However, none of the FR combinations were able to maintain the binding activity towards HLA-DQ2.5/gluten peptides compared with DQN0385ee. It seems to be a challenge to humanize DQN0385ee without compromising on the binding activity towards HLA-DQ2.5/gluten peptides. From the numerous variants generated, 0054H and 009L were eventually selected as a FR combination for DQN0385He and DQN0385Le (shown in Table 2-1), and named as DQN0385ee0054 (DQN0385ee0054H/009L (heavy chain SEQ ID NO: 87, light chain SEQ ID NO: 86)).

TABLE 2-1

Selected FR sequences in humanization

| Name of VH or VL | CDRs | SEQ ID NO: | | | | Full length |
| --- | --- | --- | --- | --- | --- | --- |
| | | FR1 | FR2 | FR3 | FR4 | |
| DQN034425H | Identical to DQN0344Hx | 4 | 9 | 14 | 18 | 84 |
| DQN034409L | Identical to DQN0344Lx | 20 | 24 | 28 | 30 | 85 |
| DQN0385ee0054H | Identical to DQN0385He | 4 | 33 | 14 | 19 | 87 |
| DQN0385ee009L | Identical to DQN0385Le | 20 | 34 | 28 | 30 | 86 |

Fab Optimization

To improve the binding affinity towards HLA-DQ2.5/gluten peptides without increasing the binding against HLA-DQ2.5/irrelevant peptides, comprehensive mutagenesis in the CDRs and several positions in FRs was performed. Multiple mutations and mutation combinations were then performed to improve multidimensional properties such as selectivity of binding against HLA-DQ2.5/multiple gluten peptides over irrelevant peptides as well as physicochemical properties such as antibody expression level and ECM binding, which may affect the antibody pharmacokinetics (US2014/0080153).

Although both DQN0344xx and DQN0385ee were humanized, two cysteine residues located in CDRH1 (position 35a according to Kabat numbering, Kabat et al., Sequence of proteins of immunological interest, 5th Ed., Public Health Service, National Institutes of Health, Bethesda, Md. (1991)) and CDRH2 (position 50 according to Kabat numbering), commonly found in rabbit antibody sequences might cause the heterogeneity of disulfide bond formation. Thus substitution of these cysteine residues to other amino acids was performed. However, such substitutions (C35aV/C50A in DQN034425H and C35aS/C50S in DQN0385ee0054H) significantly decreased the binding affinity towards HLA-DQ2.5/gluten peptides and/or decreased antibody expression level. To improve the binding affinity, S32A, N73T and D95E were introduced into DQN034425H; N28E, A55Y, S56E, H92E, I94V and N95aA were introduced into DQN034409L; S30A, S32W, W34F and S61G were introduced into DQN0385ee0054H and A25T, L54K and S67L were introduced into DQN0385ee009L. To improve antibody expression level, R16G, S61K, K64E and L102V were introduced into DQN034425H, and S31E and I35M were introduced into DQN0385ee0054H. In addition, to reduce ECM binding and the binding against HLA-DQ2.5/irrelevant peptides such as HLA-DQ2.5/CLIP, R16G and K64E were introduced into DQN034425H; S56Y were introduced into DQN034409L; T28E, S30A, S61E and G65E were introduced into DQN0385ee0054H, and S56E, and Y94K were introduced into DQN0385ee009L. To reduce pI, S30E, N64E were introduced into DQN0385ee0054H, and to reduce negative charge, E79Q was introduced into DQN0385ee009L.

All antibodies were transiently expressed in mammalian cells by the method known to those skilled in the art using the genes constructed and were purified by the method known to those skilled in the art. The combination of amino acid substitutions was summarized in Table 2-2.

Generation of Bispecific Antibodies

To further expand the peptide coverage, bispecific antibodies which demonstrated broad cross-reactive binding to the multiple HLA-DQ2.5/gluten peptide complex were generated. To generate bispecific antibodies, thirteen multi-gluten peptide selective HLA-DQ2.5 bivalent antibodies were used (DQN0344xx, DQN0385ee, DQN034425H/09L, DQN0385ee0054H/009L, DQN0344H0976/L0591, DQN0344H1013/L0620, DQN0385H1270/L0722, DQN0385H1521/L0605, DQN0385H1270/L0681, DQN0385H1352/L0681, DQN0385H1527/L0605, DQN0385H1353/L0681, and DQN0385H1255/L0605). These purified bivalent antibodies were subjected to Fab-arm exchange technology (as described in Igawa et al. WO2016/159213) to generate sixteen bispecific antibodies; DQN0344xx//DQN0385ee (bispecific antibody of DQN0344xx and DQN0385ee), DQN034425// DQN0385ee0054 (bispecific antibody of DQN034425H/09L and DQN0385ee0054H/009L), DQN0344H0976/L0591//DQN0385H1270/L0722-F6 (bispecific antibody of DQN0344H0976/L0591 and DQN0385H1270/L0722), DQN0344H0976/L0591//DQN0385H1270/L0681-F6 (bispecific antibody of DQN0344H0976/L0591 and DQN0385H1270/L0681), DQN0344H0976/L0591// DQN0385H1352/L0681-F6 (bispecific antibody of DQN0344H0976/L0591 and DQN0385H1352/L0681), DQN0344H0976/L0591//DQN0385H1527/L0605-F6 (bispecific antibody of DQN0344H0976/L0591 and DQN0385H1527/L0605), DQN0344H0976/L0591// DQN0385H1255/L0605-F6 (bispecific antibody of DQN0344H0976/L0591 and DQN0385H1255/L0605), DQN0344H1013/L0620//DQN0385H1270/L0722-F6 (bispecific antibody of DQN0344H1013/L0620 and DQN0385H1270/L0722), DQN0344H1013// DQN0385H1521/L0605-F6 (bispecific antibody of DQN0344H1013/L0620 and DQN0385H1521/L0605), DQN0344H1013/L0620//DQN0385H1270/L0681-F6 (bispecific antibody of DQN0344H1013/L0620 and DQN0385H1270/L0681), DQN0344H1013/L0620// DQN0385H1352/L0681-F6 (bispecific antibody of DQN0344H1013/L0620 and DQN0385H1352/L0681),

TABLE 2-2

Summary of introduced mutations

| H/L | VH name | Amino acid substitutions compared with DQN034425H | SEQ ID NO | VL name | Amino acid substitutions compared with DQN034409L | SEQ ID NO |
| --- | --- | --- | --- | --- | --- | --- |
| DQN0344H0976/L0591 | DQN0344H0976 | R16G/S32A/C35aV/C50A/S61K/K64E/N73T/D95E | 88 | DQN0344L0591 | N28E/A55Y/S56E/H92E/I94V/E95aA | 90 |
| DQN0344H1013/L0620 | DQN0344H1013 | S32A/C35aV/C50A/S61K/K64E/N73T/D95E/L102V | 89 | DQN0344L0620 | S56Y/H92E/I94V/E95aA | 91 |

| H/L | VH name | Amino acid substitutions compared with DQN0385ee0054H | SEQ ID NO | VL name | Amino acid substitutions compared with DQN0385ee009L | SEQ ID NO |
| --- | --- | --- | --- | --- | --- | --- |
| DQN0385H1270/L0722 | DQN0385H1270 | S31E/S32W/W34F/I35M/C35aS/C50S/S61E/N64E | 92 | DQN0385L0722 | A25T/L54K/S56E/S67L/E79Q/Y94K | 98 |
| DQN0385H1270/L0681 | DQN0385H1270 | S31E/S32W/W34F/I35M/C35aS/C50S/S61E/N64E | 92 | DQN0385L0681 | A25T/L54K/S56E/S67L/Y94K | 99 |
| DQN0385H1352/L0681 | DQN0385H1352 | T28E/S31E/S32W/W34F/I35M/C35aS/C50S/S61E/N64E | 93 | DQN0385L0681 | A25T/L54K/S56E/S67L/Y94K | 99 |
| DQN0385H1527/L0605 | DQN0385H1527 | S30A/S32W/W34F/I35M/C35aS/C50S/S61E/N64E | 94 | DQN0385L0605 | A25T/L54K/S56E/Y94K | 100 |
| DQN0385H1255/L0605 | DQN0385H1255 | S31E/S32W/W34F/I35M/C35aS/C50S/S61G/N64E/G65E | 95 | DQN0385L0605 | A25T/L54K/S56E/Y94K | 100 |
| DQN0385H1521/L0605 | DQN0385H1521 | S30E/S32W/W34F/I35M/C35aS/C50S/S61E/N64E | 96 | DQN0385L0605 | A25T/L54K/S56E/Y94K | 100 |
| DQN0385H1353/L0681 | DQN0385H1353 | S30A/S31E/S32W/W34F/I35M/C35aS/C50S/S61E/N64E | 97 | DQN0385L0681 | A25T/L54K/S56E/S67L/Y94K | 99 |

DQN0344H1013/L0620//DQN0385H1353/L0681-F6 (bispecific antibody of DQN0344H1013/L0620 and DQN0385H1353/L0681), DQN0344H0976/L0591// DQN0385H1521/L0605-F6 (bispecific antibody of DQN0344H0976/L0591 and DQN0385H1521/L0605), DQN0344H0976/L0591//DQN0385H1353/L0681-F6 (bispecific antibody of DQN0344H0976/L0591 and DQN0385H1353/L0681), DQN0344H1013/L0620// DQN0385H1255/L0605-F6 (bispecific antibody of DQN0344H1013/L0620 and DQN0385H1255/L0605), and DQN0344H1013/L0620//DQN0385H1527/L0605-F6 (bispecific antibody of DQN0344H1013/L0620 and DQN0385H1527/L0605). The combination and sequences of bispecific antibodies produced were summarized in Tables 2-3 to 2-6.

As described above, bispecific antibody was generated by Fab-arm exchange technology. Alternatively, it can also be generated by transfecting two different heavy and two different light chains plasmids into mammalian cells. To efficiently obtain a bispecific antibody of interest, there are known amino acid substitutions and combinations in the CH1-CL domain interface that promote desired H chain-L chain association (WO2019065795). The above described variable region sequences with such constant regions (heavy chain constant region for DQN0344 arm: SEQ ID NO: 162, light chain constant region for DQN0344 arm: SEQ ID NO: 106, heavy chain constant region for DQN0385 arm: SEQ ID NO: 163, light chain constant region for DQN0385 arm: SEQ ID NO: 107. SEQ ID NOs of the full length were summarized in Tables 2-3 to 2-6) are known to show similar binding properties towards HLA-DQ2.5/multiple gluten peptides.

TABLE 2-3

Summary and sequences of bispecific antibodies

| | | Bispecific Ab name | DQN0344xx// DQN0385ee | DQN034425// DQN0385ee0054 |
|---|---|---|---|---|
| | | Arm A | DQN0344xx | DQN034425H/09L |
| | | Arm B | DQN0385ee | DQN0385ee0054H/009L |
| SEQ ID NO | Arm A | HCDR1 | 68 | 112 |
| | | HCDR2 | 69 | 113 |
| | | HCDR3 | 70 | 114 |
| | | H chain VR | 71 | 84 |
| | | H chain CR | 101 | 101 |
| | | full length H | 35 | 38 |
| | | full length H (different Fc) | 36 | 39 |
| | | LCDR1 | 72 | 108 |
| | | LCDR2 | 73 | 109 |
| | | LCDR3 | 74 | 110 |
| | | L chain VR | 75 | 111 |
| | | L chain CR | 103 | 103 |
| | | full length L | 37 | 40 |
| | Arm B | HCDR1 | 76 | 115 |
| | | HCDR2 | 77 | 116 |
| | | HCDR3 | 78 | 117 |
| | | H chain VR | 79 | 87 |
| | | H chain CR | 102 | 102 |
| | | full length H | 47 | 50 |
| | | full length H (different Fc) | 48 | 51 |
| | | LCDR1 | 80 | 118 |
| | | LCDR2 | 81 | 119 |
| | | LCDR3 | 82 | 120 |
| | | L chain VR | 83 | 86 |
| | | L chain CR | 103 | 103 |
| | | full length L | 49 | 52 |

TABLE 2-4

Summary and sequences of bispecific antibodies

| | | | Bispecific Ab name | | | | |
|---|---|---|---|---|---|---|---|
| | | | DQN0344 H0976/L0591// DQN0385 H1270/L0722-F6 | DQN0344 H0976/L0591// DQN0385 H1270/L0681-F6 | DQN0344 H0976/L0591// DQN0385 H1352/L0681-F6 | DQN0344 H0976/L0591// DQN0385 H1527/L0605-F6 | DQN0344 H0976/L0591// DQN0385 H1255/L0605-F6 |
| | | | | | Arm A | | |
| | | | DQN0344 H0976/L0591 | DQN0344H0976/ L0591 | DQN0344 H0976/L0591 | DQN0344 H0976/L0591 | DQN0344 H0976/L0591 |
| | | | | | Arm B | | |
| | | | DQN0385 H1270/L0722 | DQN0385H1270/ L0681 | DQN0385 H1352/L0681 | DQN0385 H1527/L0605 | DQN0385 H1255/L0605 |
| SEQ ID NO | Arm A | HCDR1 | 129 | 129 | 129 | 129 | 129 |
| | | HCDR2 | 130 | 130 | 130 | 130 | 130 |
| | | HCDR3 | 131 | 131 | 131 | 131 | 131 |
| | | H chain VR | 88 | 88 | 88 | 88 | 88 |
| | | H chain CR | 105 | 105 | 105 | 105 | 105 |
| | | full length H | 41 | 41 | 41 | 41 | 41 |
| | | full length H (different Fc) | 42 | 42 | 42 | 42 | 42 |
| | | LCDR1 | 132 | 132 | 132 | 132 | 132 |
| | | LCDR2 | 133 | 133 | 133 | 133 | 133 |
| | | LCDR3 | 134 | 134 | 134 | 134 | 134 |
| | | L chain VR | 90 | 90 | 90 | 90 | 90 |
| | | L chain CR | 106 | 106 | 106 | 106 | 106 |
| | | full length L | 43 | 43 | 43 | 43 | 43 |
| | Arm B | HCDR1 | 135 | 135 | 144 | 147 | 153 |
| | | HCDR2 | 136 | 136 | 145 | 148 | 154 |
| | | HCDR3 | 137 | 137 | 146 | 149 | 155 |
| | | H chain VR | 92 | 92 | 93 | 94 | 95 |
| | | H chain CR | 104 | 104 | 104 | 104 | 104 |
| | | full length H | 53 | 53 | 57 | 59 | 62 |
| | | full length H (different Fc) | 54 | 54 | 58 | 60 | 63 |

TABLE 2-4-continued

Summary and sequences of bispecific antibodies

| | | Bispecific Ab name | | | | |
|---|---|---|---|---|---|---|
| | | DQN0344 H0976/L0591// DQN0385 H1270/L0722-F6 | DQN0344 H0976/L0591// DQN0385 H1270/L0681-F6 | DQN0344 H0976/L0591// DQN0385 H1352/L0681-F6 Arm A | DQN0344 H0976/L0591// DQN0385 H1527/L0605-F6 | DQN0344 H0976/L0591// DQN0385 H1255/L0605-F6 |
| | | DQN0344 H0976/L0591 | DQN0344H0976/ L0591 | DQN0344 H0976/L0591 Arm B | DQN0344 H0976/L0591 | DQN0344 H0976/L0591 |
| | | DQN0385 H1270/L0722 | DQN0385H1270/ L0681 | DQN0385 H1352/L0681 | DQN0385 H1527/L0605 | DQN0385 H1255/L0605 |
| | LCDR1 | 138 | 141 | 141 | 150 | 150 |
| | LCDR2 | 139 | 142 | 142 | 151 | 151 |
| | LCDR3 | 140 | 143 | 143 | 152 | 152 |
| | L chain VR | 98 | 99 | 99 | 100 | 100 |
| | L chain CR | 107 | 107 | 107 | 107 | 107 |
| | full length L | 55 | 56 | 56 | 61 | 61 |

TABLE 2-5

Summary and sequences of bispecific antibodies

| | | | Bispecific Ab name | | | | |
|---|---|---|---|---|---|---|---|
| | | | DQN0344 H1013/L0620// DQN0385 H1270/L0722-F6 | DQN0344 H1013/L0620// DQN0385 H1521/L0605-F6 | DQN0344 H1013/L0620// DQN0385 H1270/L0681-F6 Arm A | DQN0344 H1013/L0620// DQN0385 H1352/L0681-F6 | DQN0344 H1013/L0620// DQN0385 H1353/L0681-F6 |
| | | | DQN0344 H1013/L0620 | DQN0344 H1013/L0620 | DQN0344 H1013/L0620 Arm B | DQN0344 H1013/L0620 | DQN0344 H1013/L0620 |
| | | | DQN0385 H1270/L0722 | DQN0385 H1521/L0605 | DQN0385 H1270/L0681 | DQN0385 H1352/L0681 | DQN0385 H1353/L0681 |
| SEQ ID NO | Arm A | HCDR1 | 164 | 164 | 164 | 164 | 164 |
| | | HCDR2 | 165 | 165 | 165 | 165 | 165 |
| | | HCDR3 | 166 | 166 | 166 | 166 | 166 |
| | | H chain VR | 89 | 89 | 89 | 89 | 89 |
| | | H chain CR | 105 | 105 | 105 | 105 | 105 |
| | | full length H | 44 | 44 | 44 | 44 | 44 |
| | | full length H (different Fc) | 45 | 45 | 45 | 45 | 45 |
| | | LCDR1 | 167 | 167 | 167 | 167 | 167 |
| | | LCDR2 | 168 | 168 | 168 | 168 | 168 |
| | | LCDR3 | 169 | 169 | 169 | 169 | 169 |
| | | L chain VR | 91 | 91 | 91 | 91 | 91 |
| | | L chain CR | 106 | 106 | 106 | 106 | 106 |
| | | full length L | 46 | 46 | 46 | 46 | 46 |
| | Arm B | HCDR1 | 135 | 156 | 135 | 144 | 159 |
| | | HCDR2 | 136 | 157 | 136 | 145 | 160 |
| | | HCDR3 | 137 | 158 | 137 | 146 | 161 |
| | | H chain VR | 92 | 96 | 92 | 93 | 97 |
| | | H chain CR | 104 | 104 | 104 | 104 | 104 |
| | | full length H | 53 | 64 | 53 | 57 | 66 |
| | | full length H (different Fc) | 54 | 65 | 54 | 58 | 67 |
| | | LCDR1 | 138 | 150 | 141 | 141 | 141 |
| | | LCDR2 | 139 | 151 | 142 | 142 | 142 |
| | | LCDR3 | 140 | 152 | 143 | 143 | 143 |
| | | L chain VR | 98 | 100 | 99 | 99 | 99 |
| | | L chain CR | 107 | 107 | 107 | 107 | 107 |
| | | full length L | 55 | 61 | 56 | 56 | 56 |

TABLE 2-6

Summary and sequences of bispecific antibodies

| | | | Bispecific Ab name | | | |
|---|---|---|---|---|---|---|
| | | | DQN0344 H0976/L0591// DQN0385 H1521/L0605-F6 | DQN0344 H0976/L0591// DQN0385 H1353/L0681-F6 | DQN0344 H1013/L0620// DQN0385 H1255/L0605-F6 | DQN0344 H1013/L0620// DQN0385 H1527/L0605-F6 |
| | | | | Arm A | | |
| | | | DQN0344 H0976/L0591 | DQN0344 H0976/L0591 | DQN0344 H1013/L0620 | DQN0344 H1013/L0620 |
| | | | | Arm B | | |
| | | | DQN0385 H1521/L0605 | DQN0385 H1353/L0681 | DQN0385 H1255/L0605 | DQN0385 H1527/L0605 |
| SEQ ID NO | Arm A | HCDR1 | 129 | 129 | 164 | 164 |
| | | HCDR2 | 130 | 130 | 165 | 165 |
| | | HCDR3 | 131 | 131 | 166 | 166 |
| | | H chain VR | 88 | 88 | 89 | 89 |
| | | H chain CR | 105 | 105 | 105 | 105 |
| | | full length H | 41 | 41 | 44 | 44 |
| | | full length H (different Fc) | 42 | 42 | 45 | 45 |
| | | LCDR1 | 132 | 132 | 167 | 167 |
| | | LCDR2 | 133 | 133 | 168 | 168 |
| | | LCDR3 | 134 | 134 | 169 | 169 |
| | | L chain VR | 90 | 90 | 91 | 91 |
| | | L chain CR | 106 | 106 | 106 | 106 |
| | | full length L | 43 | 43 | 46 | 46 |
| | Arm B | HCDR1 | 156 | 159 | 153 | 147 |
| | | HCDR2 | 157 | 160 | 154 | 148 |
| | | HCDR3 | 158 | 161 | 155 | 149 |
| | | H chain VR | 96 | 97 | 95 | 94 |
| | | H chain CR | 104 | 104 | 104 | 104 |
| | | full length H | 64 | 66 | 62 | 59 |
| | | full length H (different Fc) | 65 | 67 | 63 | 60 |
| | | LCDR1 | 150 | 141 | 150 | 150 |
| | | LCDR2 | 151 | 142 | 151 | 151 |
| | | LCDR3 | 152 | 143 | 152 | 152 |
| | | L chain VR | 100 | 99 | 100 | 100 |
| | | L chain CR | 107 | 107 | 107 | 107 |
| | | full length L | 61 | 56 | 61 | 61 |

Example 4

Binding Analysis of Antibodies to Class II HLA.

FIGS. 1-1 to 1-16 show the binding of the each anti-HLA-DQ antibodies to a panel of HLA-DQ in the form of a complex with several peptides-expressing Ba/F3 cell lines as determined by FACS. The binding of anti-HLA-DQ antibodies to Ba/F3-HLA-DQ2.5, Ba/F3-HLA-DQ2.2, Ba/F3-HLA-DQ7.5, Ba/F3-HLA-DQ8, Ba/F3-HLA-DQ7.3, Ba/F3-HLA-DQ5.1, Ba/F3-HLA-DQ6.3, Ba/F3-HLA-DR, Ba/F3-HLA-DP, Ba/F3-HLA-DQ2.5/CLIP, Ba/F3-HLA-DQ2.5/HBV1, Ba/F3-HLA-DQ2.5/*Salmonella*, Ba/F3-HLA-DQ2.5/TPO, Ba/F3-HLA-DQ2.5/*M. bovis*, Ba/F3-HLA-DQ2.5/alpha 1 gliadin, Ba/F3-HLA-DQ2.5/alpha 2 gliadin, Ba/F3-HLA-DQ2.5/gamma 1 gliadin, Ba/F3-HLA-DQ2.5/gamma 2 gliadin, Ba/F3-HLA-DQ2.5/omega 1 gliadin, Ba/F3-HLA-DQ2.5/omega 2 gliadin, Ba/F3-HLA-DQ2.5/BC hordein, Ba/F3-HLA-DQ2.5/alpha 3 gliadin, Ba/F3-HLA-DQ2.5/alpha 1b gliadin, Ba/F3-HLA-DQ2.5/gamma 4a gliadin, Ba/F3-HLA-DQ2.5/gamma 4b gliadin, Ba/F3-HLA-DQ2.5/avenin 1, Ba/F3-HLA-DQ2.5/avenin 2, Ba/F3-HLA-DQ2.5/avenin 3, Ba/F3-HLA-DQ2.5/hordein 1, Ba/F3-HLA-DQ2.5/hordein 2, Ba/F3-HLA-DQ2.5/secalin 1, Ba/F3-HLA-DQ2.5/secalin 2, Ba/F3-HLA-DQ2.5/33mer gliadin, Ba/F3-HLA-DQ2.5/26mer gliadin was tested. Anti-HLA-DQ antibodies at 50 nanogram/mL, and control DQN0139bb and IC17dK antibodies at 1 microgram/mL were incubated with each cell line for 30 minutes at room temperature. The exception is for DQN0344H0976/L0591//DQN0385H1521/L0605-F6, DQN0344H0976/L0591//DQN0385H1353/L0681-F6 and DQN0344H1013/L0620//DQN0385H1255/L0605-F6 in which these anti-HLA-DQ antibodies were used at 313 nanogram/mL and respective control DQN0139bb and IC17dK antibodies at 20 microgram/mL for Ba/F3-HLA-DQ2.5 and Ba/F3-HLA-DQ2.5/CLIP only. Cell lines were washed with FACS buffer (2% FBS, 2 mM EDTA in PBS) after incubation. Goat F(ab')2 anti-Human IgG, Mouse ads-PE (Southern Biotech, Cat. 2043-09) was then added and incubated for 20 minutes at 4 degrees C., following which was washed with FACS buffer. Data acquisition was performed on LSRFortessa™ X-20 cell analyzer (Becton Dickinson), followed by analysis using the FlowJo™ software (Tree Star) and Microsoft® Office Excel® 2013 software. % MFI of antibodies was determined by taking the MFI value of IC17dK as 0% and the MFI value of DQN0139bb as 100%.

FIGS. 1-1 to 1-13 show the binding of the 13 bispecific anti-HLA-DQ antibodies (variants DQN0344H0976/L0591//DQN0385H1270/L0722-F6, DQN0344H0976/L0591//DQN0385H1270/L0681-F6, DQN0344H0976/L0591//DQN0385H1352/L0681-F6, DQN0344H0976/L0591//DQN0385H1527/L0605-F6, DQN0344H0976/

L0591//DQN0385H1255/L0605-F6, DQN0344H1013/L0620//DQN0385H1270/L0722-F6, DQN0344H1013/L0620//DQN0385H1521/L0605-F6, DQN0344H1013/L0620//DQN0385H1270/L0681-F6, DQN0344H1013/L0620//DQN0385H1352/L0681-F6, DQN0344H1013/L0620//DQN0385H1353/L0681-F6, DQN0344H0976/L0591//DQN0385H1521/L0605-F6, DQN0344H0976/L0591//DQN0385H1353/L0681-F6, DQN0344H1013/L0620//DQN0385H1255/L0605-F6) to the panel of Ba/F3 cell lines as previously described. These 13 bispecific anti-HLA-DQ antibodies have significant binding activity of various degree to HLA-DQ2.5 only when it is in the form of a complex with gluten derived peptides tested (i.e. 33mer gliadin peptide, alpha 1 gliadin peptide, alpha 2 gliadin peptide, gamma 1 gliadin peptide, gamma 2 gliadin peptide, omega 1 gliadin peptide, omega 2 gliadin peptide, BC Hordein peptide, alpha 3 gliadin peptide, alpha 1b gliadin peptide, gamma 4a gliadin peptide, gamma 4b gliadin peptide, avenin 1 peptide, avenin 2 peptide, avenin 3 peptide, hordein 1 peptide, hordein 2 peptide, secalin 1 peptide, secalin 2 peptide and 26mer gliadin peptide). The binding of the 13 bispecific anti-HLA-DQ antibodies to gamma 2 gliadin peptide is modest. On the other hand, the 13 bispecific anti-HLA-DQ antibodies have substantially no binding activity to HLA-DQ2.5 when it is in the form of a complex with peptides which are irrelevant to gluten peptides or when subjected to non-HLA-DQ2.5 haplotypes (including FIG. 1-14).

FIGS. 1-15 and 1-16 are the positive binding control (DQN0139bb) and negative binding control (IC17dK), respectively.

Example 5

Binding analysis of antibodies to HLA-DQ2.5+ PBMC B cell.

FIG. 2 shows the binding of the each anti-HLA-DQ antibodies to HLA-DQ2.5 positive PBMC-B cells as determined by FACS.

Human FcR blocking reagent (Miltenyi, Cat. 130-059-901) was added and incubated for 10 minutes at 4 degrees C. Anti-HLA-DQ antibodies at 50 nanogram/mL, and control DQN0139bb and IC17dK antibodies at 1 microgram/mL were incubated with each cell line for 30 minutes at room temperature. The exception is for DQN0344H0976/L0591//DQN0385H1521/L0605-F6, DQN0344H0976/L0591//DQN0385H1353/L0681-F6 and DQN0344H1013/L0620//DQN0385H1255/L0605-F6 in which these anti-HLA-DQ antibodies were used at 313 nanograms/mL and respective control DQN0139bb and IC17dK antibodies at 20 microgram/mL. Cells were washed with FACS buffer (2% FBS, 2 mM EDTA in PBS) after incubation. Biotin conjugated anti-human antibody (Chugai, BIO12-deltaGK Ab) and Pacific Blue™ anti-human CD19 antibody mouse IgG1k (Biolegend, Cat. 302232) were simultaneously added and incubated for 30 minutes at 4 degrees C., following which were washed with FACS buffer. PE Streptavidin (Biolegend, Cat. 405203) was then added and incubated for 15 minutes at 4 degrees C., following which were washed with FACS buffer. Data acquisition was performed on LSRFortessa™ X-20 cell analyzer (Becton Dickinson), followed by analysis using the FlowJo™ software (Tree Star) and GraphPad Prism software (GraphPad). % MFI of antibodies was determined by taking the MFI value of IC17dK as 0% and the MFI value of DQN0139bb as 100%

FIG. 2 shows that the 13 bispecific anti-HLA-DQ antibodies (variants DQN0344H0976/L0591//DQN0385H1270/L0722-F6, DQN0344H0976/L0591//DQN0385H1270/L0681-F6, DQN0344H0976/L0591//DQN0385H1352/L0681-F6, DQN0344H0976/L0591//DQN0385H1527/L0605-F6, DQN0344H0976/L0591//DQN0385H1255/L0605-F6, DQN0344H1013/L0620//DQN0385H1270/L0722-F6, DQN0344H1013/L0620//DQN0385H1521/L0605-F6, DQN0344H1013/L0620//DQN0385H1270/L0681-F6, DQN0344H1013/L0620//DQN0385H1352/L0681-F6, DQN0344H1013/L0620//DQN0385H1353/L0681-F6, DQN0344H0976/L0591//DQN0385H1521/L0605-F6, DQN0344H0976/L0591//DQN0385H1353/L0681-F6, DQN0344H1013/L0620//DQN0385H1255/L0605-F6) have substantially no binding to HLA-DQ2.5 positive PBMC-B cells.

Example 6

6.1 Establishment of αβTCR KO Jurkat NFAT-Luc Cell Line

Ribonucleoprotein (RNP) complex (Takara Bio), which is composed of Cas9 and single guide RNAs targeting TCR constant region (Blood. 2018; 131:311-22.) was introduced to NFAT-RE-luc2 Jurkat cell line (Promega corporation, CS176401) by electroporation (LONZA, the Nucleofector™ 2b apparatus). All single guide RNAs for TCR alpha chain and TCR beta chain were mixed and introduced simultaneously. RNP introduced cells were cultured in media containing Hygromycin B, followed by single cell cloning with the FACSAria™ III cell sorter (Becton, Dickinson and Company). TCR alpha chain and TCR beta chain sequences were then checked and identified Jurkat NFAT-Luc derived clones which TCR alpha chain and TCR beta chain were knocked out. Established clone was named TCR KO Jurkat NFAT-Luc.

6.2 Establishment of αβTCR KO Jurkat NFAT-Luc Cell Line Transiently Expressing HLA-DQ2.5/Gluten Peptide Restricted TCR TCR amino sequence information was obtained from public information, or Oslo University based on material transfer agreement. Amino acid sequence information of HLA-DQ2.5/alpha 1 gliadin restricted TCR (TCC ID: 387.9), HLA-DQ2.5/alpha 1b gliadin restricted TCR (TCC ID: 370.2.25), HLA-DQ2.5/omega 1 gliadin restricted TCR (TCC ID: 442D. A.2), HLA-DQ2.5/omega 2 gliadin restricted TCR (TCC ID: 578.42), HLA-DQ2.5/gamma 1 gliadin restricted TCR (TCC ID: 820.27), HLA-DQ2.5/gamma 2 gliadin restricted TCR (TCC ID: 430.1.41), HLA-DQ2.5/gamma 3 gliadin restricted TCR (TCC ID: /.2.23), HLA-DQ2.5/gamma 4a gliadin restricted TCR (TCC ID: 430.1.36), HLA-DQ2.5/gamma 4d gliadin restricted TCR (TCC ID: 430.1.94) was obtained from Oslo University based on material transfer agreement. Amino acid sequence information of HLA-DQ2.5/alpha 2 gliadin restricted TCR (DQ2.5/alpha 2 gliadin restricted TCR) was obtained from Nat Struct Mol Biol. 2014; 21:480-8, and amino acid sequence information of HLA-DQ2.5/BC hordein restricted TCR (TCC ID: 1468.2) was obtained from Eur J Immunol. 2020; 50: 256-269. Each TCR beta chain sequence was linked with corresponding TCR alpha chain sequence by 2A self-cleaving peptide sequence (P2A, amino acid sequence: GSGATNFSLLKQAGDVEENPGP, SEQ ID NO: 203). All TCR alpha chain and TCR beta chain have these own native signal peptide sequence except for HLA-DQ2.5/gamma 2 gliadin restricted TCR and HLA-DQ2.5/alpha 2 gliadin restricted TCR. Native signal sequence of HLA-DQ2.5/gamma 2 gliadin restricted TCR was replaced by Campath signal sequence (MGWSCIILFLVATATGVHS, SEQ ID NO: 170). Campath signal sequence was also attached N-terminus of HLA-DQ2.5/alpha 2 gliadin restricted TCR. Each codon optimized TCR beta chain-P2A-TCR alpha chain cDNA was then inserted into the expression vector pCXZD1 (US/20090324589) at Genscript. Electroporation of vectors into αβTCR-KO Jurkat-NFAT-luc2 was done by following to the protocol of SE Cell Line 4D-Nucleofector™ Kit.

6.3 Inhibitory Effect of Anti-HLA DQ Antibodies on HLA-DQ2.5/Alpha 1 Gliadin Peptide Dependent Jurkat T Cell Activation was Confirmed.

50 μL of the mixture of IHW09023 cell (International Histocompatibility Working Group, Fred Hutch) ($8.0 \times 10^4$ cells/well) and 33mer gliadin peptide (LQLQPFPQPELPYPQPELPYPQPELPYPQPQPF, SEQ ID NO: 201, 250 nM) was distributed in 96 well plates (Corning, 3799). 25 μL of serially diluted anti-HLA DQ antibodies were then added, and 25 μL of alpha 1 gliadin restricted TCR transfected αβTCR-KO Jurkat-NFAT-luc2 ($2.0 \times 10^4$ cells/well) were finally added and incubated at 37 degrees C., at 5% CO2 for overnight. After overnight culture, 50 μL of cultured cells were harvested and redistributed in OptiPlate™-96 (PerkinElmer, 6005299) 96-well microplate. 50 μL of Bio-Glo™ luciferase assay system (Promega, G7491) was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 3-1 and Table 2-7, all tested anti-HLA DQ antibodies demonstrated inhibitory effect on HLA-DQ2.5/alpha 1 gliadin peptide dependent Jurkat T cell activation by dose dependent manner. Especially, DQN0344H0976/L0591//DQN0385H1270/L0722-F6, DQN0344H0976/L0591//DQN0385H1270/L0681-F6, DQN0344H0976/L0591//DQN0385H1352/L0681-F6, DQN0344H0976/L0591//DQN0385H1527/L0605-F6, DQN0344H0976/L0591//DQN0385H1255/L0605-F6, DQN0344H1013/L0620//DQN0385H1270/L0722-F6, DQN0344H1013/L0620//DQN0385H1521/L0605-F6, DQN0344H1013/L0620//DQN0385H1270/L0681-F6, DQN0344H1013/L0620//DQN0385H1352/L0681-F6, DQN0344H1013/L0620//DQN0385H1353/L0681-F6) demonstrated stronger neutralizing activity on HLA-DQ2.5/alpha 1 gliadin peptide dependent Jurkat T cell activation compared to DQN0344xx, DQN0344xx//DQN0385ee, DQN034425, and DQN034425//DQN0385ee0054.

6.4 Inhibitory Effect of Anti-HLA DQ Antibodies on HLA-DQ2.5/Alpha 2 Gliadin Peptide Dependent Jurkat T Cell Activation was Confirmed.

50 μL of the mixture of IHW09023 cell ($8.0 \times 10^4$ cells/well) and 33mer gliadin peptide (LQLQPFPQPELPYPQPELPYPQPELPYPQPQPF, SEQ ID NO: 201, 250 nM) was distributed in 96 well plates (Corning, 3799). 25 μL of serially diluted anti-HLA DQ antibodies were then added, and 25 μL of alpha 2 gliadin restricted TCR transfected αβTCR-KO Jurkat-NFAT-luc2 ($2.0 \times 10^4$ cells/well) were finally added and incubated at 37 degrees C., at 5% CO2 for overnight. After overnight culture, 50 μL of cultured cells were harvested and redistributed in OptiPlate-96m (PerkinElmer, 6005299) 96-well microplate. 50 μL of Bio-Glo™ luciferase assay system (Promega, G7491) was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 3-2 and Table 2-7, all tested anti-HLA DQ antibodies demonstrated inhibitory effect on HLA-DQ2.5/alpha 2 gliadin peptide dependent Jurkat T cell activation by dose dependent manner. Especially, DQN0344H0976/L0591//DQN0385H1270/L0722-F6, DQN0344H0976/L0591//DQN0385H1270/L0681-F6, DQN0344H0976/L0591//DQN0385H1352/L0681-F6, DQN0344H0976/L0591//DQN0385H1527/L0605-F6, DQN0344H0976/L0591//DQN0385H1255/L0605-F6, DQN0344H1013/L0620//DQN0385H1270/L0722-F6, DQN0344H1013/L0620//DQN0385H1521/L0605-F6, DQN0344H1013/L0620//DQN0385H1270/L0681-F6, DQN0344H1013/L0620//DQN0385H1352/L0681-F6, DQN0344H1013/L0620//DQN0385H1353/L0681-F6) stronger neutralizing activity on HLA-DQ2.5/alpha 2 gliadin peptide dependent Jurkat T cell activation compared to DQN0344xx, DQN0344xx//DQN0385ee, DQN034425, and DQN034425//DQN0385ee0054.

6.5 Inhibitory Effect of Anti-HLA DQ Antibodies on HLA-DQ2.5/Alpha 1b Gliadin Peptide Dependent Jurkat T Cell Activation was Confirmed.

50 μL of the mixture of IHW09023 cell ($8.0 \times 10^4$ cells/well) and 33mer gliadin peptide (LQLQPFPQPELPYPQPELPYPQPELPYPQPQPF, SEQ ID NO: 201, 250 nM) was distributed in 96 well plates (Corning, 3799). 25 μL of serially diluted anti-HLA DQ antibodies were then added, and 25 μL of alpha 1b gliadin restricted TCR transfected αβTCR-KO Jurkat-NFAT-luc2 ($2.0 \times 10^4$ cells/well) were finally added and incubated at 37 degrees C., at 5% CO2 for overnight. After overnight culture, 50 μL of cultured cells were harvested and redistributed in OptiPlate-96m (PerkinElmer, 6005299) 96-well microplate. 50 μL of Bio-Glo™ luciferase assay system (Promega, G7491) was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 3-3 and Table 2-7, all tested anti-HLA DQ antibodies demonstrated inhibitory effect on HLA-DQ2.5/alpha 1b gliadin peptide dependent Jurkat T cell activation by dose dependent manner. Especially, DQN0344H0976/L0591//DQN0385H1270/L0722-F6, DQN0344H0976/L0591//DQN0385H1270/L0681-F6,
DQN0344H0976/L0591//DQN0385H1352/L0681-F6,
DQN0344H0976/L0591//DQN0385H1527/L0605-F6,
DQN0344H0976/L0591//DQN0385H1255/L0605-F6,
DQN0344H1013/L0620//DQN0385H1270/L0722-F6,
DQN0344H1013/L0620//DQN0385H1521/L0605-F6,
DQN0344H1013/L0620//DQN0385H1270/L0681-F6,
DQN0344H1013/L0620//DQN0385H1352/L0681-F6,
DQN0344H1013/L0620//DQN0385H1353/L0681-F6) demonstrated stronger neutralizing activity on HLA-DQ2.5/alpha 1b gliadin peptide dependent Jurkat T cell activation compared to DQN0344xx, DQN0344xx//DQN0385ee, DQN034425, and DQN034425//DQN0385ee0054.

6.6 Inhibitory Effect of Anti-HLA DQ Antibodies on HLA-DQ2.5/Omega 1 Gliadin Peptide Dependent Jurkat T Cell Activation was Confirmed.

50 μL of the mixture of IHW09023 cell ($8.0 \times 10^4$ cells/well) and omega1/2 gliadin peptide (EQPFPQPEQPFPWQP, SEQ ID NO: 204, 25 uM) was distributed in 96 well plates (Corning, 3799). 25 μL of serially diluted anti-HLA DQ antibodies were then added, and 25 μL of omega 1 gliadin restricted TCR transfected αβTCR-KO Jurkat-NFAT-luc2 ($2.0 \times 10^4$ cells/well) were finally added and incubated at 37 degrees C., at 5% CO2 for overnight. After overnight culture, 50 μL of cultured cells were harvested and redistributed in OptiPlate-96™ (PerkinElmer, 6005299) 96-well microplate. 50 μL of Bio-Glo™ (Promega, G7491) luciferase assay system was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. $IC_{50}$ value was determined using XLFIT (registered trademark) Excel add-in software (IDBS)

As shown in FIG. 3-4 and Table 2-7, all tested anti-HLA DQ antibodies demonstrated inhibitory effect on HLA-DQ2.5/omega 1 gliadin peptide dependent Jurkat T cell activation by dose dependent manner. Especially, DQN0344H0976/L0591//DQN0385H1270/L0722-F6, DQN0344H0976/L0591//DQN0385H1270/L0681-F6, DQN0344H0976/L0591//DQN0385H1352/L0681-F6, DQN0344H0976/L0591//DQN0385H1527/L0605-F6, DQN0344H0976/L0591//DQN0385H1255/L0605-F6, DQN0344H1013/L0620//DQN0385H1270/L0722-F6, DQN0344H1013/L0620//DQN0385H1521/L0605-F6, DQN0344H1013/L0620//DQN0385H1270/L0681-F6, DQN0344H1013/L0620//DQN0385H1352/L0681-F6, DQN0344H1013/L0620//DQN0385H1353/L0681-F6) demonstrated stronger neutralizing activity on HLA-DQ2.5/omega 1 gliadin peptide dependent Jurkat T cell activation compared to DQN0344xx, DQN0344xx//DQN0385ee, DQN034425, and DQN034425//DQN0385ee0054.

6.7 Inhibitory Effect of Anti-HLA DQ Antibodies on HLA-DQ2.5/Omega 2 Gliadin Peptide Dependent Jurkat T Cell Activation was Confirmed.

50 μL of the mixture of IHW09023 cell ($8.0 \times 10^4$ cells/well) and omega1/2 gliadin peptide (EQPFPQPEQPFPWQP, SEQ ID NO: 204, 250 nM) was distributed in 96 well plates (Corning, 3799). 25 μL of serially diluted anti-HLA DQ antibodies were then added, and 25 μL of omega 2 gliadin restricted TCR transfected αβTCR-KO Jurkat-NFAT-luc2 ($2.0 \times 10^4$ cells/well) were finally added and incubated at 37 degrees C., at 5% CO2 for overnight. After overnight culture, 50 μL of cultured cells were harvested and redistributed in OptiPlate-96™ (PerkinElmer, 6005299) 96-well microplate. 50 μL of Bio-Glo™ (Promega, G7491) luciferase assay system was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 3-5 and Table 2-7, all tested anti-HLA DQ antibodies except for DQN0344xx and DQN034425 demonstrated inhibitory effect on HLA-DQ2.5/omega 2 gliadin peptide dependent Jurkat T cell activation by dose dependent manner. Especially, DQN0344H0976/L0591//DQN0385H1270/L0722-F6, DQN0344H0976/L0591//DQN0385H1270/L0681-F6, DQN0344H0976/L0591//DQN0385H1352/L0681-F6, DQN0344H0976/L0591//DQN0385H1527/L0605-F6, DQN0344H0976/L0591//DQN0385H1255/L0605-F6, DQN0344H1013/L0620//DQN0385H1270/L0722-F6, DQN0344H1013/L0620//DQN0385H1521/L0605-F6, DQN0344H1013/L0620//DQN0385H1270/L0681-F6, DQN0344H1013/L0620//DQN0385H1352/L0681-F6, DQN0344H1013/L0620//DQN0385H1353/L0681-F6) demonstrated stronger neutralizing activity on HLA-DQ2.5/omega 2 gliadin peptide dependent Jurkat T cell activation compared to DQN0344xx, DQN0344xx//DQN0385ee, DQN034425, and DQN034425//DQN0385ee0054.

6.8 Inhibitory Effect of Anti-HLA DQ Antibodies on HLA-DQ2.5/BC Hordein Peptide Dependent Jurkat T Cell Activation was Confirmed.

50 μL of the mixture of IHW09023 cell ($8.0 \times 10^4$ cells/well) and BC hordein peptide (EPEQPIPEQPQPYPQQ, SEQ ID NO: 205, 250 nM) was distributed in 96 well plates (Corning, 3799). 25 μL of serially diluted anti-HLA DQ antibodies were then added, and 25 μL of BC hordein restricted TCR transfected αβTCR-KO Jurkat-NFAT-luc2 ($2.0 \times 10^4$ cells/well) were finally added and incubated at 37 degrees C., at 5% CO2 for overnight. After overnight culture, 50 μL of cultured cells were harvested and redistributed in OptiPlate-96m (PerkinElmer, 6005299) 96-well microplate. 50 μL of Bio-Glo™ (Promega, G7491) luciferase assay system was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 3-6 and Table 2-7, all tested anti-HLA DQ antibodies except for DQN0344xx and DQN034425 demonstrated inhibitory effect on HLA-DQ2.5/BC hordein peptide dependent Jurkat T cell activation by dose dependent manner. Especially, DQN0344H0976/L0591//DQN0385H1270/L0722-F6, DQN0344H0976/L0591//DQN0385H1270/L0681-F6, DQN0344H0976/L0591//

DQN0385H1352/L0681-F6, DQN0344H0976/L0591//
DQN0385H1527/L0605-F6, DQN0344H0976/L0591//
DQN0385H1255/L0605-F6, DQN0344H1013/L0620//
DQN0385H1270/L0722-F6, DQN0344H1013/L0620//
DQN0385H1521/L0605-F6, DQN0344H1013/L0620//
DQN0385H1270/L0681-F6, DQN0344H1013/L0620//
DQN0385H1352/L0681-F6, DQN0344H1013/L0620//
DQN0385H1353/L0681-F6) demonstrated stronger neutralizing activity on HLA-DQ2.5/BC hordein peptide dependent Jurkat T cell activation compared to DQN0344xx, DQN0344xx//DQN0385ee, DQN034425, and DQN034425//DQN0385ee0054.

6.9 Inhibitory Effect of Anti-HLA DQ Antibodies on HLA-DQ2.5/Gamma 1 Gliadin Peptide Dependent Jurkat T Cell Activation was Confirmed.

50 μL of the mixture of IHW09023 cell ($8.0 \times 10^4$ cells/well) and gamma 1 gliadin peptide (PQQPQQSFPEQEQPA, SEQ ID NO: 206, 250 nM) was distributed in 96 well plates (Corning, 3799). 25 μL of serially diluted anti-HLA DQ antibodies were then added, and 25 μL of gamma 1 gliadin restricted TCR transfected αβTCR-KO Jurkat-NFAT-luc2 ($2.0 \times 10^4$ cells/well) were finally added and incubated at 37 degrees C., at 5% CO2 for overnight. After overnight culture, 50 μL of cultured cells were harvested and redistributed in OptiPlate-96™ (PerkinElmer, 6005299) 96-well microplate. 50 μL of Bio-Glo™ (Promega, G7491) luciferase assay system was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 3-7 and Table 2-7, all tested anti-HLA DQ antibodies except for DQN0344xx and DQN034425 demonstrated inhibitory effect on HLA-DQ2.5/gamma 1 gliadin peptide dependent Jurkat T cell activation by dose dependent manner. Especially, DQN0344H0976/L0591//DQN0385H1270/L0722-F6, DQN0344H0976/L0591//
DQN0385H1270/L0681-F6, DQN0344H0976/L0591//
DQN0385H1352/L0681-F6, DQN0344H0976/L0591//
DQN0385H1527/L0605-F6, DQN0344H0976/L0591//
DQN0385H1255/L0605-F6, DQN0344H1013/L0620//
DQN0385H1270/L0722-F6, DQN0344H1013/L0620//
DQN0385H1521/L0605-F6, DQN0344H1013/L0620//
DQN0385H1270/L0681-F6, DQN0344H1013/L0620//
DQN0385H1352/L0681-F6, DQN0344H1013/L0620//
DQN0385H1353/L0681-F6) demonstrated stronger neutralizing activity on HLA-DQ2.5/gamma 1 gliadin peptide dependent Jurkat T cell activation compared to DQN0344xx, DQN0344xx//DQN0385ee, DQN034425, and DQN034425//DQN0385ee0054.

6.10 Inhibitory Effect of Anti-HLA DQ Antibodies on HLA-DQ2.5/Gamma 2 Gliadin Peptide Dependent Jurkat T Cell Activation was Confirmed.

50 μL of the mixture of IHW09023 cell ($8.0 \times 10^4$ cells/well) and gamma 2 gliadin peptide (GQGIIQPEQPAQLIR, SEQ ID NO: 207, 250 nM) was distributed in 96 well plates (Corning, 3799). 25 μL of serially diluted anti-HLA DQ antibodies were then added, and 25 μL of gamma 2 gliadin restricted TCR transfected αβTCR-KO Jurkat-NFAT-luc2 ($2.0 \times 10^4$ cells/well) were finally added and incubated at 37 degrees C., at 5% CO2 for overnight. After overnight culture, 50 μL of cultured cells were harvested and redistributed in OptiPlate-96™ (PerkinElmer, 6005299) 96-well microplate. 50 μL of Bio-Glo™ (Promega, G7491) luciferase assay system was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 3-8 and Table 2-7, all tested anti-HLA DQ antibodies except for DQN0344xx and DQN034425 demonstrated inhibitory effect on HLA-DQ2.5/gamma 2 gliadin peptide dependent Jurkat T cell activation by dose dependent manner. Especially, DQN0344H0976/L0591//
DQN0385H1270/L0722-F6, DQN0344H0976/L0591//
DQN0385H1270/L0681-F6, DQN0344H0976/L0591//
DQN0385H1352/L0681-F6, DQN0344H0976/L0591//
DQN0385H1527/L0605-F6, DQN0344H0976/L0591//
DQN0385H1255/L0605-F6, DQN0344H1013/L0620//
DQN0385H1270/L0722-F6, DQN0344H1013/L0620//
DQN0385H1521/L0605-F6, DQN0344H1013/L0620//
DQN0385H1270/L0681-F6, DQN0344H1013/L0620//
DQN0385H1352/L0681-F6, DQN0344H1013/L0620//
DQN0385H1353/L0681-F6) demonstrated stronger neutralizing activity on HLA-DQ2.5/gamma 2 gliadin peptide dependent Jurkat T cell activation compared to DQN0344xx, DQN0344xx//DQN0385ee, DQN034425, and DQN034425//DQN0385ee0054.

6.11 Inhibitory Effect of Anti-HLA DQ Antibodies on HLA-DQ2.5/Gamma 3 Gliadin Peptide Dependent Jurkat T Cell Activation was Confirmed.

50 μL of the mixture of IHW09023 cell ($8.0 \times 10^4$ cells/well) and gamma 3 gliadin peptide (EQPFPEQPEQPYPEQPEQPFPQP, SEQ ID NO: 208, 100 uM) was distributed in 96 well plates (Corning, 3799). 25 μL of serially diluted anti-HLA DQ antibodies were then added, and 25 μL of gamma 3 gliadin restricted TCR transfected αβTCR-KO Jurkat-NFAT-luc2 ($2.0 \times 10^4$ cells/well) were finally added and incubated at 37 degrees C., at 5% CO2 for overnight. After overnight culture, 50 μL of cultured cells were harvested and redistributed in OptiPlate-96m (PerkinElmer, 6005299) 96-well microplate. 50 μL of Bio-Glom (Promega, G7491) luciferase assay system was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 3-9 and Table 2-7, all tested anti-HLA DQ antibodies demonstrated inhibitory effect on HLA-DQ2.5/gamma 3 gliadin peptide dependent Jurkat T cell activation by dose dependent manner. Especially, DQN0344H0976/L0591//DQN0385H1270/L0722-F6, DQN0344H0976/L0591//DQN0385H1270/L0681-F6, DQN0344H0976/L0591//DQN0385H1352/L0681-F6, DQN0344H0976/L0591//DQN0385H1527/L0605-F6, DQN0344H0976/L0591//DQN0385H1255/L0605-F6, DQN0344H1013/L0620//DQN0385H1270/L0722-F6, DQN0344H1013/L0620//DQN0385H1521/L0605-F6, DQN0344H1013/L0620//DQN0385H1270/L0681-F6, DQN0344H1013/L0620//DQN0385H1352/L0681-F6, DQN0344H1013/L0620//DQN0385H1353/L0681-F6) demonstrated stronger neutralizing activity on HLA-DQ2.5/gamma 3 gliadin peptide dependent Jurkat T cell activation compared to DQN0344xx, DQN0344xx//DQN0385ee, DQN034425, and DQN034425//DQN0385ee0054.

6.12 Inhibitory Effect of Anti-HLA DQ Antibodies on HLA-DQ2.5/Gamma 4a Gliadin Peptide Dependent Jurkat T Cell Activation was Confirmed.

50 μL of the mixture of IHW09023 cell ($8.0 \times 10^4$ cells/well) and gamma 4a gliadin peptide (FSQPEQEFPQPQ, SEQ ID NO: 209, 25 uM) was distributed in 96 well plates (Corning, 3799). 25 μL of serially diluted anti-HLA DQ antibodies were then added, and 25 μL of gamma 4a gliadin restricted TCR transfected αβTCR-KO Jurkat-NFAT-luc2 ($2.0 \times 10^4$ cells/well) were finally added and incubated at 37 degrees C., at 5% CO2 for overnight. After overnight culture, 50 μL of cultured cells were harvested and redistributed in OptiPlate-96m (PerkinElmer, 6005299) 96-well microplate. 50 μL of Bio-Glo™ (Promega, G7491) luciferase assay system was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 3-10 and Table 2-7, all tested anti-HLA DQ antibodies except for DQN0344xx, DQN034425, and DQN034425//DQN0385ee0054 demonstrated inhibitory effect on HLA-DQ2.5/gamma 4a gliadin peptide dependent Jurkat T cell activation by dose dependent manner. Especially, DQN0344H0976/L0591//DQN0385H1270/L0722-F6, DQN0344H0976/L0591//DQN0385H1270/L0681-F6, DQN0344H0976/L0591//DQN0385H1352/L0681-F6, DQN0344H0976/L0591//DQN0385H1527/L0605-F6, DQN0344H0976/L0591//DQN0385H1255/L0605-F6, DQN0344H1013/L0620//DQN0385H1270/L0722-F6, DQN0344H1013/L0620//DQN0385H1521/L0605-F6, DQN0344H1013/L0620//DQN0385H1270/L0681-F6, DQN0344H1013/L0620//DQN0385H1352/L0681-F6, DQN0344H1013/L0620//DQN0385H1353/L0681-F6) demonstrated stronger neutralizing activity on HLA-DQ2.5/gamma 4a gliadin peptide dependent Jurkat T cell activation compared to DQN0344xx, DQN0344xx//DQN0385ee, DQN034425, and DQN034425//DQN0385ee0054.

6.13 Inhibitory Effect of Anti-HLA DQ Antibodies on HLA-DQ2.5/Gamma 4d Gliadin Peptide Dependent Jurkat T Cell Activation was Confirmed.

50 μL of the mixture of IHW09023 cell ($8.0 \times 10^4$ cells/well) and gamma 4d gliadin peptide (WPQQQPFPQPEQPFCEQPQR, SEQ ID NO: 210, 100 uM) was distributed in 96 well plates (Corning, 3799). 25 μL of serially diluted anti-HLA DQ antibodies were then added, and 25 μL of gamma 4d gliadin restricted TCR transfected αβTCR-KO Jurkat-NFAT-luc2 ($2.0 \times 10^4$ cells/well) were finally added and incubated at 37 degrees C., at 5% CO2 for overnight. After overnight culture, 50 μL of cultured cells were harvested and redistributed in OptiPlate-96m (PerkinElmer, 6005299) 96-well microplate. 50 μL of Bio-Glom (Promega, G7491) luciferase assay system was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in Table 2-7, all tested anti-HLA DQ antibodies except for DQN0344xx, DQN0344xx//DQN0385ee, DQN034425, and DQN034425//DQN0385ee0054 demonstrated inhibitory effect on HLA-DQ2.5/gamma 4d gliadin peptide dependent Jurkat T cell activation by dose dependent manner.

As shown in FIGS. 3-1 to 3-10 and Table 2-7, neutralizing activity of DQN0344H0976/L0591//DQN0385H1270/L0722-F6, DQN0344H0976/L0591//DQN0385H1270/L0681-F6, DQN0344H0976/L0591//DQN0385H1352/L0681-F6, DQN0344H0976/L0591//DQN0385H1527/L0605-F6, DQN0344H0976/L0591//DQN0385H1255/L0605-F6, DQN0344H1013/L0620//DQN0385H1270/L0722-F6, DQN0344H1013/L0620//DQN0385H1521/L0605-F6, DQN0344H1013/L0620//DQN0385H1270/L0681-F6, DQN0344H1013/L0620//DQN0385H1352/L0681-F6, DQN0344H1013/L0620//DQN0385H1353/L0681-F6) against all tested gluten peptide was stronger than DQN0344xx, DQN0344xx//DQN0385ee, DQN034425, and DQN034425//DQN0385ee0054.

Additionally, DQN0344H0976/L0591//DQN0385H1270/L0722-F6, DQN0344H0976/L0591//DQN0385H1270/L0681-F6, DQN0344H0976/L0591//DQN0385H1352/L0681-F6, DQN0344H0976/L0591//DQN0385H1527/L0605-F6, DQN0344H0976/L0591//DQN0385H1255/L0605-F6, DQN0344H1013/L0620//DQN0385H1270/L0722-F6, DQN0344H1013/L0620//DQN0385H1521/L0605-F6, DQN0344H1013/L0620//DQN0385H1270/L0681-F6, DQN0344H1013/L0620//DQN0385H1352/L0681-F6, DQN0344H1013/L0620//DQN0385H1353/L0681-F6) demonstrated much extensive neutralizing activity against gluten peptides compared to DQN0344xx, DQN0344xx//DQN0385ee, DQN034425, and DQN034425//DQN0385ee0054.

In view of Table 2-7, the ten tested anti-HLA-DQ antibodies demonstrated inhibitory effect (neutralizing activities) on Jurkat T cell activation dependent on, in particular, omega 2 gliadin peptide, BC hordein peptide, gamma 1 gliadin peptide, gamma 2 gliadin peptide, gamma 4a gliadin peptide, and gamma 4d gliadin peptide. The prior antibodies before the modifications of the invention did not show neutralizing activities against these gluten peptides. That is, in the antigen-binding molecules of the invention, a cross reactivity towards gluten peptides has been enhanced compared to before the modification.

TABLE 2-7

Neutralizing activity (inhibitory effect) of the anti-HLA-DQ antibodies on HLA-DQ2.5/gluten peptide dependent Jurkat T cell activation

| | IC50 (ng/mL) | | | | | | | | | | |
|---|---|---|---|---|---|---|---|---|---|---|---|
| Ab name | α1a gliadin TCR 250 nM 33mer gliadin | α2 gliadin TCR 250 nM 33mer gliadin | α1b gliadin TCR 250 nM 33mer gliadin | ω1 gliadin TCR 25 μM ω1/2 gliadin | ω2 gliadin TCR 250 nM ω1/2 gliadin | BC hordein TCR 250 nM BC hordein | γ1 gliadin TCR 250 nM γ1 gliadin | γ2 gliadin TCR 250 nM γ2 gliadin | γ3 gliadin TCR 100 nM γ3 gliadin | γ4a gliadin TCR 25 μM γ4a gliadin | γ4d gliadin TCR 100 μM γ4d gliadin |
| DQN0344H0976/L0591//DQN0385H1270/L0722-F6 | 0.38 | 0.31 | 1.41 | 2.55 | 0.26 | 13.16 | 0.66 | 281.04 | 2.88 | 726.43 | 16.31 |
| DQN0344H0976/L0591//DQN0385H1270/L0681-F6 | 0.58 | 0.34 | 1.36 | 2.07 | 0.26 | 12.03 | 1.05 | 181.56 | 2.40 | 748.78 | 11.81 |
| DQN0344H0976/L0591//DQN0385H1352/L0681-F6 | 0.29 | 0.31 | 1.37 | 1.48 | 0.24 | 10.82 | 1.11 | 284.12 | 2.99 | 801.85 | 9.82 |
| DQN0344H0976/L0591//DQN0385H1527/L0605-F6 | 0.70 | 0.51 | 1.84 | 3.25 | 0.30 | 6.54 | 0.59 | 636.88 | 2.09 | 1207.42 | 11.40 |
| DQN0344H0976/L0591//DQN0385H1255/L0605-F6 | 0.49 | 0.56 | 2.66 | 2.62 | 0.25 | 13.57 | 0.91 | 440.28 | 2.31 | 1425.94 | 12.45 |
| DQN0344H1013/L0620//DQN0385H1270/L0722-F6 | 0.27 | 0.33 | 1.25 | 2.17 | 0.22 | 9.70 | 1.03 | 276.71 | 3.31 | 1146.02 | 10.09 |
| DQN0344H1013/L0620//DQN0385H1521/L0605-F6 | 0.28 | 0.33 | 1.76 | 1.91 | 0.19 | 8.98 | 0.68 | 852.68 | 1.40 | 1349.11 | 13.01 |
| DQN0344H1013/L0620//DQN0385H1270/L0681-F6 | 0.38 | 0.33 | 1.78 | 2.51 | 0.20 | 7.54 | 1.11 | 322.12 | 2.63 | 1164.09 | 13.05 |
| DQN0344H1013/L0620//DQN0385H1352/L0681-F6 | 0.26 | 0.38 | 1.13 | 1.88 | 0.27 | 11.58 | 1.71 | 279.48 | 3.15 | 1728.33 | 3.15 |
| DQN0344H1013/L0620//DQN0385H1353/L0681-F6 | 0.29 | 0.34 | 1.13 | 1.17 | 0.17 | 8.78 | 0.56 | 100.28 | 2.29 | 1250.38 | 2.06 |
| DQN0344xx | 31.11 | 3.68 | 112.82 | 6.85 | >500 | >20000 | >20000 | >20000 | 3825.09 | >20000 | >20000 |
| DQN0344xx//DQN0385ee | 38.29 | 2.14 | 74.59 | 6.78 | 3.18 | 18.40 | 15.84 | >20000 | 9.94 | 11216.66 | 784.22 |
| DQN034425 | 10.57 | 1.75 | 46.36 | 3.12 | >500 | >20000 | >20000 | >20000 | 3104.55 | >20000 | >20000 |
| DQN034425//DQN0385ee0054 | 102.29 | 6.46 | 437.53 | 16.06 | 16.33 | 979.74 | 28.32 | >20000 | 18.65 | >20000 | >20000 |

Example 7

Example 7-1

The affinity of anti-HLA-DQ2.5 antibodies binding to human HLA-DQ2.5/33mer gliadin peptide complex, HLA-DQ2.5/gamma 2 gliadin peptide complex and HLA-DQ2.5/BC Hordein gliadin peptide complex at pH 7.4 were determined at 37 degrees C. using BIACORE (registered trademark) 8k instrument (GE Healthcare). Anti-human Fc antibody (GE Healthcare) was immobilized onto all flow cells of a CM4 sensor chip using amine coupling kit (GE Healthcare). All antibodies and analytes were prepared in ACES pH 7.4 containing 20 mM ACES, 150 mM NaCl, 0.05% Tween 20, 0.005% NaN₃. Each antibody was captured onto the sensor surface by anti-human Fc antibody. Antibody capture levels were aimed at 200 resonance unit (RU). Human HLA-DQ2.5/33 mer gliadin peptide complex were injected at 12.5 to 200 nM prepared by two-fold serial dilution, followed by dissociation. Human HLA-DQ2.5/gamma 2 gliadin peptide complex was injected at 25 to 400 nM prepared by two-fold serial dilution, followed by dissociation. Human HLA-DQ2.5/BC Hordein gliadin peptide complex was injected at 25 to 400 nM prepared by two-fold serial dilution, followed by dissociation. Sensor surface was regenerated each cycle with 3M MgCl₂. Binding affinity were determined by processing and fitting the data to 1:1 binding model using BIACORE (registered trademark) Insight Evaluation software (GE Healthcare).

The affinity of anti-HLA-DQ2.5 antibodies binding to human HLA-DQ2.5/33mer gliadin peptide complex, HLA-DQ2.5/gamma 2 gliadin peptide complex and HLA-DQ2.5/BC Hordein gliadin peptide complex are shown in Table 3-1.

TABLE 3-1

Affinity of anti-HLA-DQ2.5 antibodies to HLA-DQ2.5/gluten peptide complexes

| | HLA-DQ2.5/33mer gliadin peptide complex | | | HLA-DQ2.5/γ2 gliadin peptide complex | | | HLA-DQ2.5/BC Hordein peptide complex | | |
|---|---|---|---|---|---|---|---|---|---|
| Ab name | ka ($M^{-1} s^{-1}$) | kd ($s^{-1}$) | KD (M) | ka ($M^{-1} s^{-1}$) | kd ($s^{-1}$) | KD (M) | ka ($M^{-1} s^{-1}$) | kd ($s^{-1}$) | KD (M) |
| DQN0344xx | 1.86E+05 | 1.43E−03 | 7.71E−09 | N.D. | N.D. | N.D. | N.D. | N.D. | N.D. |
| DQN0385ee | 6.36E+04 | 3.41E−04 | 5.36E−09 | 9.69E+04 | 1.25E−02 | 1.29E−07 | 1.67E+05 | 6.85E−04 | 4.10E−09 |
| DQN034425H/09L0012 | 2.23E+05 | 1.27E−03 | 5.70E−09 | N.D. | N.D. | N.D. | N.D. | N.D. | N.D. |
| DQN0385ee0054H/009L | 4.06E+04 | 6.18E−04 | 1.52E−08 | 3.34E+04 | 4.42E−02 | 1.32E−06 | 8.18E+04 | 1.21E−02 | 1.48E−07 |
| DQN0344H0976/L0591//DQN0385H1270/L0722-F6 | 3.62E+05 | 1.27E−03 | 3.50E−09 | 5.62E+05 | 4.72E−03 | 8.39E−09 | 4.00E+05 | 2.42E−03 | 6.06E−09 |
| DQN0344H0976/L0591//DQN0385H1270/L0681-F6 | 3.59E+05 | 1.24E−03 | 3.46E−09 | 5.80E+05 | 4.68E−03 | 8.06E−09 | 3.78E+05 | 2.46E−03 | 6.52E−09 |
| DQN0344H0976/L0591//DQN0385H1352/L0681-F6 | 3.67E+05 | 1.23E−03 | 3.35E−09 | 6.56E+05 | 6.15E−03 | 9.37E−09 | 4.23E+05 | 2.78E−03 | 6.57E−09 |
| DQN0344H0976/L0591//DQN0385H1527/L0605-F6 | 3.69E+05 | 1.28E−03 | 3.48E−09 | 5.66E+05 | 8.25E−03 | 1.46E−08 | 3.55E+05 | 2.65E−03 | 7.46E−09 |
| DQN0344H0976/L0591//DQN0385H1255/L0605-F6 | 3.66E+05 | 1.25E−03 | 3.41E−09 | 6.40E+05 | 7.51E−03 | 1.17E−08 | 4.01E+05 | 3.29E−03 | 8.20E−09 |
| DQN0344H1013/L0620//DQN0385H1270/L0722-F6 | 3.54E+05 | 1.44E−03 | 4.09E−09 | 5.37E+05 | 4.58E−03 | 8.54E−09 | 3.62E+05 | 2.37E−03 | 6.53E−09 |
| DQN0344H1013/L0620//DQN0385H1521/L0605-F6 | 3.52E+05 | 1.44E−03 | 4.08E−09 | 4.46E+05 | 8.46E−03 | 1.90E−08 | 3.05E+05 | 2.62E−03 | 8.59E−09 |
| DQN0344H1013/L0620//DQN0385H1270/L0681-F6 | 3.64E+05 | 1.46E−03 | 4.02E−09 | 5.62E+05 | 4.62E−03 | 8.22E−09 | 3.64E+05 | 2.43E−03 | 6.67E−09 |
| DQN0344H1013/L0620//DQN0385H1352/L0681-F6 | 3.66E+05 | 1.44E−03 | 3.93E−09 | 6.10E+05 | 5.91E−03 | 9.69E−09 | 4.48E+05 | 2.72E−03 | 6.06E−09 |
| DQN0344H1013/L0620//DQN0385H1353/L0681-F6 | 3.73E+05 | 1.37E−03 | 3.69E−09 | 5.36E+05 | 3.94E−03 | 7.36E−09 | 3.78+E05 | 2.16E−03 | 5.71E−09 |

*N.D.: not determined

Example 7-2

The affinity of anti-HLA-DQ2.5 antibodies binding to 33mer gliadin peptide at pH 7.4 was determined at 25 degrees C. using BIACORE (registered trademark) 8k instrument (GE Healthcare). Anti-human Fc antibody (GE Healthcare) was immobilized onto all flow cells of a CM4 sensor chip using amine coupling kit (GE Healthcare). All antibodies and analyte were prepared in ACES pH 7.4 containing 20 mM ACES, 150 mM NaCl, 0.05% Tween 20, 0.005% $NaN_3$. Each antibody was captured onto the sensor surface by anti-human Fc antibody. Antibody capture levels were aimed at 600 resonance unit (RU). 33mer gliadin peptide was injected at 2.5 to 40 nM prepared by two-fold serial dilution, followed by dissociation. Sensor surface was regenerated each cycle with 3M $MgCl_2$. Binding affinity were determined by processing and fitting the data to 1:1 binding model using BIACORE (registered trademark) Insight Evaluation software (GE Healthcare).

The affinity of anti-HLA-DQ2.5 antibodies binding to 33mer gliadin peptide is shown in Table 3-2. All tested antibodies except for DQN0315hh did not demonstrate antibody binding to 33mer gliadin peptide itself.

TABLE 3-2

Affinity of anti-HLA-DQ2.5 antibodies to 33mer gliadin peptide

| | 33mer gliadin peptide | | |
|---|---|---|---|
| Ab name | ka ($M^{-1}s^{-1}$) | kd ($s^{-1}$) | KD (M) |
| DQN0315hh | 6.13E+06 | 6.15E−04 | 1.00E−10 |
| DQN0344H0976/L0591//DQN0385H1270/L0722-F6 | N.D. | N.D. | N.D. |
| DQN0344H0976/L0591//DQN0385H1270/L0681-F6 | N.D. | N.D. | N.D. |
| DQN0344H0976/L0591//DQN0385H1352/L0681-F6 | N.D. | N.D. | N.D. |

TABLE 3-2-continued

Affinity of anti-HLA-DQ2.5 antibodies to 33mer gliadin peptide

| Ab name | 33mer gliadin peptide | | |
|---|---|---|---|
| | ka (M⁻¹s⁻¹) | kd (s⁻¹) | KD (M) |
| DQN0344H0976/L0591//DQN0385H1527/L0605-F6 | N.D. | N.D. | N.D. |
| DQN0344H0976/L0591//DQN0385H1255/L0605-F6 | N.D. | N.D. | N.D. |
| DQN0344H1013/L0620//DQN0385H1270/L0722-F6 | N.D. | N.D. | N.D. |
| DQN0344H1013/L0620//DQN0385H1521/L0605-F6 | N.D. | N.D. | N.D. |
| DQN0344H1013/L0620//DQN0385H1270/L0681-F6 | N.D. | N.D. | N.D. |
| DQN0344H1013/L0620//DQN0385H1352/L0681-F6 | N.D. | N.D. | N.D. |
| DQN0344H1013/L0620//DQN0385H1353/L0681-F6 | N.D. | N.D. | N.D. |

*N.D.: not determined

Example 8

8.1 Establishment of Alpha/Beta TCR KO Jurkat NFAT-Luc Cell Line

Ribonucleoprotein (RNP) complex, which is composed of Cas9 and single guide RNAs targeting TCR constant region (Blood. 2018; 131:311-22.) was introduced to NFAT-RE-luc2 Jurkat cell line (Promega corporation, CS176401) by electroporation (LONZA, the Nucleofector™ 2b apparatus). All single guide RNAs for TCR alpha chain and TCR beta chain were mixed and introduced simultaneously. RNP introduced cells were cultured in media containing Hygromycin B, followed by single cell cloning with FACSAria™ III cell sorter (Becton, Dickinson and Company). TCR alpha chain and TCR beta chain sequences were then checked and identified Jurkat NFAT-Luc derived clones which TCR alpha chain and TCR beta chain were knocked out. Established clone was named TCR KO Jurkat NFAT-Luc.

8.2 Establishment of Alpha/Beta TCR KO Jurkat NFAT-Luc Cell Line Transiently Expressing HLA-DQ2.5/Gluten Peptide Restricted TCR TCR amino sequence information was obtained from public information, or Oslo University based on material transfer agreement. Amino acid sequence information of HLA-DQ2.5/alpha 1a gliadin restricted TCR (TCC ID: 387.9), HLA-DQ2.5/alpha 1b gliadin restricted TCR (TCC ID: 370.2.25), HLA-DQ2.5/omega 1 gliadin restricted TCR (TCC ID: 442D. A.2), HLA-DQ2.5/omega 2 gliadin restricted TCR (TCC ID: 578.42), HLA-DQ2.5/gamma 1 gliadin restricted TCR (TCC ID: 820.27), HLA-DQ2.5/gamma 2 gliadin restricted TCR (TCC ID: 430.1.41), HLA-DQ2.5/gamma 3 gliadin restricted TCR (TCC ID: /.2.23), HLA-DQ2.5/gamma 4a gliadin restricted TCR (TCC ID: 430.1.36), HLA-DQ2.5/gamma 4d gliadin restricted TCR (TCC ID: 430.1.94) was obtained from Oslo University based on material transfer agreement. Amino acid sequence information of HLA-DQ2.5/alpha 2 gliadin restricted TCR (HLA-DQ2.5/alpha 2 gliadin restricted TCR) was obtained from Nat Struct Mol Biol. 2014; 21:480-8, and amino acid sequence information of HLA-DQ2.5/BC hordein restricted TCR (TCC ID: 1468.2) was obtained from Eur J Immunol. 2020; 50: 256-269. Each TCR beta chain sequence was linked with corresponding TCR alpha chain sequence by 2A self-cleaving peptide sequence (P2A, amino acid sequence: GSGATNFSLLKQAGDVEENPGP SEQ ID NO: 203). All TCR alpha chain and TCR beta chain have these own native signal peptide sequence except for HLA-DQ2.5/gamma 2 gliadin restricted TCR and HLA-DQ2.5/alpha 2 gliadin restricted TCR. Native signal sequence of HLA-DQ2.5/gamma 2 gliadin restricted TCR was replaced by Campath signal sequence (MGWSCIILFLVATATGVHS SEQ ID NO: 170). Campath signal sequence was also attached N-terminus of HLA-DQ2.5/alpha 2 gliadin restricted TCR. Each codon optimized TCR beta chain-P2A-TCR alpha chain cDNA was then inserted into the expression vector pCXZD1 (US/20090324589) at Genscript.

Electroporation of vectors into αβTCR-KO Jurkat-NFAT-luc2 was done by following to the protocol of SE Cell Line 4D-Nucleofector™ Kit.

8.3 Inhibitory Effect of Anti-HLA DQ Antibodies on HLA-DQ2.5/Alpha 1a Gliadin Peptide Dependent Jurkat T Cell Activation was Confirmed.

50 μL of the mixture of IHW09023 cell (8.0×10⁴ cells/well) and 33mer gliadin peptide (LQLQPFPQPELPYPQPELPYPQPELPYPQPQPF SEQ ID NO: 201, 250 nM) was distributed in 96 well plates. 25 μL of serially diluted anti-HLA DQ antibodies were then added, and 25 μL of alpha 1a gliadin restricted TCR transfected αβTCR-KO Jurkat-NFAT-luc2 (2.0×10⁴ cells/well) were finally added and incubated at 37 degrees C., at 5% CO2 for overnight. After overnight culture, 50 μL of cultured cells were harvested and redistributed in OptiPlate-96m (PerkinElmer, 6005299) 96-well microplate. 50 μL of Bio-Glom (Promega, G7491) luciferase assay system was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 4-1 and Table 4, all tested anti-HLA DQ antibodies (DQN0344H0976/L0591//DQN0385H1255/L0605-F6.v2, DQN0344H1013/L0620//DQN0385H1521/L0605-F6.v2, DQN0344H1013/L0620//DQN0385H1270/L0681-F6.v2) mediated concentration-dependent neutralization on HLA-DQ2.5/alpha 1a gliadin peptide dependent Jurkat T cell activation with IC50 values in the picogram/mL range.

8.4 Inhibitory Effect of Anti-HLA DQ Antibodies on HLA-DQ2.5/Alpha 2 Gliadin Peptide Dependent Jurkat T Cell Activation was Confirmed.

50 μL of the mixture of IHW09023 cell (8.0×10⁴ cells/well) and 33mer gliadin peptide (LQLQPFPQPELPYPQPELPYPQPELPYPQPQPF SEQ ID NO: 201, 250 nM) was distributed in 96 well plates. 25 μL of serially diluted anti-HLA DQ antibodies were then added, and 25 μL of alpha 2 gliadin restricted TCR transfected αβTCR-KO Jurkat-NFAT-luc2 (2.0×10⁴ cells/well) were finally added and incubated at 37 degrees C., at 5% CO2 for overnight. After overnight culture, 50 μL of cultured cells were harvested and redistributed in OptiPlate-96™ (PerkinElmer, 6005299) 96-well microplate. 50 μL of Bio-Glo™ (Promega, G7491) luciferase assay system was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%)

of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 4-2 and Table 4, all tested anti-HLA DQ antibodies (DQN0344H0976/L0591//DQN0385H1255/L0605-F6.v2, DQN0344H1013/L0620//DQN0385H1521/L0605-F6.v2, DQN0344H1013/L0620//DQN0385H1270/L0681-F6.v2) mediated concentration-dependent neutralization on HLA-DQ2.5/alpha 2 gliadin peptide dependent Jurkat T cell activation with IC50 values in the picogram/mL range.

8.5 Inhibitory Effect of Anti-HLA DQ Antibodies on HLA-DQ2.5/Alpha 1b Gliadin Peptide Dependent Jurkat T Cell Activation was Confirmed.

50 μL of the mixture of IHW09023 cell ($8.0 \times 10^4$ cells/well) and 33mer gliadin peptide (LQLQPFPQPELPYPQPELPYPQPELPYPQPQPF SEQ ID NO: 201, 250 nM) was distributed in 96 well plates. 25 μL of serially diluted anti-HLA DQ antibodies were then added, and 25 μL of alpha 1b gliadin restricted TCR transfected αβTCR-KO Jurkat-NFAT-luc2 ($2.0 \times 10^4$ cells/well) were finally added and incubated at 37 degrees C., at 5% $CO_2$ for overnight. After overnight culture, 50 μL of cultured cells were harvested and redistributed in OptiPlate-96m (PerkinElmer, 6005299) 96-well microplate. 50 μL of Bio-Glom (Promega, G7491) luciferase assay system was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 4-3 and Table 4, all tested anti-HLA DQ antibodies (DQN0344H0976/L0591//DQN0385H1255/L0605-F6.v2, DQN0344H1013/L0620//DQN0385H1521/L0605-F6.v2, DQN0344H1013/L0620//DQN0385H1270/L0681-F6.v2) mediated concentration-dependent neutralization on HLA-DQ2.5/alpha 1b gliadin peptide dependent Jurkat T cell activation with IC50 values in the low nanogram/mL range.

8.6 Inhibitory Effect of Anti-HLA DQ Antibodies on HLA-DQ2.5/Omega 1 Gliadin Peptide Dependent Jurkat T Cell Activation was Confirmed.

50 μL of the mixture of IHW09023 cell ($8.0 \times 10^4$ cells/well) and omega1/2 gliadin peptide (EQPFPQPEQPFPWQP SEQ ID NO: 204, 25 μM) was distributed in 96 well plates. 25 μL of serially diluted anti-HLA DQ antibodies were then added, and 25 μL of omega 1 gliadin restricted TCR transfected αβTCR-KO Jurkat-NFAT-luc2 ($2.0 \times 10^4$ cells/well) were finally added and incubated at 37 degrees C., at 5% $CO_2$ for overnight. After overnight culture, 50 μL of cultured cells were harvested and redistributed in OptiPlate-96™ (PerkinElmer, 6005299) 96-well microplate. 50 μL of Bio-Glo™ (Promega, G7491) luciferase assay system was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 4-4 and Table 4, all tested anti-HLA DQ antibodies (DQN0344H0976/L0591//DQN0385H1255/L0605-F6.v2, DQN0344H1013/L0620//DQN0385H1521/L0605-F6.v2, DQN0344H1013/L0620//DQN0385H1270/L0681-F6.v2) mediated concentration-dependent neutralization on HLA-DQ2.5/omega 1 gliadin peptide dependent Jurkat T cell activation with IC50 values in the low nanogram/mL range.

8.7 Inhibitory Effect of Anti-HLA DQ Antibodies on HLA-DQ2.5/Omega 2 Gliadin Peptide Dependent Jurkat T Cell Activation was Confirmed.

50 μL of the mixture of IHW09023 cell ($8.0 \times 10^4$ cells/well) and omega1/2 gliadin peptide (EQPFPQPEQPFPWQP SEQ ID NO: 204, 250 nM) was distributed in 96 well plates. 25 μL of serially diluted anti-HLA DQ antibodies were then added, and 25 μL of omega 2 gliadin restricted TCR transfected αβTCR-KO Jurkat-NFAT-luc2 ($2.0 \times 10^4$ cells/well) were finally added and incubated at 37 degrees C., at 5% $CO_2$ for overnight. After overnight culture, 50 μL of cultured cells were harvested and redistributed in OptiPlate-96™ (PerkinElmer, 6005299) 96-well microplate. 50 μL of Bio-Glo™ (Promega, G7491) luciferase assay system was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 4-5 and Table 4, all tested anti-HLA DQ antibodies (DQN0344H0976/L0591//DQN0385H1255/L0605-F6.v2, DQN0344H1013/L0620//DQN0385H1521/L0605-F6.v2, DQN0344H1013/L0620//DQN0385H1270/L0681-F6.v2) mediated concentration-dependent neutralization on HLA-DQ2.5/omega 2 gliadin peptide dependent Jurkat T cell activation with IC50 values in the picogram/mL range.

8.8 Inhibitory Effect of Anti-HLA DQ Antibodies on HLA-DQ2.5/BC Hordein Peptide Dependent Jurkat T Cell Activation was Confirmed.

50 μL of the mixture of IHW09023 cell ($8.0 \times 10^4$ cells/well) and BC hordein peptide (EPEQPIPEQPQPYPQQ SEQ ID NO: 205, 250 nM) was distributed in 96 well plates. 25 μL of serially diluted anti-HLA DQ antibodies were then added, and 25 μL of BC hordein restricted TCR transfected αβTCR-KO Jurkat-NFAT-luc2 ($2.0 \times 10^4$ cells/well) were finally added and incubated at 37 degrees C., at 5% $CO_2$ for overnight. After overnight culture, 50 μL of cultured cells were harvested and redistributed in OptiPlate-96™ (PerkinElmer, 6005299) 96-well microplate. 50 μL of Bio-Glo™ (Promega, G7491) luciferase assay system was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 4-6 and Table 4, all tested anti-HLA DQ antibodies (DQN0344H0976/L0591//DQN0385H1255/L0605-F6.v2, DQN0344H1013/L0620//DQN0385H1521/L0605-F6.v2, DQN0344H1013/L0620//DQN0385H1270/L0681-F6.v2) mediated concentration-dependent neutralization on HLA-DQ2.5/BC hordein peptide dependent Jurkat T cell activation with IC50 values in the nanogram/mL range.

8.9 Inhibitory Effect of Anti-HLA DQ Antibodies on HLA-DQ2.5/Gamma 1 Gliadin Peptide Dependent Jurkat T Cell Activation was Confirmed.

50 μL of the mixture of IHW09023 cell ($8.0 \times 10^4$ cells/well) and gamma 1 gliadin peptide (PQQPQQSFPEQEQPA SEQ ID NO: 206, 250 nM) was distributed in 96 well plates. 25 μL of serially diluted anti-HLA DQ antibodies were then added, and 25 μL of gamma 1 gliadin restricted TCR transfected αβTCR-KO Jurkat-NFAT-luc2 ($2.0 \times 10^4$ cells/well) were finally added and incubated at 37 degrees C., at 5% CO2 for overnight. After overnight culture, 50 μL of cultured cells were harvested and redistributed in OptiPlate-96™ (PerkinElmer, 6005299) 96-well microplate. 50 μL of Bio-Glo™ (Promega, G7491) luciferase assay system was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 4-7 and Table 4, all tested anti-HLA DQ antibodies (DQN0344H0976/L0591//DQN0385H1255/L0605-F6.v2, DQN0344H1013/L0620//DQN0385H1521/L0605-F6.v2, DQN0344H1013/L0620//DQN0385H1270/L0681-F6.v2) mediated concentration-dependent neutralization on HLA-DQ2.5/gamma 1 gliadin peptide dependent Jurkat T cell activation with IC50 values in the low nanogram/mL range.

8.10 Inhibitory Effect of Anti-HLA DQ Antibodies on HLA-DQ2.5/Gamma 2 Gliadin Peptide Dependent Jurkat T Cell Activation was Confirmed.

50 μL of the mixture of IHW09023 cell ($8.0 \times 10^4$ cells/well) and gamma 2 gliadin peptide (GQGIIQPEQPAQLIR SEQ ID NO: 207, 250 nM) was distributed in 96 well plates. 25 μL of serially diluted anti-HLA DQ antibodies were then added, and 25 μL of gamma 2 gliadin restricted TCR transfected αβTCR-KO Jurkat-NFAT-luc2 ($2.0 \times 10^4$ cells/well) were finally added and incubated at 37 degrees C., at 5% CO2 for overnight. After overnight culture, 50 μL of cultured cells were harvested and redistributed in OptiPlate-96™ (PerkinElmer, 6005299) 96-well microplate. 50 μL of Bio-Glo™ (Promega, G7491) luciferase assay system was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 4-8 and Table 4, all tested anti-HLA DQ antibodies (DQN0344H0976/L0591//DQN0385H1255/L0605-F6.v2, DQN0344H1013/L0620//DQN0385H1521/L0605-F6.v2, DQN0344H1013/L0620//DQN0385H1270/L0681-F6.v2) mediated concentration-dependent neutralization on HLA-DQ2.5/gamma 2 gliadin peptide dependent Jurkat T cell activation with IC50 values in the nanogram/mL range.

8.11 Inhibitory Effect of Anti-HLA DQ Antibodies on HLA-DQ2.5/Gamma 3 Gliadin Peptide Dependent Jurkat T Cell Activation was Confirmed.

50 μL of the mixture of IHW09023 cell ($8.0 \times 10^4$ cells/well) and gamma 3 gliadin peptide (EQPFPEQPEQPYPEQPEQPFPQP SEQ ID NO: 208, 100 μM) was distributed in 96 well plates. 25 μL of serially diluted anti-HLA DQ antibodies were then added, and 25 μL of gamma 3 gliadin restricted TCR transfected αβTCR-KO Jurkat-NFAT-luc2 ($2.0 \times 10^4$ cells/well) were finally added and incubated at 37 degrees C., at 5% CO2 for overnight. After overnight culture, 50 μL of cultured cells were harvested and redistributed in OptiPlate-96m (PerkinElmer, 6005299) 96-well microplate. 50 μL of Bio-Glo™ (Promega, G7491) luciferase assay system was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 4-9 and Table 4, all tested anti-HLA DQ antibodies (DQN0344H0976/L0591//DQN0385H1255/L0605-F6.v2, DQN0344H1013/L0620//DQN0385H1521/L0605-F6.v2, DQN0344H1013/L0620//DQN0385H1270/L0681-F6.v2) mediated concentration-dependent neutralization on HLA-DQ2.5/gamma 3 gliadin peptide dependent Jurkat T cell activation with IC50 values in the low nanogram/mL range.

8.12 Inhibitory Effect of Anti-HLA DQ Antibodies on HLA-DQ2.5/Gamma 4a Gliadin Peptide Dependent Jurkat T Cell Activation was Confirmed.

50 μL of the mixture of IHW09023 cell ($8.0 \times 10^4$ cells/well) and gamma 4a gliadin peptide (FSQPEQEFPQPQ SEQ ID NO: 209, 25 μM) was distributed in 96 well plates. 25 μL of serially diluted anti-HLA DQ antibodies were then added, and 25 μL of gamma 4a gliadin restricted TCR transfected αβTCR-KO Jurkat-NFAT-luc2 ($2.0 \times 10^4$ cells/well) were finally added and incubated at 37 degrees C., at 5% CO2 for overnight. After overnight culture, 50 μL of cultured cells were harvested and redistributed in OptiPlate-96™ (PerkinElmer, 6005299) 96-well microplate. 50 μL of Bio-Glo™ (Promega, G7491) luciferase assay system was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 4-10 and Table 4, all tested anti-HLA DQ antibodies (DQN0344H0976/L0591//DQN0385H1255/L0605-F6.v2, DQN0344H1013/L0620//DQN0385H1521/L0605-F6.v2, DQN0344H1013/L0620//DQN0385H1270/L0681-F6.v2) mediated concentration-dependent neutralization on HLA-DQ2.5/gamma 4a gliadin peptide dependent Jurkat T cell activation with IC50 values in the low microgram/mL to nanogram/mL range.

8.13 Inhibitory Effect of Anti-HLA DQ Antibodies on HLA-DQ2.5/Gamma 4d Gliadin Peptide Dependent Jurkat T Cell Activation was Confirmed.

50 μL of the mixture of IHW09023 cell ($8.0\times10^4$ cells/well) and gamma 4d gliadin peptide (WPQQQPFPQPEQPFCEQPQR SEQ ID NO: 210, 100 μM) was distributed in 96 well plates. 25 μL of serially diluted anti-HLA DQ antibodies were then added, and 25 μL of gamma 4d gliadin restricted TCR transfected αβTCR-KO Jurkat-NFAT-luc2 ($2.0\times10^4$ cells/well) were finally added and incubated at 37 degrees C., at 5% CO2 for overnight. After overnight culture, 50 μL of cultured cells were harvested and redistributed in OptiPlate-96™ (PerkinElmer, 6005299) 96-well microplate. 50 μL of Bio-Glo™ (Promega, G7491) luciferase assay system was then added and incubated at room temperature for 10 minutes, and luminescence was measured with ENVISION (registered trademark, PerkinElmer) plate reader, followed by analysis using Outlook Excel® 2013 (Microsoft) and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in Table 4, all tested anti-HLA DQ antibodies (DQN0344H0976/L0591//DQN0385H1255/L0605-F6.v2, DQN0344H1013/L0620//DQN0385H1521/L0605-F6.v2, DQN0344H1013/L0620//DQN0385H1270/L0681-F6.v2) mediated concentration-dependent neutralization on HLA-DQ2.5/gamma 4d gliadin peptide dependent Jurkat T cell activation with IC50 values in the nanogram/mL range.

Example 9

9.1 Establishment of αβTCR KO Jurkat NFAT-Luc Cell Line Transiently Expressing HLA-DQ2.5/Gluten Peptide Restricted TCRs TCR amino sequence information was obtained from public information, or Oslo University based on material transfer agreement. Amino acid sequence information of HLA-DQ2.5/alpha 1a gliadin restricted TCR (TCC ID: 387.9) was obtained from Oslo University based on material transfer agreement. Amino acid sequence information of HLA-DQ2.5/alpha 2 gliadin restricted TCR (HLA-DQ2.5/alpha 2 gliadin restricted TCR) was obtained from Nat Struct Mol Biol. 2014; 21:480-8. Although those TCRs are HLA-DQ2.5 restricted, but crossreactive to HLA-DQ2.2 when HLA-DQ2.2 is in the form of a complex with alpha 1a gliadin, alpha 2 gliadin (FIGS. 5-1 and 5-2). Each TCR beta chain sequence was linked with corresponding TCR alpha chain sequence by 2A self-cleaving peptide sequence (P2A, amino acid sequence: GSGATNFSLLKQAGDVEENPGP SEQ ID NO: 203). TCR alpha chain and TCR beta chain for HLA-DQ2.5/alpha 1a gliadin restricted TCR have these own native signal peptide sequence. Campath signal sequence (MGWSCIILFLVATATGVHS SEQ ID NO: 170) was attached N-terminus of HLA-DQ2.5/alpha 2 gliadin restricted TCR. Each codon optimized TCR beta chain-P2A-TCR alpha chain cDNA was then inserted into the expression vector pCXZD1 (US/20090324589) at Genscript. Electroporation of vectors into αβTCR-KO Jurkat-NFAT-luc2 was done by following to the protocol of SE Cell Line 4D-Nucleofector™ Kit.

9.2 Establishment of HLA-DQ2.2+Human Blood B Booster B Cell (HBBB2.2)

B-cell was isolated from HLA-DQ2.2+ PBMC (Precision for Medicines). Isolated B-cells were then immortalized by using Human Blood B Booster® kit (DENDRITICS)

9.3 Inhibitory Effect of Anti-HLA DQ Antibodies on HLA-DQ2.2/Alpha 1a Gliadin Peptide Dependent Jurkat T Cell Activation was Confirmed.

50 μL of the mixture of HBBB2.2 cell ($8.0\times10^4$ cells/well) and 33mer gliadin peptide (LQLQPFPQPELPYPQPELPYPQPELPYPQPQPF SEQ ID NO: 201, 25 μM) was distributed in 96 well plates. 25 μL of serially diluted anti-HLA DQ antibodies were then added, and 25 μL of alpha 1a gliadin restricted TCR transfected

TABLE 4

| | IC50 (ng/mL) | | | | | | | | | | |
|---|---|---|---|---|---|---|---|---|---|---|---|
| Ab name | α1a gliadin TCR 250 nM 33mer gliadin | α2 gliadin TCR 250 nM 33mer gliadin | α1b gliadin TCR 250 nM 33mer gliadin | ω1 gliadin TCR 25 μM ω1/2 gliadin | ω2 gliadin TCR 250 nM ω1/2 gliadin | BC hordein TCR 250 nM BC hordein | γ1 gliadin TCR 250 nM γ1 gliadin | γ2 gliadin TCR 250 nM γ2 gliadin | γ3 gliadin TCR 100 μM γ3 gliadin | γ4a gliadin TCR 25 μM γ4a gliadin | γ4d gliadin TCR 100 μM γ4d gliadin |
| DQN0344H0976/ L0591// DQN0385H1255/ L0605-F6.v2 | 0.46 | 0.29 | 1.33 | 1.62 | 0.18 | 9.52 | 1.62 | 252.22 | 1.55 | 636.21 | 8.69 |
| DQN0344H1013/ L0620// DQN0385H1521/ L0605-F6.v2 | 0.60 | 0.33 | 1.81 | 1.96 | 0.20 | 11.41 | 1.90 | 785.29 | 1.21 | 1249.93 | 9.23 |
| DQN0344H1013/ L0620/ DQN0385H1270/ L0681-F6.v2 | 0.63 | 0.53 | 1.42 | 3.19 | 0.49 | 25.25 | 5.85 | 279.61 | 4.84 | 1979.98 | 27.83 |

αβTCR-KO Jurkat-NFAT-luc2 (2.0×10⁴ cells/well) were finally added and incubated at 37 degrees C., at 5% CO2 for overnight. After overnight culture, 50 µL of cultured cells were harvested and redistributed in OptiPlate-96m (PerkinElmer, 6005299) 96-well microplate. 50 µL of Bio-Glom (Promega, G7491) luciferase assay system was then added and incubated at room temperature for 10 minutes, and luminescence was measured with ENVISION (registered trademark, PerkinElmer) plate reader, followed by analysis using Microsoft® Excel® for Office 365 MSO and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS)

As shown in FIG. 5-3 and Table 5, all tested anti-HLA DQ antibodies (DQN0344H0976/L0591//DQN0385H1255/L0605-F6.v2, DQN0344H1013/L0620//DQN0385H1521/L0605-F6.v2, DQN0344H1013/L0620//DQN0385H1270/L0681-F6.v2) mediated concentration-dependent neutralization on HLA-DQ2.2/alpha 1a gliadin dependent Jurkat T cell activation with IC50 values in the low nanogram/mL range.

9.4 Inhibitory Effect of Anti-HLA DQ Antibodies on HLA-DQ2.2/Alpha 2 Gliadin Peptide Dependent Jurkat T Cell Activation was Confirmed.

50 µL of the mixture of HBBB2.2 cell (8.0×10⁴ cells/well) and 33mer gliadin peptide (LQLQPFPQPELPYPQPELPYPQPELPYPQPQPF SEQ ID NO: 201, 1 µM) was distributed in 96 well plates. 25 µL of serially diluted anti-HLA DQ antibodies were then added, and 25 µL of alpha 2 gliadin restricted TCR transfected αβTCR-KO Jurkat-NFAT-luc2 (2.0×10⁴ cells/well) were finally added and incubated at 37 degrees C., at 5% CO2 for overnight. After overnight culture, 50 µL of cultured cells were harvested and redistributed in OptiPlate-96™ (PerkinElmer, 6005299) 96-well microplate. 50 µL of Bio-Glo™ (Promega, G7491) luciferase assay system was then added and incubated at room temperature for 10 minutes, and luminescence was measured with ENVISION (registered trademark, PerkinElmer) plate reader, followed by analysis using Microsoft® Excel® for Office 365 MSO and GraphPad Prism software (GraphPad). Inhibitory effect (%) of anti-HLA DQ antibodies was determined when taking a mean counts per second (cps) of well in the absence of antigen peptide without antibody as 100%, and a cps of well in the presence of antigen without antibody as 0%. IC50 value was determined using XLFIT (registered trademark) Excel add-in software (IDBS).

As shown in FIG. 5-4 and Table 5, all tested anti-HLA DQ antibodies (DQN0344H0976/L0591//DQN0385H1255/L0605-F6.v2, DQN0344H1013/L0620//DQN0385H1521/L0605-F6.v2, DQN0344H1013/L0620//DQN0385H1270/L0681-F6.v2) mediated concentration-dependent neutralization on HLA-DQ2.2/alpha 2 gliadin dependent Jurkat T cell activation with IC50 values in the low nanogram/mL range.

As shown in FIGS. 5-3 to 5-4 and Table 5, DQN0344H0976/L0591//DQN0385H1255/L0605-F6.v2, DQN0344H1013/L0620//DQN0385H1521/L0605-F6.v2, DQN0344H1013/L0620//DQN0385H1270/L0681-F6.v2 mediated concentration-dependent neutralization on HLA-DQ2.2/alpha 1 gliadin, and alpha 2 gliadin.

As shown in FIGS. 4-1 to 5-4, Table 4[[,]] and Table 5 DQN0344H0976/L0591//DQN0385H1255/L0605-F6.v2, DQN0344H1013/L0620//DQN0385H1521/L0605-F6.v2, DQN0344H1013/L0620//DQN0385H1270/L0681-F6.v2 mediated concentration-dependent neutralization to all tested gluten epitopes. In addition, as shown in Table 2-7 and Table 4, neutralizing activity of DQN0344H0976/L0591//DQN0385H1255/L0605-F6.v2, DQN0344H1013/L0620//DQN0385H1521/L0605-F6.v2, DQN0344H1013/L0620//DQN0385H1270/L0681-F6.v2 was comparable to that of DQN0344H0976/L0591//DQN0385H1255/L0605-F6, DQN0344H1013/L0620//DQN0385H1521/L0605-F6, DQN0344H1013/L0620//DQN0385H1270/L0681-F6, respectively.

TABLE 5

| | IC50 (ng/mL) HLA-DQ2.2 | |
|---|---|---|
| | α1a gliadin TCR 25 µM | α2 gliadin TCR 1 µM |
| Ab name | 33mer gliadin | 33mer gliadin |
| DQN0344H0976/L0591// DQN0385H1255/L0605-F6.v2 | 1.72 | 9.48 |
| DQN0344H1013/L0620// DQN0385H1521/L0605-F6.v2 | 1.16 | 6.51 |
| DQN0344H1013/L0620// DQN0385H1270/L0681-F6.v2 | 1.62 | 4.60 |

The invention claimed is:

1. A bispecific antibody that comprises
    a first arm that comprises a first antibody heavy chain variable region (VH) and a first antibody light chain variable region (VL), and
    a second arm that comprises a second VH and a second VL,
wherein the first VH, first VL, second VH, and second VL are as described in any one of (1) to (14) below:
   (1) the first VH comprises the amino acid sequence of SEQ ID NO: 88; the first VL comprises the amino acid sequence of SEQ ID NO: 90; the second VH comprises the amino acid sequence of SEQ ID NO: 92; and the second VL comprises the amino acid sequence of SEQ ID NO: 98;
   (2) the first VH comprises the amino acid sequence of SEQ ID NO: 88; the first VL comprises the amino acid sequence of SEQ ID NO: 90; the second VH comprises the amino acid sequence of SEQ ID NO: 92; and the second VL comprises the amino acid sequence of SEQ ID NO: 99;
   (3) the first VH comprises the amino acid sequence of SEQ ID NO: 88; the first VL comprises the amino acid sequence of SEQ ID NO: 90; the second VH comprises the amino acid sequence of SEQ ID NO: 93; and the second VL comprises the amino acid sequence of SEQ ID NO: 99;
   (4) the first VH comprises the amino acid sequence of SEQ ID NO: 88; the first VL comprises the amino acid sequence of SEQ ID NO: 90; the second VH comprises the amino acid sequence of SEQ ID NO: 94; and the second VL comprises the amino acid sequence of SEQ ID NO: 100;
   (5) the first VH comprises the amino acid sequence of SEQ ID NO: 88; the first VL comprises the amino acid sequence of SEQ ID NO: 90; the second VH comprises the amino acid sequence of SEQ ID NO: 95; and the second VL comprises the amino acid sequence of SEQ ID NO: 100;
   (6) the first VH comprises the amino acid sequence of SEQ ID NO: 88; the first VL comprises the amino acid sequence of SEQ ID NO: 90; the second VH comprises the amino acid sequence of SEQ ID NO: 96; and the second VL comprises the amino acid sequence of SEQ ID NO: 100;
   (7) the first VH comprises the amino acid sequence of SEQ ID NO: 88; the first VL comprises the amino acid sequence of SEQ ID NO: 90; the second VH comprises the amino acid sequence of SEQ ID NO: 97; and the second VL comprises the amino acid sequence of SEQ ID NO: 99;
   (8) the first VH comprises the amino acid sequence of SEQ ID NO: 89; the first VL comprises the amino acid sequence of SEQ ID NO: 91; the second VH comprises the amino acid sequence of SEQ ID NO: 92; and the second VL comprises the amino acid sequence of SEQ ID NO: 98;
   (9) the first VH comprises the amino acid sequence of SEQ ID NO: 89; the first VL comprises the amino acid sequence of SEQ ID NO: 91; the second VH comprises the amino acid sequence of SEQ ID NO: 92; and the second VL comprises the amino acid sequence of SEQ ID NO: 99;
   (10) the first VH comprises the amino acid sequence of SEQ ID NO: 89; the first VL comprises the amino acid sequence of SEQ ID NO: 91; the second VH comprises the amino acid sequence of SEQ ID NO: 93; and the second VL comprises the amino acid sequence of SEQ ID NO: 99;
   (11) the first VH comprises the amino acid sequence of SEQ ID NO: 89; the first VL comprises the amino acid sequence of SEQ ID NO: 91; the second VH comprises the amino acid sequence of SEQ ID NO: 94; and the second VL comprises the amino acid sequence of SEQ ID NO: 100;
   (12) the first VH comprises the amino acid sequence of SEQ ID NO: 89; the first VL comprises the amino acid sequence of SEQ ID NO: 91; the second VH comprises the amino acid sequence of SEQ ID NO: 95; and the second VL comprises the amino acid sequence of SEQ ID NO: 100;
   (13) the first VH comprises the amino acid sequence of SEQ ID NO: 89; the first VL comprises the amino acid sequence of SEQ ID NO: 91; the second VH comprises the amino acid sequence of SEQ ID NO: 96; and the second VL comprises the amino acid sequence of SEQ ID NO: 100; and
   (14) the first VH comprises the amino acid sequence of SEQ ID NO: 89; the first VL comprises the amino acid sequence of SEQ ID NO: 91; the second VH comprises the amino acid sequence of SEQ ID NO: 97; and the second VL comprises the amino acid sequence of SEQ ID NO: 99.

2. The bispecific antibody of claim 1, wherein the first VH, first VL, second VH, and second VL are as described in any one of (1) to (14) below:

(1) the first VH consists of the amino acid sequence of SEQ ID NO: 88; the first VL consists of the amino acid sequence of SEQ ID NO: 90; the second VH consists of the amino acid sequence of SEQ ID NO: 92; and the second VL consists of the amino acid sequence of SEQ ID NO: 98;

(2) the first VH consists of the amino acid sequence of SEQ ID NO: 88; the first VL consists of the amino acid sequence of SEQ ID NO: 90; the second VH consisting of the amino acid sequence of SEQ ID NO: 92; and the second VL consists of the amino acid sequence of SEQ ID NO: 99;

(3) the first VH consists of the amino acid sequence of SEQ ID NO: 88; the first VL consists of the amino acid sequence of SEQ ID NO: 90; the second VH consists of the amino acid sequence of SEQ ID NO: 93; and the second VL consists of the amino acid sequence of SEQ ID NO: 99;

(4) the first VH consists of the amino acid sequence of SEQ ID NO: 88; the first VL consists of the amino acid sequence of SEQ ID NO: 90; the second VH consists of the amino acid sequence of SEQ ID NO: 94; and the second VL consists of the amino acid sequence of SEQ ID NO: 100;

(5) the first VH consists of the amino acid sequence of SEQ ID NO: 88; the first VL consists of the amino acid sequence of SEQ ID NO: 90; the second VH consists of the amino acid sequence of SEQ ID NO: 95; and the second VL consists of the amino acid sequence of SEQ ID NO: 100;

(6) the first VH consists of the amino acid sequence of SEQ ID NO: 88; the first VL consists of the amino acid sequence of SEQ ID NO: 90; the second VH consists of the amino acid sequence of SEQ ID NO: 96; and the second VL consists of the amino acid sequence of SEQ ID NO: 100;

(7) the first VH consists of the amino acid sequence of SEQ ID NO: 88; the first VL consists of the amino acid sequence of SEQ ID NO: 90; the second VH consists of the amino acid sequence of SEQ ID NO: 97; and the second VL consists of the amino acid sequence of SEQ ID NO: 99;

(8) the first VH consists of the amino acid sequence of SEQ ID NO: 89; the first VL consists of the amino acid sequence of SEQ ID NO: 91; the second VH consists of the amino acid sequence of SEQ ID NO: 92; and the second VL consists of the amino acid sequence of SEQ ID NO: 98;

(9) the first VH consists of the amino acid sequence of SEQ ID NO: 89; the first VL consists of the amino acid sequence of SEQ ID NO: 91; the second VH consists of the amino acid sequence of SEQ ID NO: 92; and the second VL consists of the amino acid sequence of SEQ ID NO: 99;

(10) the first VH consists of the amino acid sequence of SEQ ID NO: 89; the first VL consists of the amino acid sequence of SEQ ID NO: 91; the second VH consists of the amino acid sequence of SEQ ID NO: 93; and the second VL consists of the amino acid sequence of SEQ ID NO: 99;

(11) the first VH consists of the amino acid sequence of SEQ ID NO: 89; the first VL consists of the amino acid sequence of SEQ ID NO: 91; the second VH consists of the amino acid sequence of SEQ ID NO: 94; and the second VL consists of the amino acid sequence of SEQ ID NO: 100;

(12) the first VH consists of the amino acid sequence of SEQ ID NO: 89; the first VL consists of the amino acid sequence of SEQ ID NO: 91; the second VH consists of the amino acid sequence of SEQ ID NO: 95; and the second VL consists of the amino acid sequence of SEQ ID NO: 100;

(13) the first VH consists of the amino acid sequence of SEQ ID NO: 89; the first VL consists of the amino acid sequence of SEQ ID NO: 91; the second VH consists of the amino acid sequence of SEQ ID NO: 96; and the second VL consists of the amino acid sequence of SEQ ID NO: 100; and

(14) the first VH consists of the amino acid sequence of SEQ ID NO: 89; the first VL consists of the amino acid sequence of SEQ ID NO: 91; the second VH consists of the amino acid sequence of SEQ ID NO: 97; and the second VL consists of the amino acid sequence of SEQ ID NO: 99.

3. The bispecific antibody of claim 1, wherein the bispecific antibody comprises at least one Fab, Fab', or single-chain variable fragment (scFv).

4. A pharmaceutical composition comprising the bispecific antibody of claim 1.

5. The bispecific antibody of claim 1, wherein the first VH comprises the amino acid sequence of SEQ ID NO: 88; the first VL comprises the amino acid sequence of SEQ ID NO: 90; the second VH comprises the amino acid sequence of SEQ ID NO: 95; and the second VL comprises the amino acid sequence of SEQ ID NO: 100.

6. The bispecific antibody of claim 1, wherein the first arm binds to a complex of HLA-DQ2.5 and a first gluten peptide, and the second arm binds to a complex of HLA-DQ2.5 and a second gluten peptide.

7. The bispecific antibody of claim 6,
wherein the first and second gluten peptides are the same or different and are independently selected from the following list: a 33mer gliadin peptide comprising the amino acid sequence of SEQ ID NO: 201, an alpha 1 gliadin peptide comprising the amino acid sequence of SEQ ID NO: 182, an alpha 2 gliadin peptide comprising the amino acid sequence of SEQ ID NO: 183, a gamma 1 gliadin peptide comprising the amino acid sequence of SEQ ID NO: 184 or 206, a gamma 2 gliadin peptide comprising the amino acid sequence of SEQ ID NO: 175, 185 or 207, an omega 1 gliadin peptide comprising the amino acid sequence of SEQ ID NO: 186 or 204, an omega 2 gliadin peptide comprising the amino acid sequence of SEQ ID NO: 187 or 204, a BC hordein peptide comprising the amino acid sequence of SEQ ID NO: 176, 188 or 205, an alpha 3 gliadin peptide comprising the amino acid sequence of SEQ ID NO: 189, an alpha 1b gliadin peptide comprising the amino acid sequence of SEQ ID NO: 190, a gamma 4a gliadin peptide comprising the amino acid sequence of SEQ ID NO: 191 or 209, a gamma 4b gliadin peptide comprising the amino acid sequence of SEQ ID NO: 192, an avenin 1 peptide comprising the amino acid sequence of SEQ ID NO: 193, an avenin 2 peptide comprising the amino acid sequence of SEQ ID NO: 194, an avenin 3 peptide comprising the amino acid sequence of SEQ ID NO: 195, a hordein 1 peptide comprising the amino acid sequence of SEQ ID NO: 196, a hordein 2 peptide comprising the amino acid sequence of SEQ ID NO: 197, a secalin 1 peptide comprising the amino acid sequence of SEQ ID NO: 198, a secalin 2 peptide comprising the amino acid sequence of SEQ ID NO: 199, and a 26mer gliadin peptide comprising the amino acid sequence of SEQ ID NO: 202.

8. The bispecific antibody of claim 6,
wherein the first arm has binding activity to multiple different complexes of HLA-DQ2.5 with any of two or more different gluten peptides, including at least two gluten peptides from the group below; and
wherein the second arm has binding activity to multiple different complexes of HLA-DQ2.5 with any of two or more different gluten peptides, including at least two gluten peptides from the group below:
a 33mer gliadin peptide comprising the amino acid sequence of SEQ ID NO: 201, an alpha 1 gliadin peptide comprising the amino acid sequence of SEQ ID NO: 182, an alpha 2 gliadin peptide comprising the amino acid sequence of SEQ ID NO: 183, a gamma 1 gliadin peptide comprising the amino acid sequence of SEQ ID NO: 184 or 206, a gamma 2 gliadin peptide comprising the amino acid sequence of SEQ ID NO: 175, 185 or 207, an omega 1 gliadin peptide comprising the amino acid sequence of SEQ ID NO: 186 or 204, an omega 2 gliadin peptide comprising the amino acid sequence of SEQ ID NO: 187 or 204, a BC hordein peptide comprising the amino acid sequence of SEQ ID NO: 176, 188 or 205, an alpha 3 gliadin peptide comprising the amino acid sequence of SEQ ID NO: 189, an alpha 1b gliadin peptide comprising the amino acid sequence of SEQ ID NO: 190, a gamma 4a gliadin peptide comprising the amino acid sequence of SEQ ID NO: 191 or 209, a gamma 4b gliadin peptide comprising the amino acid sequence of SEQ ID NO: 192, an avenin 1 peptide comprising the amino acid sequence of SEQ ID NO: 193, an avenin 2 peptide comprising the amino acid sequence of SEQ ID NO: 194, an avenin 3 peptide comprising the amino acid sequence of SEQ ID NO: 195, a hordein 1 peptide comprising the amino acid sequence of SEQ ID NO: 196, a hordein 2 peptide comprising the amino acid sequence of SEQ ID NO: 197, a secalin 1 peptide comprising the amino acid sequence of SEQ ID NO: 198, a secalin 2 peptide comprising the amino acid sequence of SEQ ID NO: 199, and a 26mer gliadin peptide comprising the amino acid sequence of SEQ ID NO: 202.

9. A bispecific antibody comprising:
a first arm that comprises a first antibody heavy chain and a first antibody light chain, and
a second arm that comprises a second antibody heavy chain and a second antibody light chain,
wherein the first and second heavy and light chains are as described in any one of (1) to (14) below:
(1) the first heavy chain comprises the amino acid sequence of SEQ ID NO: 42, the first light chain comprises the amino acid sequence of SEQ ID NO: 43, the second heavy chain comprises the amino acid sequence of SEQ ID NO: 54, and the second light chain comprises the amino acid sequence of SEQ ID NO: 55;
(2) the first heavy chain comprises the amino acid sequence of SEQ ID NO: 42, the first light chain comprises the amino acid sequence of SEQ ID NO: 43, the second heavy chain comprises the amino acid sequence of SEQ ID NO: 54, and the second light chain comprises the amino acid sequence of SEQ ID NO: 56;
(3) the first heavy chain comprises the amino acid sequence of SEQ ID NO: 42, the first light chain comprises the amino acid sequence of SEQ ID NO: 43, the second heavy chain comprises the amino acid sequence of SEQ ID NO: 58, and the second light chain comprises the amino acid sequence of SEQ ID NO: 56;
(4) the first heavy chain comprises the amino acid sequence of SEQ ID NO: 42, the first light chain comprises the amino acid sequence of SEQ ID NO: 43, the second heavy chain comprises the amino acid sequence of SEQ ID NO: 60, and the second light chain comprises the amino acid sequence of SEQ ID NO: 61;
(5) the first heavy chain comprises the amino acid sequence of SEQ ID NO: 42, the first light chain comprises the amino acid sequence of SEQ ID NO: 43, the second heavy chain comprises the amino acid sequence of SEQ ID NO: 63, and the second light chain comprises the amino acid sequence of SEQ ID NO: 61;
(6) the first heavy chain comprises the amino acid sequence of SEQ ID NO: 45, the first light chain comprises the amino acid sequence of SEQ ID NO: 46, the second heavy chain comprises the amino acid sequence of SEQ ID NO: 54, and the second light chain comprises the amino acid sequence of SEQ ID NO: 55;
(7) the first heavy chain comprises the amino acid sequence of SEQ ID NO: 45, the first light chain comprises the amino acid sequence of SEQ ID NO: 46, the second heavy chain comprises the amino acid sequence of SEQ ID NO: 65, and the second light chain comprises the amino acid sequence of SEQ ID NO: 61;
(8) the first heavy chain comprises the amino acid sequence of SEQ ID NO: 45, the first light chain comprises the amino acid sequence of SEQ ID NO: 46, the second heavy chain comprises the amino acid sequence of SEQ ID NO: 54, and the second light chain comprises the amino acid sequence of SEQ ID NO: 56;
(9) the first heavy chain comprises the amino acid sequence of SEQ ID NO: 45, the first light chain comprises the amino acid sequence of SEQ ID NO: 46, the second heavy chain comprises the amino acid sequence of SEQ ID NO: 58, and the second light chain comprises the amino acid sequence of SEQ ID NO: 56;
(10) the first heavy chain comprises the amino acid sequence of SEQ ID NO: 45, the first light chain comprises the amino acid sequence of SEQ ID NO: 46, the second heavy chain comprises the amino acid sequence of SEQ ID NO: 67, and the second light chain comprises the amino acid sequence of SEQ ID NO: 56;
(11) the first heavy chain comprises the amino acid sequence of SEQ ID NO: 42, the first light chain comprises the amino acid sequence of SEQ ID NO: 43, the second heavy chain comprises the amino acid sequence of SEQ ID NO: 65, and the second light chain comprises the amino acid sequence of SEQ ID NO: 61;
(12) the first heavy chain comprises the amino acid sequence of SEQ ID NO: 42, the first light chain comprises the amino acid sequence of SEQ ID NO: 43, the second heavy chain comprises the amino acid sequence of SEQ ID NO: 67, and the second light chain comprises the amino acid sequence of SEQ ID NO: 56;

(13) the first heavy chain comprises the amino acid sequence of SEQ ID NO: 45, the first light chain comprises the amino acid sequence of SEQ ID NO: 46, the second heavy chain comprises the amino acid sequence of SEQ ID NO: 63, and the second light chain comprises the amino acid sequence of SEQ ID NO: 61; and

(14) the first heavy chain comprises the amino acid sequence of SEQ ID NO: 45, the first light chain comprises the amino acid sequence of SEQ ID NO: 46, the second heavy chain comprises the amino acid sequence of SEQ ID NO: 60, and the second light chain comprises the amino acid sequence of SEQ ID NO: 61.

10. The bispecific antibody of claim 9, wherein the two antibody heavy chains and two antibody light chains are as described in any one of (1) to (14) below:

(1) the first heavy chain consists of the amino acid sequence of SEQ ID NO: 42, the first light chain consists of the amino acid sequence of SEQ ID NO: 43, the second heavy chain consists of the amino acid sequence of SEQ ID NO: 54, and the second light chain consists of the amino acid sequence of SEQ ID NO: 55;

(2) the first heavy chain consists of the amino acid sequence of SEQ ID NO: 42, the first light chain consists of the amino acid sequence of SEQ ID NO: 43, the second heavy chain consists of the amino acid sequence of SEQ ID NO: 54, and the second light chain consists of the amino acid sequence of SEQ ID NO: 56;

(3) the first heavy chain consists of the amino acid sequence of SEQ ID NO: 42 the first light chain consists of the amino acid sequence of SEQ ID NO: 43, the second heavy chain consists of the amino acid sequence of SEQ ID NO: 58, and the second light chain consists of the amino acid sequence of SEQ ID NO: 56;

(4) the first heavy chain consists of the amino acid sequence of SEQ ID NO: 42 the first light chain consists of the amino acid sequence of SEQ ID NO: 43, the second heavy chain consists of the amino acid sequence of SEQ ID NO: 60, and the second light chain consists of the amino acid sequence of SEQ ID NO: 61;

(5) the first heavy chain consists of the amino acid sequence of SEQ ID NO: 42, the first light chain consists of the amino acid sequence of SEQ ID NO: 43, the second heavy chain consists of the amino acid sequence of SEQ ID NO: 63, and the second light chain consists of the amino acid sequence of SEQ ID NO: 61;

(6) the first heavy chain consists of the amino acid sequence of SEQ ID NO: 45, the first light chain consists of the amino acid sequence of SEQ ID NO: 46, the second heavy chain consists of the amino acid sequence of SEQ ID NO: 54, and the second light chain consists of the amino acid sequence of SEQ ID NO: 55;

(7) the first heavy chain consists of the amino acid sequence of SEQ ID NO: 45, the first light chain consists of the amino acid sequence of SEQ ID NO: 46, the second heavy chain consists of the amino acid sequence of SEQ ID NO: 65, and the second light chain consists of the amino acid sequence of SEQ ID NO: 61;

(8) the first heavy chain consists of the amino acid sequence of SEQ ID NO: 45, the first light chain consists of the amino acid sequence of SEQ ID NO: 46, the second heavy chain consists of the amino acid sequence of SEQ ID NO: 54, and the second light chain consists of the amino acid sequence of SEQ ID NO: 56;

(9) the first heavy chain consists of the amino acid sequence of SEQ ID NO: 45, the first light chain consists of the amino acid sequence of SEQ ID NO: 46, the second heavy chain consists of the amino acid sequence of SEQ ID NO: 58, and the second light chain consists of the amino acid sequence of SEQ ID NO: 56;

(10) the first heavy chain consists of the amino acid sequence of SEQ ID NO: 45, the first light chain consists of the amino acid sequence of SEQ ID NO: 46, the second heavy chain consists of the amino acid sequence of SEQ ID NO: 67, and the second light chain consists of the amino acid sequence of SEQ ID NO: 56;

(11) the first heavy chain consists of the amino acid sequence of SEQ ID NO: 42, the first light chain consists of the amino acid sequence of SEQ ID NO: 43, the second heavy chain consists of the amino acid sequence of SEQ ID NO: 65, and the second light chain consists of the amino acid sequence of SEQ ID NO: 61;

(12) the first heavy chain consists of the amino acid sequence of SEQ ID NO: 42, the first light chain consists of the amino acid sequence of SEQ ID NO: 43, the second heavy chain consists of the amino acid sequence of SEQ ID NO: 67, and the second light chain consists of the amino acid sequence of SEQ ID NO: 56;

(13) the first heavy chain consists of the amino acid sequence of SEQ ID NO: 45, the first light chain consists of the amino acid sequence of SEQ ID NO: 46, the second heavy chain consists of the amino acid sequence of SEQ ID NO: 63, and the second light chain consists of the amino acid sequence of SEQ ID NO: 61; and

(14) the first heavy chain consists of the amino acid sequence of SEQ ID NO: 45, the first light chain consists of the amino acid sequence of SEQ ID NO: 46, the second heavy chain consists of the amino acid sequence of SEQ ID NO: 60, and the second light chain consists of the amino acid sequence of SEQ ID NO: 61.

11. A pharmaceutical composition comprising the bispecific antibody of claim 9.

12. The bispecific antibody of claim 9, wherein the first heavy chain comprises the amino acid sequence of SEQ ID NO: 42, the first light chain comprises the amino acid sequence of SEQ ID NO: 43, the second heavy chain comprises the amino acid sequence of SEQ ID NO: 63, and the second light chain comprises the amino acid sequence of SEQ ID NO: 61.

13. The bispecific antibody of claim 9, wherein the first arm binds to a complex of HLA-DQ2.5 and a first gluten peptide, and the second arm binds to a complex of HLA-DQ2.5 and a second gluten peptide.

14. The bispecific antibody of claim 13,
wherein the first and second gluten peptides are the same or different and are independently selected from the following list: a 33mer gliadin peptide comprising the amino acid sequence of SEQ ID NO: 201, an alpha 1 gliadin peptide comprising the amino acid sequence of SEQ ID NO: 182, an alpha 2 gliadin peptide comprising the amino acid sequence of SEQ ID NO: 183, a gamma 1 gliadin peptide comprising the amino acid sequence of SEQ ID NO: 184 or 206, a gamma 2 gliadin peptide comprising the amino acid sequence of SEQ ID NO: 175, 185 or 207, an omega 1 gliadin peptide comprising the amino acid sequence of SEQ ID NO: 186 or 204, an omega 2 gliadin peptide comprising the amino acid sequence of SEQ ID NO: 187 or 204, a BC hordein peptide comprising the amino acid sequence of SEQ ID NO: 176, 188 or 205, an alpha 3 gliadin peptide comprising the amino acid sequence of SEQ ID NO: 189, an alpha 1b gliadin peptide comprising the amino acid sequence of SEQ ID NO: 190, a gamma 4a gliadin peptide comprising the amino acid sequence of SEQ ID NO: 191 or 209, a gamma 4b gliadin peptide comprising the amino acid sequence of SEQ ID NO: 192, an avenin 1 peptide comprising the amino acid sequence of SEQ ID NO: 193, an avenin 2 peptide comprising the amino acid sequence of SEQ ID NO: 194, an avenin 3 peptide comprising the amino acid sequence of SEQ ID NO: 195, a hordein 1 peptide comprising the amino acid sequence of SEQ ID NO: 196, a hordein 2 peptide comprising the amino acid sequence of SEQ ID NO: 197, a secalin 1 peptide comprising the amino acid sequence of SEQ ID NO: 198, a secalin 2 peptide comprising the amino acid sequence of SEQ ID NO: 199, and a 26mer gliadin peptide comprising the amino acid sequence of SEQ ID NO: 202.

15. The bispecific antibody of claim 13,
wherein the first arm has binding activity to multiple different complexes of HLA-DQ2.5 with any of two or more different gluten peptides, including at least two gluten peptides from the group below; and
wherein the second arm has binding activity to multiple different complexes of HLA-DQ2.5 with any of two or more different gluten peptides, including at least two gluten peptides from the group below:
a 33mer gliadin peptide comprising the amino acid sequence of SEQ ID NO: 201, an alpha 1 gliadin peptide comprising the amino acid sequence of SEQ ID NO: 182, an alpha 2 gliadin peptide comprising the amino acid sequence of SEQ ID NO: 183, a gamma 1 gliadin peptide comprising the amino acid sequence of SEQ ID NO: 184 or 206, a gamma 2 gliadin peptide comprising the amino acid sequence of SEQ ID NO: 175, 185 or 207, an omega 1 gliadin peptide comprising the amino acid sequence of SEQ ID NO: 186 or 204, an omega 2 gliadin peptide comprising the amino acid sequence of SEQ ID NO: 187 or 204, a BC hordein peptide comprising the amino acid sequence of SEQ ID NO: 176, 188 or 205, an alpha 3 gliadin peptide comprising the amino acid sequence of SEQ ID NO: 189, an alpha 1b gliadin peptide comprising the amino acid sequence of SEQ ID NO: 190, a gamma 4a gliadin peptide comprising the amino acid sequence of SEQ ID NO: 191 or 209, a gamma 4b gliadin peptide comprising the amino acid sequence of SEQ ID NO: 192, an avenin 1 peptide comprising the amino acid sequence of SEQ ID NO: 193, an avenin 2 peptide comprising the amino acid sequence of SEQ ID NO: 194, an avenin 3 peptide comprising the amino acid sequence of SEQ ID NO: 195, a hordein 1 peptide comprising the amino acid sequence of SEQ ID NO: 196, a hordein 2 peptide comprising the amino acid sequence of SEQ ID NO: 197, a secalin 1 peptide comprising the amino acid sequence of SEQ ID NO: 198, a secalin 2 peptide comprising the amino acid sequence of SEQ ID NO: 199, and a 26mer gliadin peptide comprising the amino acid sequence of SEQ ID NO: 202.

16. A bispecific antibody that comprises
a first arm that binds to a complex of HLA-DQ2.5 and a first gluten peptide, wherein the first arm comprises a first VH and a first VL, and
a second arm that binds to a complex of HLA-DQ2.5 and a second gluten peptide,
wherein the second arm comprises a second VH and a second VL,
wherein the first VH and VL and the second VH and VL comprise complementarity determining region (CDR) sequences as specified in any one of (1) to (14) below:

(1) the first VH comprises a CDR 1 comprising the amino acid sequence of SEQ ID NO: 129, a CDR 2 comprising the amino acid sequence of SEQ ID NO: 130, and a CDR 3 comprising the amino acid sequence of SEQ ID NO: 131; the first VL comprises a CDR 1 comprising the amino acid sequence of SEQ ID NO: 132, a CDR 2 comprising the amino acid sequence of SEQ ID NO: 133, and a CDR 3 comprising the amino acid sequence of SEQ ID NO: 134; the second VH comprises a CDR 1 comprising the amino acid sequence of SEQ ID NO: 135, a CDR 2 comprising the amino acid sequence of SEQ ID NO: 136, and a CDR 3 comprising the amino acid sequence of SEQ ID NO: 137; and the second VL comprises a CDR 1 comprising the amino acid sequence of SEQ ID NO: 138, a CDR 2 comprising the amino acid sequence of SEQ ID NO: 139, and a CDR 3 comprising the amino acid sequence of SEQ ID NO: 140;

(2) the first VH comprises a CDR 1 comprising the amino acid sequence of SEQ ID NO: 129, a CDR 2 comprising the amino acid sequence of SEQ ID NO: 130, and a CDR 3 comprising the amino acid sequence of SEQ ID NO: 131; the first VL comprises a CDR 1 comprising the amino acid sequence of SEQ ID NO: 132, a CDR 2 comprising the amino acid sequence of SEQ ID NO: 133, and a CDR 3 comprising the amino acid sequence of SEQ ID NO: 134; the second VH comprises a CDR 1 comprising the amino acid sequence of SEQ ID NO: 135, a CDR 2 comprising the amino acid sequence of SEQ ID NO: 136, and a CDR 3 comprising the amino acid sequence of SEQ ID NO: 137; and the second VL comprises a CDR 1 comprising the amino acid sequence of SEQ ID NO: 141, a CDR 2 comprising the amino acid sequence of SEQ ID NO: 142, and a CDR 3 comprising the amino acid sequence of SEQ ID NO: 143;

(3) the first VH comprises a CDR 1 comprising the amino acid sequence of SEQ ID NO: 129, a CDR 2 comprising the amino acid sequence of SEQ ID NO: 130, and a CDR 3 comprising the amino acid sequence of SEQ ID NO: 131; the first VL comprises a CDR 1 comprising the amino acid sequence of SEQ ID NO: 132, a CDR 2 comprising the amino acid sequence of SEQ ID NO: 133, and a CDR 3 comprising the amino acid sequence of SEQ ID NO: 134; the second VH comprises a CDR 1 comprising the amino acid sequence of SEQ ID NO: 144, a CDR 2 comprising the amino acid sequence of SEQ ID NO: 145, and a CDR 3 comprising the amino acid sequence of SEQ ID NO: 146; and the second VL comprises a CDR 1 comprising the amino acid sequence of SEQ ID NO: 141, a CDR 2 comprising the amino acid sequence of SEQ ID NO: 142, and a CDR 3 comprising the amino acid sequence of SEQ ID NO: 143;

(4) the first VH comprises a CDR 1 comprising the amino acid sequence of SEQ ID NO: 129, a CDR 2 comprising the amino acid sequence of SEQ ID NO: 130, and a CDR 3 comprising the amino acid sequence of SEQ ID NO: 131; the first VL comprises a CDR 1 comprising the amino acid sequence of SEQ ID NO: 132, a CDR 2 comprising the amino acid sequence of SEQ ID NO: 133, and a CDR 3 comprising the amino acid sequence of SEQ ID NO: 134; the second VH comprises a CDR 1 comprising the amino acid sequence of SEQ ID NO: 147, a CDR 2 comprising the amino acid sequence of SEQ ID NO: 148, and a CDR 3 comprising the amino acid sequence of SEQ ID NO: 149; and the second VL comprises a CDR 1 comprising the amino acid sequence of SEQ ID NO: 150, a CDR 2 comprising the amino acid sequence of SEQ ID NO: 151, and a CDR 3 comprising the amino acid sequence of SEQ ID NO: 152;

(5) the first VH comprises a CDR 1 comprising the amino acid sequence of SEQ ID NO: 129, a CDR 2 comprising the amino acid sequence of SEQ ID NO: 130, and a CDR 3 comprising the amino acid sequence of SEQ ID NO: 131; the first VL comprises a CDR 1 comprising the amino acid sequence of SEQ ID NO: 132, a CDR 2 comprising the amino acid sequence of SEQ ID NO: 133, and a CDR 3 comprising the amino acid sequence of SEQ ID NO: 134; the second VH comprises a CDR 1 comprising the amino acid sequence of SEQ ID NO: 153, a CDR 2 comprising the amino acid sequence of SEQ ID NO: 154, and a CDR 3 comprising the amino acid sequence of SEQ ID NO: 155; and the second VL comprises a CDR 1 comprising the amino acid sequence of SEQ ID NO: 150, a CDR 2 comprising the amino acid sequence of SEQ ID NO: 151, and a CDR 3 comprising the amino acid sequence of SEQ ID NO: 152;

(6) the first VH comprises a CDR 1 comprising the amino acid sequence of SEQ ID NO: 129, a CDR 2 comprising the amino acid sequence of SEQ ID NO: 130, and a CDR 3 comprising the amino acid sequence of SEQ ID NO: 131; the first VL comprises a CDR 1 comprising the amino acid sequence of SEQ ID NO: 132, a CDR 2 comprising the amino acid sequence of SEQ ID NO: 133, and a CDR 3 comprising the amino acid sequence of SEQ ID NO: 134; the second VH comprises a CDR 1 comprising the amino acid sequence of SEQ ID NO: 156, a CDR 2 comprising the amino acid sequence of SEQ ID NO: 157, and a CDR 3 comprising the amino acid sequence of SEQ ID NO: 158; and the second VL comprises a CDR 1 comprising the amino acid sequence of SEQ ID NO: 150, a CDR 2 comprising the amino acid sequence of SEQ ID NO: 151, and a CDR 3 comprising the amino acid sequence of SEQ ID NO: 152;

(7) the first VH comprises a CDR 1 comprising the amino acid sequence of SEQ ID NO: 129, a CDR 2 comprising the amino acid sequence of SEQ ID NO: 130, and a CDR 3 comprising the amino acid sequence of SEQ ID NO: 131; the first VL comprises a CDR 1 comprising the amino acid sequence of SEQ ID NO: 132, a CDR 2 comprising the amino acid sequence of SEQ ID NO: 133, and a CDR 3 comprising the amino acid sequence of SEQ ID NO: 134; the second VH comprises a CDR 1 comprising the amino acid sequence of SEQ ID NO: 159, a CDR 2 comprising the amino acid sequence of SEQ ID NO: 160, and a CDR 3 comprising the amino acid sequence of SEQ ID NO: 161; and the second VL comprises a CDR 1 comprising the amino acid sequence of SEQ ID NO: 141, a CDR 2 comprising the amino acid sequence of SEQ ID NO: 142, and a CDR 3 comprising the amino acid sequence of SEQ ID NO: 143;

(8) the first VH comprises a CDR 1 comprising the amino acid sequence of SEQ ID NO: 164, a CDR 2 comprising the amino acid sequence of SEQ ID NO: 165, and a CDR 3 comprising the amino acid sequence of SEQ ID NO: 166; the first VL comprises a CDR 1 comprising the amino acid sequence of SEQ ID NO: 167, a CDR 2 comprising the amino acid sequence of SEQ ID NO: 168, and a CDR 3 comprising the amino acid sequence of SEQ ID NO: 169; the second VH comprises a CDR 1 comprising the amino acid sequence of SEQ ID NO: 135, a CDR 2 comprising the amino acid sequence of SEQ ID NO: 136, and a CDR 3 comprising the amino acid sequence of SEQ ID NO: 137; and the second VL comprises a CDR 1 comprising the amino acid sequence of SEQ ID NO: 138, a CDR 2 comprising the amino acid sequence of SEQ ID NO: 139, and a CDR 3 comprising the amino acid sequence of SEQ ID NO: 140;

(9) the first VH comprises a CDR 1 comprising the amino acid sequence of SEQ ID NO: 164, a CDR 2 comprising the amino acid sequence of SEQ ID NO: 165, and a CDR 3 comprising the amino acid sequence of SEQ ID NO: 166; the first VL comprises a CDR 1 comprising the amino acid sequence of SEQ ID NO: 167, a CDR 2 comprising the amino acid sequence of SEQ ID NO: 168, and a CDR 3 comprising the amino acid sequence of SEQ ID NO: 169; the second VH comprises a CDR 1 comprising the amino acid sequence of SEQ ID NO: 135, a CDR 2 comprising the amino acid sequence of SEQ ID NO: 136, and a CDR 3 comprising the amino acid sequence of SEQ ID NO: 137; and the second VL comprises a CDR 1 comprising the amino acid sequence of SEQ ID NO: 141, a CDR 2 comprising the amino acid sequence of SEQ ID NO: 142, and a CDR 3 comprising the amino acid sequence of SEQ ID NO: 143;

(10) the first VH comprises a CDR 1 comprising the amino acid sequence of SEQ ID NO: 164, a CDR 2 comprising the amino acid sequence of SEQ ID NO: 165, and a CDR 3 comprising the amino acid sequence of SEQ ID NO: 166; the first VL comprises a CDR 1 comprising the amino acid sequence of SEQ ID NO: 167, a CDR 2 comprising the amino acid sequence of SEQ ID NO: 168, and a CDR 3 comprising the amino acid sequence of SEQ ID NO: 169; the second VH comprises a CDR 1 comprising the amino acid sequence of SEQ ID NO: 144, a CDR 2 comprising the amino acid sequence of SEQ ID NO: 145, and a CDR 3 comprising the amino acid sequence of SEQ ID NO: 146; and the second VL comprises a CDR 1 comprising the amino acid sequence of SEQ ID NO: 141, a CDR 2 comprising the amino acid sequence of SEQ ID NO: 142, and a CDR 3 comprising the amino acid sequence of SEQ ID NO: 143;

(11) the first VH comprises a CDR 1 comprising the amino acid sequence of SEQ ID NO: 164, a CDR 2 comprising the amino acid sequence of SEQ ID NO: 165, and a CDR 3 comprising the amino acid sequence of SEQ ID NO: 166; the first VL comprises a CDR 1 comprising the amino acid sequence of SEQ ID NO: 167, a CDR 2 comprising the amino acid sequence of SEQ ID NO: 168, and a CDR 3 comprising the amino acid sequence of SEQ ID NO: 169; the second VH comprises a CDR 1 comprising the amino acid sequence of SEQ ID NO: 147, a CDR 2 comprising the amino acid sequence of SEQ ID NO: 148, and a CDR 3 comprising the amino acid sequence of SEQ ID NO: 149; and the second VL comprises a CDR 1 comprising the amino acid sequence of SEQ ID NO: 150, a CDR 2 comprising the amino acid sequence of SEQ ID NO: 151, and a CDR 3 comprising the amino acid sequence of SEQ ID NO: 152;

(12) the first VH comprises a CDR 1 comprising the amino acid sequence of SEQ ID NO: 164, a CDR 2 comprising the amino acid sequence of SEQ ID NO:

165, and a CDR 3 comprising the amino acid sequence of SEQ ID NO: 166; the first VL comprises a CDR 1 comprising the amino acid sequence of SEQ ID NO: 167, a CDR 2 comprising the amino acid sequence of SEQ ID NO: 168, and a CDR 3 comprising the amino acid sequence of SEQ ID NO: 169; the second VH comprises a CDR 1 comprising the amino acid sequence of SEQ ID NO: 153, a CDR 2 comprising the amino acid sequence of SEQ ID NO: 154, and a CDR 3 comprising the amino acid sequence of SEQ ID NO: 155; and the second VL comprises a CDR 1 comprising the amino acid sequence of SEQ ID NO: 150, a CDR 2 comprising the amino acid sequence of SEQ ID NO: 151, and a CDR 3 comprising the amino acid sequence of SEQ ID NO: 152;

(13) the first VH comprises a CDR 1 comprising the amino acid sequence of SEQ ID NO: 164, a CDR 2 comprising the amino acid sequence of SEQ ID NO: 165, and a CDR 3 comprising the amino acid sequence of SEQ ID NO: 166; the first VL comprises a CDR 1 comprising the amino acid sequence of SEQ ID NO: 167, a CDR 2 comprising the amino acid sequence of SEQ ID NO: 168, and a CDR 3 comprising the amino acid sequence of SEQ ID NO: 169; the second VH comprises a CDR 1 comprising the amino acid sequence of SEQ ID NO: 156, a CDR 2 comprising the amino acid sequence of SEQ ID NO: 157, and a CDR 3 comprising the amino acid sequence of SEQ ID NO: 158; and the second VL comprises a CDR 1 comprising the amino acid sequence of SEQ ID NO: 150, a CDR 2 comprising the amino acid sequence of SEQ ID NO: 151, and a CDR 3 comprising the amino acid sequence of SEQ ID NO: 152; and

(14) the first VH comprises a CDR 1 comprising the amino acid sequence of SEQ ID NO: 164, a CDR 2 comprising the amino acid sequence of SEQ ID NO: 165, and a CDR 3 comprising the amino acid sequence of SEQ ID NO: 166; the first VL comprises a CDR 1 comprising the amino acid sequence of SEQ ID NO: 167, a CDR 2 comprising the amino acid sequence of SEQ ID NO: 168, and a CDR 3 comprising the amino acid sequence of SEQ ID NO: 169; the second VH comprises a CDR 1 comprising the amino acid sequence of SEQ ID NO: 159, a CDR 2 comprising the amino acid sequence of SEQ ID NO: 160, and a CDR 3 comprising the amino acid sequence of SEQ ID NO: 161; and the second VL comprises a CDR 1 comprising the amino acid sequence of SEQ ID NO: 141, a CDR 2 comprising the amino acid sequence of SEQ ID NO: 142, and a CDR 3 comprising the amino acid sequence of SEQ ID NO: 143.

17. The bispecific antibody of claim 16, wherein the bispecific antibody is humanized.

18. The bispecific antibody of claim 16, wherein the bispecific antibody comprises at least one Fab, Fab', or single-chain variable fragment (scFv).

19. A pharmaceutical composition comprising the bispecific antibody of claim 16.

20. The bispecific antibody of claim 16, wherein the first and second gluten peptides are the same or different and are independently selected from the following list: a 33mer gliadin peptide comprising the amino acid sequence of SEQ ID NO: 201, an alpha 1 gliadin peptide comprising the amino acid sequence of SEQ ID NO: 182, an alpha 2 gliadin peptide comprising the amino acid sequence of SEQ ID NO: 183, a gamma 1 gliadin peptide comprising the amino acid sequence of SEQ ID NO: 184 or 206, a gamma 2 gliadin peptide comprising the amino acid sequence of SEQ ID NO: 175, 185 or 207, an omega 1 gliadin peptide comprising the amino acid sequence of SEQ ID NO: 186 or 204, an omega 2 gliadin peptide comprising the amino acid sequence of SEQ ID NO: 187 or 204, a BC hordein peptide comprising the amino acid sequence of SEQ ID NO: 176, 188 or 205, an alpha 3 gliadin peptide comprising the amino acid sequence of SEQ ID NO: 189, an alpha 1b gliadin peptide comprising the amino acid sequence of SEQ ID NO: 190, a gamma 4a gliadin peptide comprising the amino acid sequence of SEQ ID NO: 191 or 209, a gamma 4b gliadin peptide comprising the amino acid sequence of SEQ ID NO: 192, an avenin 1 peptide comprising the amino acid sequence of SEQ ID NO: 193, an avenin 2 peptide comprising the amino acid sequence of SEQ ID NO: 194, an avenin 3 peptide comprising the amino acid sequence of SEQ ID NO: 195, a hordein 1 peptide comprising the amino acid sequence of SEQ ID NO: 196, a hordein 2 peptide comprising the amino acid sequence of SEQ ID NO: 197, a secalin 1 peptide comprising the amino acid sequence of SEQ ID NO: 198, a secalin 2 peptide comprising the amino acid sequence of SEQ ID NO: 199, and a 26mer gliadin peptide comprising the amino acid sequence of SEQ ID NO: 202.

21. The bispecific antibody of claim 16,
wherein the first arm has binding activity to multiple different complexes of HLA-DQ2.5 with any of two or more different gluten peptides, including at least two gluten peptides from the group below; and
wherein the second arm has binding activity to multiple different complexes of HLA-DQ2.5 with any of two or more different gluten peptides, including at least two gluten peptides from the group below:
a 33mer gliadin peptide comprising the amino acid sequence of SEQ ID NO: 201, an alpha 1 gliadin peptide comprising the amino acid sequence of SEQ ID NO: 182, an alpha 2 gliadin peptide comprising the amino acid sequence of SEQ ID NO: 183, a gamma 1 gliadin peptide comprising the amino acid sequence of SEQ ID NO: 184 or 206, a gamma 2 gliadin peptide comprising the amino acid sequence of SEQ ID NO: 175, 185 or 207, an omega 1 gliadin peptide comprising the amino acid sequence of SEQ ID NO: 186 or 204, an omega 2 gliadin peptide comprising the amino acid sequence of SEQ ID NO: 187 or 204, a BC hordein peptide comprising the amino acid sequence of SEQ ID NO: 176, 188 or 205, an alpha 3 gliadin peptide comprising the amino acid sequence of SEQ ID NO: 189, an alpha 1b gliadin peptide comprising the amino acid sequence of SEQ ID NO: 190, a gamma 4a gliadin peptide comprising the amino acid sequence of SEQ ID NO: 191 or 209, a gamma 4b gliadin peptide comprising the amino acid sequence of SEQ ID NO: 192, an avenin 1 peptide comprising the amino acid sequence of SEQ ID NO: 193, an avenin 2 peptide comprising the amino acid sequence of SEQ ID NO: 194, an avenin 3 peptide comprising the amino acid sequence of SEQ ID NO: 195, a hordein 1 peptide comprising the amino acid sequence of SEQ ID NO: 196, a hordein 2 peptide comprising the amino acid sequence of SEQ ID NO: 197, a secalin 1 peptide comprising the amino acid sequence of SEQ ID NO: 198, a secalin 2 peptide comprising the amino acid sequence of SEQ ID NO: 199, and a 26mer gliadin peptide comprising the amino acid sequence of SEQ ID NO: 202.

22. The bispecific antibody of claim 16, wherein the first VH comprises a CDR 1 comprising the amino acid sequence of SEQ ID NO: 129, a CDR 2 comprising the amino acid sequence of SEQ ID NO: 130, and a CDR 3 comprising the amino acid sequence of SEQ ID NO: 131; the first VL comprises a CDR 1 comprising the amino acid sequence of SEQ ID NO: 132, a CDR 2 comprising the amino acid sequence of SEQ ID NO: 133, and a CDR 3 comprising the amino acid sequence of SEQ ID NO: 134; the second VH comprises a CDR 1 comprising the amino acid sequence of SEQ ID NO: 153, a CDR 2 comprising the amino acid sequence of SEQ ID NO: 154, and a CDR 3 comprising the amino acid sequence of SEQ ID NO: 155; and the second VL comprises a CDR 1 comprising the amino acid sequence of SEQ ID NO: 150, a CDR 2 comprising the amino acid sequence of SEQ ID NO: 151, and a CDR 3 comprising the amino acid sequence of SEQ ID NO: 152.

* * * * *